US009504684B2

United States Patent
Blomgren et al.

(10) Patent No.: US 9,504,684 B2
(45) Date of Patent: *Nov. 29, 2016

(54) SYK INHIBITORS

(71) Applicant: Gilead Sciences, Inc., Foster City, CA (US)

(72) Inventors: Peter A. Blomgren, North Branford, CT (US); Astrid Clarke, Guilford, CT (US); Kevin S. Currie, North Branford, CT (US); Julie Di Paolo, Northford, CT (US); Jeffrey E. Kropf, Branford, CT (US); Seung H. Lee, Branford, CT (US); Jennifer R. Lo, Branford, CT (US); Scott A. Mitchell, East Haven, CT (US); Aaron C. Schmitt, Hamden, CT (US); Sundaramoorthi Swaminathan, Burlingame, CA (US); Jin-Ming Xiong, Guilford, CT (US); Jianjun Xu, Madison, CT (US); Zhongdong Zhao, Guilford, CT (US)

(73) Assignee: Gilead Sciences, Inc., Foster City, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/795,123

(22) Filed: Jul. 9, 2015

(65) Prior Publication Data

US 2016/0058758 A1  Mar. 3, 2016

Related U.S. Application Data

(60) Provisional application No. 62/024,284, filed on Jul. 14, 2014.

(51) Int. Cl.
*A61K 31/4985* (2006.01)
*A61K 31/5377* (2006.01)
*A61K 31/475* (2006.01)
*A61K 31/519* (2006.01)

(52) U.S. Cl.
CPC ......... *A61K 31/4985* (2013.01); *A61K 31/475* (2013.01); *A61K 31/519* (2013.01); *A61K 31/5377* (2013.01)

(58) Field of Classification Search
CPC .................... A61K 31/4985; A61K 31/5377; A61K 31/475; A61K 31/519
See application file for complete search history.

(56) References Cited

U.S. PATENT DOCUMENTS

| 8,440,667 B2 | 5/2013 | Mitchell et al. |
| 8,455,493 B2 | 6/2013 | Mitchell et al. |
| 2013/0267496 A1 | 10/2013 | Mitchell et al. |

FOREIGN PATENT DOCUMENTS

WO  WO-2015/100217 A1  7/2015

OTHER PUBLICATIONS

Currie, Kevin S. et al, (2014) "Discovery of GS-9973, a Selective end Orally Efficacious Inhibitor of Spleen Tyrosine Kinase" Journal of Medicinal Chemistry, vol. 57, No. 9, pp. 3856-3873.
International Search Report—Written Opinion dated Nov. 2, 2015 for PCT/US2015/039677.
Gorodetskly, Vadim et al. (2015) "Primary Diffuse Large B-Cell Lymphoma of the Liver in a Patient with Sjogren Syndrome" Oncological Medicine. vol. 2016, Article. ID 205357, 5 pages.

*Primary Examiner* — Sahar Javanmard
(74) *Attorney, Agent, or Firm* — Roy Issac

(57) ABSTRACT

The present disclosure relates to compounds that are Syk inhibitors and to their use in the treatment of various disease states, including cancer and inflammatory conditions. In particular embodiments, the structure of the compounds is given by Formula I:

Formula I wherein $R^1$, $R^2$, $R^3$, and $R^4$ are as described herein. The present disclosure further provides pharmaceutical compositions that include a compound of Formula I, or pharmaceutically acceptable salts thereof, and methods of using these compounds and compositions to treat conditions mediated by Syk. In certain embodiments, also disclosed are methods for treating a cancer in a subject (e.g., a human) in need thereof, comprising administering to the subject a therapeutically effective amount of a compound of formula I, or a pharmaceutically acceptable salt thereof, in combination with a vinca-alkaloid, or a pharmaceutically acceptable salt thereof.

30 Claims, 4 Drawing Sheets

FIGURE 1 (A and B).
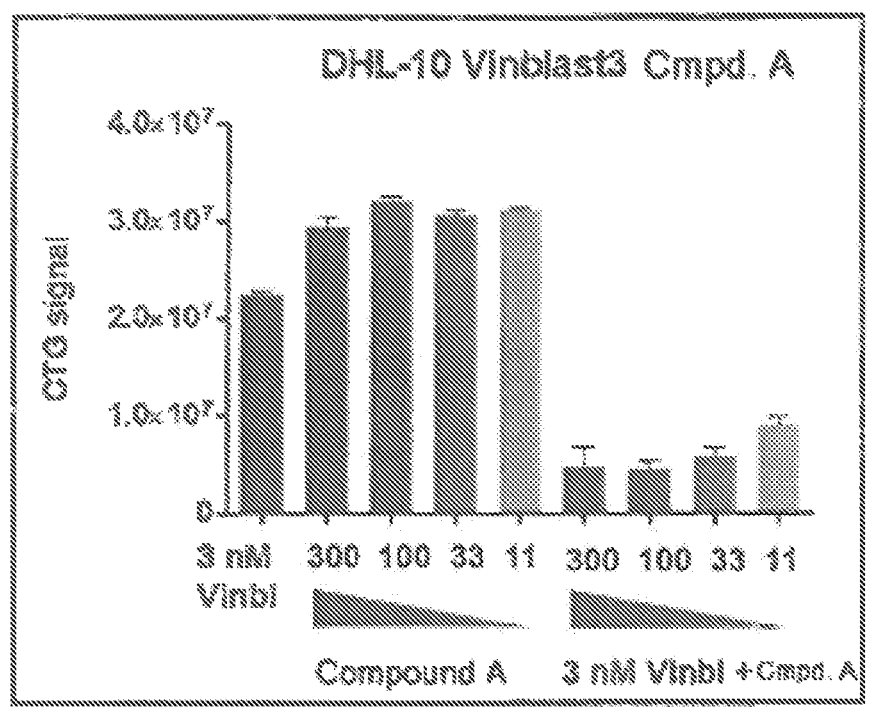
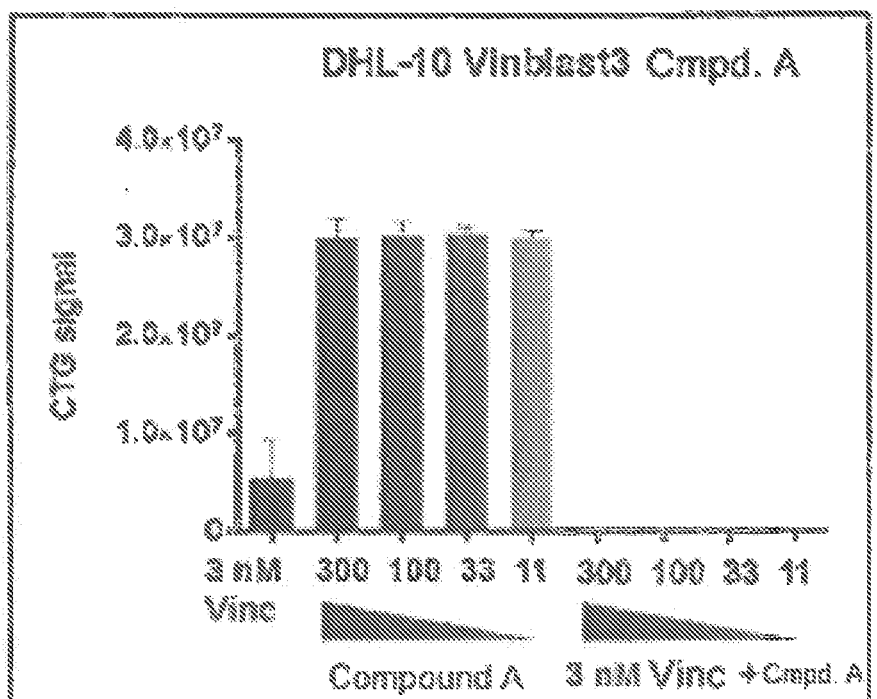

Figure 2 (A and B)
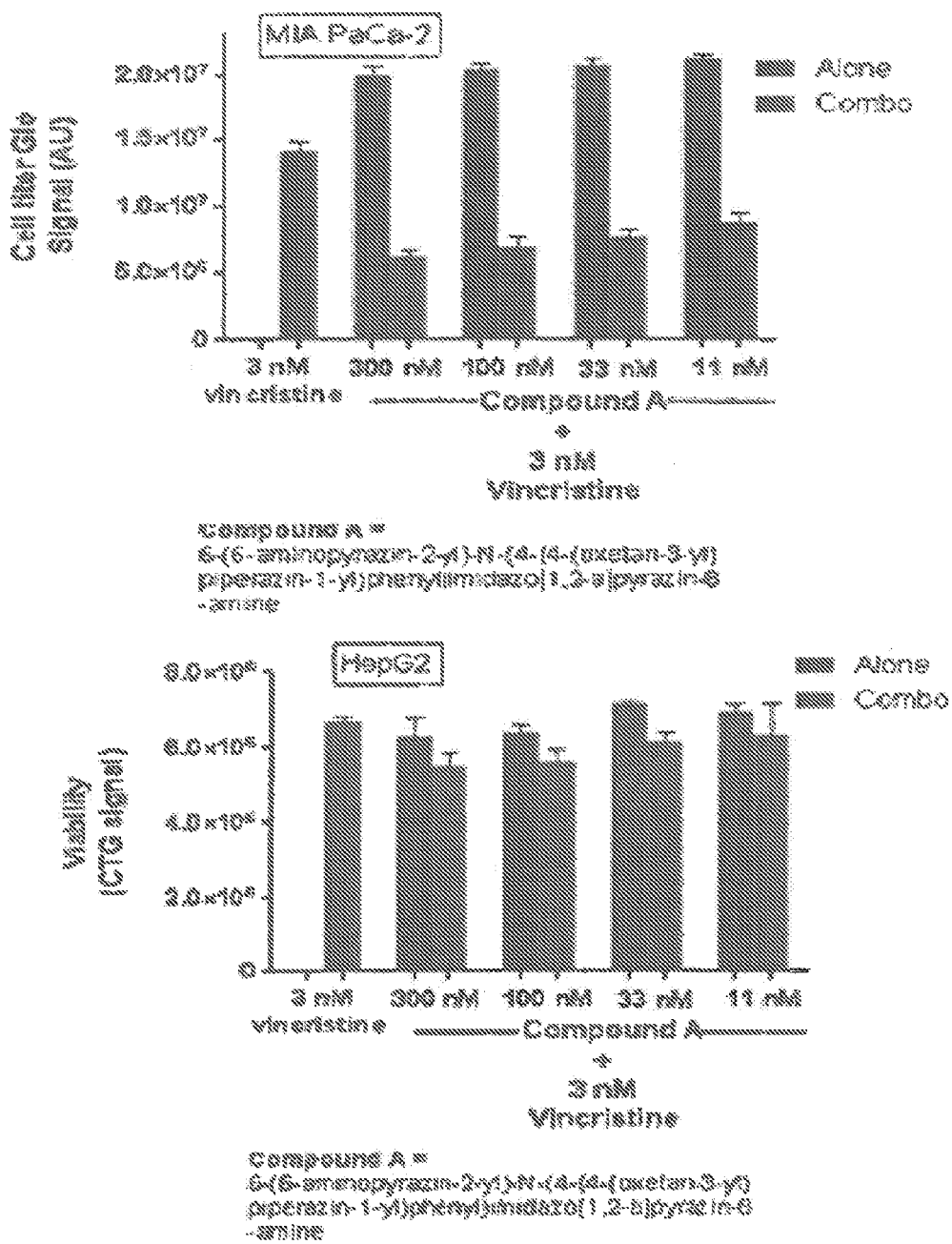

SYK INHIBITORS

CROSS REFERENCE TO RELATED APPLICATIONS

This application claims priority to and the benefit of U.S. Provisional Application No. 62/024,284, filed Jul. 14, 2014, which is hereby incorporated by reference in its entirety

FIELD

The present disclosure relates to compounds and to their use in the treatment of various diseases, including cancer and inflammatory conditions. The disclosure also relates to methods for preparation of the compounds and to pharmaceutical compositions comprising such compounds.

BACKGROUND

Protein kinases, the largest family of human enzymes, encompass well over 500 proteins. Spleen Tyrosine Kinase (Syk) is a member of the Syk family of tyrosine kinases, and is a regulator of early B-cell development as well as mature B-cell activation, signaling, and survival.

The inhibition of Syk activity can be useful for the treatment of allergic disorders, autoimmune diseases and inflammatory diseases such as: SLE, rheumatoid arthritis, multiple vasculitides, idiopathic thrombocytopenic purpura (ITP), myasthenia gravis, allergic rhinitis, chronic obstructive pulmonary disease (COPD), adult respiratory distress syndrome (ARDs) and asthma. In addition, Syk has been reported to play an important role in ligand-independent tonic signaling through the B-cell receptor, known to be an important survival signal in B-cells. Thus, inhibition of Syk activity may also be useful in treating certain types of cancer, including B-cell lymphoma and leukemia. U.S. Pat. Nos. 8,455,493 and 8,440,667 disclose Syk inhibitors, the disclosures of which are hereby incorporated by reference in their entirety.

There is a continued need to provide compounds that are effective Syk inhibitors. including compounds having desirable pharmacokinetic properties for use as therapeutics for treating cancers and other diseases, including for use as potential combinations with other therapeutics or chemotherapeutica agents for treating hematologic and solid tumor cancers.

SUMMARY

Accordingly, the present disclosure provides compounds that function as Syk inhibitors. In one embodiment, the disclosure provides a compound, of Formula I:

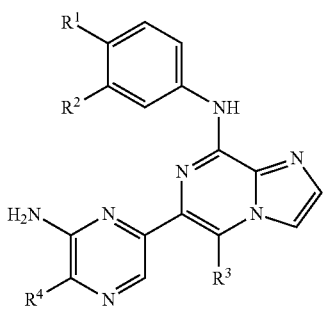

Formula I or a pharmaceutically acceptable salt thereof, wherein:

$R^1$ is selected from the group consisting of

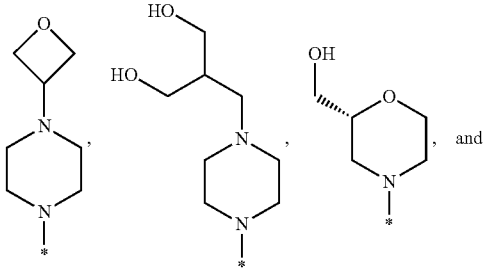

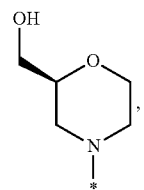

wherein * indicates the carbon atom of the indicated phenyl ring of Formula I to which $R^1$ is attached;

$R^2$ is H or 2-hydroxyethoxyl;

$R^3$ is H or methyl; and $R^4$ is H or methyl.

In some embodiments of the compound of Formula I, or a pharmaceutically acceptable salt thereof, $R^1$ is selected from the group consisting of

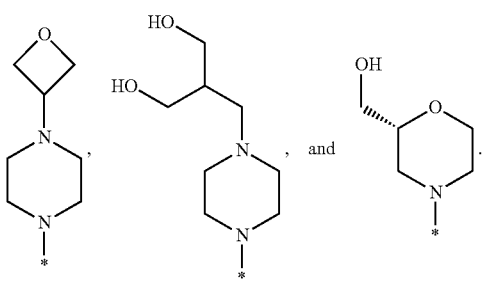 [SMILES: *N1CCN(C2COC2)CC1 ; *N1CCN(CC(CO)CO)CC1 ; *N1CCO[C@@H](CO)C1]

In some embodiments, $R^1$ is

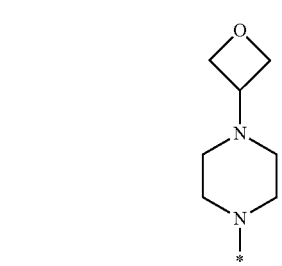

In some embodiments, $R^1$ is

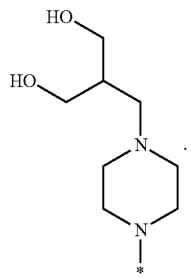

In some embodiments, $R^1$ is

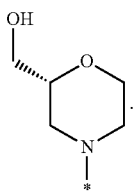

In some embodiments of the compound of Formula I, or a pharmaceutically acceptable salt thereof, $R^2$ is H. In some embodiments of the compound of Formula I, or a pharmaceutically acceptable salt thereof, $R^2$ is 2-hydroxyethoxyl.

In some embodiments of the compound of Formula I, or a pharmaceutically acceptable salt thereof, $R^3$ is H. In some embodiments of the compound of Formula I, or a pharmaceutically acceptable salt thereof, $R^3$ is methyl.

In some embodiments of the compound of Formula I, or a pharmaceutically acceptable salt thereof, $R^4$ is H or methyl. In some embodiments of the compound of Formula I, or a pharmaceutically acceptable salt thereof, $R^4$ is H. In some embodiments of the compound of Formula I, or a pharmaceutically acceptable salt thereof, $R^4$ is methyl.

In some embodiments of the compound of Formula I, or a pharmaceutically acceptable salt thereof, $R^1$ is

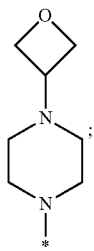

$R^2$ is H or 2-hydroxyethoxyl; $R^3$ is H or methyl; and $R^4$ is H or methyl. In one variation of Formula I, or a pharmaceutically acceptable salt thereof, $R^1$ is

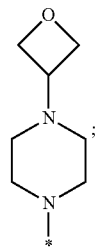

$R^2$ is H; $R^3$ is H or methyl; and $R^4$ is H or methyl. In another variation of Formula I, or a pharmaceutically acceptable salt thereof, $R^1$ is

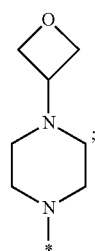

$R^2$ is 2-hydroxyethoxyl; $R^3$ is H; and $R^4$ is H or methyl.

In some embodiments of the compound of Formula I, or a pharmaceutically acceptable salt thereof, $R^1$ is

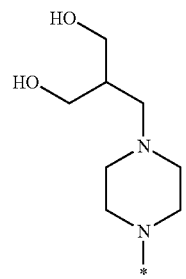 [SMILES: *N1CCN(CC(CO)CO)CC1]

and any one of $R^2$, $R^3$ and $R^4$ is H. In another variation of Formula I, or a pharmaceutically acceptable salt thereof, $R^1$ is

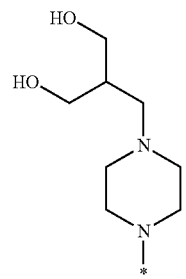 [SMILES: *N1CCN(CC(CO)CO)CC1]

and any two of $R^2$, $R^3$ and $R^4$ is H.

In some embodiments of the compound of Formula I, or a pharmaceutically acceptable salt thereof, $R^1$ is

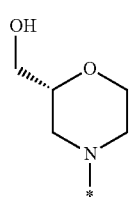 [SMILES: *N1CCO[C@@H](CO)C1]

and any one of $R^2$, $R^3$ and $R^4$ is H. In some embodiments of the compound of Formula I, or a pharmaceutically acceptable salt thereof, $R^1$ is

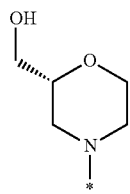 [SMILES: *N1CCO[C@@H](CO)C1]

and any two of $R^2$, $R^3$ and $R^4$ is H.

In some embodiments of the compound of Formula I, or a pharmaceutically acceptable salt thereof, $R^1$ is selected from the group consisting of

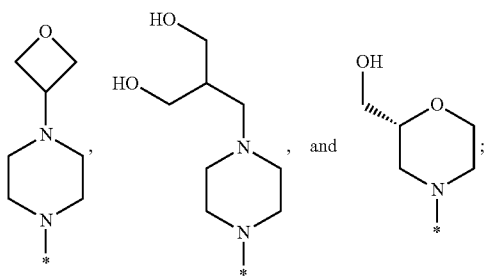 [SMILES: *N1CCN(C2COC2)CC1 ; *N1CCN(CC(CO)CO)CC1 ; *N1CCO[C@@H](CO)C1]

$R^2$ and $R^3$ are each H and $R^4$ is H or methyl.

In some embodiments, the compound of Formula I is selected from the group consisting of:

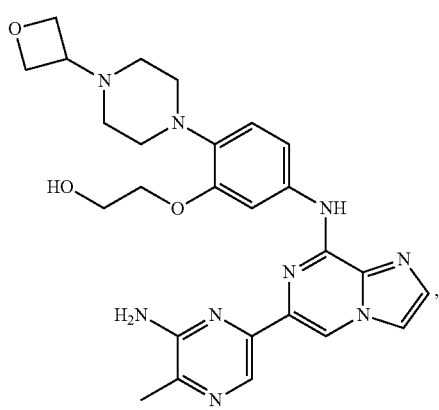

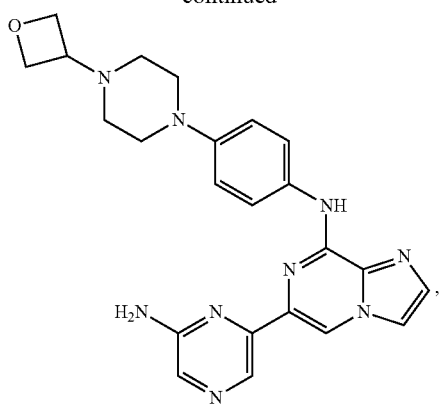

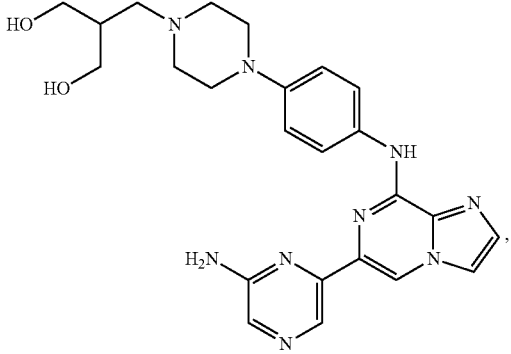

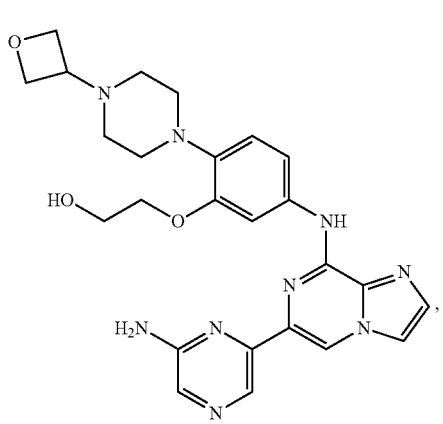

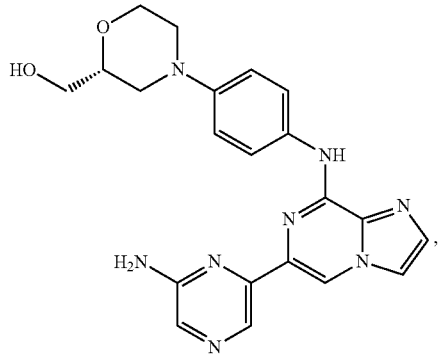

-continued

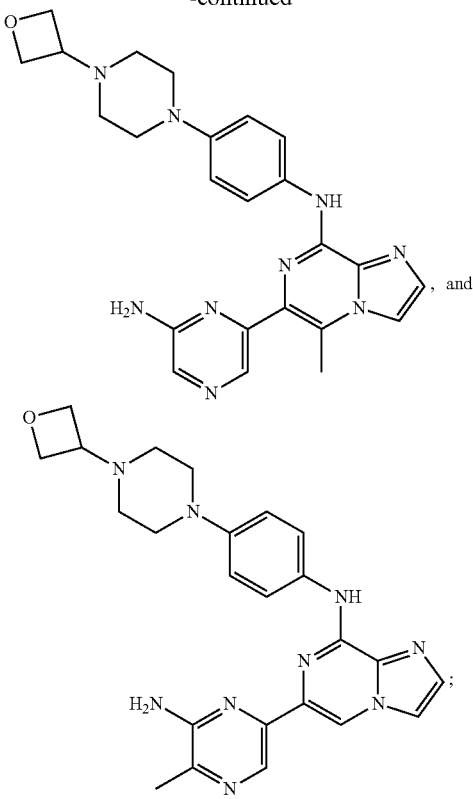

or a pharmaceutically acceptable salt thereof.

In some embodiments, the compound of Formula I is selected from the group consisting of:

2-(5-((6-(6-amino-5-methylpyrazin-2-yl)imidazo[1,2-a]pyrazin-8-yl)amino)-2-(4-(oxetan-3-yl)piperazin-1-yl)phenoxy)ethanol;

6-(6-aminopyrazin-2-yl)-N-(4-(4-(oxetan-3-yl)piperazin-1-yl)phenyl)imidazo[1,2-a]pyrazin-8-amine;

2-((4-(4-((6-(6-aminopyrazin-2-yl)imidazo[1,2-a]pyrazin-8-yl)amino)phenyl)piperazin-1-yl)methyl)propane-1,3-diol;

2-(5-((6-(6-aminopyrazin-2-yl)imidazo[1,2-a]pyrazin-8-yl)amino)-2-(4-(oxetan-3-yl)piperazin-1-yl)phenoxy)ethanol;

(R)-(4-(4-(((6-aminopyrazin-2-yl)imidazo[1,2-a]pyrazin-8 yl)amino)phenyl)morpholin-2-yl)methanol;

6-(6-aminopyrazin-2-yl)-5-methyl-N-(4-(4-(oxetan-3-yl)piperazin-1-yl)phenyl)imidazo[1,2-a]pyrazin-8-amine; and 6-(6-amino-5-methylpyrazin-2-yl)-N-(4-(4-(oxetan-3-yl)piperazin-1-yl)phenyl)imidazo[1,2-a]pyrazin-8-amine;

or a pharmaceutically acceptable salt thereof.

Provided herein are also methods of using the compound of Formula I, or a pharmaceutically acceptable salt thereof, in the treatment of a disease or condition in a subject, such as a human. Such diseases and conditions include inflammatory disorders, allergic disorders, autoimmune diseases, or a cancer (including carcinoma, sarcoma, melanoma, lymphoma and leukemia).

In some instances, the diseases and conditions that may be treated with the compounds disclosed herein include cancers such as bladder cancer, breast cancer, colorectal cancer, endometrial cancer, kidney/renal-cell cancer, lung cancer, pancreatic cancer, prostate cancer, thyroid cancer, leukemia, melanoma, and non-Hodgkin's lymphoma.

In some embodiments, the disease is cancer, including a hematologic malignancy or a solid tumor. In some embodiments, the cancer is lymphoma, multiple myeloma, or leukemia. In some embodiments, the hematologic malignancy is leukemia or lymphoma.

In some embodiments, the disease or condition that may be treated is a hematologic malignancy selected from the group consisting of lymphoma (e.g. small lymphocytic lymphoma (SLL), non-Hodgkin's lymphoma (NHL) indolent non-Hodgkin's lymphoma (iNHL), refractory iNHL, mantle cell lymphoma (MCL), follicular lymphoma (FL), lymphoplasmacytic lymphoma (LPL), marginal zone lymphoma (MZL), immunoblastic large cell lymphoma, lymphoblastic lymphoma, Splenic marginal zone B-cell lymphoma (+/− villous lymphocytes), Nodal marginal zone lymphoma (+/− monocytoid B-cells), Extranodal marginal zone B-cell lymphoma of mucosa-associated lymphoid tissue (MALT) type, T-cell lymphoma (e.g. cutaneous T-cell lymphoma, extranodal T-cell lymphoma, anaplastic large cell lymphoma, angioimmunoblastic T-cell lymphoma, mycosis fungoides), B-cell lymphoma, diffuse large B-cell lymphoma (DLBCL), Mediastinal large B-cell lymphoma, Intravascular large B-cell lymphoma, Primary effusion lymphoma, small non-cleaved cell lymphoma, or Burkitt's lymphoma), multiple myeloma, plasmacytoma, and leukemia (e.g. acute lymphocytic leukemia (ALL), T-cell acute lymphoblastic leukemia (T-ALL), B-cell acute lymphoblastic leukemia (B-ALL), B-cell prolymphocytic leukemia, acute myeloid leukemia (AML), chronic lymphocytic leukemia (CLL), juvenile myelomonocytic leukemia (JMML), minimal residual disease (MRD), hairy cell leukemia, myelofibrosis (e.g. primary or secondary myelofibrosis), or chronic myeloid leukemia (CML), myelodysplastic syndrome (MDS), myeloproliferative disease (MPD), and Waldestrom's macroglobulinemia (WM).

In some embodiments, the cancer is a solid tumor. In some embodiments, the solid tumor is from a cancer selected from the group consisting of pancreatic cancer, urological cancer, bladder cancer, colorectal cancer, colon cancer, breast cancer, prostate cancer, renal cancer, hepatocellular cancer, thyroid cancer, gall bladder cancer, lung cancer (e.g. non-small cell lung cancer, small-cell lung cancer), ovarian cancer, cervical cancer, gastric cancer, endometrial cancer, esophageal cancer, head and neck cancer, melanoma, neuroendocrine cancer, CNS cancer, brain tumors (e.g., glioma, anaplastic oligodendroglioma, adult glioblastoma multiforme, and adult anaplastic astrocytoma), bone cancer, soft tissue sarcoma, retinoblastomas, neuroblastomas, peritoneal effusions, malignant pleural effusions, mesotheliomas, Wilms tumors, trophoblastic neoplasms, hemangiopericytomas, Kaposi's sarcomas, myxoid carcinoma, round cell carcinoma, squamous cell carcinomas, esophageal squamous cell carcinomas, oral carcinomas, cancers of the adrenal cortex, and ACTH-producing tumors.

In some embodiments, the disease or condition that may be treated is selected from the group consisting of systemic lupus erythematosus (SLE), myestenia gravis, Goodpasture's syndrome, glomerulonephritis, hemorrhage, pulmonary hemorrhage, atherosclerosis, rheumatoid arthritis (RA), psoriatic arthritis, monoarticular arthritis, osteoarthritis, gouty arthritis, spondylitis, Behçet disease, autoimmune thyroiditis, Reynaud's syndrome, acute disseminated encephalomyelitis, chronic idiopathic thrombocytopenic purpura, multiple sclerosis (MS), Sjögren's syndrome, autoimmune hemolytic anemia, tissue graft rejection, hyperacute rejection of transplanted organs, allograft rejection, graft-versus-host disease, diseases involving leukocyte diapedesis, disease states due to leukocyte dyscrasia and metastasis, granulocyte transfusion-associated syndromes, cytokine-induced toxicity, scleroderma, vasculitis, asthma, psoriasis, inflammatory bowel disease (e.g. chronic inflammatory bowel disease, ulcerative colitis, Crohn's disease, necrotizing enterocolitis), irritable bowel syndrome, dermatomyositis, Addison's disease, Parkinson's disease, Alzheimer's disease, diabetes, type I diabetes mellitus, sepsis, septic shock, endotoxic shock, gram negative sepsis, gram positive sepsis, and toxic shock syndrome, multiple organ injury syndrome secondary to septicemia, trauma, hypovolemic shock, allergic conjunctivitis, vernal conjunctivitis, and thyroid-associated ophthalmopathy, easinophilic granuloma, eczema, chronic bronchitis, acute respiratory distress syndrome, allergic rhinitis, coryza, hay fever, bronchial asthma, silicosis, pulmonary sarcoidosis, plearisy, alveolitis, emphysema, pneumonia, bacterial pneumonia, bronchiectasis, and pulmonary oxygen toxicity, reperfusion injury of the myocardium, brain, or extremities, thermal injury, cystic fibrosis, keloid formation or scar tissue formation, fever and myalgias due to infection, and brain or spinal cord injury due to minor trauma, diseases involving leukocyte diapedesis, acute hypersensitivity, delayed hypersensitivity, urticaria, food allergies, skin sunburn, inflammatory pelvic disease, urethritis, uveitis, sinusitis, pneumonitis, encephalitis, meningitis, myocarditis, nephritis, osteomyelitis, myositis, hepatitis, alcoholic hepatitis, gastritis, enteritis, con tact dermatitis, atopic dermatitis, gingivitis, appendicitis, pancreatitis, cholocystitis, polycythemia vera, essential thrombocythemia, and polycystic kidney disease.

In some embodiments, the disease is an autoimmune disease. In some embodiments, the autoimmune disease is systemic lupus erythematosus (SLE), myestenia gravis, rheumatoid arthritis (RA), acute disseminated encephalomyelitis, idiopathic thrombocytopenic purpura, multiple sclerosis (MS), Sjoegren's syndrome, psoriasis, autoimmune hemolytic anemia, asthma, ulcerative colitis, Crohn's disease, irritable bowel disease, or chronic obstructive pulmonary disease (COPD). In some embodiments, the disease is excessive or destructive immune reactions, such as asthma, rheumatoid arthritis, multiple sclerosis, chronic obstructive pulmonary disease (COPD), or systemic lupus erythematosus.

In some embodiments, the disclosure provides pharmaceutical compositions comprising a compound of Formula I, or a pharmaceutically acceptable salt thereof, and a pharmaceutically acceptable vehicle.

In some embodiments, the disclosure provides pharmaceutical compositions comprising a therapeutically effective amount of a compound of Formula I, or a pharmaceutically acceptable salt, pharmaceutically acceptable ester, stereoisomer, mixture of stereoisomers or tautomer thereof, and at least one pharmaceutically acceptable vehicle.
Examples of pharmaceutically acceptable vehicle may be selected from carriers and other excipients, adjuvants and the like.

Also provided are methods of treating a disease or condition in a subject in need thereof by administering to the subject a therapeutically effective amount of a compound of Formula I, or a pharmaceutically acceptable salt, pharmaceutically acceptable ester, stereoisomer, mixture of stereoisomers or tautomer thereof, or a pharmaceutical composition thereof. In one variation of a method of treating a disease or condition in a subject in need thereof (e.g., a human in need thereof), the method comprises administering to the subject a therapeutically effective amount of a compound of Formula I, or a pharmaceutically acceptable salt thereof. In some embodiments, the disease or condition is an inflammatory disorder, an allergic disorder, an autoimmune disease, or a cancer.

Also provided is a method of inhibiting kinase activity of a Syk kinase polypeptide by contacting the polypeptide with a compound of Formula I or a pharmaceutically acceptable salt, pharmaceutically acceptable ester, stereoisomer, mixture of stereoisomers or tautomer thereof. In one aspect is provided a method of inhibiting kinase activity of a Syk kinase polypeptide by contacting the polypeptide with a compound of Formula I or a pharmaceutically acceptable salt thereof.

Also provided are methods of methods for treating cancer in a subject in need thereof, comprising administering to the subject a therapeutically effective amount of a compound of formula I, or a pharmaceutically acceptable salt thereof, in combination with a vinca-alkaloid, or a pharmaceutically acceptable salt thereof. In some embodiments, the subject is a human who has a cancer responsive to Syk activity. In another embodiment, the subject is a human who has a solid cancer tumor which expresses Syk. In some embodiments, the subject is a human who has a 17p deletion, a TP53 mutation, NOTCH1, a SF3B1 mutation, a 11q deletion, or any combination thereof. In one embodiment, the subject is a human who has a 17p deletion, a TP53 mutation, or a combination thereof. In another embodiment, the subject is a human who has NOTCH1, a SF3B1 mutation, a 11q deletion, or any combination thereof.

In some embodiments, the vinca-alkaloid is selected from the group consisting of vincristine, vinblastine, vindesine, vinorelbine, desoxyvincaminol, vincaminol, vinburnine, vincamajine, and vineridine, and pharmaceutically acceptable salts thereof. In certain embodiments, at least one vinca-alkaloid is selected from the group consisting of vincristine, vinblastine, vindesine, vinorelbine, desoxyvincaminol, vincaminol, vinburnine, vincamajine, and vineridine and pharmaceutically acceptable salts thereof. In some embodiments, the vinca-alkaloid is selected from the group consisting of vincristine, vinblastine, vindesine, and vinorelbine, and pharmaceutically acceptable salts thereof. In other embodiments, the vinca-alkaloid is selected from the group consisting of vincristine and vinblastine, and pharmaceutically acceptable salts thereof. In one embodiment, the vinca-alkaloid is vincristine and pharmaceutically acceptable salts thereof. In another embodiment, the vinca-alkaloid is vinblastine and pharmaceutically acceptable salts thereof.

Provided herein are also methods for treating cancer in a subject in need thereof, comprising administering to the subject a therapeutically effective amount of a compound of formula I, or a pharmaceutically acceptable salt thereof, and a therapeutically effective amount of a vinca-alkaloid, or a pharmaceutically acceptable salt thereof. In certain embodiments, the compound of formula I is

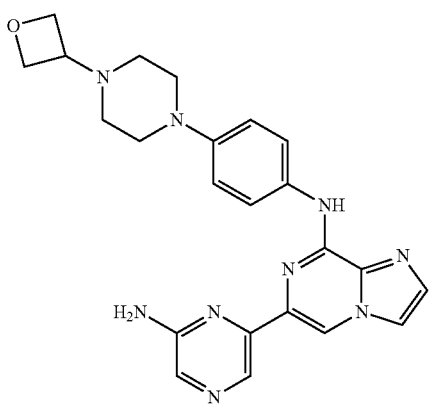 [SMILES: Nc1cncc(-c2cn3ccnc3c(Nc3ccc(N4CCN(C5COC5)CC4)cc3)n2)n1]

and the vinca-alkaloid is selected from the group of vincristine or vinblastine. In one embodiment, the compound of formula I is

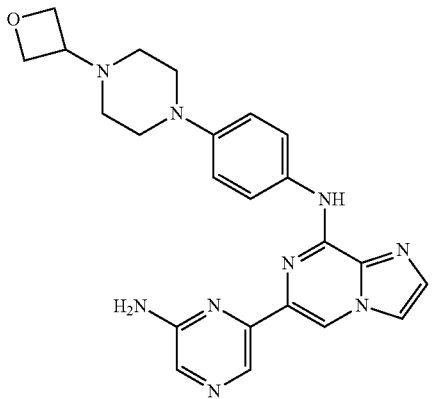 [SMILES: Nc1cncc(-c2cn3ccnc3c(Nc3ccc(N4CCN(C5COC5)CC4)cc3)n2)n1]

and the vinca-alkalod is vincristine. In another embodiment, the compound of formula I is

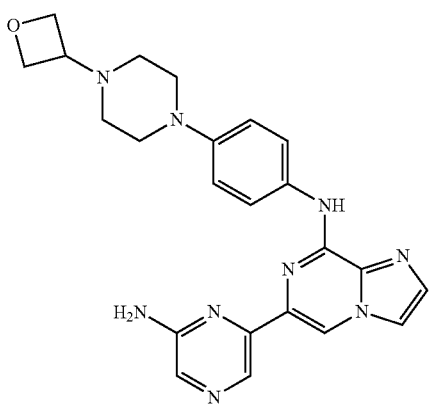 [SMILES: Nc1cncc(-c2cn3ccnc3c(Nc3ccc(N4CCN(C5COC5)CC4)cc3)n2)n1]

and the vinca-alkaloid is vinblastine.

Provided herein are also methods for treating cancer in a subject in need thereof comprising administering to the subject a therapeutically effective amount of a compound of formula I, or a pharmaceutically acceptable salt thereof, and a therapeutically effective amount of a vinca-alkaloid, or a pharmaceutically acceptable salt thereof, wherein: the subject is a human who is not undergoing any other anti-cancer treatments; and the subject is (i) refractory to at least one anti-cancer treatment, or (ii) in relapse after treatment with at least one anti-cancer therapy, or a combination thereof. In certain embodiments, the compound of formula I is

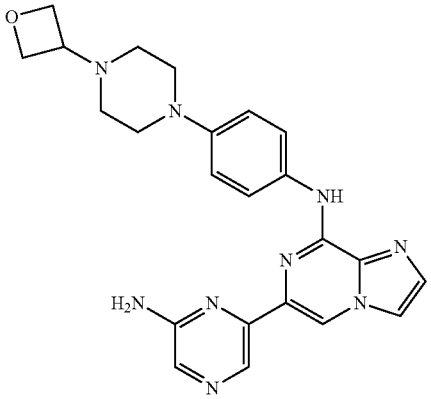 [SMILES: Nc1cncc(-c2cn3ccnc3c(Nc3ccc(N4CCN(C5COC5)CC4)cc3)n2)n1]

and the vinca-alkaloid is selected from the group consisting of vincristine or vinblastine. In one embodiment, the compound of formula I is

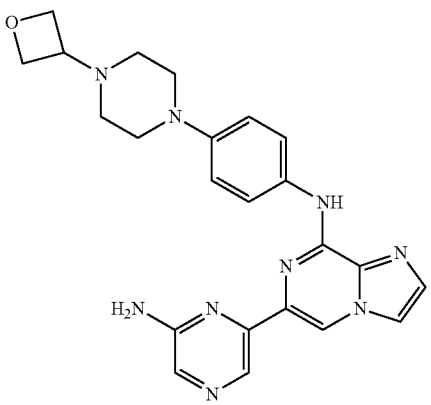 [SMILES: Nc1cncc(-c2cn3ccnc3c(Nc3ccc(N4CCN(C5COC5)CC4)cc3)n2)n1]

and the vinca-alkaloid is vincristine. In another embodiment, the compound of formula I is and the vinca-alkaloid is vinblastine.

Provided herein are also figures and examples illustrating that the combination of the compound of formula I, or a pharmaceutically acceptable salt thereof, and a therapeutically effective amount of a vinca-alkaloid, or a pharmaceutically acceptable salt thereto, has unexpected improvements over the effects of the compound of formula I, or the vinca-alkaloid, alone in monotherapy or administered as a sole agent in the treatment of certain cancers and their respective cell lines. In some embodiments, the vinca-alkaloid is selected from the group consisting of vincristine and vinblastine.

In some embodiments, the subject is refractory to at least one anti-cancer treatment. In other embodiments, the subject is in relapse after treatment with at least one anti-cancer treatment.

In some embodiments, about 50 mg to 300 mg of the compound of formula I, or a pharmaceutically acceptable salt thereof; is administered to subject once daily. In other embodiments, about 100 mg to 250 mg of the compound of formula I, or a pharmaceutically acceptable salt thereof, is administered to the subject once daily. In one embodiment, about 180-200 mg of the compound of formula I, or a pharmaceutically acceptable salt thereof, is administered to subject once daily.

In one variation, the subject is a human who has a 17p deletion, a TP53 mutation, or a combination thereof; and about 50 mg to 300 mg of the compound of Formula I, or a pharmaceutically acceptable salt thereof, is administered to the subject once daily. In another variation, the subject is a human who has a 17p deletion, a TP53 mutation, or a combination thereof; and about 100 mg to 250 mg of the compound of formula I, or a pharmaceutically acceptable salt thereof, is administered to the subject once daily. In yet another variation, the subject is a human who has a 17p deletion, a TP53 mutation, or a combination thereof; and about 180 to about 200 mg of the compound of formula I, or a pharmaceutically acceptable salt thereof is administered to the subject once daily.

In other embodiments, the vinca-alkaloid, or a pharmaceutically acceptable salt thereof, is administered to the subject once a week at clinically approved or sub-clinically approved amounts. In some embodiments, the amount of the vinca-alkaloid is administered to the subject once a, week at a sub-clinically approved amount. In other embodiments, the vinca-alkaloid is vincristine and the amount of vincristine, or a pharmaceutically acceptable salt thereof, is administered at a dose between 0.1 mg-$M^2$ and 1.5 mg-$M^2$. In other embodiments, the vinca-alkaloid is administered to the subject once a week at a dose of between 0.25 mg-M2 and 1.0 mg-M2 and the vinca-alkaloid is selected from the group consisting of vincristine and vinblastine. In other embodiments, the vinca-alkaloid is administered to the subject once daily at a dose of between 0.1 mg-M2 and 0.2 mg-M2 and the vinca-alkaloid is selected from the group consisting of vincristine and vinblastine.

In certain embodiments, the compound of formula (I) or a pharmaceutically acceptable salt thereof is administered before the vinca-alkaloid, or a pharmaceutically acceptable salt thereof. In other embodiments, the vinca alkaloid, or a pharmaceutically acceptable salt thereof, is administered before the compound of formula (I) or a pharmaceutically acceptable salt thereof.

In one embodiment, the compound of formula (I) or a pharmaceutically acceptable salt thereof, and the vinca-alkaloid, or a pharmaceutically acceptable salt thereof, are administered simultaneously, wherein the vinca-alkaloid is administered via IV and the compound of formula I is administered via tablet. In other embodiments, the compound of formula (I) or a pharmaceutically acceptable salt thereof, and the vinca-alkaloid, or a pharmaceutically acceptable salt thereof, are administered once a day. In other embodiments, the compound of formula (I) or a pharmaceutically acceptable salt thereof, and the vinca-alkaloid, or a pharmaceutically acceptable salt thereof, are administered once a week. In one embodiment, the compound of formula (I) or a pharmaceutically acceptable salt thereof, is administered once a day, and the vinca-alkaloid, or a pharmaceutically acceptable salt thereof, is administered once a week.

In some embodiments, the cancer is a hematologic malignancy. In certain embodiments, the cancer is a leukemia. In one embodiment, the leukemia is chronic lymphocytic leukemia (CLL). In certain embodiments, the cancer is a lymphoma. In one embodiment, the lymphoma is non-Hodgkin's lymphoma (NHL). In one variation, the NHL is diffuse large B-cell lymphoma (DLBCL), mantle cell lymphoma (MCL), follicular lymphoma (FL), small lymphocytic lymphoma (SLL), lymphoplasmacytic lymphoma (LPL), and/or marginal zone lymphoma (MZL). Thus, it is understood that in one aspect the subject is a human who has a hematologic malignancy, such as leukemia or lymphoma.

In certain embodiments, the cancer is selected from the group consisting of acute lymphocytic leukemia (ALL), acute myeloid leukemia (AML), chronic lymphocytic leukemia (CLL), small lymphocytic lymphoma (SLL), myelodysplastic syndrome (MDS), myeloproliferative disease (MPD), chronic myeloid leukemia (CML), multiple myeloma (MM), non-Hodgkin's lymphoma (NHL), indolent non-Hodgkin's lymphoma (iNHL), refractory iNHL, mantle cell lymphoma (MCL), follicular lymphoma (FL), Waldestrom's macroglobulinemia (WM), T-cell lymphoma, B-cell lymphoma, diffuse large B-cell lymphoma (DLBCL), lymphoplasmacytic lymphoma (LPL), and marginal zone lymphoma (MZL).

In some embodiments, the cancer is a solid tumor cancer (or solid cancer tumor). In certain embodiments the cancer is a solid tumor and expresses spleen tyrosine kinase (Syk) activity. In other embodiments, the solid tumor cancer is selected from the group consisting of pancreatic, lung, colorectal cancer, ovarian, and hepatocellular.

Also provided is a kit that includes a compound of Formula I, or a pharmaceutically acceptable salt, pharmaceutically acceptable ester, stereoisomer, mixture of stereoisomers or tautomer thereof. In one aspect, the kit comprises a compound of Formula I, or a pharmaceutically acceptable salt thereof. The kit may comprise a label and/or instructions for use of the compound in the treatment of a disease or condition in a subject (e.g., human) in need thereof. In some embodiments, the disease or condition may be associated with or mediated by Syk activity. In other embodiments, the kit may also contain instructions for use of a vinca-alkaloid in combination with the compound of Formula I in the treatment of a disease or condition in a subject (e.g., human) in need thereof. In certain of these embodiments, the disease or condition is cancer (e.g. hematologic malignancy, solid tumor cancers) that may be associated with or mediated by Syk activity.

Also provided are articles of manufacture that include a compound of Formula I, or a pharmaceutically acceptable salt, pharmaceutically acceptable ester, stereoisomer, mixture of stereoisomers or tautomer thereof; and a container. In one aspect, the article of manufacture comprises a compound of Formula I, or a pharmaceutically acceptable salt thereof. In one embodiment, the container may be a vial, jar, ampoule, preloaded syringe, or an intravenous bag.

Additional aspects and embodiments of this disclosure are described throughout.

DESCRIPTION OF THE FIGURES

FIGS. 1A and 1B depict and summarize the inhibitory effects of the combination of a compound of FIG. 1, 6-(6-aminopyrazin-2-yl)-N-(4-(4-(oxetan-3-yl)piperazin-1-yl)phenyl)imidazo[1,2-a]pyrazin-8-amine, and one of two of the vinca-alkaloids, vincristine (1A) and vinblastine (1B), respectively, in the DLBCL cell line, DHL-10 when compounds were co-administered.

FIGS. 2A and 2B summarize the inhibition of cell viability by the combination of a compound of Formula I, 6-(6-aminopyrazin-2-yl)-N-(4-(4-(oxetan-3-yl)piperazin-1-yl)phenyl)imidazo[1,2-a]pyrazin-8-amine, and vincristine in the Syk-expressing malignant colon cell line, MiaPaca, and in the non-Syk expressing malignant colon cell line, HepG2.

DETAILED DESCRIPTION

Figure 3:
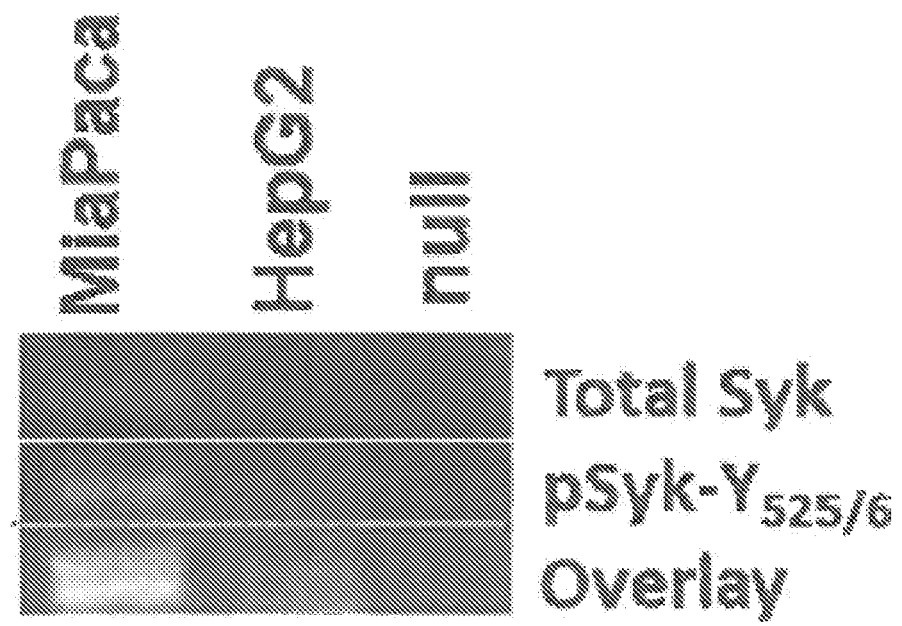
FIG. 3 depicts the level of Syk expression in the MiaPaca and HepG2 malignant colon cell lines.

It has surprisingly been discovered that compounds of Formula I, or pharmaceutically acceptable salts thereof, possess advantageous properties, making them attractive compounds for use as described herein. The compounds, in addition to being Syk inhibitors, possess desirable solubility and pharmacokinetic properties. These findings are particularly striking in view of the properties of comparable parameters of compounds of similar base structure.

The following description sets forth exemplary compositions, methods, parameters and the like. It should be recognized, however, that such description is not intended as a limitation on the scope of the present disclosure but is instead provided as a description of exemplary embodiments.

Also described for a compound of Formula I are the pharmaceutically acceptable salts, pharmaceutically acceptable esters, pharmaceutically acceptable solvates, hydrates, isomers (including optical isomers, racemates, or other mixtures thereof), tautomers, isotopes, polymorphs, and pharmaceutically acceptable prodrugs of such compounds.

The compounds of the disclosure may possess an asymmetric center, and can be produced as a racemic mixture or as individual enantiomers. The individual enantiomers may be obtained by asymmetric synthesis or by resolving a racemic or non-racemic mixture of an intermediate at some appropriate stage of the synthesis. The individual enantiomers may also be obtained by resolution of the compound by conventional means, such as crystallization in the presence of a resolving agent, or chromatography, using, for example a chiral high pressure liquid chromatography (HPLC) column. The individual enantiomers as well as racemic and non-racemic mixtures of enantiomers are within the scope of the present disclosure, all of which are intended to be included within the structures depicted in this specification unless otherwise specifically indicated.

Provided herein are also methods for treating cancer in a certain population of subjects (e.g., humans) in need thereof, comprising administering to such subjects a therapeutically effective amount of a compound of formula I, or a pharmaceutically acceptable salt, in combination with a vinca-alkaloid, or a pharmaceutically acceptable salt thereof. In certain embodiments, the compound of formula I is

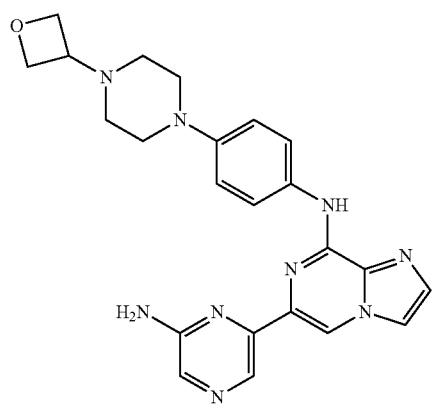 [SMILES: Nc1cncc(-c2cn3ccnc3c(Nc3ccc(N4CCN(C5COC5)CC4)cc3)n2)n1]

which may also be referred to by its compound name 6-(6-aminopyrazin-2-yl)-N-(4-(4-(oxetan-3-yl)piperazin-1-yl)phenyl)imidazo[1,2-a]pyrazin-8-amine. One skilled in the art understands that the compound structure may be named or identified using other commonly recognized nomenclature systems and symbols including CAS and IUPAC.

Provided herein are also figures and examples illustrating that the combination of a compound of formula I, or a pharmaceutically acceptable salt thereof, and a therapeutically effective amount of a vinca-alkaloid, or a pharmaceutically acceptable salt thereto, has unexpected improvements over the effects of the compound of formula I, or the vinca-alkaloid, alone in monotherapy or administered as a sole agent in the treatment of certain cancers and their respective cell lines. In some embodiments, the compound of formula I is 6-(6-aminopyrazin-2-yl)-N-(4-(4-oxetan-3-yl)piperazin-1-yl)phenyl)imidazo[1,2-a]pyrazin-8-amine, and the vinca-alkaloid is selected from the group consisting of vincristine and vinblastine.

Definitions

As used in the present disclosure, the following words and phrases are generally intended to have the meanings as set forth below, except to the extent that the context in which they are used indicates otherwise.

"Isomers" are different compounds that have the same molecular formula. Isomers include stereoisomers, enantiomers and diastereomers.

"Stereoisomers" are isomers that differ only in the way the atoms are arranged in space.

"Enantiomers" are a pair of stereoisomers that are non-superimposable mirror images of each other. A 1:1 mixture of a pair of enantiomers is a "racemic" mixture. The term "(±)" is used to designate a racemic mixture where appropriate.

The absolute stereochemistry is specified according to the Cahn Ingold Prelog R S system. When the compound is a pure enantiomer the stereochemistry at each chiral carbon may be specified by either R or S. Resolved compounds whose absolute configuration is unknown are designated (+) or (−) depending on the direction (dextro- or levorotary) that they rotate the plane of polarized light at the wavelength of the sodium D line.

The term "therapeutically effective amount" refers to an amount that is sufficient to effect treatment, as defined below, when administered to a subject (e.g., a mammal, such as a human) in need of such treatment. The therapeutically effective amount will vary depending upon the subject and disease condition being treated, the weight and age of subject, the severity of the disease condition, the manner of administration and the like, which can readily be determined by one of ordinary skill in the art. For example, a "therapeutically effective amount" of a compound of Formula I, or a pharmaceutically acceptable salt thereof, is an amount sufficient to modulate Syk expression or activity, and thereby treat a subject (e.g., a human) suffering an indication, or to ameliorate or alleviate the existing symptoms of the indication. For example, a therapeutically effective amount may be an amount sufficient to decrease a symptom of a disease or condition responsive to inhibition of Syk activity.

The term "polymorph" refers to different crystal structures of a crystalline compound. The different polymorphs may result from differences in crystal packing (packing polymorphism) or differences in packing between different conformers of the same molecule (conformational polymorphism). It is understood that any polymorph of a compound of Formula I, or a pharmaceutically acceptable salt thereof, used in the treatment of a disease or condition as described herein, while possibly providing varied properties, including pharmacokinetic properties, once absorbed into the subject, results in the compound of Formula I, such that the use of a compound of Formula I encompasses the use of any polymorph of a compound of Formula I, or a pharmaceutically acceptable salt thereof.

The term "solvate" refers to a complex formed by the combining of a compound of Formula I and a solvent. It is understood that any solvate of a compound of Formula I used in the treatment of a disease or condition as described herein, while possibly providing varied properties, including pharmacokinetic properties, once absorbed into the subject, results in the compound of Formula I, such that the use of a compound of Formula I encompasses the use of any solvate of a compound of Formula I.

The term "hydrate" refers to the complex formed by the combining of a compound of Formula I and water. It is understood that any hydrate of a compound of Formula I used in the treatment of a disease or condition as described herein, while possibly providing varied properties, including pharmacokinetic properties, once absorbed into the subject, results in the compound of Formula I, such that the use of a compound of Formula I encompasses the use of any hydrate of a compound of Formula I.

The term "prodrug" refers to a compound derived from or readily converted to a compound of Formula I that include chemical groups which, in vivo, can be converted and/or can be split off from the remainder of the molecule to provide a compound of Formula I or active moiety of the drug, or a pharmaceutically acceptable salt thereof or a biologically active metabolite thereof. It is understood that any prodrug of a compound of Formula I used in the treatment of a disease or condition as described herein, while possibly providing varied properties, including pharmacokinetic properties, once absorbed into the subject, results in the compound of Formula I, such that the use of a compound of Formula I encompasses the use of any prodrug of a compound of Formula I.

Also provided herein are isotopically labeled forms of compounds detailed herein. Isotopically labeled compounds have structures depicted by the formulas given herein except that one or more atoms are replaced by an atom having a selected atomic mass or mass number. Examples of isotopes that can be incorporated into compounds of the disclosure include isotopes of hydrogen, carbon, nitrogen, oxygen, phosphorous, fluorine and chlorine, such as, but not limited to $^{2}H$ (deuterium, D), $^{3}H$ (tritium), $^{11}C$, $^{13}C$, $^{14}C$, $^{15}N$, $^{18}F$, $^{31}P$, $^{32}P$, $^{35}S$, $^{36}Cl$ and $^{125}I$. Various isotopically labeled compounds of the present disclosure, for example those into which radioactive isotopes such as $^{3}H$, $^{13}C$ and $^{14}C$ are incorporated, are provided. Such isotopically labeled compounds may be useful in metabolic studies, reaction kinetic studies, detection or imaging techniques, such as positron emission tomography (PET) or single-photon emission computed tomography (SPECT) including drug or substrate tissue distribution assays or in radioactive treatment of subjects (e.g. humans). Also provided for isotopically labeled compounds described herein are any pharmaceutically acceptable salts, pharmaceutically acceptable esters, pharmaceutically acceptable solvates, hydrates, enantiomers, mixture of enantiomers, tautomers, polymorphs, and pharmaceutically acceptable prodrugs thereof.

The disclosure also includes the compound of Formula I, or a pharmaceutically acceptable salt thereof, in which from 1 to n hydrogens attached to a carbon atom is/are replaced by deuterium, in which n is the number of hydrogens in the molecule. Such compounds may exhibit increased resistance to metabolism and are thus useful for increasing the half life of the compound of Formula I, or a pharmaceutically acceptable salt thereof, when administered to a mammal. See, for example, Foster, "Deuterium Isotope Effects in Studies of Drug Metabolism", Trends Pharmacol. Sci. 5(12): 524-527 (1984). Such compounds are synthesized by means well known in the art, for example by employing starting materials in which one or more hydrogens have been replaced by deuterium.

Deuterium labeled or substituted therapeutic compounds of the disclosure may have improved DMPK (drug metabolism and pharmacokinetics) properties, relating to distribution, metabolism and excretion (ADME). Substitution with heavier isotopes such as deuterium may afford certain therapeutic advantages resulting from greater metabolic stability, for example increased in vivo half-life, reduced dosage requirements and/or an improvement in therapeutic index. An $^{18}F$ labeled compound may be useful for PET or SPECT studies. Isotopically labeled compounds of this disclosure and prodrugs thereof can generally be prepared by carrying out the procedures disclosed in the schemes or in the examples and preparations described below by substituting a readily available isotopically labeled reagent for a non-isotopically labeled reagent. It is understood that deuterium in this context is regarded as a substituent in the compound of Formula I.

The concentration of such a heavier isotope, specifically deuterium, may be defined by an isotopic enrichment factor. In the compounds of this disclosure any atom not specifically designated as a particular isotope is meant to represent any stable isotope of that atom. Unless otherwise stated, when a position is designated specifically as "H" or "hydrogen", the position is understood to have hydrogen at its natural abundance isotopic composition. Accordingly, in the compounds of this disclosure any atom specifically designated as a deuterium (D) is meant to represent deuterium.

The term "inhibition" indicates a decrease, such as a significant decrease, in the baseline activity of a biological activity or process. "Inhibition of Syk activity" refers to a decrease in Syk activity as a, direct or indirect response to the presence of a compound of Formula I, or a pharmaceutically acceptable salt thereof, relative to the activity of Syk in the absence of such compound or a pharmaceutically acceptable salt thereof. The decrease in activity may be due to the direct interaction of the compound with Syk, or due to the interaction of the compound(s) described herein with one or more other factors that in turn affect Syk activity. For example, the presence of the compound(s) may decrease Syk activity by directly binding to the Syk, by causing (directly or indirectly) another factor to decrease Syk activity, or by (directly or indirectly) decreasing the amount of Syk present in the cell or organism. In some embodiments, the inhibition of Syk activity may be compared in the same subject prior to treatment, or other subjects not receiving the treatment.

Inhibition of Syk activity also refers to observable inhibition of Syk activity in a standard biochemical assay for Syk activity, such as the ATP hydrolysis assay described in Example 8 below.

In some embodiments, the compound described herein, e.g. a compound of Formula I, or a pharmaceutically acceptable salt thereof, inhibits Syk kinase activity with an $IC_{50}$ value less than or equal to 1 micromolar, such as 0.1 nM to 1 μM or 1 nM to 1 μM. In some embodiments, the compound or a pharmaceutically acceptable salt thereof has an $IC_{50}$ value less than or equal to less than 500 nanomolar, such as 0.1 nM to 500 nM or 1 nM to 500 nM. In some embodiments, the compound or a pharmaceutically acceptable salt thereof has an $IC_{50}$ value less than or equal to less than 200 nanomolar, such as 0.1 nM to 200 nM or 1 nM to 200 nM. In some embodiments, the compound or a pharmaceutically acceptable salt thereof has an $IC_{50}$ value less than or equal to less than 100 nanomolar, such as 0.1 nM to 100 nM or 1 nM to 100 nM. In some embodiments, the compound or a pharmaceutically acceptable salt thereof has an $IC_{50}$ value less than or equal to 50 nanomola, such as 0.1 nM to 50 nM or 1 nM to 50 nM. In some embodiments, the compound or a pharmaceutically acceptable salt thereof has an $IC_{50}$ value less than or equal to 20 nanomolar, such as 0.1 nM to 20 nM or 1 nM to 20 nM. In some embodiments, the compound or a pharmaceutically acceptable salt thereof has an $IC_{50}$ value less than or equal to 10 nanomolar, such as 0.1 nM to 10 nM or 1 nM to 10 nM. In some embodiments, the $IC_{50}$ value is measured as described in the assay of Example 8.

"Inhibition of B-cell activity" refers to a decrease in B-cell activity as a direct or indirect response to the presence of a compound of Formula I, or a pharmaceutically acceptable salt thereof, relative to the activity of B-cells in the absence of such compound or a pharmaceutically acceptable salt thereof. The decrease in activity may be due to the direct interaction of the compound with Syk or with one or more other factors that in turn affect B-cell activity.

Inhibition of B-cell activity also refers to observable inhibition of CD86 expression in a standard assay. In some embodiments, the compound described herein has an $IC_{50}$ value less than or equal to 10 micromolar, such as 1 nM to 10 μM or 10 nM to 10 μM. In some embodiments, the compound has an $IC_{50}$ value less than or equal to less than 1 micromolar, such as 1 nM to 1 μM or 10 nM to 1 μM. In some embodiments, the compound has an $IC_{50}$ value less than or equal to 500 nanomolar, such as 1 nM to 500 nM or 10 nM to 500 nM.

"B cell activity" also includes activation, redistribution, reorganization, or capping of one or more various B cell membrane receptors, or membrane-bound immunoglobulins, e.g., IgM, IgG, and IgD. Most B cells also have membrane receptors for the Fc portion of IgG in the form of either antigen-antibody complexes or aggregated IgG. B cells also carry membrane receptors for the activated components of complement, e.g., C3b, C3d, C4, and C1q. These various membrane receptors and membrane-bound immunoglobulins have membrane mobility and can undergo redistribution and capping that can initiate signal transduction.

B cell activity also includes the synthesis or production of antibodies or immunoglobulins. Immunoglobulins are synthesized by the B cell series and have common structural features and structural units. Five immunoglobulin classes, i.e., IgG, IgA, IgM, IgD, and IgE, are recognized on the basis of structural differences of their heavy chains including the amino acid sequence and length of the polypeptide chain. Antibodies to a given antigen may be detected in all or several classes of immunoglobulins or may be restricted to a single class or subclass of immunoglobulin. Autoantibodies or autoimmune antibodies may likewise belong to one or several classes of immunoglobulins. For example, rheumatoid factors (antibodies to IgG) are most often recognized as an IgM immunoglobulin, but can also consist of IgG or IgA.

In addition, B cell activity also is intended to include a series of events leading to B cell clonal expansion (proliferation) from precursor B lymphocytes and differentiation into antibody-synthesizing plasma cells which takes place in conjunction with antigen-binding and with cytokine signals from other cells.

"Inhibition of B-cell proliferation" refers to inhibition of proliferation of abnormal B-cells, such as cancerous B-cells, e.g. lymphoma B-cells and/or inhibition of normal, non-diseased B-cells. The term "inhibition of B-cell proliferation" indicates any significant decrease in the number of B-cells, either in vitro or in vivo. Thus an inhibition of B-cell proliferation in vitro would be any significant decrease in the number of B-cells in an in vitro sample contacted with a compound of Formula I, or a pharmaceutically acceptable salt thereof as compared to a matched sample not contacted with the compound(s).

Inhibition of B-cell proliferation also refers to observable inhibition of B-cell proliferation in a standard thymidine incorporation assay for B-cell proliferation, e.g. such assay as known in the art. In some embodiments, the compounds described herein, e.g. a compound of Formula I, or a pharmaceutically acceptable salt thereof, has an $IC_{50}$ value less than or equal to 10 micromolar, such as 1 nM to 10 μM or 10 nM to 10 μM. In some embodiments, the compound or a pharmaceutically acceptable salt thereof has an $IC_{50}$ value less than or equal to less than 1 micromolar, such as 1 nM to 1 μM or 10 nM to 1 μM. In some embodiments, the compound or a pharmaceutically acceptable salt thereof has an $IC_{50}$ value less than or equal to 500 nanomolar, such as 1 nM to 500 nM or 10 nM to 500 nM. In some embodiments, the compound or a pharmaceutically acceptable salt thereof has an $IC_{50}$ value less than or equal to 200 nanomolar, such as 1 nM to 200 nM or 10 nM to 200 nM. In some embodiments, the compound or a pharmaceutically acceptable salt thereof has an $IC_{50}$ value less than or equal to 100 nanomolar, such as 1 nM to 100 nM or 10 nM to 100 nM.

The "reduction in basophil activation" refers to the ability of compounds as described herein to reduce the activation of basophils. Basophil activation is involved, for example, in inflammatory and autoimmune diseases as described herein, and the reduction of activation of basophils is desired in compounds as described herein, e.g. a compound of Formula I, or a pharmaceutically acceptable salt thereof. The activation of basophils can be assessed by the measurement of CD63 expression by basophils, such as by a CD63 human whole blood basophil cellular assay (25% blood), e.g. such as the assay described in Example 9 below.

In some embodiments, the compound described herein e.g. a compound of Formula I, or a pharmaceutically acceptable salt thereof, has at $EC_{50}$ value in a suitable CD63 assay of less than or equal to 10 micromolar, such as 1 nM to 10 μM or 10 nM to 10 μM. In some embodiments, the compound or a pharmaceutically acceptable salt thereof, has an $EC_{50}$ value less than or equal to less than 1 micromolar, such as 1 nM to 1 µM or 10 nM to 1 µM. In some embodiments, the compound or a pharmaceutically acceptable salt thereof has an $EC_{50}$ value less than or equal to 500 nanomolar, such as 1 nM to 500 nM or 10 nM to 500 nM. In some embodiments, the compound or a pharmaceutically acceptable salt thereof has an $EC_{50}$ value less than or equal to 200 nanomolar, such as 1 nM to 200 nM or 10 nM to 200 nM. In some embodiments, the compound or a pharmaceutically acceptable salt thereof has an $EC_{50}$ value less than or equal to 150 nanomolar, such as 1 nM to 150 nM or 10 nM to 150 nM. In some embodiments, the compound or a pharmaceutically acceptable salt thereof has an $IC_{50}$ value less than or equal to 100 nanomolar, such as 1 nM to 100 nM or 10 nM to 100 nM. In some embodiments, the compound or a pharmaceutically acceptable salt thereof has an $EC_{50}$ value less than or equal to 75 nanomolar, such as 1 nM to 75 nM or 10 nM to 75 nM. In some embodiments, the $EC_{50}$ value is measured as described in the assay of Example 9.

The "kinetic solubility" refers to an assessment of the solubility of a compound in a suitable buffer, such as phosphate buffer at pH 7.4, at a given temperature, for example at 37° C. In on instance, kinetic solubility is measured at 37° C. in phosphate buffer at pH 7.4, such as by the assay as described in Example 10.

In some embodiments, the compounds described herein, e.g. a compound of Formula I, or a pharmaceutically acceptable salt thereof, has a kinetic solubility at 37° C. in phosphate buffer at pH 74 of greater than or equal to 10 µM, such as 10 µM to 500 µM or 10 µM to 250 µM. In some embodiments, the compound or a pharmaceutically acceptable salt thereof has a kinetic solubility at 37° C. in phosphate buffer at pH 7.4 of greater than or equal to 20 µM, such as 20 µM to 500 µM or 20 µM to 250 µM. In some embodiments, the compound or a pharmaceutically acceptable salt thereof has a kinetic solubility at 37° C. in phosphate buffer at pH 7.4 of greater than or equal to 30 µM, such as 30 µM to 500 µM or 30 µM to 250 µM. In some embodiments, the compound or a pharmaceutically acceptable salt thereof has a kinetic solubility at 37° C. in phosphate buffer at pH 7.4 of greater than or equal to 40 µM, such as 40 µM to 500 µM or 40 µM to 250 µM. In some embodiments, the compound or a pharmaceutically acceptable salt thereof has a kinetic solubility at 37° C. in phosphate buffer pH 7.4 of greater than or equal to 50 µM, such as 50 µM to 500 µM or 50 µM to 250 µM. In some embodiments, the compound or a pharmaceutically acceptable salt thereof has a kinetic solubility at 37° C. in phosphate buffer at pH 7.4 of greater than or equal to 60 µM, such as 60 µM to 500 µM or 60 µM to 250 µM. In some embodiments, the compound or a pharmaceutically acceptable salt thereof has a kinetic solubility at 37° C. in phosphate buffer at pH 7.4 of greater than or equal to 70 µM, such as 70 µM to 500 µM or 70 µM to 250 µM. In some embodiments, the compound or a pharmaceutically acceptable salt thereof has a kinetic solubility at 37° C. in phosphate buffer at pH 7.4 of greater than or equal to 80 µM, such as 80 µM to 500 µM or 80 µM to 250 µM. In some embodiments, the compound or a pharmaceutically acceptable salt thereof has a kinetic solubility at 37° C. in phosphate buffer at pH 7.4 of greater than or equal to 90 µM, such as 90 µM to 500 µM or 90 µM to 250 µM. In some embodiments, the kinetic solubility is measured by the assay as described in Example 10.

The "human hepatocyte stability" is a measure of the stability of the compounds to metabolism by human hepatocytes, and is assessed as the predicted hepatic plasma clearance of the compounds in L/hr/kg. The predicted hepatocyte clearance can be measured, for example, by the assay described in Example 11.

In some embodiments, the compounds described herein, e.g. a compound of Formula I has a predicted hepatic plasma clearance of less than or equal to 0.50 L/hr/kg, such as 0.005 L/hr/kg to 0.50 L/hr/kg or 0.0 L/hr/kg to 0.50 L/hr/kg. In some embodiments, the compound has a predicted hepatic plasma clearance of less than or equal to 0.40 L/hr/kg, such as 0.005 L/hr/kg to 0.40 L/hr/kg or 0.01 L/hr/kg to 0.40 L/hr/kg. In some embodiments, the compound has a predicted hepatic plasma clearance of less than or equal to 0.30 L/hr/kg, such as 0.005 L/hr/kg to 0.30 L/hr/kg or 0.01 L/hr/kg to 0.30 L/hr/kg. In some embodiments, the compound has a predicted hepatic plasma clearance of less than or equal to 0.20 L/hr/kg, such as 0.005 L/hr/kg to 0.20 L/hr/kg or 0.01 L/hr/kg to 0.20 L/hr/kg. In some embodiments, the compound has a predicted hepatic plasma clearance of less than or equal to 0.10 L/hr/kg, such as 0.005 L/hr/kg to 0.10 L/hr/kg or 0.01 L/hr/kg to 0.10 L/hr/kg. In some embodiments, the compound has a predicted hepatic plasma clearance of less than or equal to 0.09 L/hr/kg, such as 0.005 L/hr/kg to 0.09 L/hr/kg or 0.01 L/hr/kg to 0.09 L/hr/kg. In some embodiments, the compound has a predicted hepatic plasma clearance of less than or equal to 0.08 L/hr/kg, such as 0.005 L/hr/kg to 0.08 L/hr/kg or 0.01/hr/kg to 0.08 L/hr/kg. In some embodiments, the compound has a predicted hepatic plasma clearance of less than or equal to 0.07 L/hr/kg, such as 0.005 L/hr/kg to 0.07 L/r/kg or 0.01 L/hr/kg to 0.07 L/hr/kg. In some embodiments, the compound has a predicted hepatic plasma clearance of or less than or equal to 0.06 L/hr/kg, such as 0.005 L/hr/kg to 0.06 L/hr/kg or 0.01 L/hr/kg to 0.06 h/hr/kg. In some embodiments, the predicted hepatocyte clearance is measured by the assay described in Example 11.

An "allergy" or "allergic disorder" refers to acquired hypersensitivity to a substance (allergen). Allergic conditions include eczema, allergic rhinitis or coryza, hay fever, bronchial asthma, urticaria (hives) and food allergies, and other atopic conditions.

"Asthma" refers to a disorder of the respiratory system characterized by inflammation, narrowing of the airways and increased reactivity of the airways to inhaled agents. Asthma is frequently, although not exclusively associated with atopic or allergic symptoms.

By "significant" is meant any detectable change that is statistically significant in a standard parametric test of statistical significance such as Student's T-test, where $p<0.05$.

A "disease responsive to inhibition of Syk activity" is a disease in which inhibiting Syk kinase provides a therapeutic benefit such as an amelioration of symptoms, decrease in disease progression, delay of disease onset, or inhibition of aberrant activity of certain cell-types (monocytes, B-cells, and mast cells).

"Subject" refers to an animal, such as a mammal, that has been or will be the object of treatment, observation or experiment. The methods described herein may be useful in both human therapy and veterinary applications. In some embodiments, the subject is a mammal; in some embodiments the subject is human; and in some embodiments the subject is chosen from cats and dogs. "Subject in need thereof" or "human in need thereof" refers to a subject, such as a human, who may have or is suspected to have diseases or conditions that would benefit from certain treatment; for example treatment with a compound of Formula I, or a pharmaceutically acceptable salt thereof, as described herein. This includes a subject who may be determined to be at risk of or susceptible to such diseases or conditions, such that treatment would prevent the disease or condition from developing.

"Treatment" or "treating" is an approach for obtaining beneficial or desired results including clinical results. Beneficial or desired clinical results may include one or more of the following:
  (i) inhibiting the disease or condition (e.g., decreasing one or more symptoms resulting from the disease or condition, and/or diminishing the extent of the disease or condition);
  (ii) slowing or arresting the development of one or more clinical symptoms associated with the disease or condition (e.g., stabilizing the disease or condition, preventing or delaying the worsening or progression of the disease or condition, and/or preventing or delaying the spread (e.g., metastasis) of the disease or condition); and/or
  (iii) relieving the disease, that is, causing the regression of clinical symptoms (e.g., ameliorating the disease state, providing partial or total remission of the disease or condition, enhancing effect of another medication, delaying the progression of the disease, increasing the quality of life, and/or prolonging survival).

"Delaying" the development of a disease or condition means to defer, hinder, slow, retard, stabilize, and/or postpone development of the disease or condition. This delay can be of varying lengths of time, depending on the history of the disease or condition, and/or subject being treated. A method that "delays" development of a disease or condition is a method that reduces probability of disease or condition development in a given time frame and/or reduces the extent of the disease or condition in a given time frame, when compared to not using the method. Such comparisons are typically based on clinical studies, using a statistically significant number of subjects. Disease or condition development can be detectable using standard methods, such as routine physical exams, mammography, imaging, or biopsy. Development may also refer to disease or condition progression that may be initially undetectable and includes occurrence, recurrence, and onset.

In many cases, the compounds of this disclosure are capable of forming acid and/or base salts by virtue of the presence of amino and/or carboxyl groups or groups similar thereto.

"Pharmaceutically acceptable salts" include, for example, salts with inorganic acids and salts with an organic acid. Examples of salts may include hydrochloride, phosphate, diphosphate, hydrobromide, sulfate, sulfinate, nitrate, malate, maleate, fumarate, tartrate, succinate, citrate, acetate, lactate, methanesulfonate (mesylate), benzenesulfonate (besylate), p-toluenesulfonate (tosylate), 2-hydroxyethylsulfonate, benzoate, salicylate, stearate, and alkanoate (such as acetate, HOOC—$(CH_2)_n$—COOH where n is 0-4). In addition, if the compounds described herein are obtained as an acid addition salt, the free base can be obtained by basifying a solution of the acid salt. Conversely, if the product is a free base, an addition salt, particularly a pharmaceutically acceptable addition salt, may be produced by dissolving the free base in a suitable organic solvent and treating the solution with an acid, in accordance with conventional procedures for preparing acid addition salts from base compounds. Those skilled in the art will recognize various synthetic methodologies that may be used to prepare nontoxic pharmaceutically acceptable addition salts.

In some embodiments of the disclosure, the pharmaceutically acceptable salt of a compound of formula I is a mesylate salt. In some embodiments of the disclosure, the pharmaceutically acceptable salt of the vinca-alkaloids is a sulfate salt. In some embodiments of the disclosure, the pharmaceutically acceptable salt of a compound of formula I is a mesylate salt and the pharmaceutically acceptable salt of the vinca-alkaloids is a sulfate salt. In one embodiment of the disclosure, the pharmaceutically acceptable salt of a compound of formula I is a mesylate salt and the vinca-alkaloid is vincristine, wherein the pharmaceutically acceptable salt is vincristine sulfate.

In some embodiments of the methods described herein, the compound of formula I, or a pharmaceutically acceptable salt, is present in a pharmaceutical composition comprising the compound of formula I, or a pharmaceutically acceptable salt, and at least one pharmaceutically acceptable vehicle. Pharmaceutically acceptable vehicles may include pharmaceutically acceptable carriers, adjuvants and/or other excipients, and other ingredients can be deemed pharmaceutically acceptable insofar as they are compatible with other ingredients of the formulation and not deleterious to the recipient thereof.

The pharmaceutical compositions of the compound of formula I described herein can be manufactured using any conventional method, e.g., mixing, dissolving, granulating, dragee-making, levigating, emulsifying, encapsulating, entrapping, melt-spinning, spray-drying, or lyophilizing processes. An optimal pharmaceutical formulation can be determined by one of skill in the art depending on the route of administration and the desired dosage. Such formulations can influence the physical state, stability, rate of in vivo release, and rate of in vivo clearance of the administered agent. Depending on the condition being treated, these pharmaceutical compositions can be formulated and administered systemically or locally.

As used herein, "pharmaceutically acceptable excipient" is a pharmaceutically acceptable vehicle that includes, without limitation, any and all carriers, solvents, dispersion media, coatings, antibacterial and antifungal agents, isotonic and absorption delaying agents and the like. The use of such media and agents for pharmaceutically active substances is well known in the art. Except insofar as any conventional media or agent is incompatible with the active ingredient, its use in the therapeutic compositions is contemplated. Supplementary active ingredients can also be incorporated into the compositions.

The term "carrier" refers to an excipient or vehicle that includes without limitation diluents, disintegrants, precipitation inhibitors, surfactants, glidants, binders, lubricants, and the like with which the compound is administered. Carriers are generally described herein and also in "Remington's Pharmaceutical Sciences" by E. W. Martin. Examples of carriers include, but are not limited to, aluminum monostearate, aluminum stearate, carboxymethylcellulose, carboxymethylcellulose sodium, crospovidone, glyceryl isostearate, glyceryl monostearate, hydroxyethyl cellulose, hydroxyethyl cellulose, hydroxymethyl cellulose, hydroxyoctacosanyl hydroxystearate, hydroxypropyl cellulose, hydroxypropyl cellulose, hydroxypropyl methylcellulose, lactose, lactose monohydrate, magnesium stearate, mannitol, microcrystalline cellulose, poloxamer 124, poloxamer 181, poloxamer 182, poloxamer 188, poloxamer 237, poloxamer 407, povidone, silicon dioxide, colloidal silicon dioxide, silicone, silicone adhesive 4102, and silicone emulsion. It should be understood, however, that the carriers selected for the pharmaceutical compositions, and the amounts of such carriers in the composition, may vary depending on the method of formulation (e.g., dry granulation formulation, solid dispersion formulation).

The term "diluent" generally refers to a substance that is used to dilute the compound of interest prior to delivery. Diluents can also serve to stabilize compounds. Examples of diluents may include starch, saccharides, disaccharides, sucrose, lactose, polysaccharides, cellulose, cellulose ethers, hydroxypropyl cellulose, sugar alcohols, xylitol, sorbitol, maltitol, microcrystalline cellulose, calcium or sodium carbonate, lactose, lactose monohydrate, dicalcium phosphate, cellulose, compressible sugars, dibasic calcium phosphate dehydrate, mannitol, microcrystalline cellulose, and tribasic calcium phosphate.

The term "disintegrant" generally refers to a substance which, upon addition to a solid preparation, facilitates its break-up or disintegration after administration and permits the release of an active ingredient as efficiently as possible to allow for its rapid dissolution. Examples of disintegrants may include maize starch, sodium starch glycolate, croscarmellose sodium, crospovidone, microcrystalline cellulose, modified corn starch, sodium carboxymethyl starch, povidone, pregelatinized starch, and alginic acid.

The term "precipitation inhibitors" generally refers to a substance that prevents or inhibits precipitation of the active agent from a supersaturated solution. One example of a precipitation inhibitor includes hydroxypropylmethylcellulose (HPMC).

The term "surfactants" generally refers to a substance that lowers the surface tension between a liquid and a solid that could improve the wetting of the active agent or improve the solubility of the active agent. Examples of surfactants include poloxamer and sodium lauryl sulfate.

The term "glidant" generally refers to substances used in tablet and capsule formulations to improve flow-properties during tablet compression and to produce an anti-caking effect. Examples of glidants may include colloidal silicon dioxide, talc, fumed silica, starch, starch derivatives, and bentonite.

The term "binder" generally refers to any pharmaceutically acceptable film which can be used to bind together the active and inert components of the carrier together to maintain cohesive and discrete portions. Examples of binders may include hydroxypropylcellulose, hydroxypropylmethylcellulose, povidone, copovidone, and ethyl cellulose.

The term "lubricant" generally refers to a substance that is added to a powder blend to prevent the compacted powder mass from sticking to the equipment during the tableting or encapsulation process. A lubricant can aid the ejection of the tablet form the dies, and can improve powder flow. Examples of lubricants may include magnesium stearate, stearic acid, silica, fats, calcium stearate, polyethylene glycol, sodium stearyl fumarate, or talc; and solubilizers such as fatty acids including lauric acid, oleic acid, and $C_8/C_{10}$ fatty acid.

By the term "vinca-alkaloids" are mean those compounds, and pharmaceutically acceptable salts thereof, which are derived from the Madagascar periwinkle plant, and have been used to treat diabetes, high blood pressure, and various cancers. Examples of vinca-alkaloids include vincristine, vinblastine, vindesine, vinorelbine, desoxyvincaminol, vincaminol, vinburnine, vincamajine, and vineridine. Typically, there have been four major vinca alkaloids in clinical use: vinblastine, vinorelbine, vincristine, and vindesine. All vi ca alkaloids are administered intravenously (IV).

The vinca-alkaloids, and pharmaceutically acceptable salts thereof, of the present disclosure are cytotoxics—they halt the division of cells and cause cell death. During cell division, vinca alkaloid molecules bind to the building blocks of a protein called tubulin, inhibiting its formation. Tubulin protein normally works in cells to create microtubules. These microtubules provide cells with both the structure and flexibility they need to divide and replicate. Without microtubules, cells cannot divide. As opposed to a Syk inhibitor, which inhibits spleen tyrosine kinase, vinca-alkaloids mechanism occupying tubulin's building block structure, thus preventing, in theory, the formation of microtubules and thus interfering with cancer cells' ability to divide.

One of the vinca-alkaloids of this disclosure, vinblastine, inhibits angiogenesis, or the process by which new blood vessels grow from pre-existing ones. Angiogenesis is an essential step in a tumor's transition to malignancy. Vinblastine is generally applied to treat Hodgkin's disease, non-Hodgkin's lymphoma, breast cancer, and germ cell tumors. Side effects of vinblastine include: toxicity to white blood cells, nausea, vomiting, constipation, dyspnea, chest or tumor pain, wheezing, and fever. Vinblastine is also occasionally associated with antidiuretic hormone secretion and angina.

Another vinca alkaloid of this disclosure is vinorelbine, which is similar in its effects to vinblastine. Vinorelbine has exhibited significant antitumor activity in patients with breast cancer a and antiproliferation effects on osteosarcoma (bone tumor cells). Vinorelbine treatment can result in side effects including decreased resistance to infection, bruising or bleeding, anemia, constipation, diarrhea, nausea, numbness or tingling in the hands and feet, fatigue (also called peripheral neuropathy), and inflammation at the injection site. Less common side effects include hair loss and allergic reaction.

Another example or embodiment of the vinca alkaloids of this disclosure is vincristine, or pharmaceutically acceptable salts thereof. Vincristine has a high affinity for tubulin dimers (dimers are building blocks of a protein only two blocks long) and can attach and reattach at different sites quickly, thus in theory preventing the dimers' ability to reassemble (build) the tubules, thus destabilizing the tubulin and inhibiting microtubule formation. Vincristine is FDA approved to treat acute leukemia, rhabdomyosarcoma, neuroblastoma, Wilm's tumor, Hodgkin's disease, and other lymphomas. Vincristine's most common side effects are: peripheral neuropathy, suppression of bone marrow activity, constipation, nervous system toxicity, nausea, and vomiting, with neuropathy being the most common and serious side effect. As a result, there are reports of some subjects being treated with vincristine for oncology having had to stop vincristine treatment.

The fourth common vinca-alkaloid is vindesine, or pharmaceutically acceptable salts thereof. Vindesine has a serum half-life of only 24 hours, but similar effects (intended and side) to that of vinblastine. Vindesine is commonly administered at a dose of 3 milligrams per square meter of body surface during treatment for melanoma, lung cancers, and (combined with other drugs) uterine cancers. Additional side effects from vindesine include: anemia, blood cell toxicity, fatigue, tingling or pricking sensations in the skin, and skin toxicity.

Compounds

Compounds are provided here and elsewhere throughout, such as in the Summary and in the Examples.

The compounds provided herein are named using ChemBioDraw Ultra 12.0, and one skilled in the art understands that the compound structure may be named or identified using other commonly recognized nomenclature systems and symbols including CAS and IUPAC.

Accordingly, provided herein are compounds that function as Syk inhibitors. In one aspect, the disclosure provides a compound of Formula I:

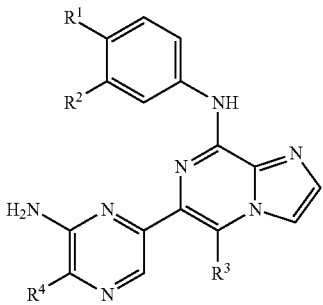

Formula I or a pharmaceutically acceptable salt thereof, wherein:
$R^1$ is selected from the group consisting of

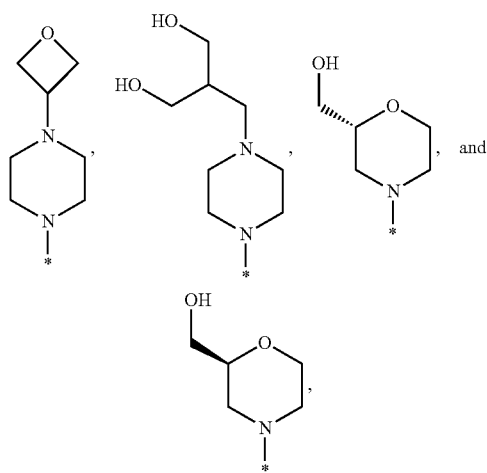

and wherein * indicates the carbon atom of the indicated phenyl ring of Formula I to which $R^1$ is attached;
$R^2$ is H or 2-hydroxyethoxyl;
$R^3$ is H or methyl; and
$R^4$ is H or methyl.

In some embodiments of the compound of Formula I, or a pharmaceutically acceptable salt thereof, $R^1$ is selected from the group consisting of

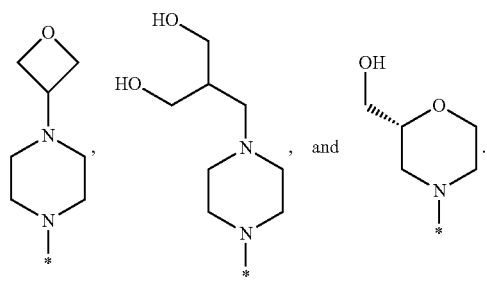 [SMILES: *N1CCN(C2COC2)CC1 ; *N1CCN(CC(CO)CO)CC1 ; *N1CCO[C@@H](CO)C1]

and

In some embodiments, $R^1$ is

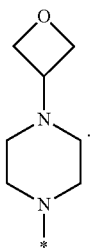

In some embodiments, $R^1$ is

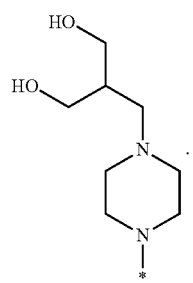

In some embodiments, $R^1$ is

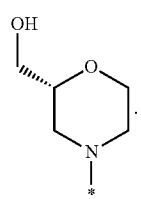

In some embodiments of the compound of Formula I, or a pharmaceutically acceptable salt thereof, $R^2$ is H. In some embodiments of the compound of Formula I or a pharmaceutically acceptable salt thereof, $R^2$ is 2-hydroxyethoxyl.

In some embodiments of the compound of Formula I, or a pharmaceutically acceptable salt thereof, $R^3$ is H. In some embodiments of the compound of Formula I, or a pharmaceutically acceptable salt thereof, $R^3$ is methyl.

In some embodiments of the compound of Formula I, or a pharmaceutically acceptable salt thereof, $R^4$ is H or methyl. In some embodiments of the compound of Formula I, or a pharmaceutically acceptable salt thereof, $R^4$ is H. In some embodiments of the compound of Formula I, or a pharmaceutically acceptable salt thereof, $R^4$ is methyl.

In some embodiments of the compound of Formula I, or a pharmaceutically acceptable salt thereof, $R^1$ is selected from the group consisting of

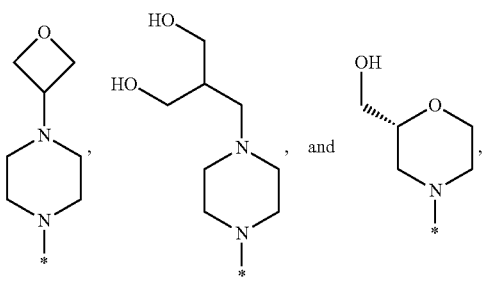 [SMILES: *N1CCN(C2COC2)CC1 ; *N1CCN(CC(CO)CO)CC1 ; *N1CCO[C@@H](CO)C1]

and $R^2$ is H. In some embodiments of the compound of Formula I, or a pharmaceutically acceptable salt thereof, $R^1$ is selected from the group consisting of

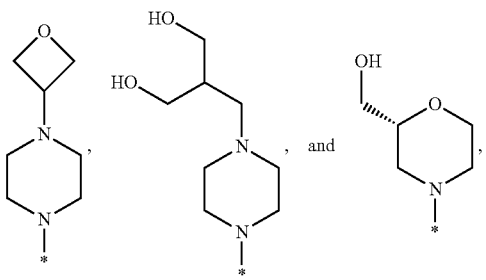 [SMILES: *N1CCN(C2COC2)CC1 ; *N1CCN(CC(CO)CO)CC1 ; *N1CCO[C@@H](CO)C1]

and $R^2$ is 2-hydroxyethoxyl.

In some embodiments of the compound of Formula I, or a pharmaceutically acceptable salt thereof, $R^1$ is selected from the group consisting of

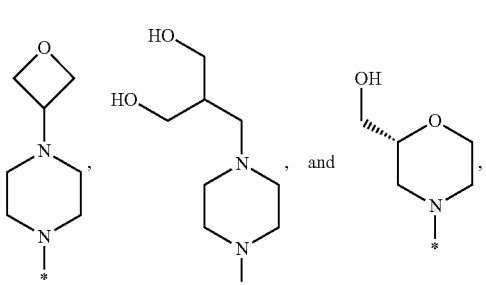

and $R^3$ is H. In some embodiments of the compound of Formula I, or a pharmaceutically acceptable salt thereof, $R^1$ is selected from the group consisting of

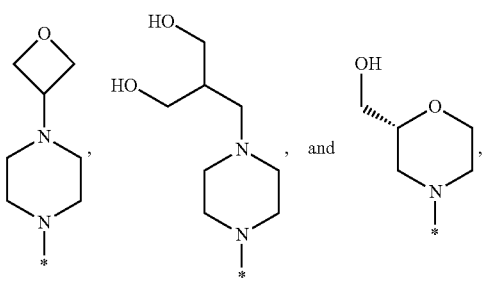 [SMILES: *N1CCN(C2COC2)CC1 ; *N1CCN(CC(CO)CO)CC1 ; *N1CCO[C@@H](CO)C1]

and $R^3$ is methyl.

In some embodiments of the compound of Formula I, or a pharmaceutically acceptable salt thereof, $R^1$ is selected from the group consisting of

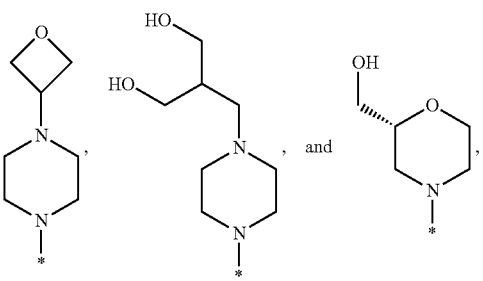 [SMILES: *N1CCN(C2COC2)CC1 ; *N1CCN(CC(CO)CO)CC1 ; *N1CCO[C@@H](CO)C1]

and $R^4$ is H or methyl. In some embodiments of the compound of Formula I, or a pharmaceutically acceptable salt thereof, $R^1$ is selected from the group consisting of

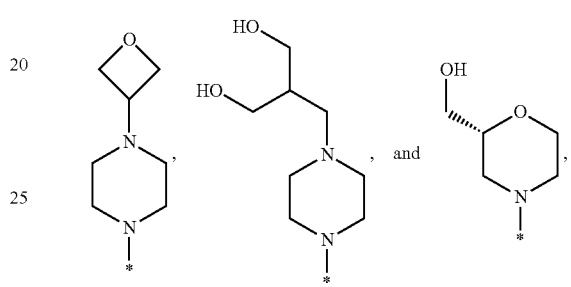

and $R^4$ is H. In some embodiments of the compound of Formula I, or a pharmaceutically acceptable salt thereof, $R^1$ is selected from the group consisting of

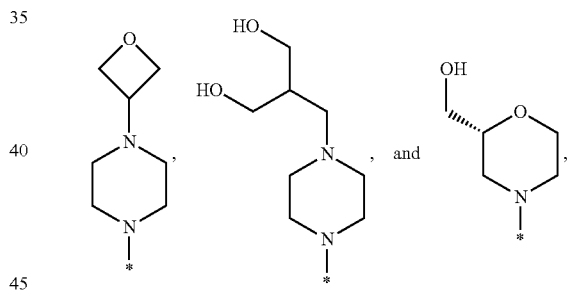

and $R^4$ is methyl.

In some embodiments of the compound of Formula I, or a pharmaceutically acceptable salt thereof, $R^1$ is selected from the group consisting of

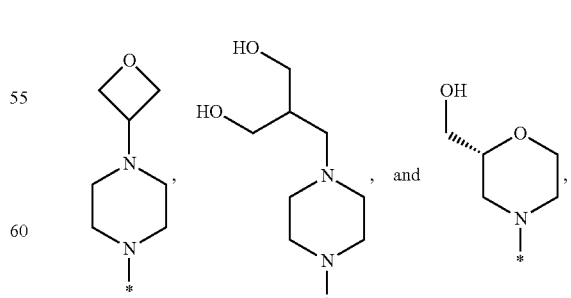

$R^2$ is H and $R^3$ is H. In some embodiments of the compound of Formula I, or a pharmaceutically acceptable salt thereof, $R^1$ is selected from the group consisting of

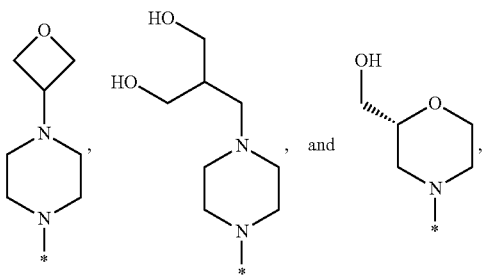 [SMILES: *N1CCN(C2COC2)CC1 ; *N1CCN(CC(CO)CO)CC1 ; *N1CCO[C@@H](CO)C1]

$R^2$ is 2-hydroxyethoxyl and $R^3$ is H. In some embodiments of the compound of Formula I, or a pharmaceutically acceptable salt thereof, $R^1$ is selected from the group consisting of

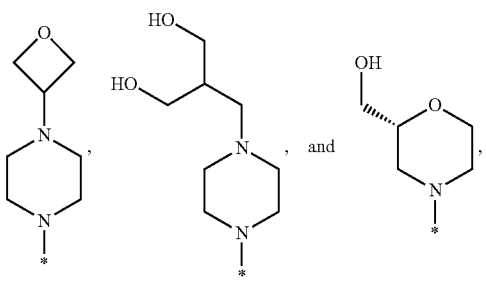

$R^2$ is H and $R^3$ is methyl. In some embodiments of the compound of Formula I, or a pharmaceutically acceptable salt thereof, $R^1$ is selected from the group consisting of

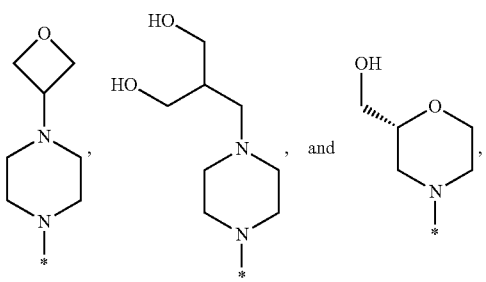 [SMILES: *N1CCN(C2COC2)CC1 ; *N1CCN(CC(CO)CO)CC1 ; *N1CCO[C@@H](CO)C1]

$R^2$ is 2-hydroxyethoxyl and $R^3$ is methyl.

In some embodiments of the compound of Formula I, or a pharmaceutically acceptable salt thereof, $R^1$ is selected from the group consisting of

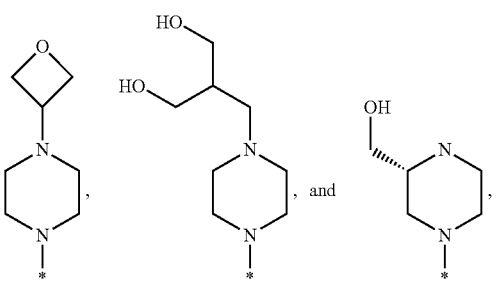 [SMILES: *N1CCN(C2COC2)CC1 ; *N1CCN(CC(CO)CO)CC1 ; *N1CCN[C@@H](CO)C1]

$R^2$ is H and $R^4$ is H or methyl. In some embodiments of the compound of Formula I, or a pharmaceutically acceptable salt thereof, $R^1$ is selected from the group consisting of

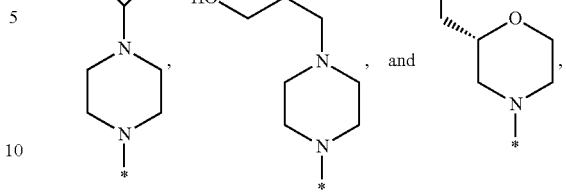

$R^2$ is 2-hydroxyethoxyl and $R^4$ is H or methyl. In some embodiments of the compound of Formula I, or a pharmaceutically acceptable salt thereof, $R^1$ is selected from the group consisting of

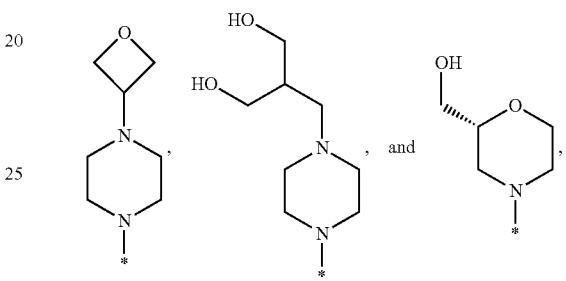

$R^2$ is H and $R^4$ is H. In some embodiments of the compound of Formula I, or a pharmaceutically acceptable salt thereof, $R^1$ is selected from the group consisting of

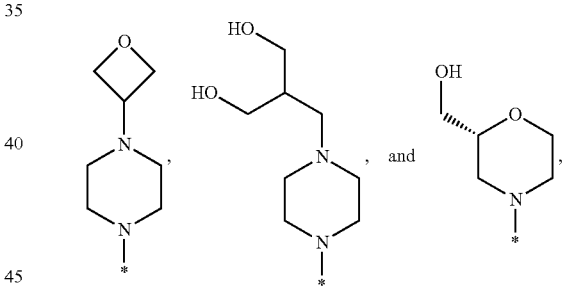

$R^2$ is 2-hydroxyethoxyl and $R^4$ is H. In some embodiments of the compound of Formula I, or a pharmaceutically acceptable salt thereof, $R^1$ is selected from the group consisting of

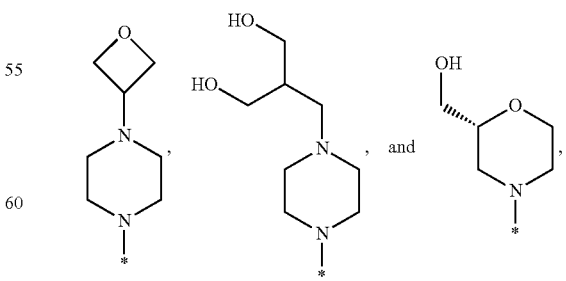

$R^2$ is H and $R^4$ is methyl. In some embodiments of the compound of Formula I, or a pharmaceutically acceptable salt thereof, $R^1$ is selected from the group consisting of

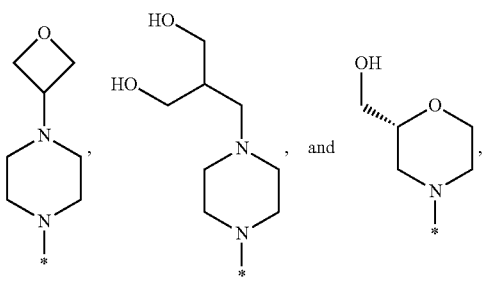 [SMILES: *N1CCN(C2COC2)CC1 ; *N1CCN(CC(CO)CO)CC1 ; *N1CCO[C@@H](CO)C1], and

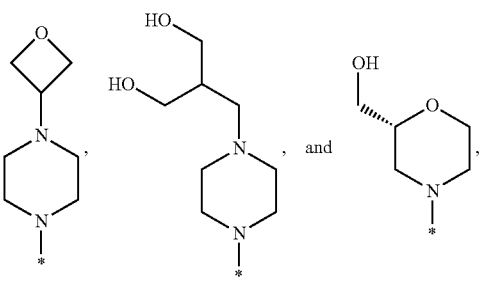 [SMILES: *N1CCN(C2COC2)CC1 ; *N1CCN(CC(CO)CO)CC1 ; *N1CCO[C@@H](CO)C1], and $R^2$ is 2-hydroxyethoxyl and $R^4$ is methyl.

In some embodiments of the compound of Formula I, or a pharmaceutically acceptable salt thereof, $R^1$ is selected from the group consisting of

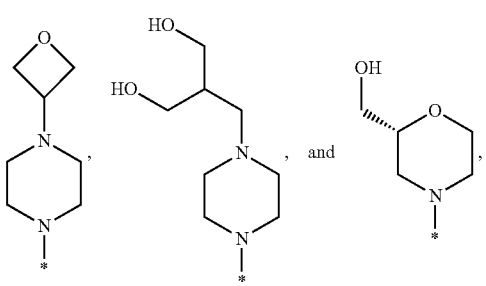 [SMILES: *N1CCN(C2COC2)CC1 ; *N1CCN(CC(CO)CO)CC1 ; *N1CCO[C@@H](CO)C1], and $R^3$ is H and $R^4$ is H or methyl. In some embodiments of the compound of Formula I, or a pharmaceutically acceptable salt thereof, $R^1$ is selected from the group consisting of

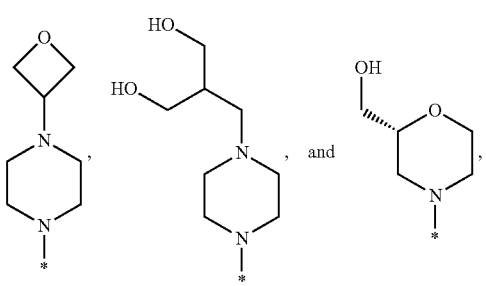 [SMILES: *N1CCN(C2COC2)CC1 ; *N1CCN(CC(CO)CO)CC1 ; *N1CCO[C@@H](CO)C1], and $R^3$ is methyl and $R^4$ is H or methyl. In some embodiments of the compound of Formula I, or a pharmaceutically acceptable salt thereof, $R^1$ is selected from the group consisting of

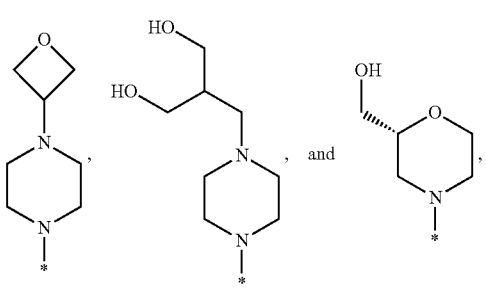 [SMILES: *N1CCN(C2COC2)CC1 ; *N1CCN(CC(CO)CO)CC1 ; *N1CCO[C@@H](CO)C1], and $R^3$ is H and $R^4$ is H. In some embodiments of the compound of Formula I, or a pharmaceutically acceptable salt thereof, $R^1$ is selected from the group consisting of $R^3$ is methyl and $R^4$ is H. In some embodiments of the compound of Formula I, or a pharmaceutically acceptable salt thereof, $R^1$ is selected from the group consisting of

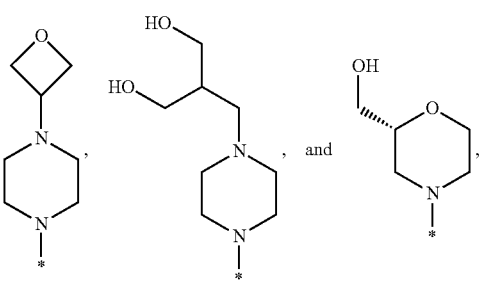 [SMILES: *N1CCN(C2COC2)CC1 ; *N1CCN(CC(CO)CO)CC1 ; *N1CCO[C@@H](CO)C1], and $R^3$ is H and $R^4$ is methyl. In some embodiments of the compound of Formula I, or a pharmaceutically acceptable salt thereof, $R^1$ is selected from the group consisting of

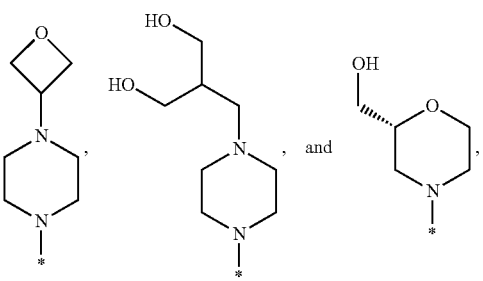 [SMILES: *N1CCN(C2COC2)CC1 ; *N1CCN(CC(CO)CO)CC1 ; *N1CCO[C@@H](CO)C1], and $R^3$ is methyl and $R^4$ is methyl.

In some embodiments of the compound of Formula I, or a pharmaceutically acceptable salt thereof, $R^1$ is selected from the group consisting of

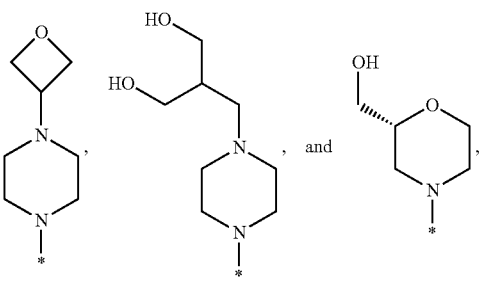 [SMILES: *N1CCN(C2COC2)CC1 ; *N1CCN(CC(CO)CO)CC1 ; *N1CCO[C@@H](CO)C1], and $R^2$ is H, $R^3$ is H and $R^4$ is H or methyl. In some embodiments of the compound of Formula I, or a pharmaceutically acceptable salt thereof, $R^1$ is selected from the group consisting of

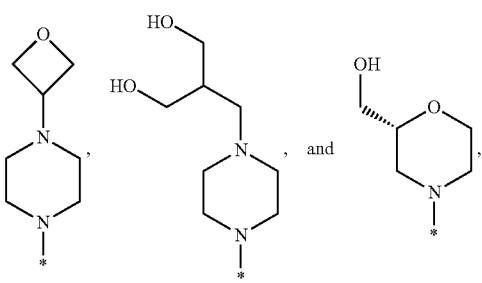 [SMILES: *N1CCN(C2COC2)CC1 ; *N1CCN(CC(CO)CO)CC1 ; *N1CCO[C@@H](CO)C1]

$R^2$ is H, $R^3$ is H and $R^4$ is H. In some embodiments of the compound of Formula I or a pharmaceutically acceptable salt thereof, $R^1$ is selected from the group consisting of

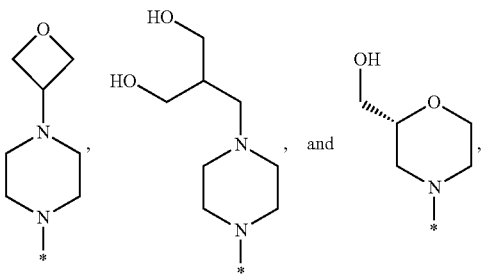 [SMILES: *N1CCN(C2COC2)CC1 ; *N1CCN(CC(CO)CO)CC1 ; *N1CCO[C@@H](CO)C1]

$R^2$ is H, $R^3$ is H and $R^4$ is methyl.

In some embodiments of the compound of Formula I, or a pharmaceutically acceptable salt thereof, $R^1$ is selected from the group consisting of

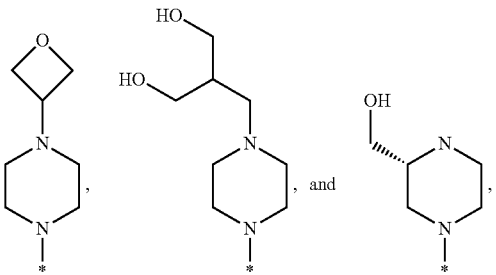 [SMILES: *N1CCN(C2COC2)CC1 ; *N1CCN(CC(CO)CO)CC1 ; *N1CCN[C@@H](CO)C1]

$R^2$ is 2-hydroxyethoxyl, $R^3$ is H and $R^4$ is H or methyl. In some embodiments of the compound of Formula I, or a pharmaceutically acceptable salt thereof, $R^1$ is selected from the group consisting of

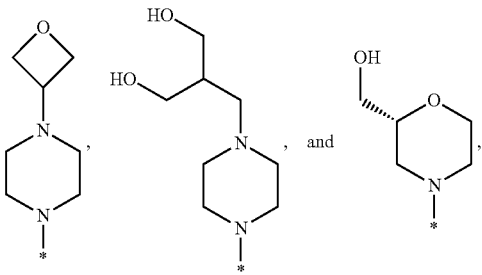 [SMILES: *N1CCN(C2COC2)CC1 ; *N1CCN(CC(CO)CO)CC1 ; *N1CCO[C@@H](CO)C1]

$R^2$ is 2-hydroxyethoxyl, $R^3$ is H and $R^4$ is H. In some embodiments of the compound of Formula I, or a pharmaceutically acceptable salt thereof, $R^1$ is selected from the group consisting of *

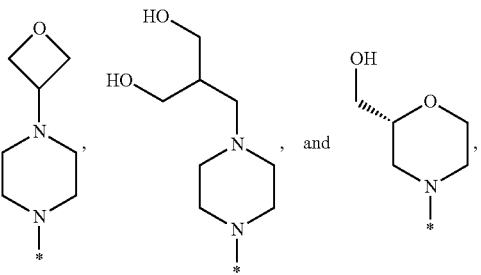 [SMILES: *N1CCN(C2COC2)CC1 ; *N1CCN(CC(CO)CO)CC1 ; *N1CCO[C@@H](CO)C1]

$R^2$ is 2-hydroxyethoxyl, $R^3$ is H and $R^4$ is methyl.

In some embodiments of the compound of Formula I, or a pharmaceutically acceptable salt thereof, $R^1$ is selected from the group consisting of

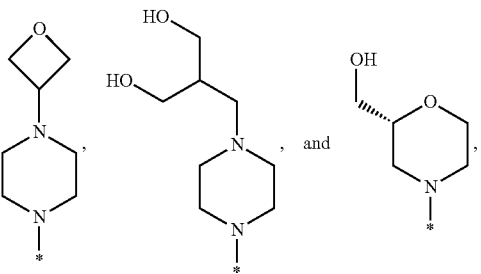 [SMILES: *N1CCN(C2COC2)CC1 ; *N1CCN(CC(CO)CO)CC1 ; *N1CCO[C@@H](CO)C1]

$R^2$ is H, $R^3$ is methyl and $R^4$ is H or methyl. In some embodiments of the compound of Formula I, or a pharmaceutically acceptable salt thereof. $R^1$ is selected from the group consisting of

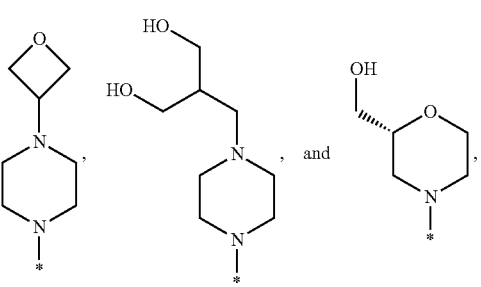 [SMILES: *N1CCN(C2COC2)CC1 ; *N1CCN(CC(CO)CO)CC1 ; *N1CCO[C@@H](CO)C1]

$R^2$ is H, $R^3$ is methyl and $R^4$ is H. In some embodiments of the compound of Formula I, or a pharmaceutically acceptable salt thereof, $R^1$ is selected from the group consisting of

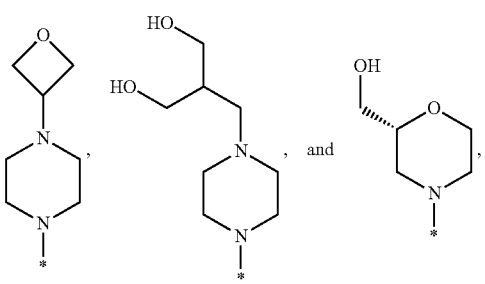

$R^2$ is H, $R$ is methyl and $R^4$ is methyl.

In some embodiments of the compound of Formula I, or a pharmaceutically acceptable salt thereof, $R^1$ is selected from the group consisting of

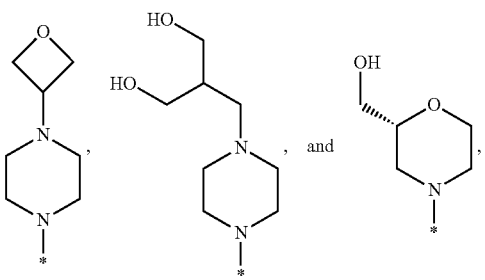 [SMILES: *N1CCN(C2COC2)CC1 ; *N1CCN(CC(CO)CO)CC1 ; *N1CCO[C@@H](CO)C1]

$R^2$ is 2-hydroxyethoxyl, $R^3$ is methyl and $R^4$ is H or methyl. In some embodiments of the compound of Formula I, or a pharmaceutically acceptable salt thereof, $R^1$ is selected from the group consisting of

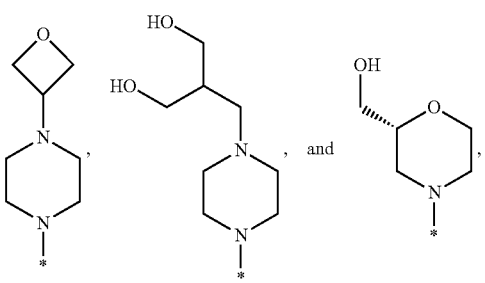 [SMILES: *N1CCN(C2COC2)CC1 ; *N1CCN(CC(CO)CO)CC1 ; *N1CCO[C@@H](CO)C1]

$R^2$ is 2-hydroxyethoxyl, $R^3$ is methyl and $R^4$ is H. In some embodiments of the compound of Formula I, or a pharmaceutically acceptable salt thereof, R is selected from the group consisting of

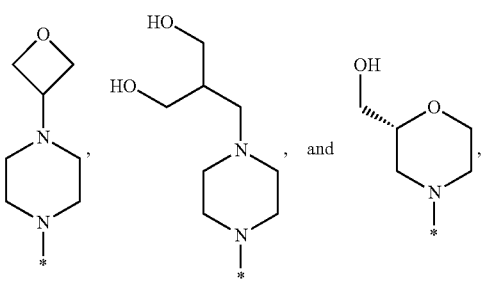 [SMILES: *N1CCN(C2COC2)CC1 ; *N1CCN(CC(CO)CO)CC1 ; *N1CCO[C@@H](CO)C1]

$R^2$ is 2-hydroxyethoxyl, $R^3$ is methyl and $R^4$ is methyl.

In some embodiments of the compound of Formula I, or a pharmaceutically acceptable salt thereof, $R^1$ is

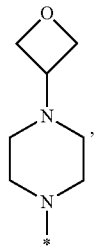

and $R^2$ is H. In some embodiments of the compound of Formula I, or a pharmaceutically acceptable salt thereof, $R^1$ is

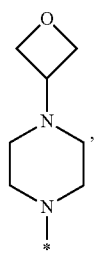

and $R^2$ is 2-hydroxyethoxyl.

In some embodiments of the compound of Formula I, or a pharmaceutically acceptable salt thereof, $R^1$ is

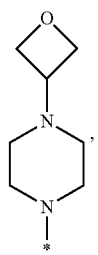

and $R^3$ is H. In some embodiments of the compound of Formula I, or a pharmaceutically acceptable salt thereof, $R^1$ is

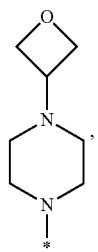

and $R^3$ is methyl.

In some embodiments of the compound of Formula I, or a pharmaceutically acceptable salt thereof, $R^1$ is

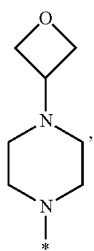

and $R^4$ is H or methyl. In some embodiments of the compound of Formula I, or a pharmaceutically acceptable salt thereof, $R^1$ is

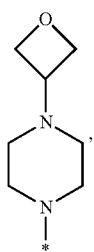

and $R^4$ is H. In some embodiments of the compound of Formula I, or a pharmaceutically acceptable salt thereof, $R^1$ is

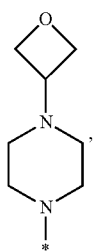

and $R^4$ is methyl.

In some embodiments of the compound of Formula I, or a pharmaceutically acceptable salt thereof, $R^1$ is

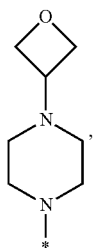

$R^2$ is H and $R^3$ is H. In some embodiments of the compound of Formula I, or a pharmaceutically acceptable salt thereof, $R^1$ is

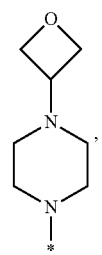

$R^2$ is 2-hydroxyethoxyl and $R^3$ is H. In some embodiments of the compound of Formula I, or a pharmaceutically acceptable salt thereof, $R^1$ is

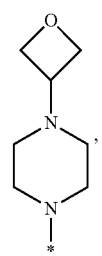

$R^2$ is H and $R^3$ is methyl. In some embodiments of the compound of Formula I, or a pharmaceutically acceptable salt thereof, $R^1$ is

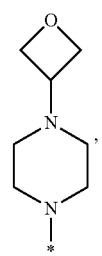

$R^2$ is 2-hydroxyethoxyl and $R^3$ is methyl.

In some embodiments of the compound of Formula I, or a pharmaceutically acceptable salt thereof, $R^1$ is

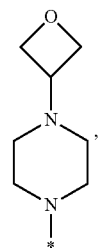

$R^2$ is H and $R^4$ is H or methyl. In some embodiments of the compound of Formula I, or a pharmaceutically acceptable salt thereof, $R^1$ is

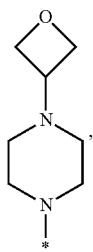

$R^2$ is 2-hydroxyethoxyl and $R^4$ is H or methyl. In some embodiments of the compound of Formula I, or a pharmaceutically acceptable salt thereof, $R^1$ is

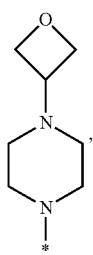

$R^2$ is H and $R^4$ is H. In some embodiments of the compound of Formula I, or a pharmaceutically acceptable salt thereof, $R^1$ is

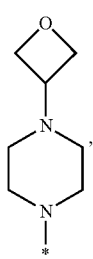

$R^2$ is 2-hydroxyethoxyl and $R^4$ is H. In some embodiments of the compound of Formula I, or a pharmaceutically acceptable salt thereof, $R^1$ is

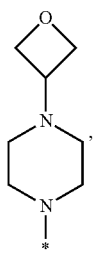

$R^2$ is H and $R^4$ is methyl. In some embodiments of the compound of Formula I, or a pharmaceutically acceptable salt thereof, $R^1$ is

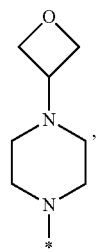

$R^2$ is 2-hydroxyethoxyl and $R^4$ is methyl.

In some embodiments of the compound of Formula I, or a pharmaceutically acceptable salt thereof, $R^1$ is

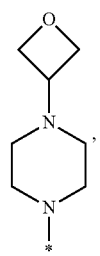

$R^3$ is H and $R^4$ is H or methyl. In some embodiments of the compound of Formula I, or a pharmaceutically acceptable salt thereof, $R^1$ is

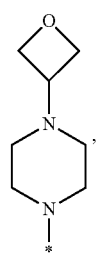

$R^3$ is methyl and $R^4$ is H or methyl. In some embodiments of the compound of Formula I, or a pharmaceutically acceptable salt thereof, $R^1$ is

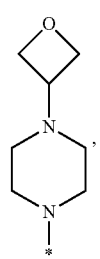

$R^3$ is H and $R^4$ is H. In some embodiments of the compound of Formula I, or a pharmaceutically acceptable salt thereof, $R^1$ is

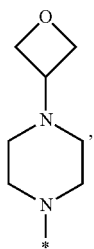

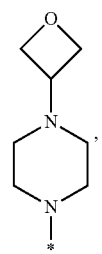

$R^3$ is methyl and $R^4$ is H. In some embodiments of the compound of Formula I, or a pharmaceutically acceptable salt thereof, $R^1$ is $R^2$ is H, $R^3$ is H and $R^4$ is H. In some embodiments of the compound of Formula I, or a pharmaceutically acceptable salt thereof, $R^1$ is

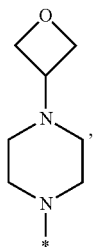

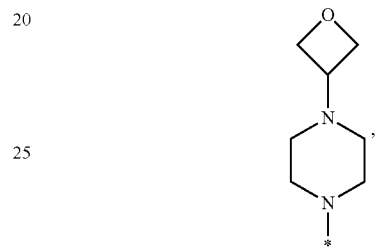

$R^3$ is H and $R^4$ is methyl. In some embodiments of the compound of Formula I, or a pharmaceutically acceptable salt thereof, $R^1$ is $R^2$ is H, $R^3$ is H and $R^4$ is methyl.

In some embodiments of the compound of Formula I, or a pharmaceutically acceptable salt thereof, $R^1$ is

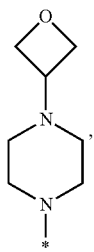

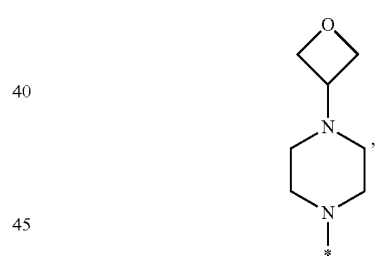

$R^3$ is methyl and $R^4$ is methyl.

In some embodiments of the compound of Formula I, or a pharmaceutically acceptable salt thereof, $R^1$ is $R^2$ is 2-hydroxyethoxyl, $R^3$ is H and $R^4$ is H or methyl. In some embodiments of the compound of Formula I, or a pharmaceutically acceptable salt thereof, $R^1$ is

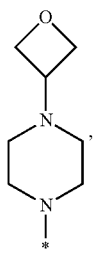

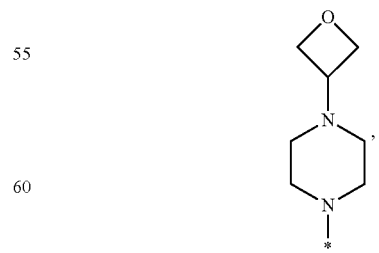

$R^2$ is H, $R^3$ is H and $R^4$ is H or methyl. In some embodiments of the compound of Formula I, or a pharmaceutically acceptable salt thereof, $R^1$ is $R^2$ is 2-hydroxyethoxyl, $R^3$ is H and $R^4$ is H. In some embodiments of the compound of Formula I, or a pharmaceutically acceptable salt thereof, $R^1$ is

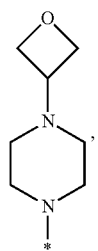

$R^2$ is 2-hydroxyethoxyl, $R^3$ is H and $R^4$ is methyl

In some embodiments of the compound of Formula I, or a pharmaceutically acceptable salt thereof, $R^1$ is

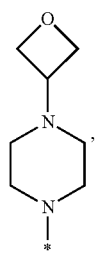

$R^2$ is H, $R^3$ is methyl and $R^4$ is H or methyl. In some embodiments of the compound of Formula I, or a pharmaceutically acceptable salt thereof, $R^1$ is

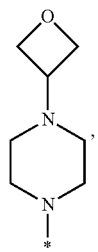

$R^2$ is H, $R^3$ is methyl and $R^4$ is methyl. In some embodiments of the compound of Formula I, or a pharmaceutically acceptable salt thereof, $R^1$ is

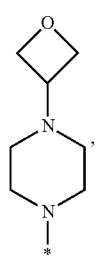

$R^2$ is H, $R^3$ is methyl and $R^4$ is methyl.

In some embodiments of the compound of Formula I, or a pharmaceutically acceptable salt thereof, $R^1$ is

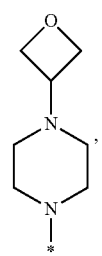

$R^2$ is 2-hydroxyethoxyl, $R^3$ is methyl and $R^4$ is H or methyl. In some embodiments of the compound of Formula I, or a pharmaceutically acceptable salt thereof, $R^1$ is

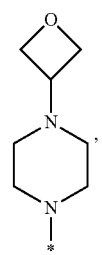

$R^2$ is 2-hydroxyethoxyl, $R^3$ is methyl and $R^4$ is H. In some embodiments of the compound of Formula I, or a pharmaceutically acceptable salt thereof, $R^1$ is

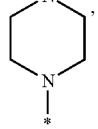

$R^2$ is 2-hydroxyethoxyl, $R^3$ is methyl and $R^4$ is methyl.

In some embodiments of the compound of Formula I, or a pharmaceutically acceptable salt thereof, $R^1$ is

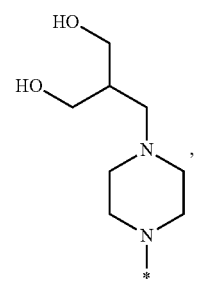

and $R^2$ is H. In some embodiments of the compound of Formula I, or a pharmaceutically acceptable salt thereof, $R^1$ is

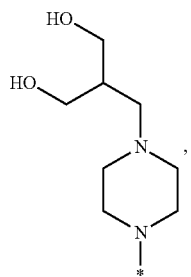

and $R^2$ is 2-hydroxyethoxyl.

In some embodiments of the compound of Formula I, or a pharmaceutically acceptable salt thereof, $R^1$ is

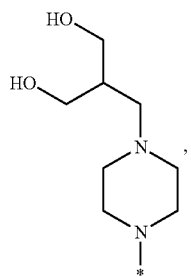

and $R^3$ is H. In some embodiments of the compound of Formula I, or a pharmaceutically acceptable salt thereof, $R^1$ is

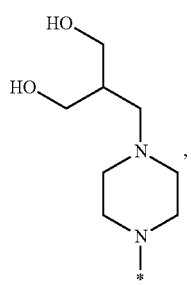

and $R^3$ is methyl.

In some embodiments of the compound of Formula I, or a pharmaceutically acceptable salt thereof, $R^1$ is

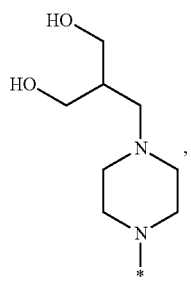

and $R^4$ is H or methyl. In some embodiments of the compound of Formula I, or a pharmaceutically acceptable salt thereof, $R^1$ is

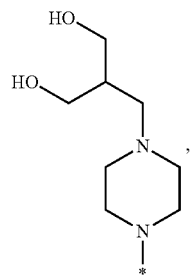

and $R^4$ is H. In some embodiments of the compound of Formula I, or a pharmaceutically acceptable salt thereof, $R^1$ is

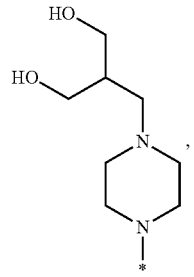

and $R^4$ is methyl

In some embodiments of the compound of Formula I, or a pharmaceutically acceptable salt thereof, $R^1$ is

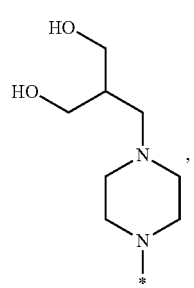

$R^2$ is H and $R^3$ is H. In some embodiments of the compound of Formula I, or a pharmaceutically acceptable salt thereof, $R^1$ is

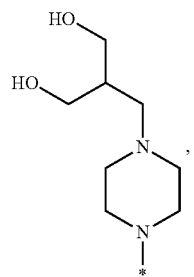

$R^2$ is 2-hydroxyethoxyl and $R^3$ is H. In some embodiments of the compound of Formula I, or a pharmaceutically acceptable salt thereof, $R^1$ is

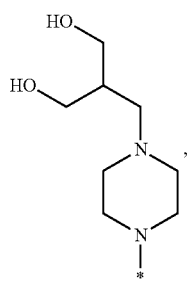

R² is H and R³ is methyl. In some embodiments of the compound of Formula I, R¹ is

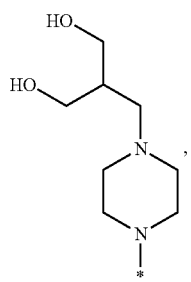

is 2-hydroxyethoxyl and R³ is methyl.

In some embodiments of the compound of Formula I, or a pharmaceutically acceptable salt thereof, R¹ is

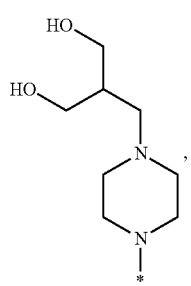

R² is H and R⁴ is H or methyl. In some embodiments of the compound of Formula I, or a pharmaceutically acceptable salt thereof, R¹ is

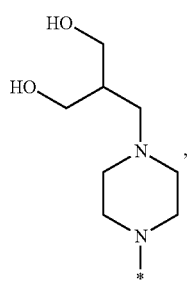

R² is 2-hydroxyethoxyl and R⁴ is H or methyl. In some embodiments of the compound of Formula I, or a pharmaceutically acceptable salt thereof, R¹ is

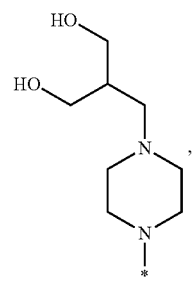

R² is H and R⁴ is H. In some embodiments of the compound of Formula I, or a pharmaceutically acceptable salt thereof, R¹ is

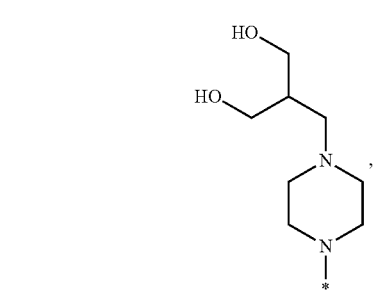

R² is 2-hydroxyethoxyl and R⁴ is H. In some embodiments of the compound of Formula I, or a pharmaceutically acceptable salt thereof, R¹ is

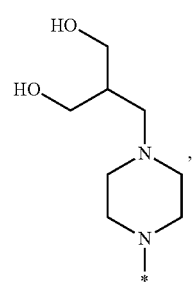

R² is H and R⁴ is methy. In some embodiments of the compound of Formula I, or a pharmaceutically acceptable salt thereof, R¹ is

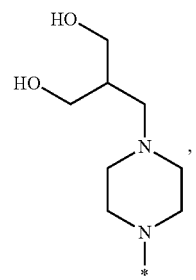

R² is 2-hydroxyethoxyl and R⁴ is methyl.

In some embodiments of the compound of Formula I, or a pharmaceutically acceptable salt thereof, R¹ is

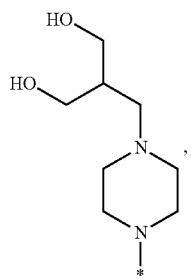

$R^3$ is H and $R^4$ is H or methyl. In some embodiments of the compound of Formula I, or a pharmaceutically acceptable salt thereof, $R^1$ is

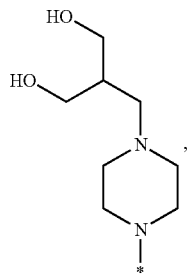

$R^3$ is methyl and $R^4$ is H or methyl. In some embodiments of the compound of Formula I, or a pharmaceutically acceptable salt thereof, $R^1$ is

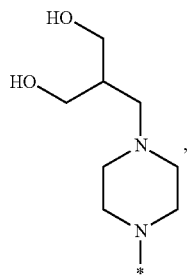

$R^3$ is H and $R^4$ is H. In some embodiments of the compound of Formula I, or a pharmaceutically acceptable salt thereof, $R^1$ is

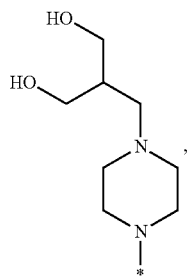

$R^3$ is methyl and $R^4$ is H. In some embodiments of the compound of Formula I, or a pharmaceutically acceptable salt thereof, $R^1$ is

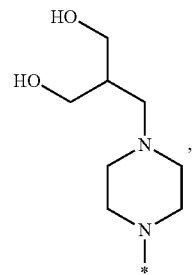

$R^3$ is H and $R^4$ is methyl. In some embodiments of the compound of Formula I, or a pharmaceutically acceptable salt thereof, $R^1$ is

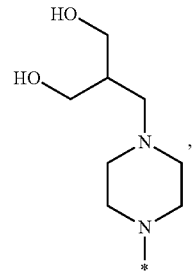

$R^3$ is methyl and $R^4$ is methyl.

In some embodiments of the compound of Formula I, or a pharmaceutically acceptable salt thereof, $R^1$ is

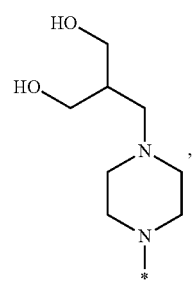

$R^2$ is H, $R^3$ is H and $R^4$ is H or methyl. In some embodiments of the compound of Formula I, or a pharmaceutically acceptable salt thereof, $R^1$ is

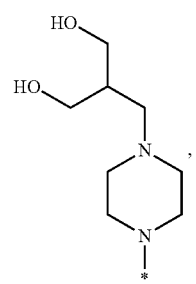

$R^2$ is H, $R^3$ is H and $R^4$ is H. In some embodiments of the compound of Formula I, or a pharmaceutically acceptable salt thereof, $R^1$ is

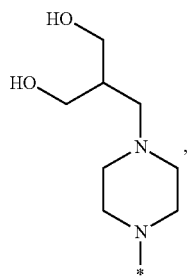

$R^2$ is H, $R^3$ is H and $R^4$ is methyl.

In some embodiments of the compound of Formula I, or a pharmaceutically acceptable salt thereof, $R^1$ is

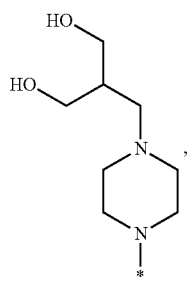

$R^2$ is 2-hydroxyethoxyl, $R^3$ is H and $R^4$ is H or methyl. In some embodiments of the compound of Formula I, or a pharmaceutically acceptable salt thereof, $R^1$ is

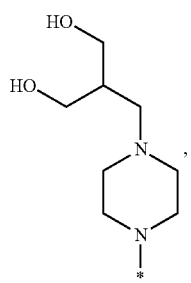

$R^2$ is 2-hydroxyethoxyl, $R^3$ is H and $R^4$ is H. In some embodiments of the compound of Formula I, or a pharmaceutically acceptable salt thereof, $R^1$ is

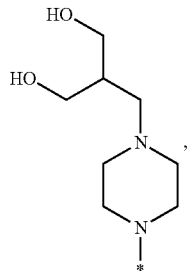

$R^2$ is 2-hydroxyethoxyl, $R^3$ is H and $R^4$ is methyl.

In some embodiments of the compound of Formula I, or a pharmaceutically acceptable salt thereof, $R^1$ is

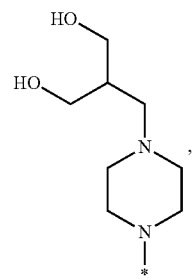

$R^2$ is H, $R^3$ is methyl and $R^4$ is H or methyl. In some embodiments of the compound of Formula I, or a pharmaceutically acceptable salt thereof, $R^1$ is

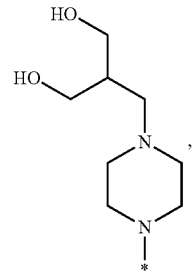

$R^2$ is H, $R^3$ is methyl and $R^4$ is H. In some embodiments of the compound of Formula I, or a pharmaceutically acceptable salt thereof, $R^1$ is

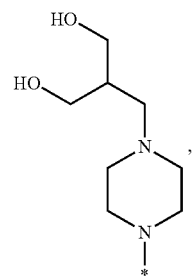

$R^2$ is H, $R^3$ is methyl and $R^4$ is methyl.

In some embodiments of the compound of Formula I, or a pharmaceutically acceptable salt thereof, $R^1$ is

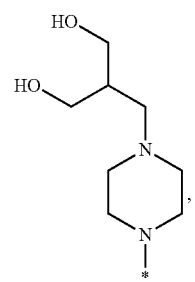

$R^2$ is 2-hydroxyethoxyl, $R^3$ is methyl and $R^4$ is H or methyl. In some embodiments of the compound of Formula I, or a pharmaceutically acceptable salt thereof, $R^1$ is

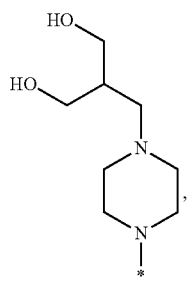 [SMILES: *N1CCN(CC(CO)CO)CC1]

$R^2$ is 2-hydroxyethoxyl, $R^3$ is methyl and $R^4$ is H. In some embodiments of the compound of Formula I, or a pharmaceutically acceptable salt thereof, $R^1$ is

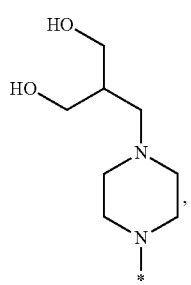 [SMILES: *N1CCN(CC(CO)CO)CC1]

$R^2$ is $R^2$-hydroxyethoxyl, $R^3$ is methyl and $R^4$ is methyl.

In some embodiments of the compound of Formula I, or a pharmaceutically acceptable salt thereof, $R^1$ is

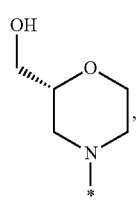

and $R^2$ is H. In some embodiments of the compound of Formula I, $R^1$ is

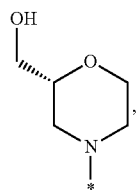

and $R^2$ is 2-hydroxyethoxyl.

In some embodiments of the compound of Formula I, or a pharmaceutically acceptable salt thereof, $R^1$ is

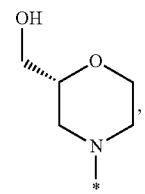

and $R^3$ is H. In some embodiments of the compound of Formula I, or a pharmaceutically acceptable salt thereof, $R^1$ is

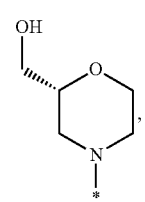

and $R^3$ is methyl.

In some embodiments of the compound of Formula I, or a pharmaceutically acceptable salt thereof, $R^1$ is

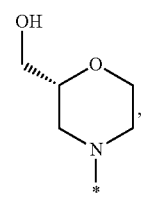 [SMILES: *N1CCO[C@@H](CO)C1]

and $R^4$ is H or methyl. In some embodiments of the compound of Formula I, or a pharmaceutically acceptable salt thereof, $R^1$ is

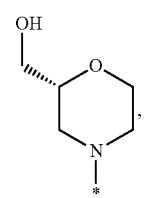 [SMILES: *N1CCO[C@@H](CO)C1]

and $R^4$ is H. In some embodiments of the compound of Formula I, or a pharmaceutically acceptable salt thereof, $R^1$ is

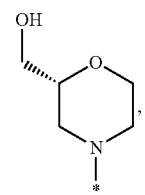 [SMILES: *N1CCO[C@@H](CO)C1]

and $R^4$ is methyl.

In some embodiments of the compound of Formula I, or a pharmaceutically acceptable salt thereof, $R^1$ is $R^2$ is H and $R^3$ is H. In some embodiments of the compound of Formula I, or a pharmaceutically acceptable salt thereof, $R^1$ is $R^2$ is 2-hydroxyethoxyl and $R^3$ is H. In some embodiments of the compound of Formula I, or a pharmaceutically acceptable salt thereof, $R^1$ is $R^2$ is H and $R^3$ is methyl. In some embodiments of the compound of Formula I, or a pharmaceutically acceptable salt thereof, $R^1$ is $R^2$ is 2-hydroxyethyl and $R^3$ is methyl.
In some embodiments of the compound of Formula I, or a pharmaceutically acceptable salt thereof, $R^1$ is $R^2$ is H and $R^4$ is H or methyl. In some embodiments of the compound of Formula I, or a pharmaceutically acceptable salt thereof, $R^1$ is $R^2$ is 2-hydroxyethoxyl and $R^4$ is H or methyl. In some embodiments of the compound of Formula I, or a pharmaceutically acceptable salt thereof, $R^1$ is $R^2$ is H and $R^4$ is H. In some embodiments of the compound of Formula I, or a pharmaceutically acceptable salt thereof, $R^1$ is $R^2$ is 2-hydroxyethoxyl and $R^4$ is H. In some embodiments of the compound of Formula I, or a pharmaceutically acceptable salt thereof. $R^1$ is $R^2$ is H and $R^4$ is methyl. In some embodiments of the compound of Formula I, or a pharmaceutically acceptable salt thereof, $R^1$ is is 2-hydroxyethoxyl and $R^4$ is methyl.
In some embodiments of the compound of Formula I, or a pharmaceutically acceptable salt thereof, $R^1$ is

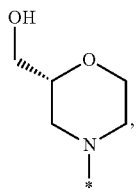

$R^3$ is H and $R^4$ is H or methyl. In some embodiments of the compound of Formula I, or a pharmaceutically acceptable salt thereof, $R^1$ is

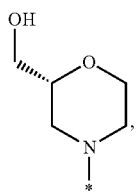

$R^3$ is methyl and $R^4$ is H or methyl. In some embodiments of the compound of Formula I, or a pharmaceutically acceptable salt thereof, $R^1$ is

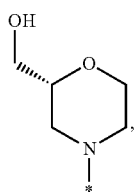

$R^3$ is H and $R^4$ is H. In some embodiments of the compound of Formula I, or a pharmaceutically acceptable salt thereof, $R^1$ is

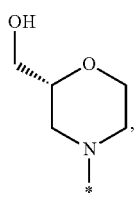

$R^3$ is methyl and $R^4$ is H. In some embodiments of the compound of Formula I, or a pharmaceutically acceptable salt thereof, $R^1$ is

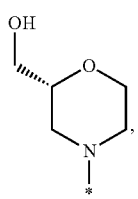

$R^3$ is H and $R^4$ is methyl. In some embodiments of the compound of Formula I, or a pharmaceutically acceptable salt thereof, $R^1$ is

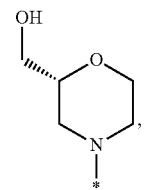 [SMILES: *N1CCO[C@@H](CO)C1]

$R^3$ is methyl and $R^4$ is methyl.

In some embodiments of the compound of Formula I, or a pharmaceutically acceptable salt thereof, $R^1$ is

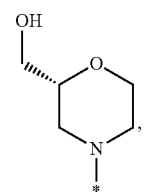

$R^2$ is H, $R^3$ is H and $R^4$ is H or methyl. In some embodiments of the compound of Formula I, or a pharmaceutically acceptable salt thereof, $R^1$ is

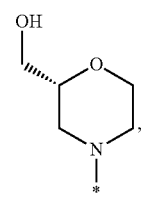

$R^2$ is H, $R^3$ is H and $R^4$ is H. In some embodiments of the compound of Formula I, or a pharmaceutically acceptable salt thereof, $R^1$ is

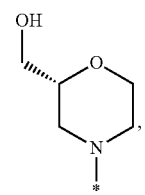 [SMILES: *N1CCO[C@@H](CO)C1]

$R^2$ is H, $R^3$ is H and $R^4$ is methyl.

In some embodiments of the compound of Formula I, or a pharmaceutically acceptable salt thereof, $R^1$ is

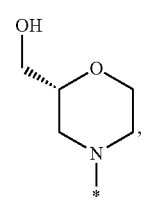 [SMILES: *N1CCO[C@@H](CO)C1]

$R^2$ is 2-hydroxyethoxyl, $R^3$ is H and $R^4$ is H or methyl. In some embodiments of the compound of Formula I, or a pharmaceutically acceptable salt thereof, $R^1$ is

61

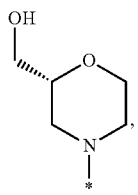

$R^2$ is 2-hydroxyethoxyl, $R^3$ is H and $R^4$ is H. In some embodiments of the compound of Formula I, or a pharmaceutically acceptable salt thereof, $R^1$ is

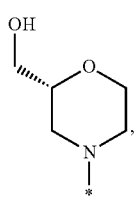

$R^2$ is 2-hydroxyethoxyl, $R^3$ is H and $R^4$ is methyl.

In some embodiments of the compound of Formula I, or a pharmaceutically acceptable salt thereof, $R^1$ is

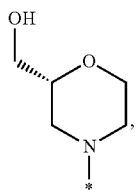

$R^2$ is H, $R^3$ is methyl and $R^4$ is H or methyl. In some embodiments of the compound of Formula I, or a pharmaceutically acceptable salt thereof, $R^1$ is

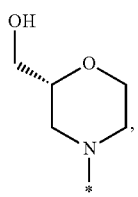

$R^2$ is H, $R^3$ is methyl and $R^4$ is H. In some embodiments of the compound of Formula I, or a pharmaceutically acceptable salt thereof, $R^1$ is

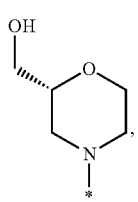

$R^2$ is H, $R^3$ is methyl and $R^4$ is methyl

In some embodiments of the compound of Formula I, or a pharmaceutically acceptable salt thereof, $R^1$ is

62

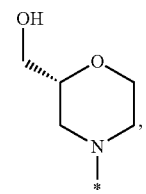 [SMILES: *N1CCO[C@@H](CO)C1]

$R^2$ is 2-hydroxyethoxyl, $R^3$ is methyl and $R^4$ is H or methyl. In some embodiments of the compound of Formula I, or a pharmaceutically acceptable salt thereof, $R^1$ is

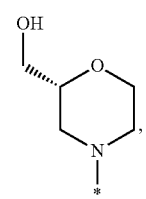

$R^2$ is 2-hydroxyethoxyl, $R^3$ is methyl and $R^4$ is H. In some embodiments of the compound of Formula I, or a pharmaceutically acceptable salt thereof, $R^1$ is

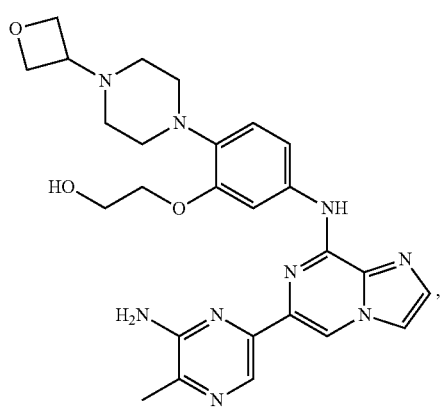

$R^2$ is 2-hydroxyethoxyl, $R^3$ is methyl and $R^4$ is methyl.

Embodiments herein that refer to the compound of Formula I in one aspect also refer to a pharmaceutically acceptable salt of the compound of Formula I, even if not explicity stated as such.

In some embodiments, the compound of Formula I is selected from the group consisting of:

-continued

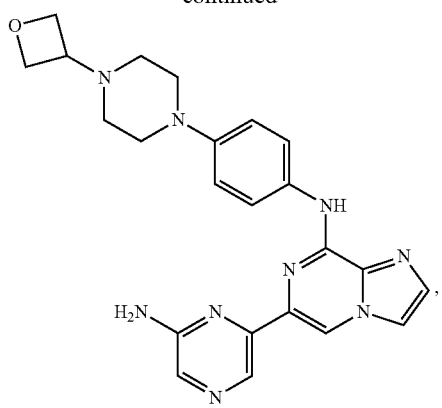

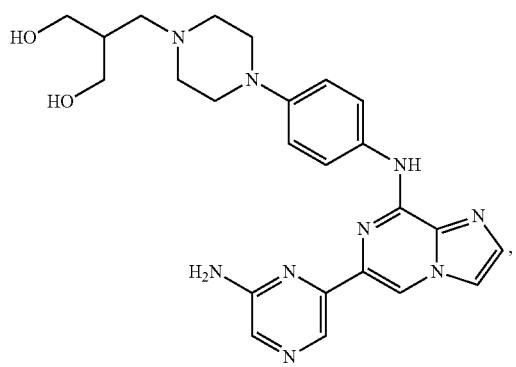

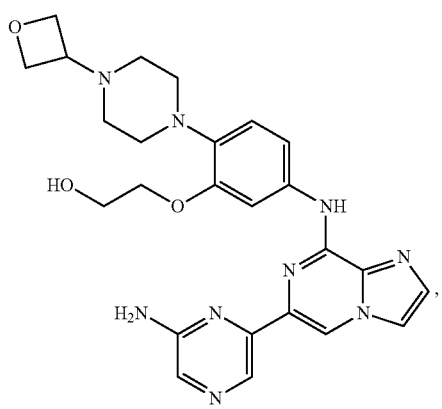

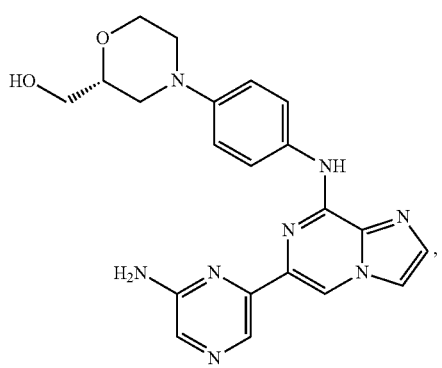

-continued

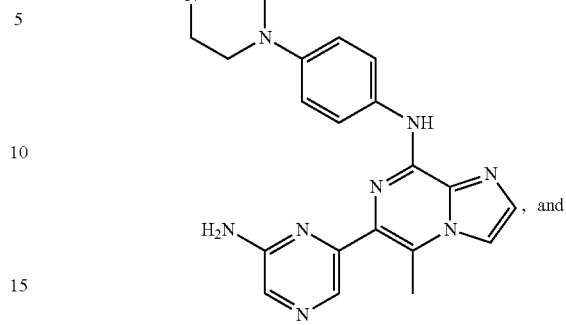, and

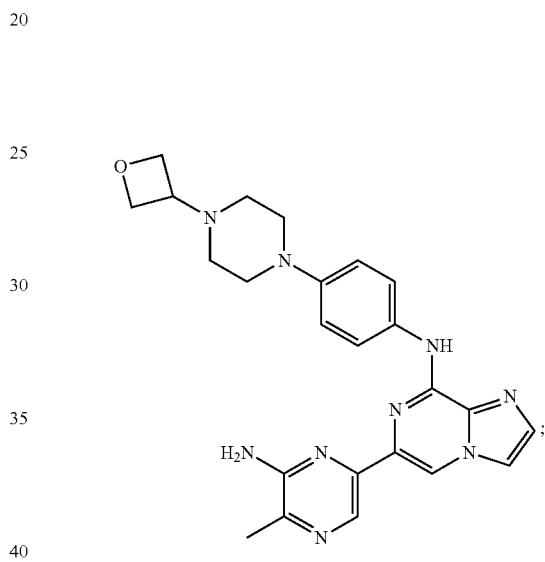

or a pharmaceutically acceptable salt thereof.

In some embodiments, the compound of Formula I is selected from the group consisting of:

2-(5-(((6-(6-amino-5-methylpyrazin-2-yl)imidazo[1,2-a]pyrazin-8-yl)amino)-2-(4-(oxetan-3-yl)piperazin-1-yl)phenoxy)ethanol;

6-(6-aminopyrazin-2-yl)-N-(4-(4-(oxetan-3-yl)piperazin-1-yl)phenyl)imidazo[1,2-a]pyrazin-8-amine;

2-((4-(4-(((6-(6-aminopyrazin-2-yl)imidazo[1,2-a]pyrazin-8-yl)amino)phenyl)piperazin-1-yl)methyl)propane-1,3-diol;

2-(5-(((6-(6-aminopyrazin-2-yl)imidazo[1,2-a]pyrazin-8-yl)amino)-2-(4-(oxetan-3-yl)piperazin-1-yl)phenoxy)ethanol;

(R)-(4-(4-(((6-(6-aminopyrazin-2-yl)imidazo[1,2a]pyrazin-8-yl)amino)phenyl)morpholin-2-yl)methanol;

6-(6-aminopyrazin-2-yl)-5-methyl-N-(4-(4-(oxetan-3-yl)piperazin-1-yl)phenyl)imidazo[1,2a]pyrazin-8-amine; and 6-(6-amino-5-methylpyrazin-2-yl)-N-(4-(4-(oxetan-3-yl)piperazin-1-yl)phenyl)imidazo[1,2-a]pyrazin-8-amine;

or a pharmaceutically acceptable salt thereof

Also provided herein is a compound of Formula II:

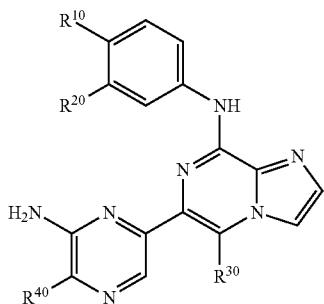

Formula II or a pharmaceutically acceptable salt thereof, wherein:
$R^{10}$ is selected from the group consisting of

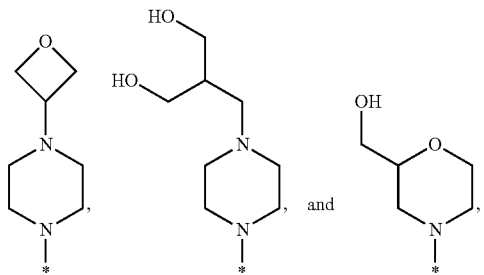

wherein * indicates the carbon atom of the indicated phenyl ring of Formula I to which $R^1$ is attached;

$R^{20}$ is H or 2-hydroxyethoxyl;

$R^{30}$ is H or methyl; and $R^4$ is H, halogen (i.e. F, Cl, Br, or I), methyl, or halo substituted methyl (i.e. methyl wherein 1 to 3 hydrogen atoms are substituted by 1 to 3 halogen atoms, which may be the same or different, e.g. fluoromethyl, chloromethyl, difluoromethyl, dichloromethyl, chlorofluoromethyl, trifluoromethyl, and the like).

Representative compounds of the invention are listed in Table A below. The compounds in Table A are named using ChemBioDraw Ultra 12.0 and it should be understood that other names be used to identify compounds of the same structure. Other compounds or radicals may be named with common names, or systematic or non-systematic names. The compounds may also be named using other nomenclature systems and symbols that are commonly recognized in the art of chemistry including, for example, Chemical Abstract Service (CAS) and International Union of Pure and Applied Chemistry (IUPAC). Any ambiguity in naming of compounds can be resolved by deferring to the structure, where provided.

TABLE A

| Representative Compounds | |
|---|---|
| Structure | Name |
| (structure) | 6-(6-amino-5-methylpyrazin-2-yl)-N-(4-(4-(oxetan-3-yl)piperazin-1-yl)phenyl)imidazo[1,2-a]pyrazin-8-amine |
| (structure) | 6-(6-aminopyrazin-2-yl)-N-(4-(4-(oxetan-3-yl)piperazin-1-yl)phenyl)imidazo[1,2-a]pyrazin-8-amine |

TABLE A-continued

Representative Compounds

| Structure | Name |
|---|---|
| 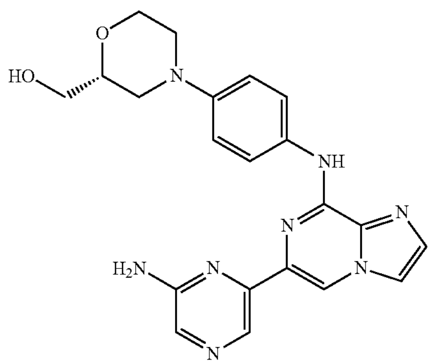 [SMILES: Nc1cncc(-c2cn3ccnc3c(Nc3ccc(N4CCO[C@@H](CO)C4)cc3)n2)n1] | (R)-(4-(4-((6-(6-aminopyrazin-2-yl)imidazo[1,2-a]pyrazin-8-yl)amino)phenyl)morpholin-2-yl)methanol |
| 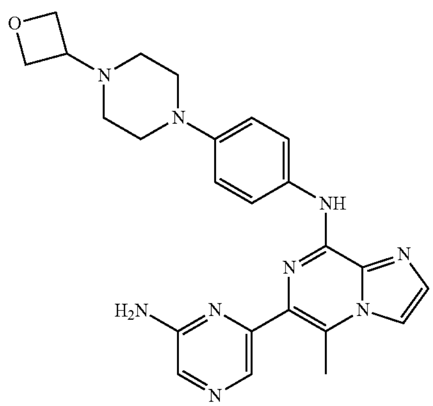 [SMILES: Cc1c(-c2cncc(N)n2)nc(Nc2ccc(N3CCN(C4COC4)CC3)cc2)c2nccn12] | 6-(6-aminopyrazin-2-yl)-5-methyl-N-(4-(4-(oxetan-3-yl)piperazin-1-yl)phenyl)imidazo[1,2-a]pyrazin-8-amine |
| 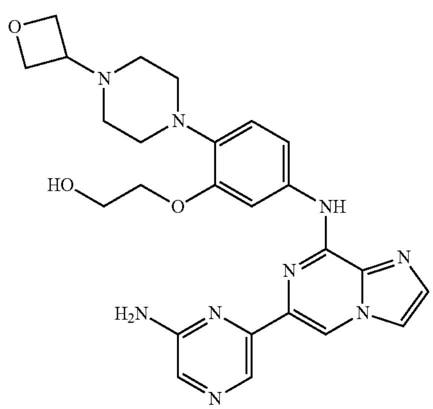 [SMILES: Nc1cncc(-c2cn3ccnc3c(Nc3ccc(N4CCN(C5COC5)CC4)c(OCCO)c3)n2)n1] | 2-(5-((6-(6-aminopyrazin-2-yl)imidazo[1,2-a]pyrazin-8-yl)amino)-2-(4-(oxetan-3-yl)piperazin-1-yl)phenoxy)ethanol |
| 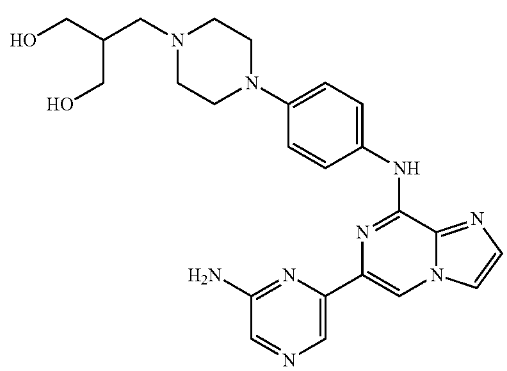 [SMILES: Nc1cncc(-c2cn3ccnc3c(Nc3ccc(N4CCN(CC(CO)CO)CC4)cc3)n2)n1] | 2-((4-(4-((6-(6-aminopyrazin-2-yl)imidazo[1,2-a]pyrazin-8-yl)amino)phenyl)piperazin-1-yl)methyl)propane-1,3-diol |

TABLE A-continued

Representative Compounds

| Structure | Name |
|---|---|
| 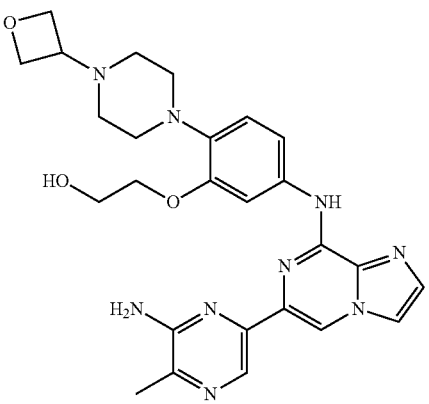 [SMILES: Cc1ncc(-c2cn3ccnc3c(Nc3ccc(N4CCN(C5COC5)CC4)c(OCCO)c3)n2)nc1N] | 2-(5-((6-(6-amino-5-methylpyrazin-2-yl)imidazo[1,2-a]pyrazin-8-yl)amino)-2-(4-(oxetan-3-yl)piperazin-1-yl)phenoxy)ethanol |

The compounds described herein, e.g. a compound of Formula I, or a pharmaceutically acceptable salt thereof, provide distinct advantage as Syk inhibitors. The compounds described herein are inhibitors of Syk kinase activity, as measured, for example as the inhibition of Syk kinase activity in a biochemical assay or as the reduction in basophil activation as measured by CD63 expression, as described in the Examples. The compounds described herein also have desirable properties for use as a pharmaceutical, including kinetic solubility at 37° C. in phosphate buffer at pH 7.4 and low levels of hepatocyte clearance. These features result in Syk inhibitors for treatment of disease with pharmacokinetic characteristics that provide a therapeutic window such that the compounds can be effective in smaller doses than currently known compounds. As such, the compounds provide effective doses with minimal off target activity, which may reduce unwanted side effects, lessen the chance of drug-drug interactions, and increase a subject's compliance with a given therapeutic regimen.

In some embodiments, the compounds described herein, e.g. a compound of Formula I, or a pharmaceutically acceptable salt thereof is effective in one or more of Syk kinase activity inhibition or reduction of basophil activation as measured by CD63 expression, for example, the compound inhibits Syk kinase activity with an $IC_{50}$ value less than or equal to 1 micromolar, less than or equal to 500 nanomolar, less than or equal to 200 nanomolar, less than or equal to 100 nanomolar, less than or equal to 50 nanomolar, less than or equal to 20 nanomolar, or less than or equal to 10 nanomolar, as demonstrated by a suitable assay for Syk kinase activity, such as the assay as described in Example 8; and/or reduces CD63 expression activity with an $EC_{50}$ value less than or equal to 1 micromolar, less than or equal to 500 nanomolar, less than or equal to 200 nanomolar, less than or equal to 150 nanomolar, less than or equal to 100 nanomolar, or less than or equal to 75 nanomolar, as demonstrated by a suitable assay for the measurement of CD63 expression in basophils, such as the assay as described in Example 9.

In some embodiments, the compound of Formula I, or a pharmaceutically acceptable salt thereof, is effective in both of Syk kinase inhibition and reduction of CD63 expression, for example, the compound has Syk kinase activity with an $IC_{50}$ value less than or equal to 1 micromolar, less than or equal to 500 nanomolar, less than or equal to 200 nanomolar, less than or equal to 100 nanomolar, less than or equal to 50 nanomolar, less than or equal to 20 nanomolar, or less than or equal to 10 nanomolar, as demonstrated by a suitable assay for Syk kinase activity, such as the assay as described in Example 8; and has reduction in CD63 expression with an $EC_{50}$ value less than or equal to 1 micromolar, less than or equal to 500 nanomolar, less than or equal to 200 nanomolar, less than or equal to 150 nanomolar, less than or equal to 100 nanomolar, or less than or equal to 75 nanomolar, as demonstrated by a suitable assay for the measurement of CD63 expression in basophils, such as the assay as described in Example 9.

In some embodiments, in addition to having the property of one or more of Syk kinase inhibition or reduction of basophil activation as measured by CD63 expression, including having both of the properties of Syk kinase inhibition and reduction of basophil activation as measured by CD63 expression, the compound of Formula I, or a pharmaceutically acceptable salt thereof, has desirable properties for use as a pharmaceutical, including one or more of kinetic solubility and low levels of hepatocyte clearance. In some embodiments, the compound of Formula I, or a pharmaceutically acceptable salt thereof has a desirable property of one or more of kinetic solubility and low levels of hepatocyte clearance, including kinetic solubility at 37° C. in phosphate buffer at pH 7.4 of greater than or equal to 10 μM, greater than er equal to 20 μM, greater than or equal to 30 μM, greater than or equal to 40 μM, greater than or equal to 50 μM, greater than or equal to 60 μM, greater than or equal to 70 μM, greater than or equal to 80 μM, or greater than or equal to 90 μM, as demonstrated by a suitable measure of kinetic solubility, such as the assay as described in Example 10; and/or predicted hepatocyte clearance of less than or equal to 0.50 L/hr/g, less than or equal to 0.40 L/hr/kg, less than or equal to 0.30 L/hr/kg, less than or equal to 0.20 L/hr/kg, less than or equal to 0.10 L/hr/kg, less than or equal to 0.09 L/hr/kg, less than or equal to 0.08 L/hr/kg, less than or equal to 0.07 L/hr/kg, or less than or equal to 0.06 L/hr/kg, as demonstrated by a suitable measure of predicted hepatocyte clearance, such as the assay as described in Example 11.

In some embodiments, the compound of Formula I, or a pharmaceutically acceptable salt thereof, has a desirable property of kinetic solubility, and low levels of hepatocyte clearance, including kinetic solubility at 37° C. in phosphate buffer at pH 7.4 of greater than or equal to 10 μM, greater than or equal to 20 μM, greater than or equal to 30 μM, greater than or equal to 40 μM, greater than or equal to 50 μM, greater than or equal to 60 μM, greater than or equal to 70 μM, greater than or equal to 80 μM, or greater than or equal to 90 μM, as demonstrated by a suitable measure of kinetic solubility, such as the assay as described in Example 10; and predicted hepatocyte clearance of less than or equal to 0.50 L/hr/kg, less than or equal to 0.40 L/hr/kg, less than or equal to 0.30 L/hr/kg, less than or equal to 0.20 L/hr/kg, less than or equal to 0.10 L/hr/kg, less than or equal to 0.09 L/hr/kg, less than or equal to 0.08 L/hr/kg, less than or equal to 0.07 L/hr/kg, or less than or equal to 0.06 L/hr/kg, as demonstrated by a suitable measure of predicted hepatocyte clearance, such as the assay as described in Example 11.

In some embodiments, the compound of Formula I, or a pharmaceutically acceptable salt thereof, is effective in both of Syk kinase inhibition and reduction of CD63 expression, and has a desirable property of kinetic solubility, and low levels of hepatocyte clearance, for example, the compound has Syk kinase activity with an $IC_{50}$ value less than or equal to 1 micromolar, less than or equal to 500 nanomolar, less than or equal to 200 nanomolar, less than or equal to 100 nanomolar, less than or equal to 50 nanomolar, less than or equal to 20 nanomolar, or less than or equal to 10 nanomolar, as demonstrated by a suitable assay for Syk kinase activity, such as the assay as described in Example 8; and has reduced CD63 expression with an $EC_{50}$ value less than or equal to 1 micromolar, less than or equal to 500 nanomolar, less than or equal to 200 nanomolar, less than or equal to 150 nanomolar, less than or equal to 100 nanomolar, or less than or equal to 75 nanomolar, as demonstrated by a suitable assay for the measurement of CD63 expression in basophils, such as the assay as described in Example 10; and kinetic solubility at 37° C. in phosphate buffer at pH 7.4 of greater than or equal to 10 μM, greater than or equal to 20 μM, greater than or equal to 30 μM, greater than or equal to 40 μM, greater than or equal to 40 μM, greater than or equal to 50 μM, greater than or equal to 60 μM, greater than or equal to 70 μM, greater than or equal to 80 μM, or greater than or equal to 90 μM, as demonstrated by a suitable measure of kinetic solubility, such as the assay as described in Example 10; and predicted hepatocyte clearance of less than or equal to 0.50 L/hr/kg, less than or equal to 0.40 L/hr/kg, less than or equal to 0.30 L/hr/kg, less than or equal to 0.20 L/hr/kg, less than or equal to 0.10 L/hr/kg, less than or equal to 0.09 L/hr/kg, less than or equal to 0.08 L/hr/kg, less than or equal to 0.07 L/hr/kg, or less than or equal to 0.06 L/hr/kg, as demonstrated by a suitable measure of predicted hepatocyte clearance, such as the assay as described in Example 11

Methods of Use

Provided is a method of treating a subject, for example, a mammal, such as a human, having a disease responsive to inhibition of Syk activity, comprising administrating to the subject having, or suspected of having, such a disease, an effective amount of a compound of Formula I, or a pharmaceutically acceptable salt thereof. In one aspect, the subject, such as a human, is administered a pharmaceutical composition comprising a compound of Formula I, or a pharmaceutically acceptable salt thereof, and a pharmaceutically acceptable vehicle.

In some embodiments, the compound of Formula I, or a pharmaceutically acceptable salt thereof, may be administered to a subject (e.g., a human) who is at risk or has a family history of the disease or condition.

In some embodiments, the compound of Formula I, or a pharmaceutically acceptable salt thereof, may also inhibit other kinases, such that disease, disease symptoms, and conditions associated with these kinases are also treated.

Methods of treatment also include inhibiting Syk activity and/or inhibiting B-cell activity, by inhibiting ATP binding or hydrolysis by Syk or by some other mechanism, in vivo, in a subject suffering from a disease responsive to inhibition of Syk activity, by administering an effective concentration of a compound of Formula I, or a pharmaceutically acceptable salt thereof. An example of an effective concentration would be that concentration sufficient to inhibit Syk activity in vitro. An effective concentration may be ascertained experimentally, for example by assaying blood concentration of the compound following administration to a human, or theoretically, by calculating bioavailability.

In some embodiments, the condition responsive to inhibition of Syk activity and/or B-cell activity is cancer, an allergic disorder and/or an autoimmune and/or inflammatory disease, and/or an acute inflammatory reaction.

Also provided is a method of inhibiting B-cell activity in a subject in need thereof comprising administering an effective amount of a compound of Formula I, or a pharmaceutically acceptable salt thereof.

Also provided is a method of inhibiting B-cell proliferation in a subject in need thereof comprising administering an effective amount of a compound of Formula I, or a pharmaceutically acceptable salt thereof.

Also provided is a method of treating a subject having cancer, an allergic disorder and/or an autoimmune and/or inflammatory disease, and/or an acute inflammatory reaction, by administering an effective amount of a compound of Formula I, or a pharmaceutically acceptable salt thereof.

In some embodiments, the conditions and diseases that can be treated using a compound of Formula I, or a pharmaceutically acceptable salt thereof, include, but are not limited tolymphoma (e.g. small lymphocytic lymphoma (SLL), non-Hodgkin's lymphoma (NHL), indolent non-Hodgkin's lymphoma (iNHL), refractory iNHL, mantle cell lymphoma (MCL), follicular lymphoma (FL), lymphoplasmacytic lymphoma (LPL), marginal zone lymphoma (MZL), immunoblastic large cell lymphoma, lymphoblastic lymphoma, Splenic marginal zone B-cell lymphoma (+/− villous lymphocytes), Nodal marginal zone lymphoma (+/− monocytoid B-cells), Extranodal marginal zone B-cell lymphoma of mucosa-associated lymphoid tissue (MALT) type, T-cell lymphoma (e.g. cutaneous T-cell lymphoma, extranodal L-cell lymphoma, anaplastic large cell lymphoma, angioimmunoblastic T-cell lymphoma, mycosis fungoides), B-cell lymphoma, diffuse large B-cell lymphoma (DLBCL), Mediastinal large B-cell lymphoma, Intravascular large B-cell lymphoma, Primary effusion lymphoma, small non-cleaved cell lymphoma, or Burkitt's lymphoma), multiple myeloma, plasmacytoma, and leukemia (e.g. acute lymphocytic leukemia (ALL), T-cell acute lymphoblastic leukemia (T-ALL), B-cell acute lymphoblastic leukemia (B-ALL), B-cell prolymphocytic leukemia, acute myeloid leukemia (AML), chronic lymphocytic leukemia (CLL), juvenile myelomonocytic leukemia (JMML), minimal residual disease (MRD), hairy cell leukemia, myelofibrosis (e.g. primary or secondary myelofibrosis), or chronic myeloid leukemia (CML), myelodysplastic syndrome (MDS), myeloproliferative disease (MPD), Waldestrom's macroglobulinemia (WM), polycythemia vera, essential thrombocythemia, pancreatic cancer, urological cancer, bladder cancer, colorectal cancer, colon cancer, breast cancer, prostate cancer, renal cancer, hepatocellular cancer, thyroid cancer, gall bladder cancer, lung cancer (e.g. non-small cell lung cancer, small-cell lung cancer), ovarian cancer, cervical cancer, gastric cancer, endometrial cancer, esophageal cancer, head and neck cancer, melanoma, neuroendocrine cancer, CNS cancer, brain tumors (e.g., glioma, anaplastic oligodendroglioma, adult glioblastoma multiforme, and adult anaplastic astrocytoma), bone cancer, soft tissue sarcoma, retinoblastomas, neuroblastomas, peritoneal effusions, malignant pleural effusions, mesotheliomas, Wilms tumors, trophoblastic neoplasms, hemangiopericytomas, Kaposi's sarcomas, myxoid carcinoma, round cell carcinoma, squamous cell carcinomas, esophageal squamous cell carcinomas, oral carcinomas, cancers of the adrenal cortex, ACTH-producing tumors, systemic lupus erythematosus (SLE), myestenia gravis, Goodpasture's syndrome, glomerulonephritis, hemorrhage, pulmonary hemorrhage, atherosclerosis, rheumatoid arthritis (RA), psoriatic arthritis, monoarticular arthritis, osteoarthritis, gouty arthritis, spondylitis, Behçet disease, autoimmune thyroiditis, Reynaud's syndrome, acute disseminated encephalomyelitis, chronic idiopathic thrombocytopenic pulpura, multiple sclerosis (MS), Sjögren's syndrome, autoimmune hemolytic anemia, tissue graft rejection, hyperacute rejection of transplanted organs, allograft rejection, graft-versus-host disease, diseases involving leukocyte diapedesis, disease states due to leukocyte dyscrasia and metastasis, granulocyte transfusion-associated syndromes, cytokine-induced toxicity, scleroderma, vasculitis, asthma, psoriasis, inflammatory bowel disease (e.g., chronic inflammatory bowel disease, ulcerative colitis, Crohn's disease, necrotizing enterocolitis), irritable bowel syndrome, dermatomyositis, Addison's disease, Parkinson's disease, Alzheimer's disease, diabetes, type I diabetes mellitus, sepsis, septic shock, endotoxic shock, gram negative sepsis, gram positive sepsis, and toxic shock syndrome, multiple organ injury syndrome secondary to septicemia, trauma, hypovolemic shock, allergic conjunctivitis, vernal conjunctivitis, and thyroid-associated ophthalmopathy, eosinophilic granuloma, eczema, chronic bronchitis, acute respiratory distress syndrome, allergic rhinitis, coryza, hay fever, bronchial asthma, silicosis, pulmonary sarcoidosis, pleurisy, alveolitis, emphysema, pneumonia, bacterial pneumonia, bronchiectasis, and pulmonary oxygen toxicity, reperfusion injury of the myocardium, brain, or extremities, thermal injury, cystic fibrosis keloid formation or scar tissue formation, fever and myalgias due to infection, and brain or spinal cord injury due to minor trauma, diseases involving leukocyte diapedesis, acute hypersensitivity, delayed hypersensitivity, articaria, food allergies, skin sunburn, inflammatory pelvic disease, urethritis, uveitis, sinusitis, pneumonitis, encephalitis, meningitis, myocarditis, nephritis, osteomyelitis, myositis, hepatitis, hepatitis, alcoholic hepatitis, gastritis, enteritis, contact dermatitis, atopic dermatitis, gingivitis, appendicitis, pancreatitis, cholocystitis, and polycystic kidney disease.

In some embodiments, provided is a method of treating a subject having an allergic disorder and/or an autoimmune and/or inflammatory disease, and/or an acute inflammatory reaction by administering an effective amount of a compound of Formula I, or a pharmaceutically acceptable salt thereof. In some embodiments, the disease is selected from the group consisting of systemic lupus erythematosus, myestenia gravis, Goodpasture's syndrome, glomerulonephritis, hemorrhage, pulmonary hemorrhage, atherosclerosis, rheumatoid arthritis, psoriatic arthritis, monoarticular arthritis, osteoarthritis, gouty arthritis, spondylitis, Behçcet disease, autoimmune thyroiditis, Reynaud's syndrome, acute disseminated encephalomyelitis, chronic idiopathic thrombocytopenic purpura, multiple sclerosis, Sjögren's syndrome, autoimmune hemolytic anemia, tissue graft rejection, hyperacute rejection of transplanted organs, allograft rejection, graft-versus-host disease, diseases involving leukocyte diapedesis, disease states due to leukocyte dyscrasia and metastasis, granulocyte transfusion-associated syndromes, cytokine-induced toxicity, scleroderma, vasculitis, asthma, psoriasis, chronic inflammatory bowel disease, ulcerative colitis, Crohn's disease, necrotizing enterocolitis, irritable bowel syndrome, dermatomyositis, Addison's disease, Parkinson's disease, Alzheimer's disease, diabetes, type I diabetes mellitus, sepsis, septic shock, endotoxic shock, gram negative sepsis, gram positive sepsis, and toxic shock syndrome, multiple organ injury syndrome secondary to septicemia, trauma, hypovolemic shock, allergic conjunctivitis, vernal conjunctivitis, and thyroid-associated ophthalmopathy, eosinophilic granuloma, eczema, chronic bronchitis, acute respiratory distress syndrome, allergic rhinitis, coryza, hay fever, bronchial asthma, silicosis, pulmonary sarcoidosis, pleurisy, alveolitis, emphysema, pneumonia, bacterial pneumonia, bronchiectasis, and pulmonary oxygen toxicity, reperfusion injury of the myocardium, brain, or extremities, thermal injury, cystic fibrosis, keloid formation or scar tissue formation, fever and myalgias due to infection, and brain or spinal cord injury due to minor trauma, diseases involving leukocyte diapedesis, acute hypersensitivity, delayed hypersensitivity, urticaria, food allergies, skin sunburn, inflammatory pelvic disease, urethritis, uveitis, sinusitis, pneumonitis, encephalitis, meningitis, myocarditis, nephritis, osteomyelitis, myositis, hepatitis, alcoholic hepatitis, gastritis, enteritis, contact dermatitis, atopic dermatitis, gingivitis, appendicitis, pancreatitis, cholocystitis, and polycystic kidney disease.

In some embodiments, provided is a method of treating a subject having an autoimmune disease selected from the group consisting of a systemic lupus erythematosus, myestenia gravis, rheumatoid arthritis, acute disseminated encephalomyelitis, idiopathic thrombocytopenic purpura, multiple sclerosis, Sjoegren's syndrome, psoriasis, autoimmune hemolytic anemia, asthma, ulcerative colitis, Crohn's disease, irritable bowel disease, and chronic obstructive pulmonary disease by administering an effective amount of a compound of Formula I, or a pharmaceutically acceptable salt thereof. In some embodiments, the autoimmune disease has excessive or destructive immune reactions, such as asthma, rheumatoid arthritis, multiple sclerosis, chronic obstructive pulmonary disease, or systemic lupus erythematosus.

In some embodiments, provided is a method of treating a subject having rheumatoid arthritis, by administering an effective amount of a compound of Formula I, or a pharmaceutically acceptable salt thereof.

Syk is a known inhibitor of apoptosis in lymphoma B-cells. Defective apoptosis contributes to the pathogenesis and drug resistance of human leukemias and lymphomas. Thus, further provided is a method of promoting or inducing apoptosis in cells expressing Syk comprising contacting the cell with a compound of Formula I, or a pharmaceutically acceptable salt thereof.

In some embodiments, provided is a method of treating a subject having cancer selected from the group consisting of carcinoma, sarcoma, melanoma, lymphoma and leukemia. In some embodiments the cancer is a solid tumor or a hematologic malignancy.

In some embodiments, provided is a method of treating a subject having a hematologic malignancy selected from the group consisting of small lymphocytic lymphoma, non- Hodgkin's lymphoma, indolent non-Hodgkin's lymphoma, refractory iNHL, mantle cell lymphoma, follicular lymphoma, lymphoplasmacytic lymphoma, marginal zone lymphoma, immunoblastic large cell lymphoma, lymnphoblastic lymphoma, Splenic marginal zone B-cell lymphoma (+/−villous lymphocytes), Nodal marginal zone lymphoma (+/−monocytoid B-cells), Extranodal marginal zone B-cell lymphoma of mucosa-associated lymphoid tissue type, cutaneous T-cell lymphoma, extranodal T-cell lymphoma, anaplastic large cell lymphoma, angioimmunoblastic T-cell lymphoma, mycosis fungoides, B-cell lymphoma, diffuse large B-cell lymphoma, Mediastinal large B-cell lymphoma, Intravascular large B-cell lymphoma, Primary effusion lymphoma, small non-cleaved cell lymphoma, Burkitt's lymphoma, multiple myeloma, plasmacytoma, acute lymphocytic leukemia, T-cell acute lymphoblastic leukemia, B-cell acute lymphoblastic leukemia, B-cell prolymphocytic leukemia, acute myeloid leukemia, chronic lymphocytic leukemia, juvenile myelomonocytic leukemia, minimal residual disease, hairy cell leukemia, primary myelofibrosis, secondary myelofibrosis, chronic myeloid leukemia, myelodysplastic syndrome, myeloproliferative disease, and Waldestrom's macroglobulinemia.

In some embodiments, provided is a method of treating a subject having cancer, wherein the cancer is leukemia or lymphoma, by administering an effective amount of a compound of Formula I, or a pharmaceutically acceptable salt thereof. In some embodiments, the cancer is selected from the group consisting of acute lymphocytic leukemia, acute myeloid leukemia, chronic lymphocytic leukemia, small lymphocytic lymphoma, myelodysplastic syndrome, myeloproliferative disease, chronic myeloid leukemia, multiple myeloma, indolent non-Hodgkin's lymphoma, refractory iNHL, non-Hodgkin's lymphoma, mantle cell lymphoma, follicular lymphoma, Waldestrom's macroglobulinemia, T-cell lymphoma, B-cell lymphoma, and diffuse large B-cell lymphoma. In one embodiment, the cancer is T-cell acute lymphoblastic leukemia, or B-cell acute lymphoblastic leukemia. The non-Hodgkin lymphoma encompasses the indolent B-cell diseases that include, for example, follicular lymphoma, lymphoplasmacytic lymphoma, Waldenstrom macroglobulinemia, and marginal zone lymphoma, as well as the aggressive lymphomas that include, for example, Burkitt's lymphoma, diffuse large B-cell lymphoma and mantle cell lymphoma. In one embodiment, the cancer is indolent non-Hodgkin's lymphoma.

In some embodiments, provided is a method of treating a subject having a hematologic malignancy by administering an effective amount of a compound of Formula I, or a pharmaceutically acceptable salt thereof. In specific embodiments, the hematologic malignancy is leukemia (e.g., chronic lymphocytic leukemia) or lymphoma (e.g., non-Hodgkin's lymphoma).

In some embodiments, provided is a method of treating a subject having chronic lymphocytic leukemia by administering an effective amount of a compound of Formula I, or a pharmaceutically acceptable salt thereof.

In some embodiments, provided is a method of treating a subject having a solid tumor by administering an effective amount of a compound of Formula I, or a pharmaceutically acceptable salt thereof. In some embodiments, the solid tumor is from a cancer selected from the group consisting of pancreatic cancer, urological cancer, bladder cancer, colorectal cancer, colon cancer, breast cancer, prostate cancer, renal cancer, hepatocellular cancer, thyroid cancer, gall bladder cancer, lung cancer (e.g. non-small cell lung cancer, small-cell lung cancer), ovarian cancer, cervical cancer, gastric cancer, endometrial cancer, esophageal cancer, head and neck cancer, melanoma, neuroendocrine cancer, CNS cancer, brain tumors (e.g., glioma, anaplastic oligodendroglioma, adult glioblastoma multiforme, and adult anaplastic astrocytoma), bone cancer, soft tissue sarcoma, retinoblastomas, neuroblastomas, peritoneal effusions, malignant pleural effusions, mesotheliomas, Wilms tumors, trophoblastic neoplasms, hemangiopericytomas, Kaposi's sarcomas, myxoid carcinoma, round cell carcinoma, squamous cell carcinomas, esophageal squamous cell carcinomas, oral carcinomas, cancers of the adrenal cortex, and ACTH-producing tumors. In some embodiments, the solid tumor is from non-small cell lung cancer, small-cell lung cancer, colon cancer, CNS cancer, melanoma, ovarian cancer, renal cancer, prostate cancer, and breast cancer.

Also provided herein is a compound as described herein, e.g. a compound of Formula I, or a pharmaceutically acceptable salt thereof, for use in the treatment of a disease or condition as described herein, e.g. a cancer (including carcinoma, sarcoma, melanoma, lymphoma and leukemia), an allergic disorder and/or an autoimmune and/or inflammatory disease, and/or a acute inflammatory reaction.

Also provided herein is a compound as described herein, e.g. a compound of Formula I, or a pharmaceutically acceptable salt thereof, for use in the manufacture of a medicament for the treatment of a disease or condition as described herein, e.g. a cancer (including carcinoma, sarcoma, melanoma, lymphoma and leukemia), an allergic disorder and/or an autoimmune and/or inflammatorydisease, and/or an acute inflammatory reaction.

Also provided herein are methods for using a compound of formula I, or a pharmaceutically acceptable salt thereof, to selectively or specifically inhibit Syk activity therapeutically or prophylactically, in combination with a vinca-alkaloid, or pharmaceutically acceptable salt thereof, to selectively or specifically inhibit tubulin or microtubule formation therapeutically or prophylactically. The method comprises administering a compound of formula I, or a pharmaceutically acceptable salt thereof, or a pharmaceutical composition thereof, in combination with a vinca-alkaloid, or a pharmaceutically acceptable salt thereof, to a subject (e.g., a human) in need thereof in an amount sufficient to inhibit Syk activity and/or inhibit tubulin or microtubule formation. The method can be employed to treat subjects (e.g., humans) suffering from, or subject to, a condition whose symptoms or pathology is mediated by Syk expression or activity.

"Treatment" or "treating" is an approach for obtaining beneficial or desired results including clinical results. Beneficial or desired clinical results may include one or more of the following:
  (i) decreasing one more symptoms resulting from the disease;
  (ii) diminishing the extent of the disease and/or stabilizing the disease (e.g., delaying the worsening of the disease);
  (iii) delaying the spread (e.g., metastasis) of the disease;
  (iv) delaying or slowing the recurrence of the disease and/or the progression of the disease;
  (v) ameliorating the disease state and/or providing a remission (whether partial or total) of the disease and/or decreasing the dose of one or more other medications required to treat the disease;
  (vi) increasing the quality of life, and/or
  (vii) prolonging survival.

"Delaying" the development of a disease or condition means to defer, hinder, slow, retard, stabilize, and/or postpone development of the disease or condition. This delay can be of varying lengths of time, depending on the history of the disease or condition, and/or subject being treated. A method that "delays" development of a disease or condition is a method that reduces probability of disease or condition development in a given time frame and/or reduces the extent of the disease or condition in a given time frame, when compared to not using the method. Such comparisons are typically based on clinical studies, using a statistically significant number of subjects. Disease or condition development can be detectable using standard methods, such as routine physical exams, mammography, imaging, or biopsy. Development may also refer to disease or condition progression that may be initially undetectable and includes occurrence, recurrence, and onset.

The compound of formula I, or a pharmaceutically acceptable salt thereof, in combination with a vinca alkaloid, or a pharmaceutically acceptable salt thereof, may, in some embodiments, be administered to a subject (e.g., a human) who is at risk or has a family history of the disease or condition.

The term "inhibition" indicates a decrease in the baseline activity of a biological activity or process. "Inhibition of activity of Syk activity" refers to a decrease in activity of Syk as a direct or indirect response to the presence of the compound of formula I, or a pharmaceutically acceptable salt thereof, relative to the activity of Syk in the absence of such compound or a pharmaceutically acceptable salt thereof. In some embodiments, the inhibition of Syk activity may be compared in the same subject prior to treatment, or other subjects not receiving the treatment. "Inhibition of activity of tubulin formation" refers to a decrease in tubulin formation as a direct or indirect response to the presence of a vinca-alkaloid, or a pharmaceutically acceptable salt thereof, relative to the activity of tubulin formation in the absence of such vinca-alkaloid or a pharmaceutically acceptable salt thereof. In some embodiments, the inhibition of tubulin formation may be compared in the same subject prior to treatment, or other subjects not receiving the treatment.

Diseases

In some embodiments, the compound of formula I, or a pharmaceutically acceptable salt thereof, or a pharmaceutical composition thereof, in combination with a vinca-alkaloid, or a pharmaceutically acceptable salt thereof, is used in the treatment of cancer. In certain embodiments, the compound of formula I, or a pharmaceutically acceptable salt thereof, in combination with a vinca-alkaloid, or a pharmaceutically acceptable salt thereof, is used in the treatment of a hematologic malignancy. In some embodiments, the compound of formula I, or a pharmaceutically acceptable salt thereof, in combination with a vinca-alkaloid, or a pharmaceutically acceptable salt thereof, inhibits the growth or proliferation of cancer cells of hematopoietic origin. In some embodiments, the cancer cells are of lymphoid origin, and in certain embodiments, the cancer cells are related to or derived from B lymphocytes or B lymphocyte progenitors.

Hematologic malignancies amenable to treatment using the method disclosed in the present disclosure include, without limitation, lymphomas (e.g., malignant neoplasms of lymphoid and reticuloendothelial tissues, such as Burkitt's lymphoma, Hodgkins' lymphoma, non-Hodgkins' lymphomas, lymphocytic lymphomas); multiple myelomas; leukemias (e.g., lymphocytic leukemias, chronic myeloid (myelogenous) leukemias). Other cancer cells, of hematopoietic origin or otherwise, that express Syk also can be treated by administration of the polymorphs and compositions thereof described herein.

In particular embodiments, the hematologic malignancy is leukemia or lymphoma. In certain embodiments, the hematologic malignancy is acute lymphocytic leukemia (ALL), acute myeloid leukemia (AML), chronic lymphocytic leukemia (CLL), small lymphocytic lymphoma (SLL), myelodysplastic syndrome (MDS), myeloproliferative disease (MPD), chronic myeloid leukemia (CML), multiple myeloma (MM), non-Hodgkin's lymphoma (NHL), indolent non-Hodgkin's lymphoma (iNL), refractory iNHL, mantle cell lymphoma (MCL), follicular lymphoma (FL), Waldestrom's macroglobulinemia (WM), T-cell lymphoma, B-cell lymphoma, diffuse large B-cell lymphoma (DLBCL), lymphoplasmacytic lymphoma (LPL), and marginal zone lymphoma (MZL).

In one embodiment, the cancer is T-cell acute lymphoblastic leukemia (T-ALL), or B-cell acute lymphoblastic leukemia (B-ALL). In another embodiment, the cancer is chronic lymphocytic leukemia (CLL). In yet another embodiment, the cancer is non-Hodgkin's lymphoma (NHL). In one embodiment, the NHL is diffuse large B-cell lymphoma (DLBCL), mantle cell lymphoma (MCL), follicular lymphoma (FL), small lymphocytic lymphoma (SLL), lymphoplasmacytic lymphoma (LPL), and marginal zone lymphoma (MZL). In one embodiment, the cancer is indolent non-Hodgkin's lymphoma (iNHL).

In some embodiments, the compound of formula I, or a pharmaceutically acceptable salt thereof, or a pharmaceutical composition thereof, in combination with a vinca-alkaloid, or a pharmaceutically acceptable salt thereof, is used in the treatment of a solid tumor cancer. In certain embodiments, the compound of formula I, or a pharmaceutically acceptable salt thereof, in combination with a vinca-alkaloid, or a pharmaceutically acceptable salt thereof, is used in the treatment of certain solid tumor cancers, such as pancreatic cancer, lung cancer, colon cancer, colo-rectal cancer, breast cancer, esophageal cancer, adenocarcinoma, hepatocellular cancer. In certain embodiments, the compound of formula I, or a pharmaceutically acceptable salt thereof, in combination with a vinca-alkaloid, or a pharmaceutically acceptable salt thereof, is used in the treatment of certain solid tumor cancers which have an expression of Syk activity or in which Syk is expressed. Other solid tumor cancer cells that express Syk also can be treated by administration of the polymorphs and compositions thereof described herein.

In yet another aspect, provided are methods of treating a subject (e.g., a human) having a Syk-mediated disorder by administering a compound of formula I, or a pharmaceutically acceptable salt thereof, or a pharmaceutical composition thereof, in combination with a vinca-alkaloid, or a pharmaceutically acceptable salt thereof, to the subject. Provided are also methods of modulating Syk in a subject (e.g., a human) by administering a compound of formula I, or a pharmaceutically acceptable salt thereof, or a pharmaceutical composition thereof, in combination with a vinca-alkaloid, or a pharmaceutically acceptable salt thereof to the subject.

In any of the methods described herein, the compound of formula I, or a pharmaceutically acceptable salt thereof, may be administered to the individual as a unit dosage, for example in the form of a tablet. In any of the methods described herein, the vinca-alkaloid, or a pharmaceutically acceptable salt thereof, may be administered to the individual via IV (intravenous) delivery.

Any of the methods of treatment provided herein may be used to treat cancer at an advanced stage. Any of the methods of treatment provided herein may be used to treat cancer at locally advanced stage. Any of the methods of treatment provided herein may be used to treat early stage cancer. Any of the methods of treatment provided herein may be used to treat cancer in remission. In some of the embodiments of any of the methods of treatment provided herein, the cancer has reoccurred after remission. In some embodiments of any of the methods of treatment provided herein, the cancer is progressive cancer.

Subjects

Any of the methods of treatment provided may be used to treat a subject who has been diagnosed with or is suspected of having an allergic disorder and/or an autoimmune and/or inflammatory disease, and/or an acute inflammatory reaction or a cancer.

In some of the embodiments of any of the methods provided herein, the subject is a human who is at risk of developing a cancer (e.g., a human who is genetically or otherwise predisposed to developing a cancer) and who has or has not been diagnosed with the cancer. As used herein, an "at risk" subject is a subject who is at risk of developing cancer (e.g., a hematologic malignancy). The subject may or may not have detectable disease, and may or may not have displayed detectable disease prior to the treatment methods described herein. An at risk subject may have one or more so-called risk factors, which are measurable parameters that correlate with development of cancer, such as described herein. A subject having one or more of these risk factors has a higher probability of developing cancer than an individual without these risk factor(s).

These risk factors may include, for example, age, sex, race, diet, history of previous disease, presence of precursor disease, genetic (e.g., hereditary) considerations, and environmental exposure. In some embodiments, a subject at risk for cancer includes, for example, a subject whose relatives have experienced this disease, and those whose risk is determined by analysis of genetic or biochemical markers. Prior history of having cancer may also be a risk factor for instances of cancer recurrence.

Provided herein are also methods for treating a subject (e.g., a human) who exhibits one or more symptoms associated with cancer (e.g., a hematologic malignancy). In some embodiments, the subject is at an early stage of cancer. In other embodiments, the subject is at an advanced stage of cancer.

Provided herein are also methods for treating a subject (e.g., a human) who is undergoing one or more standard therapies for treating cancer (e.g., a hematologic malignancy), such as chemotherapy, radiotherapy, immunotherapy, and/or surgery. Thus, in some foregoing embodiments, the compound of Formula I, or a pharmaceutically acceptable salt thereof, administered before, during, or after administration of chemotherapy, radiotherapy, immunotherapy, and/or surgery.

In another aspect, provided herein are methods for treating a subject (e.g., a human) who is "refractory" to a cancer treatment or who is in "relapse" after treatment for cancer (e.g., a hematologic malignancy). A subject "refractory" to an anti-cancer therapy means they do not respond to the particular treatment, also referred to as resistant. The cancer may be resistant to treatment from the beginning of treatment, or may become resistant during the course of treatment, for example after the treatment has shown some effect on the cancer, but not enough to be considered a remission or partial remission. A subject in "relapse" means that the cancer has returned or the signs and symptoms of cancer have returned after a period of improvement, e.g. after a treatment has shown effective reduction in the cancer, such as after a subject is in remission or partial remission.

In some embodiments, the subject may be a human who is (i) refractory to at least one anti-cancer therapy, or (ii) in relapse after treatment with at least one anti-cancer therapy, or both (i) and (ii). In some of embodiments, the subject is refractory to at least two, at least three, or at least four anti-cancer therapy (including, for example, standard or experimental chemotherapies).

In some embodiments, the subject is refractory to at least one, at least two, at least three, or at least four anti-cancer therapy (including, for example, standard or experimental chemotherapy) selected from fludarabine, rituximab, obinutuzumab, alkylating agents, alemtuzumab and other chemotherapy treatments such as CHOP (cyclophosphamide, doxorubicin, vincristine, prednisone); R-CHOP (rituximab-CHOP); hyperCVAD (hyperfractionated cyclophosphamide, vincristine, doxorabicin, dexamethasone, methotrexate, cytarabine); R-hyperCVAD (rituximab-hyperCVAD); FCM (fludarabine, cyclophosphamide, mitoxantrone); R-FCM (rituximab, fludarabine, cyclophosphamide, mitoxantrone); bortezomib and rituximab; temsirolimus and rituximab; temsirolimus and Velcade®; Iodine-131 tositumomab (Bexxar®) and CHOP; CVP (cyclophosphamide, vincristine, prednisone); R-CVP (rituximab-CVP); ICE (iphosphamide, carboplatin, etoposide); R-ICE (rituximab-ICE); FCR (fludarabine, cyclophosphamide, rituximab); FR (fludarabine, rituximab); and D.T. PACE (dexamethasone, thalidomide, cisplatin, Adriamycin®, cyclophosphamide, etoposide).

Other examples of chemotherapy treatments (including standard or experimental chemotherapies) are described below. In addition, treatment of certain lymphomas is reviewed in Cheson, B. D., Leonard, J. P., "Monoclonal Antibody Therapy for B-Cell Non-Hodgkin's Lymphoma" *The New England Journal of Medicine* 2008, 359(6), p. 613-626; and Wierda, W. G., "Current and Investigational Therapies for Patients with CLL" *Hematology* 2006, p. 285-294. Lymphoma incidence patterns in the United States is profiled in Morton, L. M., et at "Lymphoma Incidence Patterns by WHO Subtype in the United States, 1992-2001" *Blood* 2006, 107(1), p. 265-276.

For example, treatment of non-Hodgkin's lymphomas (NHL), especially of B-cell origin, include the use of monoclonal antibodies, standard chemotherapy approaches (e.g., CHOP, CVP, FCM, MCP, and the like), radioimmunotherapy, and combinations thereof, especially integration of an antibody therapy with chemotherapy. Examples of unconjugated monoclonal antibodies for Non-Hodgkin's lymphoma/B-cell cancers include rituximab, alemtuzumab, human or humanized anti-CD20 antibodies, lumiliximab, anti-TRAIL, bevacizumab, galiximab, epratuzumab, SGN-40, and anti-CD74, Examples of experimental antibody agents used in treatment of Non-Hodgkin's lymphoma/B-cell cancers include of atumumab, ha20, PRO131921, alemtuzumab, galiximab, SGN-40, CHIR-12.12, epratuzumab, lumiliximab, apolizumab, milatuzumab, and bevacizumab. Examples of standard regimens of chemotherapy for Non-Hodgkin's lymphoma B-cell cancers include CHOP (cyclophosphamide, doxorubicin, vincristine, prednisone), FCM (fludarabine, cyclophosphamide, mitoxantrone), CVP (cyclophosphamide, vincristine and prednisone), MCP (mitoxantrone, chlorambucil, and prednisolone), R-CHOP (rituximab plus CHOP), R-FCM (rituximab plus FCM), R-CVP (rituximab plus CVP), and R-MCP (R-MCP). Examples of radioimmunotherapy for Non-Hodgkin's lymphoma/B-cell cancers include yttrium-90-labeled ibritumomanab tiuxetan, and iodine-131-labeled tositumomab.

In another example, therapeutic treatments for mantle cell lymphoma (MCL) include combination chemotherapies such as CHOP (cyclophosphamide, doxorubicin, vincristine, prednisone), hyperCVAD (hyperfractionated cyclophosphamide, vincristine, doxorubicin, dexamethasone, methotrexate, cytarabine) and FCM (fludarabine, cyclophosphamide, mitoxantrone). In addition, these regimens can be supplemented with the monoclonal antibody rituximab (Rituxan) to form combination therapies R-CHOP, hyperCVAD-R, and R-FCM. Other approaches include combining any of the abovementioned therapies with stem cell transplantation or treatment with ICE (iphosphamide, carboplatin and etoposide). Other approaches to treating mantle cell lymphoma includes immunotherapy such as using monoclonal antibodies like Rituximab (Rituxan). Rituximab can be used for treating indolent B-cell cancers, including marginal-zone lymphoma, WM, CLL and small lymphocytic lymphoma. A combination of Rituximab and chemotherapy agents is especially effective. A modified approach is radioimmunotherapy, wherein a monoclonal antibody is combined with a radioisotope particle, such as Iodine-131 tositumomab (Bexxar®) and Yttrium-90 ibritumomab tiuxetan (Zevalin®). In another example, Bexxar® is used in sequential treatment with CHOP. Another immunotherapy example includes using cancer vaccines, which is based upon the genetic makeup of an individual subject's tumor. A lymphoma vaccine example is GTOP-99 (MyVax®). Yet other approaches to treating mantle cell lymphoma includes autologous stem cell transplantation coupled with high-dose chemotherapy, or treating mantle cell lymphoma includes administering proteasome inhibitors, such as Velcade® (bortezomib or PS-341), or antiangiogenesis agents, such as thalidomide, especially in combination with Rituxan. Another treatment approach is administering drugs that lead to the degradation of Bcl-2 protein and increase cancer cell sensitivity to chemotherapy, such as oblimersen (Genasense) in combination with other chemotherapeutic agents. Another treatment approach includes administering mTOR inhibitors, which can lead to inhibition of cell growth and even cell death; a non-limiting example is Temsirolimus (CCI-779), and Temsirolimus in combination with Rituxan®, Velcade® or other chemotherapeutic agents.

Other recent therapies for MCL have been disclosed (*Nature Reviews*; Jares, P. 2007). Such examples include Flavopiridol, PD0332991, R-roscovitine (Selicilib, CYC202), Styryl sulphones, Obatoclax (GX15-070), TRAIL, Anti-TRAIL DR4 and DR5 antibodies, Temsirolimus (CCI-779), Everolimus (RAD001), BMS-345541, Curcumin, Vorinostat (SAHA), Thalidomide, lenalidomide (Revlimid®, CC-5013), and Geldanamycin (17-AAG).

Examples of other therapeutic agents used to treat Waldenstrom's Macroglobulinemia (WM) include perifosine, bortezomib (Velcade®), rituximab, sildenafil citrate (Viagra®), CC-5103, thalidomide, epratuzumab (hLL2-anti-CD22 humanized antibody), simvastatin, enzastaurin, campath-1H, dexamethasone, DT PACE, oblimersen, antineoplaston A10, antineoplaston AS2-1, alemtuzumab, beta alethine, cyclophosphamide, doxorubicin hydrochloride, prednisone, vincristine sulfate, fludarabine, filgrastim, melphalan, recombinant interferon alfa, carmustine, cisplatin, cyclophosphamide, cytarabine, etoposide, melphalan, dolastatin 10, indium In 111 monoclonal antibody MN-14, yttrium Y 90 humanized epratuzumab, anti-thymocyte globulin, busulfan, cyclosporine, methotrexate, mycophenolate mofetil, therapeutic allogeneic lymphocytes, Yttrium Y 90 ibritumomab tiuxetan, sirolimus, tacrolimus, carboplatin, thiotepa, paclitaxel, aldesleukin, recombinant interferon alfa, docetaxel, ifosfamide, mesna, recombinant interleukin-12, recombinant interleukin-11, Bcl-2 family protein inhibitor ABT-263, denileukin diftitox, tanespimycin, everolimus, pegfilgrastim, vorinostat, alvocidib, recombinant flt3 ligand, recombinant human thrombopoietin, lymphokine-activated killer cells, amifostine trihydrate, aminocamptothecin, irinotecan hydrochloride, caspofungin acetate, clofarabine, epoetin alfa, nelarabine, pentostatin, sargramostim, vinorelbine ditartrate, WT-1 analog peptide vaccine, WT1 126-134 peptide vaccine, fenretinide, ixabepilone, oxaliplatin, monoclonal antibody CD19, monoclonal antibody CD20, omega-3 fatty acids, mitoxantrone hydrochloride, octreotide acetate, tositumomab and iodine I-131 tositumomab, motexafin gadolinixum, arsenic trioxide, tipifarnib, autologous human tumor-derived HSPPC-96, veltuzumab, bryostatin 1, and PEGylated liposomal doxorubicin hydrochloride, and any combination thereof.

Examples of therapeutic procedures used to treat WM include peripheral blood stem cell transplantation, autologous hematopoietic stem cell transplantation, autologous bone marrow transplantation, antibody therapy, biological therapy, enzyme inhibitor therapy, total body irradiation, infusion of stem cells, bone marrow ablation with stem cell support, in vitro-treated peripheral blood stem cell transplantation, umbilical cord blood transplantation, immunoenzyme technique, pharmacological study, low-LET cobalt-60 gamma ray therapy, bleomycin, conventional surgery, radiation therapy, and nonmyeloablative allogeneic hematopoietic stem cell transplantation.

Examples of other therapeutic agents used to treat diffuse large B-cell lymphoma (DLBCL) drug therapies (*Blood* 2005 Abramson, J.) include cyclophosphamide, doxorubicin, vincristine, prednisone, anti-CD20 monoclonal antibodies, etoposide, bleomycin, many of the agents listed for Waldenstrom's, and any combination thereof, such as ICE and R-ICE.

Examples of other therapeutic agents used to treat chronic lymphocytic leukemia (CLL) (Spectrum, 2006, Fernandes, D.) include Chlorambucil (Leukeran), Cyclophosphamide (Cyloxan, Endoxan, Endoxana, Cyclostin), Fludarabine (Fludara), Pentstatin (Nipent), Cladribine (Leustarin), Doxorubicin (Adriamycin®, Adriblastine), Vincristine (Oncovin), Prednisone, Prednisolone, Alemtuzumab (Campath, MabCampath), many of the agents listed for Waldenstrom's, and combination chemotherapy and chemoimmunotherapy, including the common combination regimen: CVP (cyclophosphamide, vincristine, prednisone); R-CVP (rituximab-CVP); ICE (iphosphamide, carboplatin, etoposide); R-ICE (rituximab-ICE); FCR (fludarabine, cyclophosphamide, rituximab); and FR (fludarabine, rituximab).

In another aspect, provided is a method of sensitizing a subject (e.g., a human) who is (i) refractory to at least one chemotherapy treatment, or (ii) in relapse after treatment with chemotherapy, or both (i) and (ii), wherein the method comprises administering a compound of Formula I, or a pharmaceutically acceptable salt thereof, or a pharmaceutical composition thereof, to the subject. A subject who is sensitized is a subject who is responsive to the treatment involving administration of the compound of Formula I, or a pharmaceutically acceptable salt thereof, or who has not developed resistance to such treatment.

In another aspect, provided herein are methods for treating a subject (e.g., a human) for a cancer, with comorbidity, wherein the treatment is also effective in treating the comorbidity. A "comorbidity" to cancer is a disease that occurs at the same time as the cancer.

In some embodiments, provided herein are methods for treating a subject (e.g., a human) for chronic lymphocytic leukemia (CLL), with comorbidity, wherein the treatment is also effective in treating the comorbidity. Many subjects with CLL will have one or more other diseases, for example diseases affecting the blood pressure system, vascular and heart systems, endocrine and metabolic systems, genitourinary system, musculoskeletal system, respiratory system, neurological system, upper and lower gastrointestinal systems, psychiatric system, ear, nose and throat systems, renal system, or liver system, Specific morbidities of CLL include, but are not limited to, one or more other cancers (e.g. breast, head and neck, lung, melanoma, non-Hodgkin's T-cell lymphoma, prostate, colon, small intestine, gynecologic and urinary tract), hypertension, hyperlipidemia, coronary artery disease, peripheral vascular diseases, cardiomyopathy, vulvular heart disease, atrial fibrillation, cerebrovascular disease (e.g. transient ischemic attack, stroke), chronic obstructive pulmonary disease, joint disease, peptic ulcer, inflammatory bowel disease, psychiatric illness, thyroid disease, benign prostate hyperplasia, diabetes mellitus, and osteoarthritis (Satram-Hoang et al., *Journal of Cancer Therapy*, 2013; 4:1321-1.329; Thurmes et al., *Leukemia & Lymphoma*, 2008; 49(1):49-56).

In some embodiments, a method of treating a comorbidity of CLL in a subject (e.g., a human), wherein the method comprises administering a compound of Formula I, or a pharmaceutically acceptable salt thereof, or a pharmaceutical composition thereof, to the subject. In some embodiments, the comorbidity is selected from the group consisting of one or more other cancers (e.g. breast, head and neck, lung, melanoma, non-Hodgkin's T-cell lymphoma, prostate, colon, small intestine, gynecologic and urinary tract), hypertension, hyperlipidemia, coronary artery disease, peripheral vascular diseases, cardiomyopathy, vulvular heart disease, atrial fibrillation, cerebrovascular disease (e.g. transient ischemic attack, stroke), chronic obstructive pulmonary disease, joint disease, peptic ulcer, inflammatory bowel disease, psychiatric illness, thyroid disease, benign prostate hyperplasia, diabetes mellitus, and osteoarthritis.

Monotherapy and Combination Therapies

Also provided are methods of treatment in which a compound of Formula I, or a pharmaceutically acceptable salt thereof, is the only active agent given to a subject and also includes methods of treatment in which a compound of Formula I, or a pharmaceutically acceptable salt thereof, is given to a subject in combination with one or more additional active agents. Both monotherapy and combination therapies are intended and described for use in the methods detailed herein, such as in a method of treating any of the diseases or conditions detailed herein and for use with any subject detailed herein.

Monotherapy

In some embodiments, a method of treating cancer, an allergic disorder and/or an autoimmune and/or inflammatory disease, and/or an acute inflammatory reaction comprises administering to a subject in need thereof an effective amount of a compound of Formula I, or a pharmaceutically acceptable salt thereof, wherein the subject is not undergoing therapy for the same disease or condition with another agent or procedure.

In some embodiments where the compound of Formula I, or a pharmaceutically acceptable salt thereof, is administered as a monotherapy to the subject who has been diagnosed with or is suspected of having a cancer, the subject may be a human who is (i) refractory to at least one anti-cancer therapy, or (ii) in relapse after treatment with at least one anti-cancer therapy, or both (i) and (ii). In some of embodiments, the subject is refractory to at least two, at least three, or at least four anti-cancer therapy (including, for example, standard or experimental chemotherapies). For example, in some embodiments, the subject may be a human who is (i) refractory to a therapy using an anti-CD20 antibody, an alkylating agent (e.g., bendamustine), a purine analog (e.g., fludarabine), an anthracycline, or any combination thereof; (ii) in relapse after treatment with an anti-CD20 antibody, an alkylating agent (e.g., bendamustine), a purine analog (e.g., fludarabine), an anthracycline, or any combination thereof, or both (i) and (ii).

A human subject who is refractory to at least one anti-cancer therapy and/or is in relapse after treatment with at least one anti-cancer therapy, as described above, may have undergone one or more prior therapies. In some embodiments, such subjects have undergone one, two, three, or four, or at least one, at least two, at least three, at least four, or at least five, or between one and ten, between one and nine, between one and eight, between one and seven, between one and six, between one and five, or between one and four, anti-cancer therapies prior to treatment using the methods described herein (e.g., prior to the administration of the compound of Formula I, or a pharmaceutically acceptable salt thereof, as a monotherapy).

It should be understood that when a subject (e.g. a human) is treated with the compound of Formula I, or a pharmaceutically acceptable salt thereof, as a monotherapy, the subject may also undergo one or more other therapies that are not anti-cancer therapies.

In some embodiments, a method of treating a comorbidity of a cancer, including but not limited to CLL, in a subject (e.g., a human) who has been diagnosed with cancer, e.g. CLL, wherein the method comprises administering a therapy to treat the comorbidity in combination with a compound of Formula I, or a pharmaceutically acceptable salt thereof, or a pharmaceutical composition thereof, to the subject. In some embodiments, the comorbidity is selected from the group consisting of one or more other cancers (e.g. breast, head and neck, lung, melanoma, non-Hodgkin's T-cell lymphoma, prostate, colon, small intestine, gynecologic and urinary tract), hypertension, hyperlipidemia, coronary artery disease, peripheral vascular diseases, cardiomyopathy, vulvular heart disease, atria fibrillation, cerebrovascular disease (e.g. transient ischemic attack, stroke), chronic obstructive pulmonary disease, joint disease, peptic ulcer, inflammatory bowel disease, psychiatric illness, thyroid disease, benign prostate hyperplasia, diabetes mellitus, and osteoarthritis.

Combination Therapies

In some embodiments, a method of treating cancer, an allergic disorder and/or an autoimmune and/or inflammatory disease, and/or an acute inflammatory reaction comprises administering to a subject in need thereof an effective amount of a compound of Formula I, or a pharmaceutically acceptable salt thereof, together with a second active agent, which can be useful for treating a cancer, an allergic disorder and/or an autoimmune and/or inflammatory disease, and/or an acute inflammatory reaction. For example the second agent may be an anti-inflammatory agent. Treatment with the second active agent may be prior to, concomitant with, or following treatment with a compound of Formula I, or a pharmaceutically acceptable salt thereof. In some embodiments, a compound of Formula I, or a pharmaceutically acceptable salt thereof is combined with another active agent in a single dosage form.

Provided herein are also methods of treatment in which the compound of Formula I, or a pharmaceutically acceptable salt thereof, administered to a subject (e.g., a human) who has been diagnosed with or is suspected of having a cancer is given to the subject in combination with one or more additional therapies, including one or more of the anti-cancer therapies described above. Thus, in some embodiments, the method for treating cancer in a subject (e.g., a human) in need thereof, comprises administering to the subject a therapeutically effective amount of a compound of Formula I, or a pharmaceutically acceptable salt thereof, or a pharmaceutical composition thereof, together with one or more additional therapies, which can be useful for treating the cancer. The one or more additional therapies may involve the administration of one or more therapeutic agents. Suitable anti-cancer therapeutics that may be used in combination with a compound of Formula I, or a pharmaceutically acceptable salt thereof include, but are not limited to, one or more agents selected from the group consisting of chemotherapeutic agents (e.g. mitomycin C, carboplatin, taxol, cisplatin, paclitaxel, etoposide, doxorubicin), radiotherapeutic antitumor agents, topoisomerase I inhibitors (e.g. camptothesin or topotecan), topoisomerase II inhibitors (e.g. daunomycin and etoposide), alkylating agents (e.g. cyclophosphamide, melphalan and BCNU), tubulin directed agents (e.g. taxol and vinblastine), PI3K inhibitors (e.g. compounds A, B, and C below), inhibitors of lysyl oxidase-like 2, and biological agents (e.g. antibodies such as anti CD20 antibody, IDEC 8, immunotoxins, and cytokines).

In some embodiments, the method for treating cancer in a subject (e.g., a human) in need thereof, comprises administering to the subject a therapeutically effective amount of a compound of Formula I, or a pharmaceutically acceptable salt thereof, or a pharmaceutical composition thereof with one or more additional therapies selected from the group consisting of fludarabine, rituximab, obinutuzumab, alemtuzumab, cyclophosphamide, chlorambucil, doxorubicin, doxorubicin hydrochloride, vincristine, vincristine sulfate, melphalan, busulfan, carmustine, prednisone, prednisolone, dexamethasone, methotrexate, cytarabine, mitoxantrone, mitoxantrone hydrochloride, bortezomib, temsirolimus, carboplatin, etoposide, thalidomide, cisplatin, lumiliximab, anti-TRAIL, bevacizumab, galiximab, epratazumab, SGN-40, anti-CD74, ofatumumab, ha20, PRO131921, CHIR-12.12, apolizumab, milatuazumab, bevacizumab, yttrium-90-labeled ibritumomab tiuxetan, tositumomab, iodine-131 tositumomab, iphosphamide, GTOP-99 vaccine, oblimersen, Flavopiridol, PD0332991, R-roscovitine, Styryl sulphones, Obatoclax, TRAIL, Anti-TRAIL DR4 and DR5 antibodies, Everolimus, BMS-345541, Curcumin, Vorinostat, lenalidomide, Geldanamycin, perifosine, sildenafil citrate, CC-5103, simvastatin, enzastaurin, campath-1H, DT PACE, antineoplaston A10, antieoplaston AS2-1, beta alethine, filgrastim, recombinant interferon alfa, dolastatin 10, indium In 111 monoclonal antibody MN-14, anti-thymocyte globulin, cyclosporine, mycophenolate mofetil, therapeutic allogeneic lymphocytes, tacrolimus, thiotepa, paclitaxel, aldesleukin, docetaxel, ifosfamide, mesna, recombinant interleukin-12, recombinant interleukin-11, ABT-263, denileukin diftitox, tanespimycin, everolimus, pegfilgrastim, vorinostat, alvocidib, recombinant flt3 ligand, recombinant human thrombopoietin, lymphokine-activated killer cells, amifostine trihydrate, aminocamptothecin, irinotecan hydrochloride, caspofungin acetate, clofarabine, epoetin alfa, nelarabine, pentostatin, sargramostim, vinorelbine ditartrate, WT-1 analog peptide vaccine, WT1 126-134 peptide vaccine, fenretinide, ixabepilone, oxaliplatin, monoclonal antibody CD19, monoclonal antibody CD20, omega-3 fatty acids, octreotide acetate, motexafin gadolinium, arsenic trioxide, tipifarnib, autologous human tumor-derived HSPPC-96, veltuzumab, bryostatin 1, PEGylated liposomal hydrochloride, peripheral blood stem cell transplantation, autologous hematopoietic stem cell transplantation, autologous bone marrow transplantation, infusion of stem cells, bone marrow ablation with stem cell support, in vitro treated peripheral blood stem cell transplantation, umbilical cord blood transplantation, low-LET cobalt-60 gamma ray therapy, bleomycin, conventional surgery, radiation therapy, and nonmyeloablative allogeneic hematopoietic stem cell transplantation.

In some embodiments, the one or more additional therapies involve the use of a phosphatidylinositol 3-kinase (PI3K) inhibitor, including for example, Compounds A, B or C, or a pharmaceutically acceptable salt of such compounds. The structures of Compounds A, B and C are provided below.

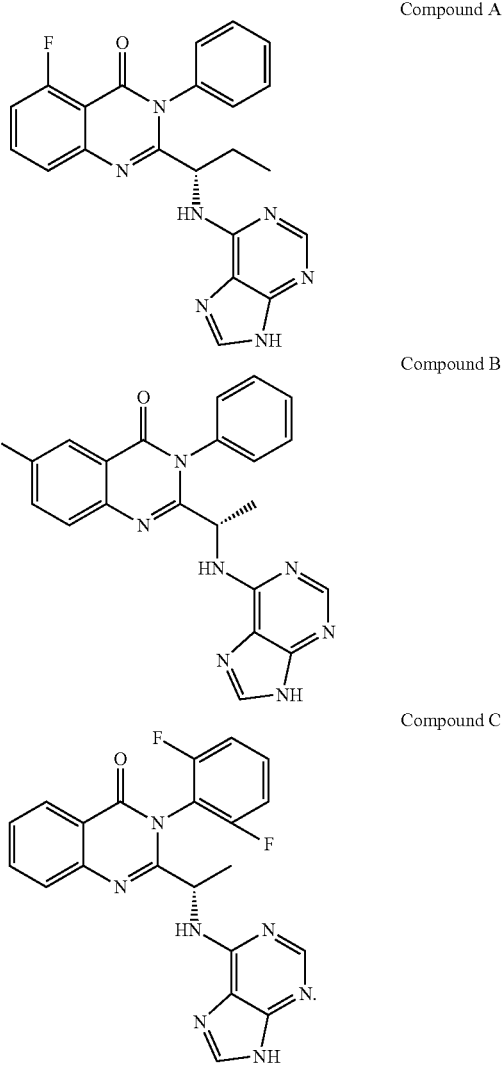

Compound A

Compound B

Compound C

In other embodiments of the methods described above involving the use of the compound of Formula I, or a pharmaceutically acceptable salt thereof, in combination with one or more additional therapies, the one or more additional therapies is other than a therapy using Compound A, Compound B, or Compound C, or a pharmaceutically acceptable salt of such compounds. In one embodiment of the methods described above involving the use of the compound of Formula I, or a pharmaceutically acceptable salt thereof, in combination with one or more additional therapies, the one or more additional therapies is other than a therapy using Compound A, or a pharmaceutically acceptable salt thereof. In another embodiment of the methods described above involving the use of the compound of Formula I, or a pharmaceutically acceptable salt thereof, in combination with one or more or more additional therapies, the one or more additional therapies is other than a therapy using Compound B, or a pharmaceutically acceptable salt thereof. In yet another embodiment of the methods described above involving the use of the compound of Formula I, or a pharmaceutically acceptable salt thereof, in combination with one or more additional therapies, the one or more additional therapies is other than a therapy using Compound C, or a pharmaceutically acceptable salt thereof.

In other embodiments, the one or more additional therapeutic agent may be an inhibitors of lysyl oxidase-like 2 (LOXL2) and a substance that bind to LOXL2, including for example, a humanized monoclonal antibody (mAb) with an immunoglobulin IgG4 isotype directed against human LOXL2.

The compound of Formula I, or a pharmaceutically acceptable salt thereof, can be useful as chemosensitizing agents, and, thus, can be useful in combination with other chemotherapeutic drugs, in particular, drugs that induce apoptosis.

A method for increasing sensitivity of cancer cells to chemotherapy, comprising administering to a subject (e.g., human) undergoing chemotherapy a chemotherapeutic agent together with a compound of Formula I, or a pharmaceutically acceptable salt thereof, or a pharmaceutical composition thereof, in an amount sufficient to increase the sensitivity of cancer cells to the chemotherapeutic agent is also provided herein. Examples of other chemotherapeutic drugs that can be used in combination with chemical entities described herein include topoisomerase I inhibitors (camptothesin or topotecan), topoisomerase II inhibitors (e.g. daunomycin and etoposide), alkylating agents (e.g. cyclophosphamide, melphalan and BCNU), tubulin directed agents (e.g. taxol and vinblastine), and biological agents (e.g. antibodies such as anti CD20 antibody, IDEC 8, immunotoxins, and cytokines). In one embodiment of the method for increasing sensitivity of cancer cells to chemotherapy, the chemotherapeutic agent is other than Compound A, or a pharmaceutically acceptable salt thereof in another embodiment of the method for increasing sensitivity of cancer cells to chemotherapy, the chemotherapeutic agent is other than Compound B, or a pharmaceutically acceptable salt thereof. In yet another embodiment of the method for increasing sensitivity of cancer cells to chemotherapy, the chemotherapeutic agent is other than Compound C, or a pharmaceutically acceptable salt thereof.

In some embodiments, the compound of Formula I, or a pharmaceutically acceptable salt thereof, or a pharmaceutical composition thereof, is used in combination with Rituxan® (Rituximab) or other agents that work by selectively depleting CD20+ B-cells.

Included herein are methods of treating cancer, an allergic disorder and/or an autoimmune and/or inflammatory disease, and/or an acute inflammatory reaction comprising administering to a subject in need thereof an effective amount of a compound of Formula I, or a pharmaceutically acceptable salt thereof, or a pharmaceutical composition thereof, in combination with an anti-inflammatory agent. Anti-inflammatory agents include but are not limited to NSAIDs, non-specific and COX-2 specific cyclooxgenase enzyme inhibitors, gold compounds, corticosteroids, methotrexate, tumor necrosis factor receptor (TNF) receptors antagonists, immunosuppressants and methotrexate. Examples of NSAIDs include, but are not limited to ibuprofen, flurbiprofen, naproxen and naproxen sodium, diclofenac, combinations of diclofenac sodium and misoprostol, sulindac, oxaprozin, diflunisal, piroxicam, indomethacin, etodolac, fenoprofen calcium, ketoprofen, sodium nabumetone, sulfasalazine, tolmetin sodium, and hydroxychloroquine. Examples of NSAIDs also include COX-2 specific inhibitors (i.e., a compound that inhibits COX-2 with an IC50 that is at least 50-fold lower than the IC50 for COX-1) such as celecoxib, valdecoxib, lumiracoxib, etoricoxib and/or rofecoxib.

In a further embodiment, the anti-inflammatory agent is a salicylate. Salicylates include but are not limited to acetylsalicylic acid or aspirin, sodium salicylate, and choline and magnesium salicylates. The anti-inflammatory agent may also be a corticosteroid. For example, the corticosteroid may be chosen from cortisone, dexamethasone, methylprednisolone, prednisolone, prednisolone sodium phosphate, and prednisone. In some embodiments, the anti-inflammatory therapeutic agent is a gold compound such as gold sodium thiomalate or auranofin. In some embodiments, the anti-inflammatory agent is a metabolic inhibitor such as a dihydrofolate reductase inhibitor, such as methotrexate or a dihydroorotate dehydrogenase inhibitor, such as leflunomide.

In some embodiments, combinations in which at least one anti-inflammatory compound is an anti-C5 monoclonal antibody (such as eculizumab or pexelizumab), a TNF antagonist, such as entanercept, or infliximab, which is an anti-TNF alpha monoclonal antibody are used.

In some embodiments, combinations in which at least one therapeutic agent is an immunosuppressant compound such as methotrexate, leflunomide, cyclosporine, tacrolimus, azathioprine, or mycophenolate mofetil are used.

Provided herein are also methods of treatment in which the compound of Formula I, or a pharmaceutically acceptable salt thereof, administered to a subject (e.g., a human) who has been diagnosed with or is suspected of having an autoimmune disease is given to the subject in combination with on one or more anti-inflammatory or immunosuppresant agents selected from the group consisting of ibuprofen, flurbiprofen, naproxen, naproxen sodium, diclofenac, diclofenac sodium, misoprostol, sulindac, oxaprozin, diflunisal, piroxicam, indomethacin, etodolac, fenoprofen calcium, ketoprofen, sodium nabumetone, sulfasalazine, tolmetin sodium, hydroxychloroquine, celecoxib, valdecoxib, lumiracoxib, etoricoxib, rofecoxib, acetylsalicylic acid, sodium salicylate, choline salicylate, magnesium salicylate, cortisone, dexamethasone, methylprednisolone, prednisolone, prednisolone sodium phosphate, prednisone, gold sodium thiomalate, auranofin, methotrexate, dihydroorotate leflunomide, leflunomide, cyclosporine, tacrolimus, azathioprine, mycophenolate mofetil, eculizumab, pexelizumab, entanercept, and infliximab.

Provided herein are methods of treatment in which the compound of formula I, or a pharmaceutically acceptable salt thereof, in combination with a vinca-alkaloid, or a pharmaceutically acceptable salt thereof, administered to a subject (e.g., a human) is the only anti-cancer therapy regimen administered to the subject. Provided herein are methods of treatment in which the compound of formula I, or a pharmaceutically acceptable salt thereof, in combination with a vinca-alkaloid, or a pharmaceutically acceptable salt thereof, administered to a subject (e.g., a human), wherein the subject is not undergoing any other anti-cancer treatments. In one variation, the subject is not undergoing any other anti-cancer treatments using one or more PI3K inhibitors. Such PI3K inhibitors may include, in certain embodiments, Compounds A, B and C, whose structures are provided below.

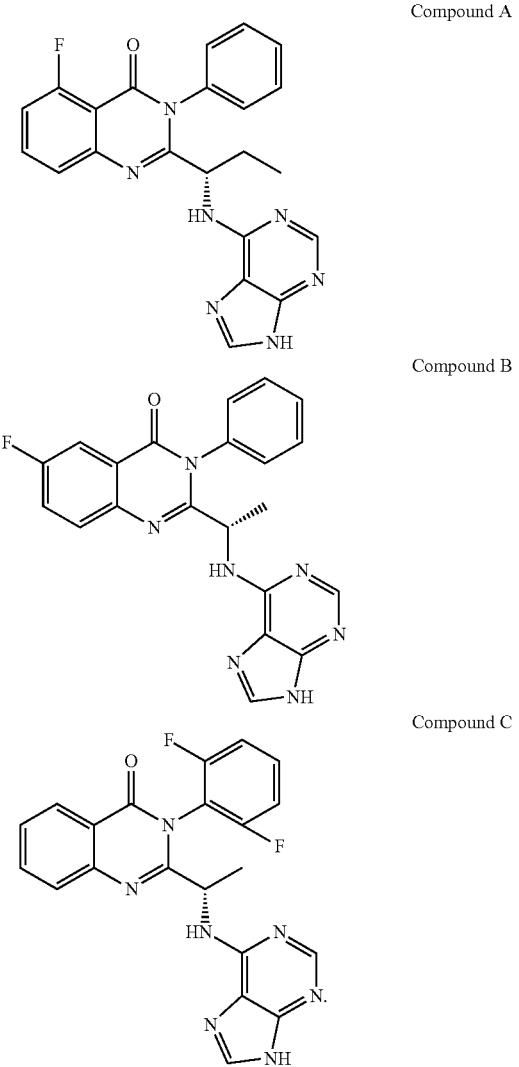

Compound A

Compound B

Compound C

In one variation, the subject is not undergoing any other anti-cancer treatments using Compound A, or a pharmaceutically acceptable salt thereof. In another variation, the subject is not undergoing any other anti-cancer treatments using Compound B, or a pharmaceutically acceptable salt thereof. In yet another variation, the subject is not undergoing any other anti-cancer treatments using Compound C, or a pharmaceutically acceptable salt thereof.

In some embodiments where the compound of formula I, or a pharmaceutically acceptable salt thereof, in combination with a vinca-alkaloid, or a pharmaceutically acceptable salt thereof is administered as a monotherapy treatment regimen to the subject, the subject may be a human who is (i) refractory to at least one anti-cancer therapy, or (ii) in relapse after treatment with at least one anti-cancer therapy, or both (i) and (ii). In some of embodiments, the subject is refractory to at least two, at least three, or at least four anti-cancer therapy (including, for example, standard or experimental chemotherapies).

It should be understood that when a subject (e.g. a human) is treated with the compound of Formula I, or a pharmaceutically acceptable salt thereof, in combination with a vinca-alkaloid, or a pharmaceutically acceptable salt thereof, as a monotherapy treatment regimen as described by this disclosure, the subject may also undergo one or more other therapies that are not anti-cancer therapies.

In some embodiments, there is provided a method for treating cancer in a subject in need thereof, comprising administering to the subject a therapeutically effective amount of a compound of formula I, or a pharmaceutically acceptable salt, and a therapeutically effective amount of a vinca-alkaloid, or a pharmaceutically acceptable salt, wherein: the vinca-alkaloid is selected from the group consisting of vincristine, vindesine, vinorelbine and vinblastine, and the subject is a human who is (i) refractory to at least one anti-cancer treatment, or (ii) in relapse after treatment with at least one anti-cancer therapy, or a combination thereof. In certain other embodiments, there is provided a method for treating cancer in a subject in need thereof, comprising administering to the subject a therapeutically effective amount of a compound of formula I, or a pharmaceutically acceptable salt, and a therapeutically effective amount of a vinca-alkaloid, or a pharmaceutically acceptable salt, wherein the vinca-alkaloid is selected from the group consisting of vincristine, vindesine, vinorelbine and vinblastine, and wherein further the subject is a human who is not undergoing any other anti-cancer treatments; and the subject is (i) refractory to at least one anti-cancer treatment, or (ii) in relapse after treatment with at least one anti-cancer therapy, or a combination thereof.

In some embodiments, there is provided a method for treating cancer in a subject in need thereof, comprising administering to the subject a therapeutically effective amount of a compound of Formula I, or a pharmaceutically acceptable salt, and a therapeutically effective amount of a vinca-alkaloid, or a pharmaceutically acceptable salt, wherein: the vinca-alkaloid is selected from the group consisting of vincristine and vinblastine, and the subject is a human who is (i) refractory to at least one anti-cancer treatment, or (ii) in relapse after treatment with at least one anti-cancer therapy, or a combination thereof. In certain other embodiments, there is provided a method for treating cancer in a subject in need thereof, comprising administering to the subject a therapeutically effective amount of a compound of formula I, or a pharmaceutically acceptable salt, and a therapeutically effective amount of a vinca-alkaloid, or a pharmaceutically acceptable salt, wherein the vinca-alkaloid is selected from the group consisting of vincristine and vinblastine, and wherein further the subject is a human who is not undergoing any other anti-cancer treatments; and the subject is (i) refractory to at least one anti-cancer treatment, or (ii) in relapse after treatment with at least one anti-cancer therapy, or a combination thereof.

In one embodiment, there is provided a method for treating cancer in a subject in need thereof, comprising administering to the subject a therapeutically effective amount of a compound of Formula I, or a pharmaceutically acceptable salt, and a therapeutically effective amount of a vinca-alkaloid, or a pharmaceutically acceptable salt, wherein: the compound of formula I is 6-(6-aminopyrazin-2-yl)-N-(4-(4-(oxetan-3-yl)piperazin-1-yl)phenyl)imidazo[1,2-a]pyrazin-8-amine, the vinca-alkaloid is vincristine, and the subject is a human who is (i) refractory to at least one anti-cancer treatment, or (ii) in relapse after treatment with at least one anti-cancer therapy, or a combination thereof. In one other embodiment, there is provided a method for treating cancer in a subject in need thereof, comprising administering to the subject a therapeutically effective amount of a compound of formula I, or a pharmaceutically acceptable salt, and a therapeutically effective amount of a vinca-alkaloid, or a pharmaceutically acceptable salt, wherein the compound of formula I is 6-(6-aminopyrazin-2-yl)-N-(4-(4-(oxetan-3-yl)piperazin-1-yl)phenyl)imidazo[1,2-a]pyrazin-8-amine, the vinca-alkaloid is vineristine, and wherein further the subject is a human who is not undergoing any other anti-cancer treatments; and the subject is (i) refractory to at least one anti-cancer treatment, or (ii) in relapse after treatment with at least one anti-cancer therapy, or a combination thereof.

In one embodiment, there is provided a method for treating cancer in a subject in need thereof, comprising administering to the subject a therapeutically effective amount of a compound of formula I, or a pharmaceutically acceptable salt, and a therapeutically effective amount of a vinca-alkaloid, or a pharmaceutically acceptable salt, wherein: wherein the compound of formula I is 6-(6-aminopyrazin-2-yl)-N-(4-(4-(oxetan-3-yl)piperazin-1-yl)phenyl)imidazo[1,2-a]pyrazin-8-amine, the vinca-alkaloid is vinblastine, and the subject is a human who is (i) refractory to at least one anti-cancer treatment, or (ii) in relapse after treatment with at least one anti-cancer therapy, or a combination thereof. In one other embodiment, there is provided a method for treating cancer in a subject in need thereof, comprising administering to the subject a therapeutically effective amount of a compound of formula I, or a pharmaceutically acceptable salt, and a therapeutically effective amount of a vinca-alkaloid, or a pharmaceutically acceptable salt, wherein the compound of formula I is 6-(6-aminopyrazin-2-yl)-N-(4-(4-(oxetan-3-yl)piperazin-1-yl)phenyl)imidazo[1,2-a]pyrazin-8-amine, the vinca-alkaloid is vinblastine, and wherein further the subject is a human who is not undergoing any other anti-cancer treatments; and the subject is (i) refractory to at least one anti-cancer treatment, or (ii) in relapse after treatment with at least one anti-cancer therapy, or a combination thereof.

In yet other embodiments where a compound of formula I, or a pharmaceutically acceptable salt thereof, in combination with a vinca-alkaloid, or a pharmaceutically acceptable salt thereof, is administered as a monotherapy treatment regimen to the subject, the subject may have a 17p deletion, a TP53 mutation, NOTCH1, a SF3B1 mutation, a 11q deletion, or any combination thereof. In some embodiments where a compound of formula I, or a pharmaceutically acceptable salt thereof, in combination with a vinca-alkaloid, or a pharmaceutically acceptable salt thereof, is administered as a monotherapy treatment regimen to the subject, the subject has a 17p deletion, a TP53 mutation, or a combination thereof. In another embodiments where a compound of formula I, or a pharmaceutically acceptable salt thereof, in combination with a vinca-alkaloid, or a pharmaceutically acceptable salt thereof, is administered as a monotherapy treatment regimen to the subject, the subject has NOTCH1, a SF3B1 mutation, a 11q deletion, or any combination thereof.

Provided herein are also methods of treatment in which the compound of formula I, or a pharmaceutically acceptable salt thereof, in combination with a vinca-alkaloid, or a pharmaceutically acceptable salt thereof, administered to a subject (e.g., a human) is given to a subject (e.g., a human) in additional combination with one or more additional therapies, including one or more of the anti-cancer therapies described above. Thus, in some embodiments, the method for treating cancer in a subject (e.g., a human) in need thereof, comprises administering to the subject a therapeutically effective amount of a compound of formula I, or a pharmaceutically acceptable salt thereof, or a pharmaceutical composition thereof, in combination with a vinca-alkaloid, or a pharmaceutically acceptable salt thereof, together with one or more additional therapies, which can be useful for treating the cancer. The one or more additional therapies may involve the administration of one or more therapeutic agents as described herein.

For example, in other embodiments, the one or more additional therapeutic agent may be an inhibitors of lysyl oxidase-like 2 (LOXL2) and a substance that bind to LOXL2, including for example, a humanized monoclonal antibody (mAb) with an immunoglobulin IgG4 isotype directed against human LOXL2.

In other embodiments, the one or more additional therapeutic agent may be an anti-inflammatory agent. Treatment with the one or more additional therapeutic agent may be prior to, concomitant with, or following treatment with the pharmaceutical composition described herein. In some embodiments, the pharmaceutical composition described herein, is combined with another therapeutic agent in a single dosage form, which is then administered prior to, concomitant with or subsequent to administration with a vinca-alkaloid, or a pharmaceutically acceptable salt thereof, of this disclosure. Suitable antitumor therapeutics that may be used in combination with at least one chemical entity described herein include, but are not limited to, chemotherapeutic agents, for example mitomycin C, carboplatin, taxol, cisplatin, paclitaxel, etoposide, doxorubicin, or a combination comprising at least one of the foregoing chemotherapeutic agents. Radiotherapeutic antitumor agents may also be used, alone or in combination with chemotherapeutic agents.

It should be understood that any combinations of the additional therapeutic agents described above may be used, as if each and every combination was individually listed. For example, in some embodiments, the additional therapeutic agents include a PI3K inhibitor and a LOXL2 inhibitor.

Pharmaceutical Compositions and Administration

Compounds of Formula I, or a pharmaceutically acceptable salt thereof, are usually administered in the form of pharmaceutical compositions. This disclosure therefore provides pharmaceutical compositions that contain, as the active ingredient, one or more of the compounds described, or a pharmaceutically acceptable salt or pharmaceutically acceptable ester thereof, and one or more pharmaceutically acceptable vehicle, such as excipients, carriers, including inert solid diluents and fillers, diluents, including sterile aqueous solution and various organic solvents, permeation enhancers, solubilizers and adjuvants. The pharmaceutical compositions may be administered alone or in combination with other therapeutic agents. Such compositions are prepared in a manner well known in the pharmaceutical art (see, e.g., Remington's Pharmaceutical Sciences, Mace Publishing Co., Philadelphia, Pa. 17th Ed. (1985); and Modern Pharmaceutics, Marcel Dekker, Inc. 3rd Ed. (G. S. Banker & C. T. Rhodes, Eds.)

The pharmaceutical compositions may be administered in either single or multiple doses by any of the accepted modes of administration of agents having similar utilities, for example as described in those patents and patent applications incorporated by reference, including rectal, buccal, intranasal and transdermal routes, by intra-arterial injection, intravenously, intraperitoneally, parenterally, intramuscularly, subcutaneously, orally, topically, as an inhalant, or via an impregnated or coated device such as a stent, for example, or an artery-inserted cylindrical polymer.

One mode for administration is parenteral, particularly by injection. The forms in which the compound of Formula I, or a pharmaceutically acceptable salt thereof, may be incorporated for administration by injection include aqueous or oil suspensions, or emulsions, with sesame oil, corn oil, cottonseed oil, or peanut oil, as well as elixirs, mannitol, dextrose, or a sterile aqueous solution, and similar pharmaceutical vehicles. Aqueous solutions in saline may also conventionally be used for injection. Ethanol, glycerol, propylene glycol, liquid polyethylene glycol, and the like (and suitable mixtures thereof), cyclodextrin derivatives, and vegetable oils may also be employed. The proper fluidity can be maintained, for example, by the use of a coating, such as lecithin, by the maintenance of the required particle size in the case of dispersion and by the use of surfactants. The prevention of the action of microorganisms can be brought about by various antibacterial and antifungal agents, for example, parabens, chlorobutanol, phenol, sorbic acid, thimerosal, and the like.

Sterile injectable solutions are prepared by incorporating a compound according to the present disclosure in the required amount in the appropriate solvent with various other ingredients as enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum-drying and freeze-drying techniques which yield a powder of the active ingredient plus any additional desired ingredient from a previously sterile-filtered solution thereof in some embodiments, for parenteral administration, sterile injectable solutions are prepared containing a therapeutically effective amount, e.g., 0.1 to 1000 mg, of the compound of Formula I, or a pharmaceutically acceptable salt thereof. It will be understood, however, that the amount of the compound actually administered usually will be determined by a physician, in the light of the relevant circumstances, including the condition to be treated, the chosen route of administration, the actual compound administered and its relative activity, the age, weight, and response of the individual subject, the severity of the subject's symptoms, and the like.

Oral administration is another route for administration of the compound of Formula I, or a pharmaceutically acceptable salt thereof. Administration may be via capsule or enteric coated tablets, or the like. In making the pharmaceutical compositions that include the compound of Formula I, or a pharmaceutically acceptable salt thereof the active ingredient is usually diluted by an excipient and/or enclosed within such a carrier that can be in the form of a capsule, sachet, paper or other container. When the excipient serves as a diluent, it can be in the form of a solid, semi-solid, or liquid material (as above), which acts as a vehicle, carrier or medium for the active ingredient. Thus, the compositions can be in the form of tablets, pills, powders, lozenges, sachets, cachets, elixirs, suspensions, emulsions, solutions, syrups, aerosols (as a solid or in a liquid medium), ointments containing, for example, up to 10% by weight of the active compound, soft and hard gelatin capsules, sterile injectable solutions, and sterile packaged powders.

Some examples of suitable excipients in an oral formulation include lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, sterile water, syrup, and methyl cellulose. The formulations can additionally include: lubricating agents such as talc, magnesium stearate, and mineral oil; wetting agents; emulsifying and suspending agents; preserving agents such as methyl and propylhydroxy-benzoates; sweetening agents; and flavoring agents.

The pharmaceutical compositions as described herein can be formulated so as to provide quick, sustained or delayed release of the active ingredient after administration to the subject by employing procedures known in the art. Controlled release drug delivery systems for oral administration include osmotic pump systems and dissolutional systems containing polymer-coated reservoirs or drug-polymer matrix formulations. Examples of controlled release systems are given in U.S. Pat. Nos. 3,845,770; 4,326,525; 4,902,514; and 5,616,345. Another formulation for use in the methods of the present disclosure employs transdermal delivery devices (patches). Such transdermal patches may be used to provide continuous or discontinuous infusion of the compounds of the present disclosure in controlled amounts. The construction and use of transdermal patches for the delivery of pharmaceutical agents is well known in the art. See, e.g., U.S. Pat. Nos. 5,023,252, 4,992,445 and 5,001,139. Such patches may be constructed for continuous, pulsatile, or on demand delivery of pharmaceutical agents.

In some embodiments, the compositions described herein are formulated in a unit dosage form. The term "unit dosage forms" refers to physically discrete units suitable as unitary dosages for human subjects and other mammals, each unit containing a predetermined quantity of active material calculated to produce the desired therapeutic effect, in association with a suitable pharmaceutical excipient (e.g., a tablet, capsule, ampoule). The compounds are generally administered in a pharmaceutically effective amount. In some embodiments, for oral administration, each dosage unit contains from about 1 mg to about 5000 mg, about 1 mg to about 4000 mg, about 1 mg to about 3000 mg, about 1 mg to about 2000 mg, about 2 mg to about 2000 mg, about 5 mg to about 2000 mg, about 10 mg to about 2000 mg, about 1 mg to about 1000 mg, about 2 mg to about 1000 mg, about 5 mg to about 1000 mg, about 10 mg to about 1000 mg, about 25 mg to about 1000 mg, about 50 mg to about 1000 mg, about 75 mg to about 1000 mg, about 100 mg to about 1000 mg, about 125 mg to about 1000 mg, about 150 mg to about 1000 mg, about 175 mg to about 1000 mg, about 200 mg to about 1000 mg, about 225 mg to about 1000 mg, about 250 mg to about 1000 mg, about 300 mg to about 1000 mg, about 350 mg to about 1000 mg, about 400 mg to about 1000 mg, about 450 mg to about 1000 mg, about 500 mg to about 1000 mg, about 550 mg to about 1000 mg, about 600 mg to about 1000 mg, about 650 mg to about 1000 mg, about 700 mg to about 1000 mg, about 750 mg to about 1000 mg, about 800 mg to about 1000 mg, about 850 mg to about 1000 mg, about 900 mg to about 1000 mg, about 950 mg to about 1000 mg, about 1 mg to about 750 mg, about 2 mg to about 750 mg, about 5 mg to about 750 mg, about 10 mg to about 750 mg, about 25 mg to about 750 mg, about 50 mg to about 750 mg, about 75 mg to about 750 mg, about 100 mg to about 750 mg, about 125 mg to about 750 mg, about 150 mg to about 750 mg, about 175 mg to about 750 mg, about 200 mg to about 750 mg, about 225 mg to about 750 mg, about 250 mg to about 750 mg, about 300 mg to about 750 mg, about 350 mg to about 750 mg, about 400 mg to about 750 mg, about 450 mg to about 750 mg, about 500 mg to about 750 mg, about 550 mg to about 750 mg, about 600 mg to about 750 mg, about 650 mg to about 750 mg, about 700 mg to about 750 mg, about 1 mg to about 500 mg, about 2 mg to about 500 mg, about 5 mg to about 500 mg, about 10 mg to about 500 mg, about 25 mg to about 500 mg, about 50 mg to about 500 mg, about 75 g to about 500 mg, about 100 mg to about 500 mg, about 125 mg to about 500 mg, about 150 mg to about 500 mg, about 175 mg to about 500 mg, about 200 mg to about 500 mg, about 225 mg to about 500 mg, about 250 mg to about 500 mg, about 300 mg to about 500 mg, about 350 mg to about 500 mg, about 400 mg to about 500 mg, about 450 mg to about 500 mg, about 1 mg to about 400 mg, about 2 mg to about 400 mg, about 5 mg to about 400 mg, about 10 mug to about 400 mg, about 25 mg to about 400 mg, about 50 mg to about 400 mg, about 75 mg to about 400 mg, about 100 mg to about 400 mg, about 125 mg to about 400 mg, about 150 mg to about 400 mg, about 175 mg to about 400 mg, about 200 mg to about 400 mg, about 225 mg to about 400 mg, about 250 mg to about 400 mg, about 300 mg to about 400 mg, about 350 mg to about 400 mg, about 1 mg to about 300 mg, about 2 mg to about 300 mg, about 5 mg to about 300 mg, about 10 mg to about 300 mg, about 25 g to about 300 mg, about 50 g to about 300 mg, about 75 mg to about 300 mg, about 100 mg to about 300 mg, about 125 mg to about 300 mg, about 150 mg to about 300 mg, about 175 mg to about 300 mg, about 200 mg to about 300 mg, about 225 mg to about 300 mg, about 250 mg to about 300 mg, about 1 tug to about 250 mg, about 2 mg to about 250 mg, about 5 mg to about 250 mg, about 10 mg to about 250 mg, about 25 mg to about 250 mg, about 50 mg to about 250 mg, about 75 mg to about 250 mg, about 100 mg to about 250 mg, about 125 mg to about 250 mg, about 150 mg to about 250 mg, about 175 mg to about 250 mg, about 200 mg to about 250 tug, about 225 mg to about 250 mg, about 1 mg to about 225 mg, about 2 mg to about 225 mg, about 5 mg to about 225 mg, about 10 mg to about 225 mg, about 25 mg to about 225 mg, about 50 mg to about 225 mg, about 75 mg to about 225 mg, about 100 mg to about 225 mg, about 125 mg to about 225 mg, about 150 mg to about 225 mg, about 175 mg to about 225 mg, about 200 mg to about 225 mg, about 1 mg to about 200 mg, about 2 mg to about 200 mg, about 5 mg to about 200 mg, about 10 mg to about 200 mg, about 25 mg to about 200 mg, about 50 mg to about 200 mg, about 75 mg to about 200 mg, about 100 mg to about 200 mg, about 125 mg to about 200 mg, about 150 mg to about 200 mg, about 175 mg to about 200 mg, about 180 mg to about 200 mg, about 1 mg to about 175 mg, about 2 mg to about 175 mg, about 5 mg to about 175 mg, about 10 mg to about 175 mg, about 25 mg to about 175 mg, about 50 mg to about 175 mg, about 75 mg to about 175 mg, about 100 mg to about 175 mg, about 125 mg to about 175 mg, about 150 mg to about 175 mg, about 1 mg to about 150 mg, about 2 mg to about 150 mg, about 5 mg to about 150 mg, about 10 mg to about 150 mg, about 25 mg to about 150 mg, about 50 mg to about 150 mg, about 75 mg to about 150 mg, about 100 mg to about 150 mg, about 125 mg to about 150 mg, about 1 mg to about 125 mg, about 2 mg to about 125 mg, about 5 mg to about 125 mg, about 10 mg to about 125 mg about 25 mg to about 125 mg, about 50 mg to about 125 mg, about 75 mg to about 125 mg, about 100 mg to about 125 mg, about 1 mg to about 100 mg, about 2 mg to about 100 mg, about 5 mg to about 100 mg, about 10 mg to about 100 mg, about 25 mg to about 100 mg, about 50 mg to about 100 mg, or about 75 rag to about 100 mg of a compound of Formula I, about or a pharmaceutically acceptable salt thereof.

In some embodiments, for oral administration, each dosage unit contains about 1 mg, about 2 mg, about 5 mg, about 10 mg, about 15 mg, about 20 mg, about 25 mg, about 30 mg, about 35 mg, about 40 mg, about 45 mg, about 50 mg, about 75 mg, about 100 mg, about 125 mg, about 150 mg, about 175 mg, about 180 mg, about 200 mg, about 225 mg, about 250 mg, about 300 mg, about 350 mg, about 400 mg, about 450 mg, about 500 mg, about 550 mg, about 600 mg, about 650 mg, about 700 mg, about 750 mg, about 800 mg, about 850 mg, about 900 mg, about 950 mg, or about 1000 mg of a compound of Formula I, or a pharmaceutically acceptable salt thereof.

The dosages for oral administration described above may be administered once daily (QD) or twice daily (BID). In some embodiments, the compound of Formula I, or a pharmaceutically acceptable salt thereof, or a pharmaceutical composition thereof, is administered orally at a unit dosage of about 1 mg QD, about 2 mg QD, about 5 mg QD, about 10 mg QD, about 15 mg QD, about 20 mg QD, about 25 mg QD, about 30 mg QD, about 35 mg QD, about 40 mg QD, about 45 mg QD, about 50 mg QD, about 60 mg QD, about 65 mg QD, about 70 mg QD, about 75 mg QD, about 80 mg QD, about 90 mg QD, about 100 mg QD, about 125 mg QD, about 150 mg QD, about 175 mg QD, about 180 mg QD, about 200 mg QD, about 225 mg QD, about 250 mg QD, about 300 mg QD, about 350 mg QD, about 400 mg QD, about 450 mg QD, about 500 mg QD, about 550 mg QD, about 600 mg QD, about 650 mg QD, about 700 mg QD, about 750 mg QD, about 800 mg QD, about 850 mg QD, about 900 mg QD, about 950 mg QD, or about 1000 mg QD. In some embodiments, the compound of formula I, or a pharmaceutically acceptable salt thereof, or a pharmaceutical composition thereof, is administered orally at a unit dosage of about 1 mg BID, about 2 mg BID, about 5 mg BID, about 10 mg BID, about 15 mg BID, about 20 mg BID, about 25 mg BID, about 30 mg BID, about 35 mg BID, about 40 mg BID, about 45 mg BID, about 50 mg BID, about 75 mg BID, about 80 mg BID, about 90 mg BID, about 100 mg BID, about 125 mg BID, about 150 mg BID, about 175 mg BID, about 200 mg BID, about 225 mg BID, about 250 mg BID, about 300 mg BID, about 350 mg BID, about 400 mg BID, about 450 mg BID, about 500 mg BID, about 550 mg BID, about 600 mg BID, about 650 mg BID, about 700 mg BID, about 750 mg BID, about 800 mg BID, about 850 mg BID, about 900 mg BID, about 950 mg BID, or about 1000 mg BID.

In some embodiments, for parenteral administration, each dosage unit contains from 0.1 mg to 1 g, 0.1 mg to 700 mg, or 0.1 mg to 100 mg of a compound of Formula I, or a pharmaceutically acceptable salt thereof.

For any of the dosage units as described herein, it will be understood, however, that the amount of the compound actually administered usually will be determined by a physician, in the light of the relevant circumstances, including the condition to be treated, the chosen route of administration, the actual compound administered and its relative activity, the age, weight, and response of the individual subject, the severity of the subject's symptoms, and the like.

For preparing solid compositions such as tablets, the principal active ingredient is mixed with a pharmaceutical excipient to form a solid preformulation composition containing a homogeneous mixture of the compound of Formula I, or a pharmaceutically acceptable salt thereof. When referring to these preformulation compositions as homogeneous, it is meant that the active ingredient is dispersed evenly throughout the composition so that the composition may be readily subdivided into equally effective unit dosage forms such as tablets, pills and capsules.

The tablets or pills as described herein may be coated or otherwise compounded to provide a dosage form affording the advantage of prolonged action, or to protect from the acid conditions of the stomach. For example, the tablet or pill can comprise an inner dosage and an outer dosage component, the latter being in the form of an envelope over the former. The two components can be separated by an enteric layer that serves to resist disintegration in the stomach and permit the inner component to pass intact into the duodenum or to be delayed in release. A variety of materials can be used for such enteric layers or coatings, such materials including a number of polymeric acids and mixtures of polymeric acids with such materials as shellac, cetyl alcohol, and cellulose acetate.

Compositions for inhalation or insufflation may include solutions and suspensions in pharmaceutically acceptable, aqueous or organic solvents, or mixtures thereof, and powders. The liquid or solid compositions comprising the compound of Formula I, or a pharmaceutically acceptable salt thereof, may contain suitable pharmaceutically acceptable excipients as described supra. Preferably, the compositions are administered by the oral or nasal respiratory route for local or systemic effect. Compositions in preferably pharmaceutically acceptable solvents may be nebulized by use of inert gases. Nebulized solutions may be inhaled directly from the nebulizing device or the nebulizing device may be attached to a facemask tent, or intermittent positive pressure breathing machine. Solution, suspension, or powder compositions may be administered, preferably orally or nasally, from devices that deliver the formulation in an appropriate manner.

Dosing Regimen

In the methods provided herein, the compound of Formula I, or a pharmaceutically acceptable salt thereof, or a pharmaceutical composition thereof is administered in a therapeutically effective amount to achieve its intended purpose. Determination of a therapeutically effective amount is well within the capability of those skilled in the art, especially in light of the detailed disclosure provided herein. In some embodiments (methods of treating cancer), a therapeutically effective amount of the compound of Formula I, or a pharmaceutically acceptable salt thereof, may (i) reduce the number of cancer cells; (ii) reduce tumor size; (iii) inhibit, retard, slow to some extent, and preferably stop cancer cell infiltration into peripheral organs; (iv) inhibit (e.g., slow to some extent and preferably stop) tumor metastasis; (v) inhibit tumor growth; (vi) delay occurrence and/or recurrence of a tumor; and/or (vii) relieve to some extent one or more of the symptoms associated with the cancer. In various embodiments, the amount is sufficient to ameliorate, palliate, lessen, and/or delay one or more of symptoms of cancer.

The therapeutically effective amount may vary depending on the subject, and disease or condition being treated, the weight and age of the subject, the severity of the disease or condition, and the manner of administering, which can readily be determined by one or ordinary skill in the art.

The dosing regimen of the compound of Formula I, or a pharmaceutically acceptable salt thereof, in the methods provided herein may vary depending upon the indication, route of administration, and severity of the condition, for example. Depending on the route of administration, a suitable dose can be calculated according to body weight, body surface area, or organ size. The final dosing regimen is determined by the attending physician in view of good medical practice, considering various factors that modify the action of drugs, e.g., the specific activity of the compound, the identity and severity of the disease state, the responsiveness of the subject, the age, condition, body weight, sex, and diet of the subject, and the severity of any infection. Additional factors that can be taken into account include time and frequency of administration, drug combinations, reaction sensitivities, and tolerance/response to therapy. Further refinement of the doses appropriate for treatment involving any of the formulations mentioned herein is done routinely by the skilled practitioner without undue experimentation, especially in light of the dosing information and assays disclosed, as well as the pharmacokinetic data observed in human clinical trials. Appropriate doses can be ascertained through use of established assays for determining concentration of the agent in a body fluid or other sample together with dose response data.

The formulation and route of administration chosen may be tailored to the individual subject, the nature of the condition to be treated in the subject, and generally, the judgment of the attending practitioner. For example, the therapeutic index of the compound of Formula I, or a pharmaceutically acceptable salt thereof, may be enhanced by modifying or derivatizing the compound for targeted delivery to cancer cells expressing a marker that identifies the cells as such. For example, the compounds can be linked to an antibody that recognizes a marker that is selective or specific for cancer cells, so that the compounds are brought into the vicinity of the cells to exert their effects locally, as previously described. See e.g., Pietersz et al., Immunol. Rev., 129:57 (1992); Trail et al, Science, 261:212 (1993); and Rowlinson-Busza et al., Curr. Opin. Oncol., 4:1142 (1992).

The therapeutically effective amount of the compound of Formula I, or a pharmaceutically acceptable salt thereof, may be provided in a single dose or multiple doses to achieve the desired treatment endpoint. As used herein, "dose" refers to the total amount of an active ingredient (e.g., the compound of Formula I, or a pharmaceutically acceptable salt thereof,) to be taken each time by a subject (e.g., a human). The dose administered, for example for oral administration described above, may be administered once daily (QD), twice daily (BID), three times daily, four times daily, or more than four times daily. In some embodiments, the dose of a compound of Formula I, or a pharmaceutically acceptable salt thereof, is administered once daily. In some embodiments, the dose of a compound of Formula I, or a pharmaceutically acceptable salt thereof, is administered twice daily.

In some embodiments, exemplary doses of the compound of Formula I, or a pharmaceutically acceptable salt thereof, for a human subject may be from about 1 mg to about 5000 mg, about 1 mg to about 4000 mg, about 1 mg to about 3000 mg, about 1 mg to about 2000 mg, about 2 mg to about 2000 mg, about 5 mg to about 2000 mg, about 1.0 mg to about 2000 mg, about 1 mg to about 1000 mg, about 2 mg to about 1000 mg, about 5 mg to about 1000 mg, about 10 mg to about 1000 mg, about 25 mg to about 1000 mg, about 50 mg to about 1000 mg, about 75 mg to about 1000 mg, about 100 mg to about 1000 mg, about 125 mg to about 1000 mg, about 150 mg to about 1000 mg, about 175 mg to about 1000 mg, about 200 mg to about 1000 mg, about 225 mg to about 1000 mg, about 250 mg to about 1000 mg, about 300 mg to about 1000 mg, about 350 mg to about 1000 mg, about 400 mg to about 1000 mg, about 450 mg to about 1000 mg, about 500 mg to about 1000 mg, about 550 mg to about 1000 mg, about 600 mg to about 1000 mg, about 650 mg to about 1000 mg, about 700 mg to about 1000 mg, about 750 mg to about 1000 mg, about 800 mg to about 1000 mg, about 850 mg to about 1000 mg, about 900 mg to about 1000 mg, about 950 mg to about 1000 mg, about 1 mg to about 750 mg, about 2 mg to about 750 mg, about 5 mg to about 750 mg, about 10 mg to about 750 mg, about 25 mg to about 750 mg, about 50 mg to about 750 mg, about 75 mg to about 750 mg, about 100 mg to about 750 mg, about 125 mg to about 750 mg, about 150 mg to about 750 mg, about 175 mg to about 750 mg, about 200 mg to about 750 mg, about 225 mg to about 750 mg, about 250 mg to about 750 mg, about 300 mg to about 750 mg, about 350 mg to about 750 mg, about 400 mg to about 750 mg, about 450 mg, to about 750 mg, about 500 mg to about 750 mg, about 550 mg to about 750 mg, about 600 mg to about 750 mg, about 650 mg to about 750 mg, about 700 mg to about 750 mg, about 1 mg to about 500 mg, about 2 mg to about 500 mg, about 5 mg to about 500 mg, about 10 mg to about 500 mg, about 25 mg to about 500 mg, about 50 ng to about 500 mg, about 75 mg to about 500 mg, about 100 mg to about 500 mg, about 125 mg to about 500 mg, about 150 mg to about 500 mg, about 175 mg to about 500 mg, about 200 mg to about 500 mg, about 225 mg to about 500 mg, about 250 mg to about 500 mg, about 300 mg to about 500 mg, about 350 mg to about 500 mg, about 400 mg to about 500 mg, about 450 mg to about 500 mg, about 1 mg to about 400 mg, about 2 mg to about 400 mg, about 5 mg to about 400 mg, about 10 mg to about 400 mg, about 25 mg, to about 400 mg, about 50 mg to about 400 mg, about 75 mg to about 400 mg, about 100 mg to about 400 mg, about 125 mg to about 400 mg, about 150 mg to about 400 mg, about 175 rag to about 400 mg, about 200 mg to about 400 mg, about 225 mg to about 400 mg, about 250 mg to about 400 mg, about 300 mg to about 400 mg, about 350 mg to about 400 mg, about 1 mg to about 300 mg, about 2 mg to about 300 mg, about 5 mg to about 300 mg, about 10 mg, to about 300 mg, about 25 mg to about 300 mg, about 50 mg to about 300 mg, about 75 mg to about 300 mg, about 100 mg to about 300 mg, about 125 mg to about 300 mg, about 150 mg to about 300 rag, about 175 mg to about 300 mg, about 200 mg to about 300 mg, about 225 arg to about 300 mg, about 250 mg to about 300 mg, about 1 mg to about 250 mg, about 2 mg to about 250 mg, about 5 g to about 250 mg, about 0 nag to about 250 mg, about 25 mg to about 250 mg, about 50 mg to about 250 mg, about 75 mg to about 250 mg, about 100 mg to about 250 mg, about 125 nag to about 250 mg, about 150 mg to about 250 mg, about 175 mg to about 250 mg, about 200 mg to about 250 mg, about 225 mg to about 250 mg, about 1 mg to about 225 mg, about 2 mg to about 225 mg, about 5 mg to about 225 mg, about 10 mg to about 225 mg, about 25 mg to about 225 mg, about 50 mg to about 225 mg, about 75 mg to about 225 mg, about 100 nag to about 225 mg, about 125 mg to about 225 mg, about 150 mg to about 225 mg, about 175 mg to about 225 mg, about 200 mg to about 225 mg, about 1 mg to about 200 mg, about 2 mg to about 200 mg, about 5 mg to about 200 mg, about 10 mg to about 200 mg, about 25 mg to about 200 mg, about 50 mg to about 200 mg, about 75 mg to about 200 mg, about 100 mg to about 200 mg, about 125 mg to about 200 mg, about 150 mg to about 200 mg, about 175 mg to about 200 mg, about 180 mug to about 200 mg, about 1 mg to about 175 mg, about 2 mg to about 175 mg, about 5 mg to about 175 mg, about 10 mg to about 175 mg, about 25 mg to about 175 mg, about 50 mg to about 175 mg, about 75 mg to about 175 mg, about 100 mg to about 175 mg, about 125 mg to about 175 mg, about 150 mg to about 175 mg, about 1 mg to about 150 mg, about 2 mg to about 150 mg, about 5 mg to about 150 mg, about 10 mg to about 150 mg, about 25 mg to about 150 mg, about 50 mg to about 150 mg, about 75 mg to about 150 mg, about 100 mg to about 150 mg, about 125 mg to about 150 mg, about 1 mg to about 125 mg, about 2 mg to about 125 mg, about 5 mg to about 125 mg, about 10 mg to about 125 mg, about 25 mg to about 125 mg, about 50 mug to about 125 mg, about 75 mg to about 125 mg, about 100 mg to about 125 mg, about 1 mg to about 100 mg, about 2 mg to about 100 mg, about 5 mg to about 100 mg, about 10 mg to about 100 mg, about 25 mg to about 100 mg, about 50 mg to about 100 mg, about 60 mug to about 100 mg, or about 75 mg to about 100 mg.

In some embodiments, exemplary doses of the compound of Formula I, or a pharmaceutically acceptable salt thereof, for a human subject may be about 1 mg, about 2 mg, about 5 mg, about 10 mg, about 15 mg, about 20 mg, about 25 mg, about 30 mg, about 35 mg, about 40 mug, about 45 mg, about 50 mg, about 60 mg, about 65 mg, about 70 mg, about 75 mg, about 100 mg, about 125 mg, about 150 mg, about 175 mg, about 180 mg, about 190 mg, about 200 mg, about 225 mg, about 250 mg, about 300 mg, about 350 mg, about 400 mg, about 450 mg, about 500 mg, about 550 mg, about 600 mg, about 650 mg, about 700 mg, about 750 mg, about 800 mg, about 850 mg, about 900 mg, about 950 mg, about 1000 mg, about 1200 mg, about 1400 mg, about 1600 mg, about 1800 mg, about 2000 mg, about 2200 mg, about 2400 mg, about 2600 mg, about 2800 mg, about 3000 mg, about 3200 mg, about 3400 mg, about 3600 mg, about 3800 mg, about 4000 mg, about 4200 mg, about 4400 mg, about 4600 mg, about 4800 mg, or about 5000 mg.

In other embodiments, the methods provided comprise continuing to treat the subject (e.g., a human) by administering the doses of the compound of Formula I, or a pharmaceutically acceptable salt thereof, at which clinical efficacy is achieved or reducing the doses by increments to a level at which efficacy can be maintained. In some embodiments, the methods provided comprise administering to the subject (e.g., a human) an initial daily dose of 50 mg to about 300 mg or the compound of formula I, or in an alternative embodiment 100 mg to 1000 mg of the compound of Formula I, or a pharmaceutically acceptable salt thereof, and administering subsequent daily doses of the compound of Formula I, or a pharmaceutically acceptable salt thereof, over at least 6 days, wherein each subsequent daily dose is increased by 25 mg to 300 mg, or by 50 mg to about 400 mg. Thus, it should also be understood that the dose of the compound of Formula I, or a pharmaceutically acceptable salt thereof, may be increased by increments until clinical efficacy is achieved. Increments of about 10 mg, about 25 mg, about 50 mg, about 100 mg, or about 125 mg, or about 150 mg, or about 200 mg, or about 250 mg, or about 300 mg can be used to increase the dose. The dose can be increased daily, every other day, two, three, four, five or six times per week, or once per week.

The frequency of dosing will depend on the pharmacokinetic parameters of the compound administered, the route of administration, and the particular disease treated. The dose and frequency of dosing may also depend on pharmacokinetic and pharmacodynamic, as well as toxicity and therapeutic efficiency data. For example, pharmacokinetic and pharmacodynamic information about the compound of Formula I, or a pharmaceutically acceptable salt thereof, can be collected through preclinical in vitro and in vivo studies, later confirmed in humans during the course of clinical trials. Thus, for the compound of Formula I, or a pharmaceutically acceptable salt thereof, used in the methods provided herein, a therapeutically effective dose can be estimated initially from biochemical and/or cell-based assays. Then, dosage can be formulated in animal models to achieve a desirable circulating concentration range that modulates Syk expression or activity. As human studies are conducted further information will emerge regarding the appropriate dosage levels and duration of treatment for various diseases and conditions.

Toxicity and therapeutic efficacy of the compound of Formula I, or a pharmaceutically acceptable salt thereof, can be determined by standard pharmaceutical procedures in cell cultures or experimental animals, e.g., for determining the $LD_{50}$ (the dose lethal to 50% of the population) and the $ED_{50}$ (the dose therapeutically effective in 50% of the population). The dose ratio between toxic and therapeutic effects is the "therapeutic index", which typically is expressed as the ratio $LD_{50}/ED_{50}$. Compounds that exhibit large therapeutic indices, i.e., the toxic dose is substantially higher than the effective dose, are preferred. The data obtained from such cell culture assays and additional animal studies can be used in formulating a range of dosage for human use. The doses of such compounds lies preferably within a range of circulating concentrations that include the $ED_{50}$ with little or no toxicity.

In the methods provided herein, the compound of Formula I, or a pharmaceutically acceptable salt thereof, or a pharmaceutical composition thereof, is administered in a therapeutically effective amount to achieve its intended purpose. As used herein, a "therapeutically effective amount" when referring to a vinca-alkaloid, or a pharmaceutically acceptable sat thereof, is an amount sufficient to inhibit tubulin growth or formation, or to inhibit or reduce microtubule formation, or to interfere with spindle formation, and thereby treat a subject (e.g. a human) suffering an indication, or to ameliorate or alleviate the existing symptoms of the indication. For example, a therapeutically effective amount of a vinca-alkaloid or a pharmaceutically acceptable salt thereof may be an amount sufficient to decrease a symptom of a disease or condition responsive to inhibit of tubulin activity and/or formation.

The therapeutically effective amount of the vinca-alkaloid of this disclosure, or its pharmaceutically acceptable salt thereof, may be provided in a single dose or multiple doses to achieve the desired treatment endpoint. As used herein, "dose" refers to the total amount of an active ingredient (e.g., vincristine or vinblastine, for example), or a pharmaceutically acceptable salt thereof) to be taken each time by a subject (e.g., a human).

Exemplary doses of the vinca-alkaloid of this disclosure, or its pharmaceutically acceptable salt thereof, for a human subject may be between about 0.01 mg-$M^2$ to about 3.0 mg-$M^2$, depending on the identity of the vinca-alkaloid, or between about 0.01 mg-$M^2$ to about 2.5 mg-$M^2$, or between about 0.01 mg-$M^2$ to about 2.0 mg-$M^2$, or between about 0.01 mg-$M^2$ to about 1.9 mg-$M^2$, or between about 0.01 mg-$M^2$ to about 1.8 mg-$M^2$, or between about 0.01 mg-$M^2$ to about 1.7 mg-$M^2$, or between about 0.01 mg-$M^2$ to about 1.6 mg-$M^2$, or between about 0.01 mg-$M^2$ to about 1.5 mg-$M^2$, or between about 0.01 mg-$M^2$ to about 1.4 mg-$M^2$, or between about 0.01 mg-$M^2$ to about 1.3 mg-$M^2$, or between about 0.01 mg-$M^2$ to about 1.2 mg-$M^2$, or between about 0.01 mg-$M^2$ to about 1.1 mg-$M^2$, or between about 0.01 mg-$M^2$ to about 1.0 mg-$M^2$, or between about 0.01 mg-$M^2$ to about 0.9 mg-$M^2$, or between about 0.01 mg-$M^2$ to about 0.8 mg-$M^2$, or between about 0.01 mg-$M^2$ to about 0.7 mg-$M^2$, or between about 0.1 mg-$M^2$ to about 0.6 mg-$M^2$, or between about 0.01 mg-$M^2$ to about 0.5 mg-$M^2$, or between about 0.01 mg-$M^2$ to about 0.45 mg-$M^2$, or between about 0.01 mg-$M^2$ to about 0.4 mg-$M^2$, or between about 0.01 mg-$M^2$ to about 0.35 mg-$M^2$ or between about 0.01 mg-$M^2$ to about 0.33 mg-$M^2$, or between about 0.01 mg-$M^2$ to about 0.3 mg-$M^2$, or between about 0.01 mg-$M^2$ to about 0.25 mg-$M^2$, or between about 0.01 mg-$M^2$ to about 0.2 mg-$M^2$, or between about 0.01 mg-$M^2$ to about 0.15 mg-$M^2$, or between about 0.01 mg-$M^2$ to about 0.01 mg-$M^2$, or between about 0.1 mg-$M^2$ to about 1.8 mg-$M^2$, or between about 0.15 mg-$M^2$ to about 7 mg-$M^2$ to about 1.7 mg-$M^2$, or between about 0.2 mg-$M^2$ to about 1.6 mg-$M^2$, or between about 0.25 mg-$M^2$ to about 1.5 mg-$M^2$, or between about 0.3 mg-$M^2$ to about 1.4 mg-$M^2$, or between about 0.33 mg-$M^2$ to about 1.3 mg-$M^2$, or between about 0.35 mg-$M^2$ to about 1.2 mg-$M^2$, or between about 0.4 mg-$M^2$ to about 1.1 mg-$M^2$, or between about 0.45 mg-$M^2$ to about 1.0 mg-$M^2$, or between about 0.5 mg-$M^2$ to about 0.9 mg-$M^2$, or between about 0.6 mg-$M^2$ to about 0.8 mg-$M^2$. In one embodiment, the dose of the vinca-alkaloid of this disclosure, or its pharmaceutically acceptable salt thereof, administered to the subject in the methods provided herein is about 1.5 mg-$M^2$. In one embodiment, the dose of the vinca-alkaloid of this disclosure, or its pharmaceutically acceptable salt thereof, administered to the subject in the methods provided herein is about 1.0 mg-$M^2$. In one embodiment, the dose of the vinca-alkaloid of this disclosure, or its pharmaceutically acceptable salt thereof, administered to the subject in the methods provided herein is about 0.5 mg-$M^2$.

In other embodiments, the methods provided comprise continuing to treat the subject (e.g., a human) by administering the doses of the vinca-alkaloid of this disclosure, or a pharmaceutically acceptable salt thereof, at which clinical efficacy is achieved or reducing the doses by increments to a level at which efficacy can be maintained. The frequency of dosing will depend on the pharmacokinetic parameters of the compound administered, the route of administration, and the particular disease treated. The dose and frequency of dosing may also depend on pharmacokinetic and pharmacodynamic, as well as toxicity and therapeutic efficiency data The vinca-alkaloid of the disclosure, or the pharmaceutically acceptable salts thereof, are administered via IV. In one embodiment, the vinca-alkaloid is vincristine sulfate and the amount of the vial is 1 mg/1 ml. In some embodiments, the vinca-alkaloid is vincristine sulfate and the vial is 2 ml containing either 1 mg or 2 mg of vincristine sulfate. In another embodiment, "Vincristine Sulfate", USP is a white to off-white powder. It is soluble in methanol, freely soluble in water, but only slightly soluble in 95% ethanol. In 98% ethanol, Vincristine Sulfate, USP has an ultraviolet spectrum with maxima at 221 nm ($\epsilon$+47,100).

"Vincristine Sulfate Injection", USP is a sterile, preservative-free, single use only solution available for intravenous use in 2 mL (1 mg and 2 mg) vials. Each mL, contains 1 mg Vincristine Sulfate, USP, 100 mg mannitol and Water for Injection, USP. Q.S. Sulfuric acid or sodium hydroxide have been added for pH control. The pH of Vincristine Sulfate Injection, USP ranges from 4.0 to 5.0.

The administration of the compound of Formula I, or a pharmaceutically acceptable salt thereof, may be administered under fed conditions. The term fed conditions or variations thereof refers to the consumption or uptake of food, in either solid or liquid forms, or calories, in any suitable form, before or at the same time when the compounds or pharmaceutical compositions thereof are administered. For example, the compound of Formula I, or a pharmaceutically acceptable salt thereof, may be administered to the subject (e.g., a human) within minutes or hours of consuming calories (e.g., a meal). In some embodiments, the compound of Formula I, or a pharmaceutically acceptable salt thereof, may be administered to the subject (e.g., a human) within 5-10 minutes, about 30 minutes, or about 60 minutes consuming calories.

Articles of Manufacture and Kits

Compositions (including, for example, formulations and unit dosages) comprising the compound of Formula I, or a pharmaceutically acceptable salt thereof, can be prepared and placed in an appropriate container, and labeled for treatment of an indicated condition. Accordingly, provided is also an article of manufacture, such as a container comprising a unit dosage form of the compound of Formula I, or a pharmaceutically acceptable salt thereof, and a label containing instructions for use of the compounds. In some embodiments, the article of manufacture is a container comprising a unit dosage form of the compound of Formula I, or a pharmaceutically acceptable salt thereof, and at least one pharmaceutically acceptable vehicle. The article of manufacture may be a bottle, vial, ampoule, single-use disposable applicator, or the like, containing the pharmaceutical composition provided in the present disclosure. The container may be formed from a variety of materials, such as glass or plastic and in one aspect also contains a label on, or associated with, the container which indicates directions for use in the treatment of cancer or inflammatory conditions. It should be understood that the active ingredient may be packaged in any material capable of improving chemical and physical stability, such as an aluminum foil bag. In some embodiments, diseases or conditions indicated on the label can include, for example, treatment of cancer.

In another embodiment, the article of manufacture is a container comprising a unit dosage form of a compound of formula iI, or a pharmaceutically acceptable salt thereof, and at least one pharmaceutically acceptable vehicle, and a vial containing a vinca-alkaloid, or a pharmaceutically acceptable salt.

Any pharmaceutical composition provided in the present disclosure may be used in the articles of manufacture, the same as if each and every composition were specifically and individually listed for use in an article of manufacture.

Kits comprising a pharmaceutical composition comprising a compound of Formula I, or a pharmaceutically acceptable salt thereof, are also provided. For example, a kit can comprise unit dosage forms of the compound of Formula I, or a pharmaceutically acceptable salt thereof, and a package insert containing instructions for use of the composition in treatment of a medical condition. In some embodiments, the kit comprises a unit dosage form of the compound of Formula I, or a pharmaceutically acceptable salt thereof, a at least one pharmaceutically acceptable vehicle. In some embodiments, the kits comprises a unit dosage form of the compound of Formula I, or a pharmaceutically acceptable salt thereof, and at least one pharmaceutically acceptable vehicle, and a vial containing a solution of vinca-alkaloid, or a pharmaceutically acceptable salt thereof. The instructions for use in the kit may be for treating a cancer, including, for example, a hematologic malignancy. In some embodiments, the instructions are directed to use of the pharmaceutical composition for the treatment of cancer, such as leukemia or lymphoma, including relapsed and refractory leukemia or lymphoma. In some embodiments, the instructions for use in the kit may be for treating a hematologic cancer selected from the group consisting of small lymphocytic lymphoma, non-Hodgkin's lymphoma, indolent non-Hodgkin's lymphoma, refractory iNHL, mantle cell lymphoma, follicular lymphoma, lymphoplasmacytic lymphoma, marginal zone lymphoma, immunoblastic large cell lymphoma, lymphoblastic lymphoma, Splenic marginal zone B-cell lymphoma (+/−villous lymphocytes), Nodal marginal zone lymphoma (+/−monocytoid B-cells), Extranodal marginal zone B-cell lymphoma of mucosa-associated lymphoid tissue type, cutaneous T-cell lymphoma, extranodal T-cell lymphoma, anaplastic large cell lymphoma, angioimmunoblastic T-cell lymphoma, mycosis fungoides, B-cell lymphoma, diffuse large B-cell lymphoma, Mediastinal large B-cell lymphoma, Intravascular large B-cell lymphoma, Primary effusion lymphoma, small non-cleaved cell lymphoma, Burkitt's lymphoma, multiple myeloma, plasmacytoma, acute lymphocytic leukemia, T-cell acute lymphoblastic leukemia, B-cell acute lymphoblastic leukemia, B-cell prolymphocytic leukemia, acute myeloid leukemia, chronic lymphocytic leukemia, juvenile myelomonocytic leukemia, minimal residual disease, hairy cell leukemia, primary myelofibrosis, secondary myelofibrosis, chronic myeloid leukemia, myelodysplastic syndrome, myeloproliferative disease, and Waldestrom's macroglobulinemia. In one embodiment, the instructions for use in the kit may be for treating chronic lymphocytic leukemia or non-Hodgkin's lymphoma. In one embodiment, the NHL is diffuse large B-cell lymphoma, mantle cell lymphoma, follicular lymphoma, small lymphocytic lymphoma, lymphoplasmacytic lymphoma, and marginal zone lymphoma. In one embodiment, the hematologic malignancy is indolent non-Hodgkin's lymphoma. In some embodiments, diseases or conditions indicated on the label can include, for example, treatment of cancer.

In some instances, the instructions are directed to use of the pharmaceutical composition for the treatment of a solid tumor, wherein the solid tumor is from a cancer selected from the group consisting of pancreatic cancer, urological cancer, bladder cancer, colorectal cancer, colon cancer, breast cancer, prostate cancer, renal cancer, hepatocellular cancer, thyroid cancer, gall bladder cancer, lung cancer (e.g. non-small cell lung cancer, small-cell lung cancer), ovarian cancer, cervical cancer, gastric cancer, endometrial cancer, esophageal cancer, head and neck cancer, melanoma, neuroendocrine cancer, CNS cancer, brain tumors (e.g., glioma, anaplastic oligodendroglioma, adult glioblastoma multiforme, and adult anaplastic astrocytoma), bone cancer, soft tissue sarcoma, retinoblastomas, neuroblastomas, peritoneal effusions, malignant pleural effusions, mesotheliomas, Wilms tumors, trophoblastic neoplasms, hemangiopericytomas, Kaposi's sarcomas, myxoid carcinoma, round cell carcinoma, squamous cell carcinomas, esophageal squamous cell carcinomas, oral carcinomas, cancers of the adrenal cortex, ACTH-producing tumors.

In some instances, the instructions are directed to use of the pharmaceutical composition for the treatment of an allergic disorder and/or an autoimmune and/or inflammatory disease, and/or an acute inflammatory reaction. In some embodiments, the instructions are directed to use of the pharmaceutical composition for the treatment of an autoimmune disease, in some embodiments, the instructions are directed to use of the pharmaceutical composition for the treatment of an autoimmune disease selected from the group consisting of systemic lupus erythematosus, myestenia gravis, rheumatoid arthritis, acute disseminated encephalomyelitis, idiopathic thrombocytopenic purpura, multiple sclerosis, Sjoegren's syndrome, psoriasis, autoimmune hemolytic anemia, asthma, ulcerative colitis, Crohn's disease, irritable bowel disease, and chronic obstructive pulmonary disease. In some embodiments, the autoimmune disease is selected from the group consisting of asthma, rheumatoid arthritis, multiple sclerosis, chronic obstructive pulmonary disease and systemic lupus erythematosus.

Any pharmaceutical composition provided in the present disclosure may be used in the kits, the same as if each and every composition were specifically and individually listed for use a kit.

Synthesis

The compounds of the disclosure may be prepared using methods disclosed herein and routine modifications thereof which will be apparent given the disclosure herein and methods well known in the art. Conventional and well-known synthetic methods may be used in addition to the teachings herein. The synthesis of typical compounds of Formula I, or a pharmaceutically acceptable salt thereof, may be accomplished as described in the following examples. If available, reagents may be purchased commercially, e.g. from Sigma Aldrich or other chemical suppliers.

General Syntheses

Typical embodiments of compounds in accordance with the present disclosure may be synthesized using the general reaction schemes described below. It will be apparent given the description herein that the general schemes may be altered by substitution of the starting materials with other materials having similar structures to result in products that are correspondingly different. Descriptions of syntheses follow to provide numerous examples of how the starting materials may vary to provide corresponding products. Given a desired product for which the substituent groups are defined, the necessary starting materials generally may be determined by inspection. Starting materials are typically obtained from commercial sources or synthesized using published methods. For synthesizing compounds which are embodiments of the present disclosure, inspection of the structure of the compound to be synthesized will provide the identity of each substituent group. The identity of the final product, will generally render apparent the identity of the necessary starting materials by a simple process of inspection, given the examples herein.

Synthetic Reaction Parameters

The compounds of this disclosure can be prepared from readily available starting materials using, for example, the following general methods and procedures. It will be appreciated that where typical or preferred process conditions (i.e., reaction temperatures, times, mole ratios of reactants, solvents, pressures, etc.) are given, other process conditions can also be used unless otherwise stated. Optimum reaction conditions may vary with the particular reactants or solvent used, but such conditions can be determined by one skilled in the art by routine optimization procedures.

Additionally, as will be apparent to those skilled in the art, conventional protecting groups may be necessary to prevent certain functional groups from undergoing undesired reactions. Suitable protecting groups for various functional group as well as suitable conditions for protecting and deprotecting particular functional groups are well known in the art. For example, numerous protecting groups are described in T. W. Greene and G. M. Wuts (1999) *Protecting Groups in Organic Synthesis*, 3rd Edition, Wiley, New York, and references cited therein.

Furthermore, the compounds of this disclosure may contain a chiral center. Accordingly, if desired, such compounds can be prepared or isolated as pure stereoisomers, i.e., as individual enantiomers or as stereoisomer-enriched mixtures. All such stereoisomers (and enriched mixtures) are included within the scope of this disclosure, unless otherwise indicated. Pure stereoisomers (or enriched mixtures) may be prepared using, for example, optically active starting materials or stereoselective reagents well-known in the art. Alternatively, racemic mixtures of such compounds can be separated using, for example, chiral column chromatography, chiral resolving agents, and the like.

The starting materials for the following reactions are generally known compounds or can be prepared by known procedures or obvious modifications thereof. For example, many of the starting materials are available from commercial suppliers such as Aldrich Chemical Co. (Milwaukee, Wis., USA). Others may be prepared by procedures or obvious modifications thereof, described in standard reference texts such as Fieser and Fieser's Reagents for Organic Synthesis, Volumes 1-15 (John Wiley, and Sons, 1991), Rodd's Chemistry of Carbon Compounds, Volumes 1-5, and Supplementals (Elsevier Science Publishers, 1989) organic Reactions, Volumes 1-40 (John Wiley, and Sons, 1991), March's Advanced Organic Chemistry, (John Wiley, and Sons, $5^{th}$ Edition, 2001), and Larock's Comprehensive Organic Transformations (VCH Publishers Inc., 1989).

The terms "solvent," "inert organic solvent" or "inert solvent" refer to a solvent inert under the conditions of the reaction being described in conjunction therewith (including, for example, benzene, toluene, acetonitrile, tetrahydrofuran ("THF"), dimethylformamide ("DMF"), chloroform, methylene chloride (or dichloromethane), diethyl ether, methanol, pyridine and the like). Unless specified to the contrary, the solvents used in the reactions of the present disclosure are inert organic solvents, and the reactions are carried out under an inert gas, preferably nitrogen.

The term "q.s." means adding a quantity sufficient to achieve a stated function, e.g., to bring a solution to the desired volume (i.e., 100%).

The following examples are included to demonstrate preferred embodiments of the disclosure. It should be appreciated by those of skill in the art that the techniques disclosed in the examples which follow represent techniques discovered by the inventor to function well in the practice of the disclosure, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the disclosure.

| List of abbreviations and acronyms. | |
|---|---|
| Abbreviation | Meaning |
| ° C. | Degree Celsius |
| anal | Analytical |
| ATP | Adenosine-5'-triphosphate |
| ATX II | Anemonia sulcata toxin |
| AcOH | Acetic acid |
| ACN | Acetonitrile |
| CAN | Ceric ammonium nitrate |
| CDI | 1,1'-carbonyldiimidazole |
| CHO | Chinese hamster ovary |
| conc. | Concentrated |
| d | Doublet |
| DABCO | 1,4-Diazabicyclo[2.2.2]octane |
| DAST | (Diethylamino)sulfur trifluoride |
| dd | Doublet of doublets |

List of abbreviations and acronyms.

| Abbreviation | Meaning |
|---|---|
| DCE | 1,2-dichloroethane |
| DCM | Dichloromethane |
| DEAD | Diethyl azodicarboxylate |
| DIPEA | N,N-diisopropylethylamine |
| DMAP | 4-dimethylaminopyridine |
| DME | 1,2-dimethoxyethane |
| DMF | Dimethylformamide |
| DMSO | Dimethylsulfoxide |
| dppf | 1,1'-Bis(diphenylphosphino)ferrocene |
| EA | Ethyl alcohol |
| ECF | Extracellular fluid |
| EDTA | Ethylenediaminetetraacetic acid |
| EGTA | Ethylene glycol tetraacetic acid |
| equiv/eq | Equivalents |
| ESI | Electrospray ionization |
| Ac | Acetate |
| Et | Ethyl |
| EtOAc | Ethyl Acetate |
| g | Grams |
| HEPES | (4-(2-Hydroxyethyl)-1-piperazineethanesulfonic acid) |
| HATU | 2-(7-Aza-1H-Benzotriazole-1-yl)-1,1,3,3-tetramethyluronium hexafluorophosphate |
| hERG | human Ether-a-go-go Related Gene |
| HMDS | hexamethyldisilazane(azide) |
| HPLC | High-performance liquid chromatography |
| h | Hours |
| Hz | Hertz |
| $IC_{50}$ | The half maximal inhibitory concentration |
| IMR-32 | Human neuroblastoma cell line |
| J | Coupling constant |
| Kg | Kilogram |
| kHz | Kilohertz |
| LAH | Lithium ammonium hydride |
| LCMS/LC-MS | Liquid chromatography-mass spectrometry |
| M | Molar |
| m | multiplet |
| m/z | mass-to-charge ratio |
| M+ | Mass peak |
| M + H | Mass peak plus hydrogen |
| mCPBA | 3-chloroperoxybenzoic acid |
| Me | Methyl |
| MeOH | Methanol |
| mg | Milligram |
| MHz | Megahertz |
| min/m | Minute |
| ml/mL | Milliliter |
| mM | Millimolar |
| mmol | Millimole |
| nmol | Nanomole |
| mOsmol | Milliosmole |
| MRM | Magnetic Resonance Microscopy |
| MS | Mass spectroscopy |
| ms | Millisecond |
| mV | Millivolt |
| mw | Microwave |
| N | Normal |
| mol | Mole |
| NMP | N-methylpyrrolidinone |
| NMR | Nuclear magnetic resonance |
| pA | Picoamps |
| Ph | Phenyl |
| ppm | Parts per million |
| prep | Preparative |
| q.s. | Quantity sufficient to achieve a stated function |
| Rf | Retention factor |
| RP | Reverse phase |
| RT/rt | Room temperature |
| s | Second |
| s | Singlet |
| SEM | 2-(Trimethylsilyl)ethoxymethyl |
| t | Triplet |
| TB | Tonic Block |
| TEA | Triethylamine |
| TFA | Trifluoroacetic acid |
| THF | Tetrahydrofuran |
| TLC | Thin layer chromatography |
| TMS | trimethylsilyl |
| TTX | Tetrodotoxin |
| UDB | Use Dependent Block |
| WT | Wild type |
| δ | Chemical shift |
| μg | Microgram |
| μL/μl | Microliter |
| μM | Micromolar |
| μm | Micrometer |
| μmol | Micromole |

EXAMPLES

Preparation of Common Intermediates

Intermediate 1.01

Preparation of tert-Butyl (6-bromoimidazo[1,2-a]pyrazin-8-yl)(4-(4-(oxetan-3-yl)piperazin-1-yl)phenyl)carbamate IV and tert-butyl 4-(4-(oxetan-3-yl)piperazin-1-yl)phenyl(6-(tributylstannyl)imidazo[1,2-a]pyrazin-8-yl)carbamate V

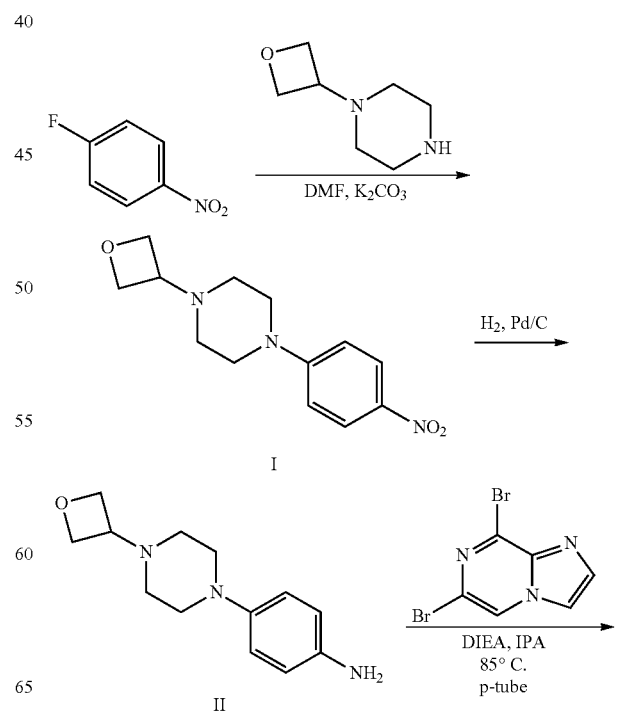

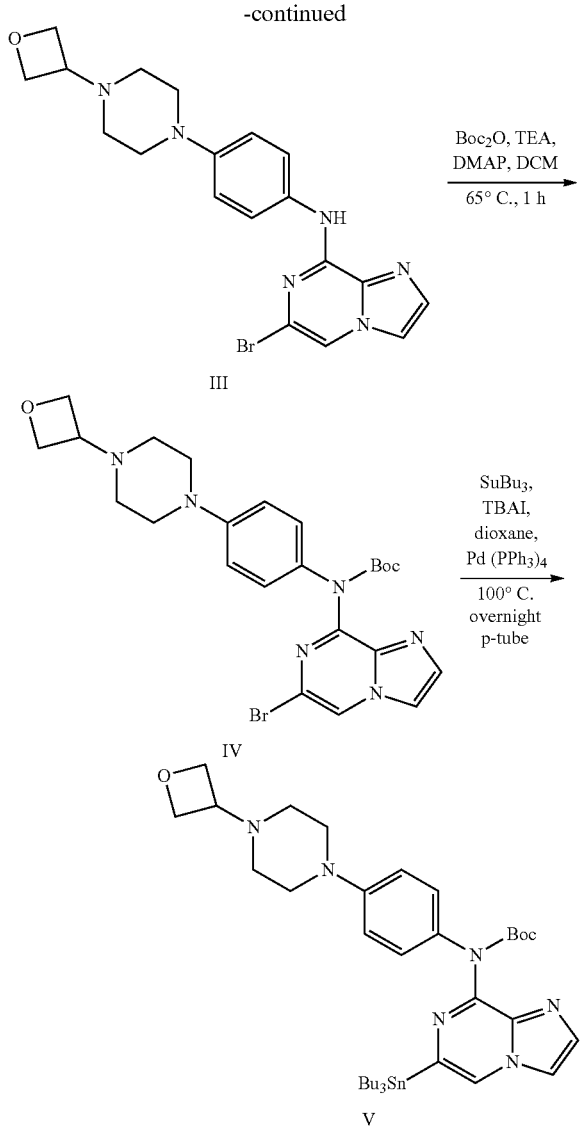

1-(4-Nitrophenyl)-4-(oxetan-3-yl)piperazine I: In a 500 mL round bottom flask, 1 (oxetan-3-yl)piperazine (3.02 g, 21.26 mmoles), potassium carbonate (5.87 g, 42.52 mmoles), 1-fluoro-4-nitrobenzene (3.00 g, 21.26 mmoles) was combined in acetonitrile (33 mL) and stirred under nitrogen overnight at 100° C. The mixture was diluted with water (100 mL) and extracted with DCM (100 mL×3), dried over anhydrous sodium carbonate, filtered and the filtrate was concentrated. The residue was dissolved in minimal DCM using a sonicator and crashed out with hexane. The precipitate was filtered, washed with hexane and dried, to provide the title compound I as an orange solid (4.70 g, 17.85 mmoles, 84%).

4-(4-(Oxetan-3-yl)piperazin-1-yl)aniline II: In a hydrogenation vessel, 1-(4-nitrophenyl)-4-(oxetan-3-yl)piperazine I (4.70 g, 17.85 mmoles) was dissolved as much as possible in MeOH (26 mL) and DCM (5 mL). Pd/C (10%) (2.85 g, 2.68 mmoles) was added and the reaction was stored under nitrogen. The reaction was shaken on the Parr hydrogenator at 45 PSI. After 15 minutes, the reaction was fully recharged to 45 PSI and shaken for an additional hour. The material was filtered over celite, washed with 25% MeOH/DCM and concentrated to provide the title compound II as a light brown solid (4.16 g, 17.85 mmoles, 98%).

6-Bromo-N-(4-(4-(oxetan-3-yl)piperazin-1-yl)phenyl)imidazo[1,2-a]pyrazin-8-amine III: To 4-(4-(oxetan-3-yl)piperazin-1-yl)aniline II (2.00 g, 8.57 mmoles), hunig's base (3.29 mL) and 6,8-dibromoimidazo[1,2-a]pyrazine (2.37 g, 8.57 mmoles) was added in DMF (43 mL). The reaction was stirred at 85° C. in a pressure tube for overnight. The material was quenched with saturated sodium bicarbonate, extracted with DCM (120 mL×3) and the organic layers were combined and washed with water (120 mL×3), dried over anhydrous sodium carbonate and concentrated. The crude material was purified using a 120 g Isco column and eluted off using a stepwise gradient of 0-60% (10% MeOH/DCM). The desired fractions were combined and concentrated to provide the title compound III as a light yellow solid (3.00 g, 6.99 mmoles, 82%).

tert-Butyl (6-bromoimidazo[1,2-a]pyrazin-8-yl)(4-(4-(oxeta-3-yl)piperazin-1-yl)phenyl)carbamate IV: 6-bromo-N-(4-(4-(oxetan-3-yl)piperazin-1-yl)phenyl)imidazo[1,2-a]pyrazin-8-amine III (1000 mg, 2.33 mmol), di-ter-butyl dicarbonate (1016.72 mg, 4.66 mmol) and N,N-dimethylpyridin-4-amine (21.34 mg, 0.17 mmol) were stirred in DCM (1.01 ml) and refluxed at 65° C. for 3 h. The reaction was diluted with 100 mL of DCM, washed with H2O (×3), dried, filtered and concentrated. The crude material was dissolved in minimal DCM, loaded onto a preloaded silica loader and eluted off a 40 g column using 0-30% MeOH/DCM over 20 column volumes. The desired fractions were combined and concentrated to provide the title compound IV (1.2 g, 97%). This compound is used in Example 2.

tert-Butyl 4-(4-(oxetan-3-yl)piperazin-1-yl)phenyl(6-(tributylstannyl)imidazo[1,2-a]pyrazin-8-yl)carbamate V: In a 350 mL p-tube, tert-butyl 6-bromoimidazo[1,2-a]pyrazin-8-yl(4-(4-(oxetan-3-yl)piperazin-1-yl)phenyl)carbamate IV (8150 mg, 15.39 mmol), 1,1,1,2,2,2-hexabutyldistannane (11.67 ml, 23.09 mmol), tetrakis(triphenylphosphine)palladium (889.43 mg, 0.77 mmol), and tetrabutylammonium iodide (5686.03 mg, 15.39 mmol) were combined in dioxane (62 ml) and heated to 110° C. overnight. According to LCMS, no starting material remained. The reaction was absorbed onto celite and eluted off a 160 g alumina column using a 0-10-20-30-100% (50% EtOAc/Hex-Hex) gradient holding at 50% for 10-15 column volumes over 50-60 column volumes to provide the title compound V (5.83 g, 51%). This compound is used in Examples 1 and 2.

Intermediate 1.02

Preparation tert-butyl (6-bromo-5-methylimidazo[1,2-a]pyrazin-8-yl)(4-(4-(oxetan-3-yl)piperazin-1-yl)phenyl)carbamate X

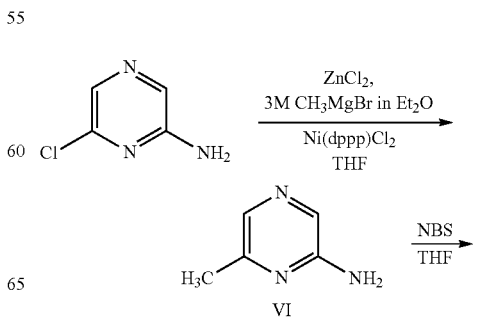

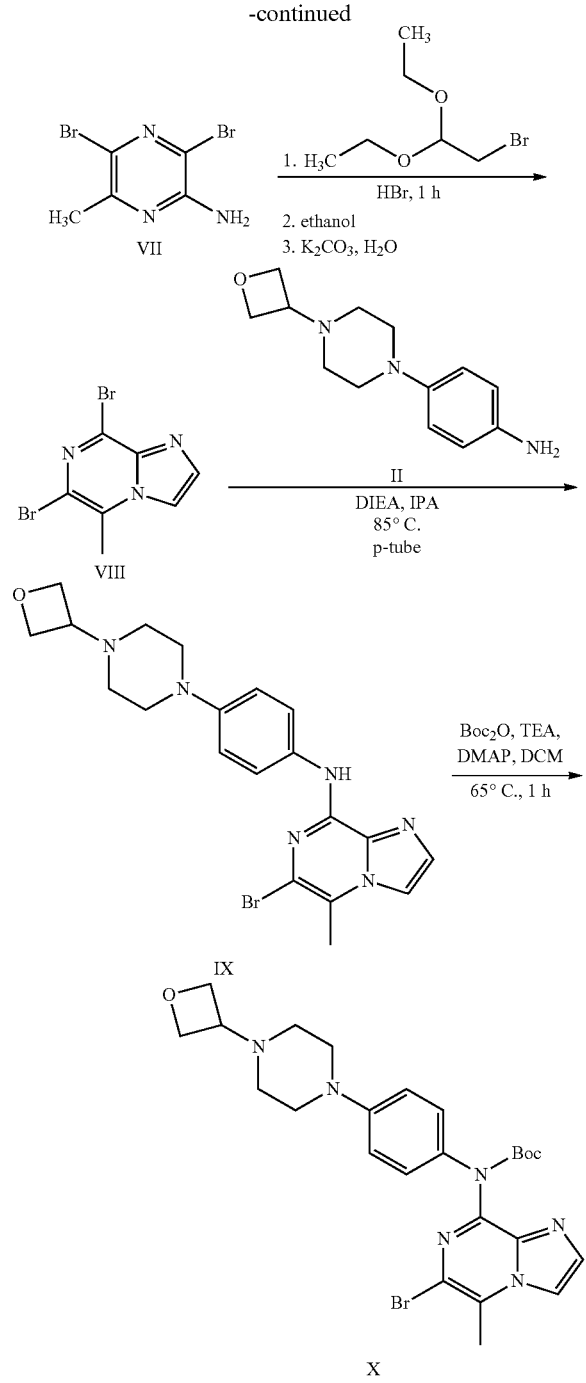

dried over sodium sulfate. The drying agent was filtered and the filtrate concentrated under reduced pressure to provide crude 6-methylpyrazin-2-amine VI (2.60 g, 62%) as a light yellow solid which was used in the next step without purification: $^1$H NMR (400 MHz, CDCl$_3$) δ: 7.63 (s, 1H), 7.53 (s, 1H), 4.96 (bs, 2H), 2.16 (s, 3H).

3,5-Dibromo-6-methylpyrazin-2-amine VII: To a solution of 6-methylpyrazin-2-anine VI (2.00 g, 18.3 mmol) in THF (40 mL) at 10° C., was added N-bromosuccinimide (6.70 g, 37.6 mmol) portion wise over 15 min and the mixture allowed to warm to room temperature while stirring. After 2 h, the reaction was concentrated under reduced pressure and the resulting residue was purified by column chromatography (silica, gradient, hexanes to EtOAc) to provide 3,5-dibromo-6-methylpyrazin-2-amine VII (3.10 g, 64%) as an orange solid: $^1$H NMR (400 MHz, CDCl$_3$) δ: 4.93 (bs, 2H), 2.38 (s, 3H).

6,8-Dibromo-5-methylimidazo[1,2-a]pyrazine VIII: A mixture of 2-bromo-1,1-diethoxyethane (3.21 mL, 20.7 mmol) and 48% aqueous hydrobromic acid (1.0 mL) was stirred at reflux for 2 h. The reaction was then cooled to room temperature and treated with sodium bicarbonate until gas evolution ceased. The mixture was filtered and the filtrate diluted with ethanol (15 mL). To this mixture, 3,5-dibromo-6-methylpyrazin-2-amine VII (3.00 g, 11.2 mmol) was added and the reaction stirred at reflux for 16 h. After this time, the reaction was cooled to room temperature and concentrated under reduced pressure to a volume of approximately 10 mL. The suspension was filtered and the filter cake washed with cold ethanol (5 mL). The filter cake was then taken into water (50 mL) and the pH was adjusted to ~8 with potassium carbonate. The resulting suspension was filtered and the filter cake dried to a constant weight under vacuum to provide 6,8-dibromo-5-methylimidazo[1,2-a]pyrazine VIII (1.97 g, 60%) as a light brown solid: $^1$H NMR (400 MHz, CDCl$_3$) δ: 7.90 (s, 1H), 7.72 (s, 1H), 2.74 (s, 3H).

6-Bromo-5-methyl-N-(4-(4-(oxetan-3yl)piperazin-1-yl)phenyl)imidazo[1,2-a]pyrazin 8-amine IX: The compound IX was prepared from 6,8-dibromo-5-methylimidazo[1,2-a]pyrazine VIII using the method as described for preparing 6-bromo-N-(4-(4-(oxetan-3-yl)piperazin-1-yl)phenyl)imidazo[1,2-a]pyrazin-4-amine III in Intermediate Example 1.01.

tert-Butyl (6-bromo-5-methylimidazo[1,2a]pyrazin-8-yl)(4-(4-(oxetan-3-yl)piperazin-1-yl)phenyl)carbamate X: The compound X was prepared from 6-bromo-5-methyl-N-(4-(4-(oxetan-3-yl)piperazin-1-yl)phenyl)imidazo[1,2-a]pyrazin-8-amine IX using the method as described for preparing tert-butyl (6-bromoimidazo[1,2-a]pyrazin-8-yl)(4-(4-(oxetan-3yl)piperazin-1-yl)phenyl)carbamate IV in Intermediate Example 1.01. This compound is used in Example 4.

Synthesis of Examples 1-7

Example 1

Preparation of 6-(6-amino-5-methylpyrazin-2-yl)-N-(4-(4-(oxetan-3-yl)piperazin-1-yl)phenyl)imidazo[1,2-a]pyrazin-8-amine (1)

6-Methylpyrazin-2-amine VI: To a solution of anhydrous zinc(II) chloride (26.3 g, 193 mmol) in THF (150 mL) at 0° C., was added 3M methyl magnesium bromide in diethyl ether (129 mL) drop wise over a period of 1 h. [1,3-Bis(diphenylphosphino)propane]nickel(II) chloride (2.08 g, 3.85 mmol) was then added and the mixture allowed to warm to room temperature. To the above mixture, a solution of 6-chloro-2-aminopyrazine (5.00 g, 38.6 mmol) in anhydrous THF (25 mL) was added and the reaction stirred, under a nitrogen atmosphere, at reflux for 6 h. After this time, the mixture was cooled to room temperature, then to 0° C. and carefully quenched with saturated aqueous ammonium chloride (50 mL). The organic layer was separated and

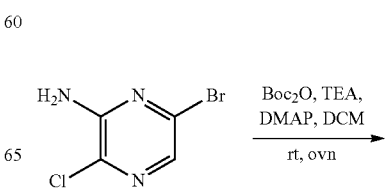

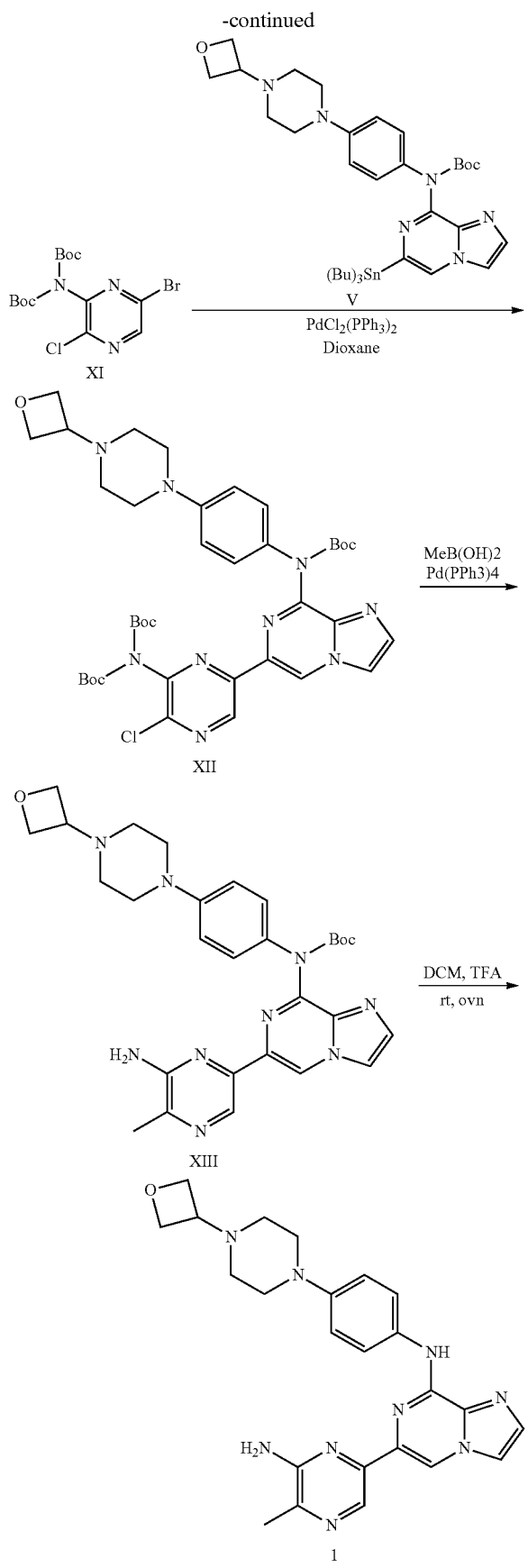

2-Bis(tert-butoxycarbonyl)amino-6-bromo-3-chloropyrazine XI: 6-bromo-3-chloropyrazin-2-amine (2000 mg, 9.59 mmol) was dissolved in DCM (48 ml) followed by Triethylamine (3.99 ml, 28.78 mmol), di-tert-butyl dicarbonate (4188.12 mg, 19.19 mmol), and N,N-dimethylpyridin-4-amine (87.91 mg, 0.72 mmol). The reaction was allowed to stir at rt for overnight. The crude material was washed with water, dried, filtered and concentrated. The crude material was dissolved in minimal DCM and loaded onto a 25 g prepacked silica loader and eluted off a 40 g column using 0-30% MeOH/DCM. The title compound XI (3900 mg, 99%) was isolated and identified by LCMS and NMR. The product was a mix of mono and bis boc-protected material, mainly bis boc-protected as seen by NMR.

tert-Butyl tert-butoxycarbonyl(6-(8-((tert-butoxycarbonyl)(4-(4-(oxetan-3-yl)piperazin-1-yl)phenyl)amino)imidazo[1,2-a]pyrazin-6-yl)-3-chloropyrazin-2-yl)carbamate XII: tert-Butyl 4-(4-(Oxetan-3-yl)piperazin-1-yl)phenyl(6-(tributylstannyl)imidazo[1,2-a]pyrazin-8-yl)carbamate V (1000 mg, 1.4 mmol), 2-Bis(tert-butoxycarbonyl)amino-6-bromo-3-chloropyrazine XI (552 mg, 1.35 mmol), and PdCl$_2$(PPh$_3$)$_2$ (142.77 mg, 0.20 mmol), in 1,4-Dioxane (11.27 ml) was irridated in the microwave for 20 min at 140° C. The reaction was absorbed onto celite and eluted off a 40 g Gold Isco column using 0-10-100% (30% MeOH/DCM) over 20 column volumes. Fractions 34-39 were collected and concentrated. According to NMR, the title compound XII was identified and isolated (590 mg, 55%).

tert-Butyl (6-(6-amino-5-methylpyrazin-2-yl)imidazo[1,2-a]pyrazin-8-yl)(4-(4-(oxetan-3-yl)piperazin-1-yl)phenyl)carbamate XIII: In a microwave vial, tert-butyl tert-butoxycarbonyl(6-(8-((tert-butoxycarbonyl)(4-(4-(oxetan-3-yl)piperazin-1-yl)phenyl)amino)imidazo[1,2-a]pyrazin-6-yl)-3-chloropyrazin-2-yl)carbamate XII (300 mg, 0.44 mmol), methylboronic acid (794.39 mg, 13.27 mmol), tetrakis(triphenylphosphine)palladium (51.12 mg, 0.04 mmol), and 2M Na$_2$CO$_3$ (0.44 ml) were combined in DME (1.77 ml) and irridated in the microwave for 20 min at 150° C. The reaction was worked up using 25% MeOH/DCM and water. The organic layers were combined, dried, filtered and concentrated. The crude material was loaded onto silica and eluted off a 40 g Gold column using 0-5-15-25-50% (30% MeOH/DCM) over 45 column volumes. The desired fractions were concentrated and provided tert-butyl (6-(6-amino-5-methylpyrazin-2-yl)imidazo[1,2-a]pyrazin-8-yl)(4-(4-(oxetan-3-yl)piperazin-1-yl)phenyl)carbamate XIII as the minor product and the desired final compound 1 as an inseparable mixture (208 mg total) and were taken in to the TFA reaction.

6-(6-Amino-5-methylpyrazin-2-yl)-N-(4-(4-(oxetan-3-yl)piperazin-1-yl)phenyl)imidazo[1,2-a]pyrazin-8-amine (1): To a solution of tert-butyl 6-(6-amino-5-methylpyrazin-2-yl)imidazo[1,2-a]pyrazin-8-yl(4-(4-(oxetan-3-yl)piperazin-1-yl)phenyl)carbamate XIII (48 mg, 0.09 mmol) and 6-(6-amino-5-methylpyrazin-2-yl)-N-(4-(4-(oxetan-3-yl)piperazin-1-yl)phenyl)imidazo[1,2-a]pyrazin-8-amine (1, 160 mg, 0.35 mmol) in DCM (2.5 ml) was added TFA (0.16 ml, 2.15 mmol). The resulting mixture was stirred at room temperature overnight. According to LCMS, the reaction was incomplete. The reaction was subjected to additional TFA (0.16 ml, 2.15 mmol) and stirred for 1 h. According to LCMS, the reaction was incomplete, the reaction was subjected to additional TFA (0.32 ml, 4.3 mmol) and stirred for 2 h more. The reaction was cooled to 0° C. and quenched with sat. NaHCO$_3$, then extracted with DCM (5 ml×3), and the combined organic layers were washed with water (5 ml×2), brine (5 ml×1), dried (Na$_2$SO$_4$), and concentrated to give the crude product. The crude material was absorbed onto silica and eluted off a 24 g Gold Isco column using 0-15-25-40-100% (30% MeOH/DCM). The desired fractions were combined and concentrated to provide the desired compound (1, 67.5 mg, 34%). LCMS-ESI$^+$ (m/z): [M+H]$^+$: 458.22. $^1$H NMR (300 MHz, d$_6$-DMSO) δ: 9.48 (s, 1H), 8.54 (s, 1H), 8.41 (s, 1H), 8.11 (s, 1H), 7.95 (d, 2H), 7.6 (s, 1H), 6.98 (d, 2H), 6.2 (s, 2H), 4.58-4.45 (dt, 4H), 3.3 (m, 1H), 3.14 (t, 4H), 2.50-2.4 (dt, 4H), 2.33 (s, 1H). Alternatively, compound XII could be taken directly to this step and similarly de-protected to provide the 5-chloropyrazine substituted analog.

Example 2

Preparation of 6-(6-aminopyrazin-2-yl)-N-(4-(4-(oxetan-3yl)piperazin-1-yl)phenyl)imidazo[1,2-a]pyrazin-8-amine (2)

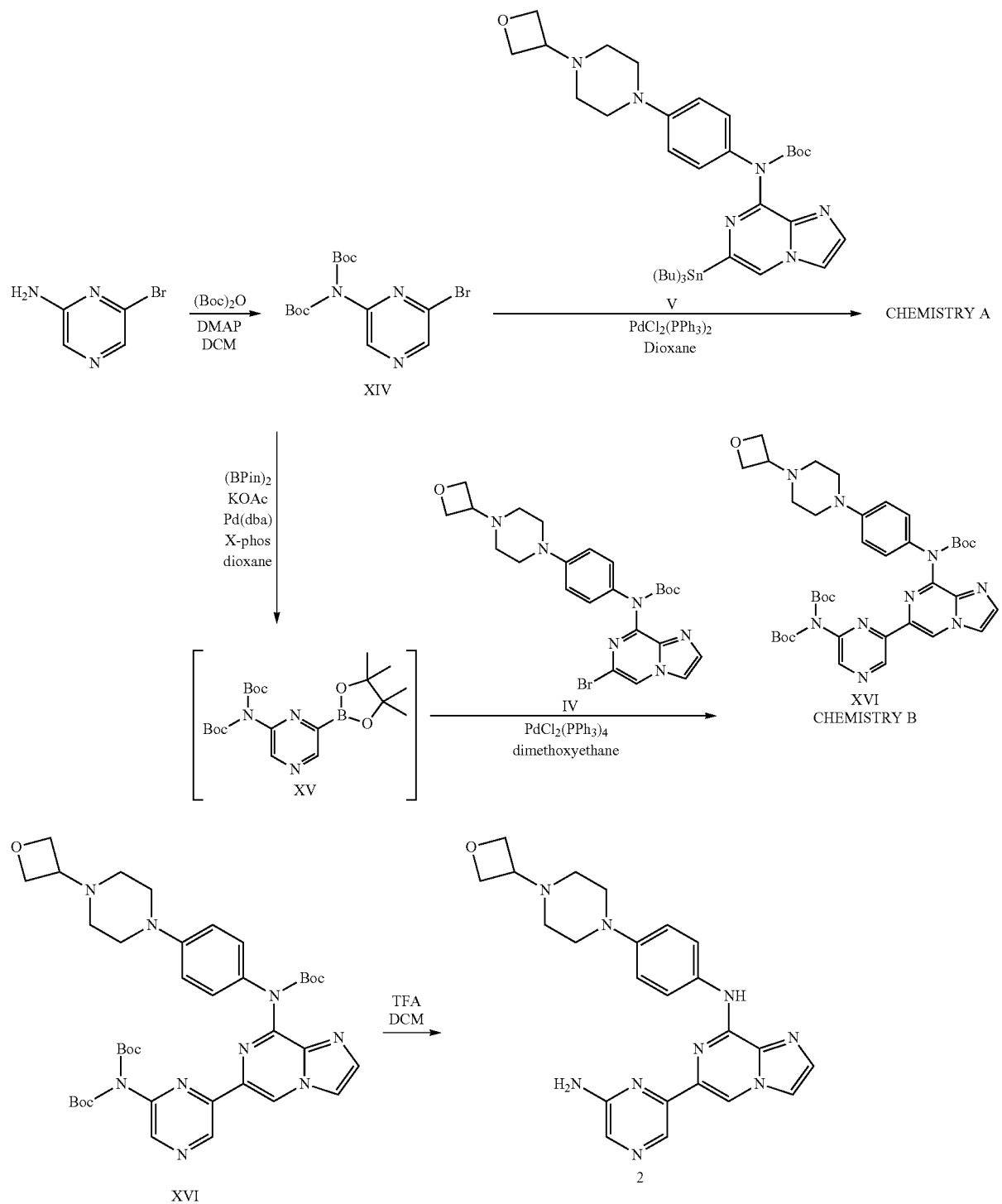

2-Bis(tert-butoxycarbonyl)amino-6-bromopyrazine XIV: To a mixture of 6-bromopyrazin-2-amine (5 g, 28.7 mmol) and di-tert-butyl dicarbonate (25.09 g, 114.94 mmol) was added DCM (10 ml) followed by DMAP (0.351 g, 29 mmol). The reaction was heated to 55° C. for 1 h, cooled to RT, the reaction was partitioned between water and DCM, purified on silica gel and concentrated to provide 10.75 g (87% yield) of 2-bis(tert-butoxycarbonyl)amino-6-bromopyrazine XIV. LCMS-ESI$^+$ (m/z): [M+H]$^+$: 374.14. $^1$H NMR (DMSO) δ: 8.84 (d, 2H), 1.39 (s, 18H).

tert-Butyl (6-(6-(bis(tert-butoxycarbonyl)amino)pyrazin-2-yl)imidazo[1,2-a]pyrazin-8-yl)(4-(4-(oxetan-3-yl)piperazin-1-yl)phenyl)carbamate XVI-CHEMISTRY A route: tert-Butyl 4-(4-(oxetan-3-yl)piperazin-1-yl)phenyl(6-(tributylstannyl)imidazo[1,2-a]pyrazin-8-yl)carbamate V (215 mg, 0.291 mmol), was combined with 2-bis(tert-butoxycarbonyl)amino-6-bromopyrazine XIV (217.58 mg, 0.581 mmol), bis(triphenylphosphine)palladium(II) dichloride (30.61 mg, 0.044 mmol) and 1,4-dioxane (5 ml). The reaction mixture was stirred in a microwave reactor at 120° C. for 30 min. The reaction mixture was quenched with saturated KF, extracted with EtOAc, purified on silica gel, eluted with EtOAc. The desired fractions were combined and concentrated to provide 100 mg (46% yield) of tert-butyl (6-(6-(bis(tert-butoxycarbonyl)amino)pyrazin-2-yl)imidazo[1,2-a]pyrazin-8-yl)(4-(4-(oxetan-3-yl)piperazin-1-yl)phenyl)carbamate XVI. LCMS-ESI$^+$ (m/z): [M+H]$^+$: 744.4. $^1$H NMR (300 MHz d$_6$-DMSO) δ: 9.37 (s, 1H), 9.18 (s, 1H), 8.77 (s, 1H), 8.33 (d, 1H), 7.87 (d, 1H), 7.28-7.25 (d, 2H), 6.92-6.89 (d, 2H), 4.55-4.41 (m, 4H) 3.4 (m, 1H), 3.14-3.11 (m, 4H), 2.37-2.34 (m, 4H), 1.37 (s, 18H), 1.3 (s, 9H).

tert-Butyl (6-(6-(bis(tert-butoxycarbonyl)amino)pyrazin-2-yl)imidazo[1,2-a]pyrazin-8-yl)(4-(4-(oxetan-3-yl)piperazin-1-yl)phenyl)carbamate XVI-CHEMISTRY B route: Step 1: To a dry 250 mL round-bottomed flask was added 2-bis(tert-butoxycarbonyl)amino-6-bromopyrazine XIV (1.0 g, 1.0 equiv, 2.67 mmol), KOAc (790 mg, 8.02 mmol, 3.0 equiv), 4,4,4',4',5,5,5',5'-octamethyl-2,2'-bi(1,3,2-dioxaborolane) (750 mg, 2.94 mmol, 1.1 equiv), Pd(dba) (171 mg, 0.187 mmol, 0.07 equiv) and X-phos (128 mg, 0.267 mmol, 0.1 equiv) followed by 1,4-dioxane (25 mL) and the solution was sonicated for 5 min and then purged with N$_2$ gas for 5 min. The flask with contents was then placed under N$_2$ atmosphere and heated at 110° C. for 90 min. Once full conversion to the pinacolboronate was achieved by LCMS, the reaction was removed from heat and allowed to cool to RT. Once cool, the reaction contents were filtered through Celite and the filter cake was washed 3×20 mL EtOAc. The resultant solution was then concentrated down to a deep red-orange syrup providing N,N-BisBoc 6-(4,4,5,5-tetramethyl-1,3,2-dioxaborolan-2-yl)pyrazin-2-amine XV, which was used directly in the next step.

Step 2: The freshly formed N,N-BisBoc 6-(4,4,5,5-tetramethyl-1,3,2-dioxaborolan-2-yl)pyrazin-2-amine XV (2.67 mmol based on 100% conversion, 2.0 equiv based on bromide) was dissolved in 20 Ml of 1,2-dimethoxyethane and to that solution was added tert-butyl (6-bromoimidazo[1,2-a]pyrazin-8-yl)(4-(4-(oxetan-3-yl)piperazin-1-yl)phenyl)carbamate IV (707 mg, 1.34 mmol, 1.0 equiv), Na$_2$CO$_3$ (283 mg, 2.67 mmol, 2.0 equiv), Pd(PPh$_3$)$_4$ (155 mg, 0.134 mmol, 0.1 equiv) and water (10 mL) and the solution was degassed for 5 min using N$_2$ gas. The reaction was then placed under N$_2$ atmosphere and heated at 110° C. for 90 min. LCMS showed complete consumption of the bromide starting material and the reaction was removed from heat and allowed to cool to RT. The reaction was diluted with 100 mL water and 100 mL 20% MeOH/DCM and the organic layer was recovered, extracted 1×sat. NaHCO$_3$, 1×sat brine and then dried over Na$_2$SO$_4$. The solution was then filtered and concentrated down to an orange-red solid. The sample was then slurried in warm MeOH, sonicated then filtered, washing 2×20 mL with cold MeOH and then the cream-colored solid was dried on hi-vacuum overnight to yield 905 mg of tert-butyl (6-(6-(bis(tert-butoxycarbonyl)amino)pyrazin-2-yl)imidazo[1,2-a]pyrazin-8-yl)(4-(4-(oxetan-3-yl)piperazin-1-yl)phenyl)carbamate XVI in a 90% yield over 2 steps (95% per step).

6-(6-Aminopyrazin-2-yl)-N-(4-(4-(oxetan-3-yl)piperazin-1-yl)phenyl)imidazol[1,2-a]pyrazin-8-amine (2): To a solution of tert-butyl (6-(6-(bis(tert-butoxycarbonyl)amino)pyrazin-2-yl)imidazo[1,2-a]pyrazin-8-yl)(4-(4-(oxetan-3-yl)piperazin-1-yl)phenyl)carbamate XVI (200 mg, 0.269 mmol) in DCM (2 ml) was added TFA (0.5 ml, 6.578 mmol). The reaction was stirred at rt for 16 h, saturated sodium bicarbonate was added, extracted with EtOAC and purified on silica gel, eluted with 5% MeOH/EtOAc, 20% MeOH/EtOAc. The desired fractions were combined and concentrated to provide 100 mg (83% yield) of the title compound 2. LCMS-ESI$^+$ (m/z): [M+H]$^+$: 444.2. $^1$H NMR (300 MHz d$_6$-DMSO) δ: 9.5 (s, 1H), 8.588 (s, 1H), 8.47 (s, 1H), 8.12 (d, 1H), 7.95-7.92 (d, 2H), 7.88 (s, 1H), 7.62 (s, 1H), 6.99-6.96 (d, 2H), 6.46 (s, 2H), 4.57-4.53 (m, 2H), 4.48-4.44 (m, 2H), 3.43 (m, 1H), 3.15-3.12 (m, 4H), 2.41-2.38 (m, 4H).

Example 3

Preparation of (R)-(4-(4-((6-(6-aminopyrazin-2-yl)imidazo[1,2-a]pyrazin-8-yl)amino)phenyl)morpholin-2-yl)methanol (3)

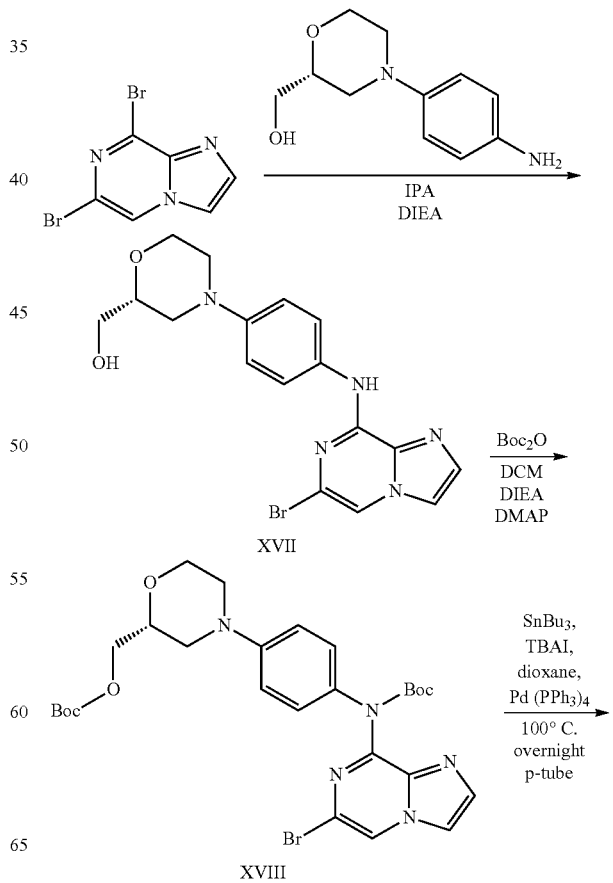

-continued

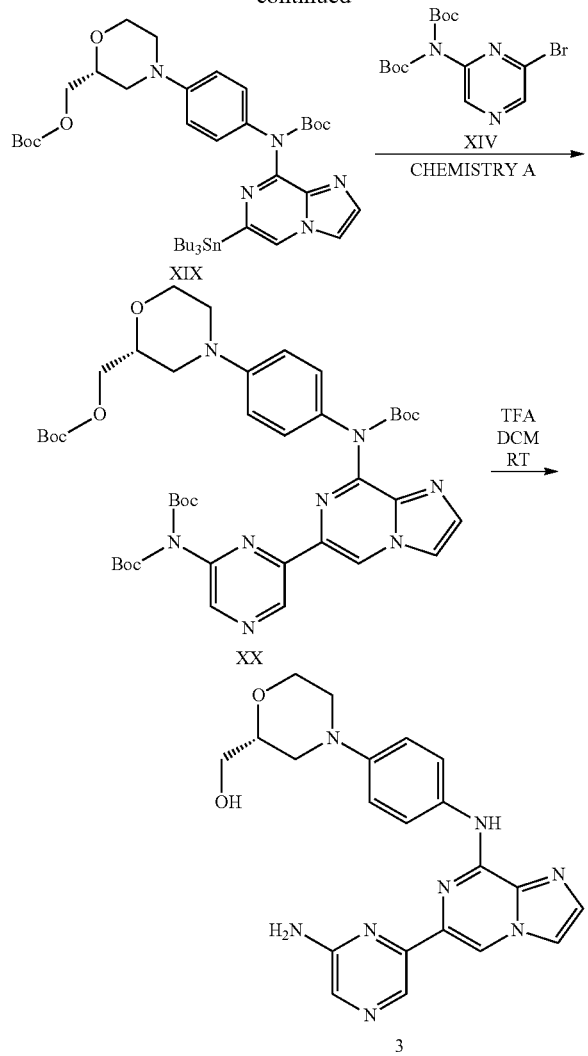

(R)-(4-(4-((6-Bromoimidazo[1,2-a]pyrazin-8-yl)amino)phenyl)morpholin-2-yl)methanol XVII: In a 250 mL round bottom flask equipped with a condenser was placed 6,8-dibromoimidazo[1,2-a]pyrazine (2000 mg, 7.22 mmol) and added 30 mL isopropanol followed by N,N-diisopropylethylamine (2.52 ml, 14.44 mmol) and (R)-(4-(4-aminophenyl)morpholin-2-yl)methanol (1504.12 mg, 7.22 mmol). The reaction was heated to reflux (oil bath 95° C.) overnight. The reaction was cooled and precipitates were collected by filtration and washed with isopropanol followed by hexanes to give the desired compound XVII, 2.92 g, 95% yield.

(R)-tert-Butyl (6-bromoimidazo[1,2-a]pyrazin-8-yl)(4-(((tert-butoxycarbonyl)oxy)methyl)morpholino)phenyl)carbamate XVIII: In a 250 mL round bottom flask was placed (R)-(4-(4-((6-bromoimidazo[1,2-a]pyrazin-8-yl)amino)phenyl)morpholin-2-yl)methanol XVII (2.80 g, 6.9 mmol) and added DCM followed by triethylamine (2.9 mL, 2.1 g, 20.8 mmol), DMAP (63 g, 0.52 mmol) and di-tert-butyl dicarbonate (3.8 g, 17.3 mmol). The reaction was stirred overnight then diluted with DCM and water, separated, washed with brine, dried over $Na_2SO_4$, filtered and concentrated under reduced pressure. The crude material was purified by chromatography: ISCO 40 g silica with 25 g silica loader, eluting with 0-100% EtOAc/hexanes to give compound XVIII (1.66 g, 40%).

(R)-tert-Butyl (4-(2-(((tert-butoxycarbonyl)oxy)methyl)morpholino)phenyl)(6-(tributylstannyl)imidazo[1,2-a]pyrazin-8-yl)carbamate XIX: (R)-tert-Buty (6-bromoimidazo[1,2-a]pyrazin-8-yl)(4-(2-(((tert-butoxycarbonyl)oxy)methyl)morpholino)phenyl)carbamate XVIII was reacted according to the analogous method of Example Intermediate 1.01 to provide (R)-tert-buty (4-(2-(((tert-butoxycarbonyl)oxy)methyl)morpholino)phenyl)(6-(tributylstannyl)imidazo[1,2-a]pyrazin-8-yl)carbamate XIX.

(R)-tert-Butyl (6-(6-(bis(tert-butoxycarbonyl)amino)pyrazin-2-yl)imidazo[1,2-a]pyrazin-8-yl)(4-(2-(((tert-butoxycarbonyl)oxy)methyl)morpholino)phenyl)carbamate XX: (R)-tert-Butyl (4-(2-(((tert-butoxycarbonyl)oxy)methyl)morpholino)phenyl)(6-(tributylstannyl)imidazo[1,2-a]pyrazin-8-yl)carbamate XIX was reacted with 2-Bis(tert-butoxycarbonyl)amino-6-bromopyrazine XIV according to the analogous method of CHEMISTRY A as described in Example 2 to provide the desired compound (R)-tert-butyl (6-(6-(bis(tert-butoxycarbonyl)amino)pyrazin-2-yl)imidazo[1,2-a]pyrazin-8-yl)(4-(2-(((tert-butoxycarbonyl)oxy)methyl)morpholino)phenyl)carbonate XX.

(R)-(4-(4-((6-(6-Amino-5-methylpyrazin-2-yl)imidazo[1,2a]pyrazin-8-yl)amino)phenyl)morpholin-2-yl)methanol (3): (R)-tert-butyl (6-(6-(bis(tert-butoxycarbonyl)amino)pyrazin-2-yl)imidazo[1,2-a]pyrazin-8-yl)(4-(2-(((tert-butoxycarbonyl)oxy)methyl)morpholino)phenyl)carbamate XX (460 mg, 0.56 mmol) in DCM was added to a round bottom flask, and TFA (1.29 ml, 16.85 mmol) was added. The reaction was partially complete after stirring ~5 hours. Added an additional 10 eq TFA and stirred overnight, then concentrated under reduced pressure. 10% MeOH/DCM (~100 mL) and sat.aq. sodium bicarbonate were added and stirred 15 min, separated, extracted with ~100 mL 10% MeOH/DCM. The organic layers were combined, washed with brine, dried over $Na_2SO_4$, filtered and concentrated under reduced pressure and dried under vacuum. The resulting solid was triturated with DCM, collected solids via filtration and dried under vacuum to give a brown solid, 125 mg, with identity confirmed as compound 3 by NMR and LC-MS. LCMS-ESI+ (m/z): [M+H]+: 419.2. $^1$H NMR (300 MHz $d_6$ DMSO) δ: 9.57 (s, 1H), 8.59 (s, 1H), 8.47 (s, 1H), 8.13 (d, J=1.2 Hz, 1H), 8.06-7.90 (m, 2H), 7.87 (s, 1H), 7.62 (d, J=1.1 Hz, 1H), 7.05-6.93 (m, 2H), 6.49 (s, 2H), 4.78 (t, J=5.8 Hz, 1H), 3.98-3.87 (m, 1H), 3.71-3.36 (m, 7H), 2.63 (td, J=11.7, 3.4 Hz, 1H), 2.37 (dd, J=12.1, 10.5 Hz, 1H). The corresponding (S) isomer, or racemic mixture of compounds is prepared similarly, using (S)-(4-(4-aminophenyl)morpholin-2-yl)methanol or a racemic mixture of (4-(4-aminophenyl)morpholino-2-yl)methanol, respectively, in the first step.

Example 4

Preparation of 6-(6-aminopyrazin-2-yl)-5-methyl-N-(4-(4-(oxetan-3-yl)piperazin-1-yl)phenyl)imidazo[1,2-a]pyrazin-8-amine (4)

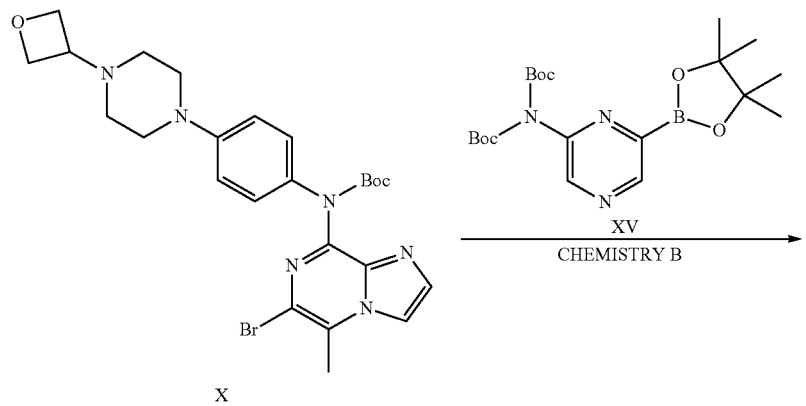

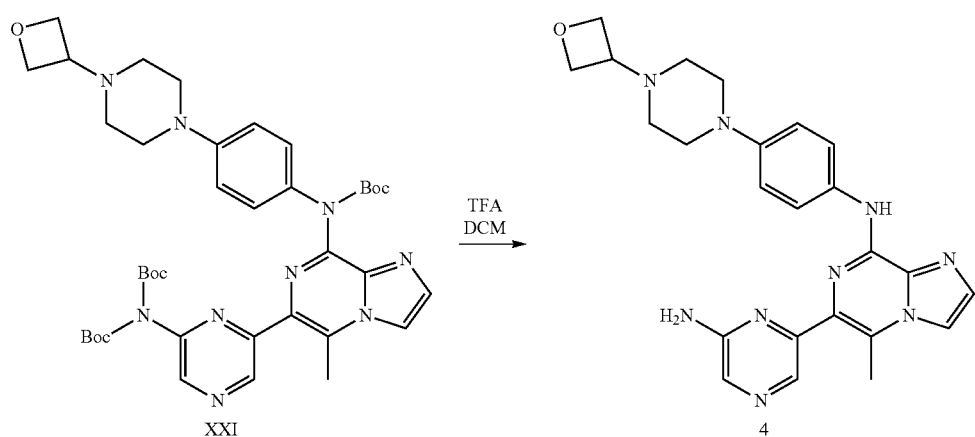

tert-Butyl (6-(6-(bis(tert-butoxycarbonyl)amino)pyrazin-2-yl)-5-methylimidazo[1,2-a]pyrazin-8-yl)(4-(4-(oxetan-3-yl)piperazin-1-yl)phenyl)carbamate XXI: tert-Butyl (6-bromo-5-methylimidazo[1,2-a]pyrazin-8-yl)(4-(4-(oxetan-3-yl)piperazin-1-yl)phenyl)carbamate X was reacted with XV according to the methods of CHEMISTRY B as described in Example 2 to provide the desired compound XXI.

6-(6-aminopyrazin-2-yl)-5-methyl-N-(4-(4-(oxetan-3-yl)piperazin-1-yl)phenyl)imidazo[1,2a]pyrazin-8-amine (4): The compound tert-butyl (6-(6-(bis(tert-butoxycarbonyl)amino)pyrazin-2-yl)-5-methylimidazo[1,2-a]pyrazin-8-yl) (4-(4-(oxetan-3-yl)piperazin-1-yl)phenyl)carbamate XXI was de-protected by the analogous method described in Example 2 to provide the desired compound 4. LCMS-ESI⁺ (m/z): [M+H]⁺: 458.32. ¹H NMR (300 MHz, d₆-DMSO) δ: 9.28 (s, 1H), 8.28 (s, 1-1), 8.04 (s, 1H), 7.89 (d, 2H), 7.83 (s, 1H), 7.7 (s, 1H), 6.91 (d, 2H), 6.46 (s, 2H), 4.6-4.4 (dt, 4H). 3.43 (m, 1H), 3.1 (t, 4H), 2.49 (s, 3H), 2.4 (t, 4H).

Example 5
Preparation of 2-(5-((6-(6-aminopyrazin-2-yl)imidazo[1,2-a]pyrazin-8-yl)amino)-2-(4-(oxetan-3-yl)piperazin-1-yl)phenoxy)ethanol (5)
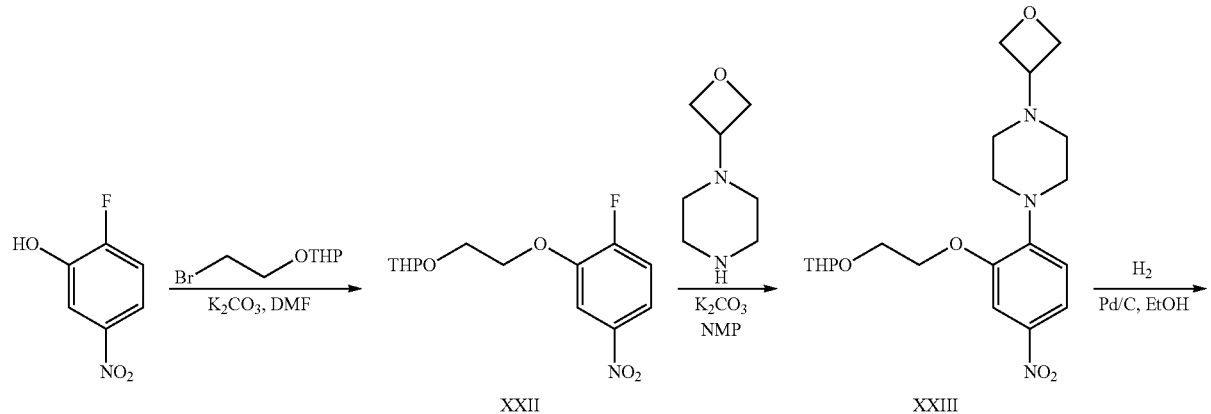
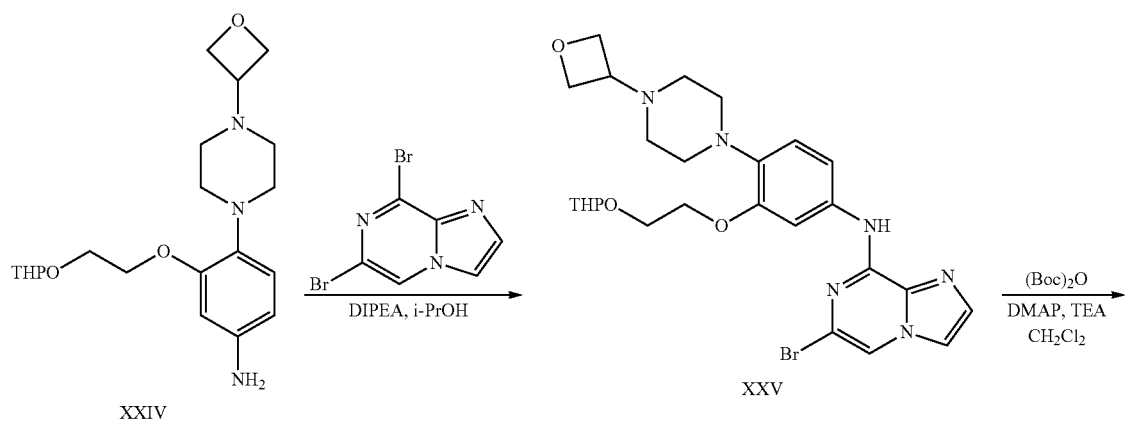
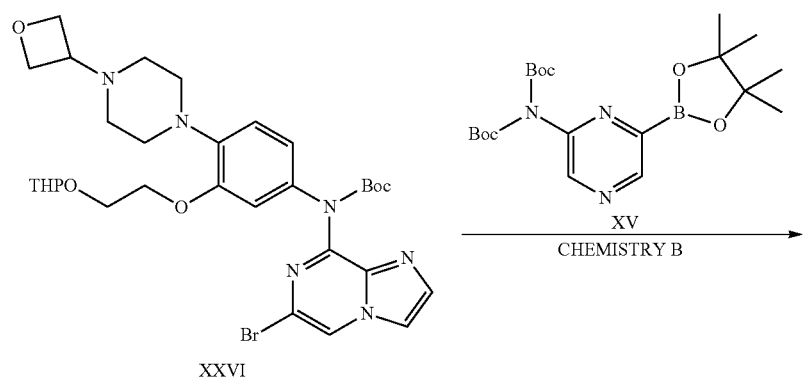

-continued

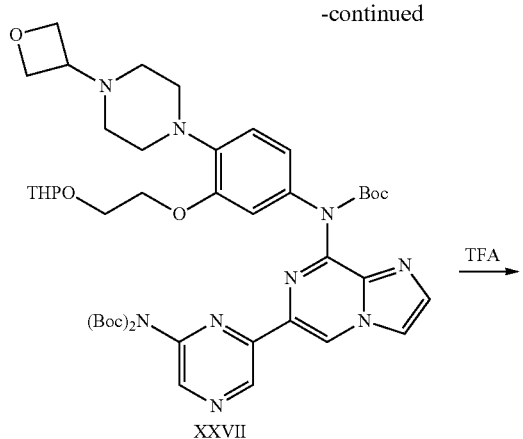

2-(2-(2-Fluoro-5-nitrophenoxy)ethoxy)tetrahydro-2H-pyran XXII: A mixture of 2-fluoro-5-nitrophenol (4 g, 25 mmol), 2-(2-bromoethoxy)tetrahydro-2H-pyran (4.4 mL, 28 mmol) and potassium carbonate (4.2 g 30 mmol) in DMF (50 mL) was stirred at 50° C. for 16 h. The reaction was cooled to room temperature, diluted with EtOAc and H$_2$O. The aqueous layer was separated ad extracted with EtOAc. The combined organic extracts were washed with H$_2$O (5×'s to remove DMF) and brine and dried over sodium sulfate. The resulting residue was purified by column chromatography ISCO Rf (40 g column) eluting with a gradient of 100% hexanes—1:1 hexanes:EtOAc to provide 2-(2-(2-fluoro-5-nitrophenoxy)ethoxy)tetrahydro-2H-pyran XXII (1.5 g, 21%).

1-(4-Nitro-2-(2-((tetrahydro-2H-pyran-2-yl)oxy)ethoxy)phenyl)-4-(oxetan-3-yl)piperazine XXIII: A mixture of 2-(2-(2-fluoro-5-nitrophenoxy)ethoxy)tetrahydro-2H-pyran XXII (1550 mg, 5.43 mmol), 1-(oxetan-3-yl)piperazine (772 mg, 5.43 mmol) and potassium carbonate (1126.41 mg, 8.15 mmol) in NMP (6 mL) was stirred at 100° C. for 8 h. The aqueous layer was separated and extracted with EtOAc. The combined organic extracts were washed with H$_2$O (5× to remove NMP) and brine and dried over sodium sulfate. The resulting residue was purified by column chromatography ISCO Rf (24 g column) eluting with a gradient of 100% DCM—60:35:5 DCM:Et$_2$O:MeOH to provide 1-(4-nitro 2-(2-((tetrahydro-2H-pyran 2-yl)oxy)ethoxy)phenyl)-4-(oxetan-3-yl)piperazine XXIII (2.1 g, 94%).

4-(4-(Oxetan-3-yl)piperazin-1-yl)-3-(2-((tetrahydro-2H-pyran-2-yl)oxy)ethoxy)aniline XXIV: To a suspension of 1-(4-nitro-2-(2-((tetrahydro-2H-pyran-2-yl)oxy)ethoxy)phenyl)-4-(oxetan-3-yl)piperazine XXIII (2100 mg, 5.1 mmol) in ethanol (50 mL) was added 10% Pd/C (50% wet, 390 mg dry weight) in a 500-mL Parr hydrogenation bottle. The bottle was evacuated, charged with hydrogen gas to a pressure of 50 psi and shaken at rt for 2 h on a Parr hydrogenation apparatus. The reaction mixture was filtered, and washed with ethanol. The filtrate was concentrated in vacuo to give 4-(4-(oxetan-3-yl)piperazin-1-yl)-3-(2-((tetrahydro-2H-pyran-2-yl)oxy)ethoxy)aniline XXIV (1850 mg, 95%).

6-Bromo-N-(4-(4-(oxetan-3-yl)piperazin-1-yl)-3-(2-((tetrahydro-2H-pyran-2 yl)oxy)ethoxy)phenyl)imidazo[1,2-a]pyrazin-8-amine XXV: To a solution of 4-(4-(oxetan-3-yl)piperazin-1-yl)-3-(2-((tetrahydro-2H-pyran-2-yl)oxy)ethoxy)aniline XXIV (619 mg, 2.17 mmol) and 6,8-dibromoimidazo[1,2-a]pyrazine (601 mg, 2.2 mmol) in IPA (15 mL) was added N,N-Diisopropylethylamine (0.95 ml, 5.43 mmol). The mixture was stirred at 110° C. for 16 h. After this time, DCM (10 mL) and sat aqueous NaHCO$_3$ (15 mL) were added. The aqueous layer was separated and extracted with DCM (2×10 mL). The combined organic extracts were washed with brine (10 mL) and dried over sodium sulfate. The resulting residue was purified by column chromatography ISCO Rf (24 g column) eluting with a gradient of 100% DCM—60:35:5 DCM:Et$_2$O:MeOH to provide 6-bromo-N-(4-(4-(oxetan-3-yl)piperazin-1-yl)-3-(2-((tetrahydro-2H-pyran-2-yl)oxy)ethoxy)phenyl)imidazo[1,2-a]pyrazin-8-amine XXV (1.2 g, quant).

tert-Butyl (6-bromoimidazo[1,2-a]pyrazin-8-yl)(4-(4-(oxetan-3-yl)piperazin-1-yl)-3-(2-((tetrahydro-2H-pyran-2-yl)oxy)ethoxy)phenyl)carbamate XXVI: 6-Bromo-N-(4-(4-(oxetan-3-yl)piperazin-1-yl)-3-(2-((tetrahydro-2H-pyran-2-yl)oxy)ethoxy)phenyl)imidazo[1,2-a]pyrazin-8-amine XXV (1.2 g, 2.4 mmol) was reacted according to the analogous method described in Intermediate Example 1.01 (conversion of III to IV) to provide tert-butyl (6-bromoimidazo[1,2-a]pyrazin-8-yl)(4-(4-(oxetan-3-yl)piperazin-1-yl)-3-(2-((tetrahydro-2H-pyran-2-yl)oxy)ethoxy)phenyl)carbamate XXVI (639 mg, 37%).

tert-butyl (6-(6-(bis(tert-butoxycarbonyl)amino)pyrazin-2-yl)imidazo[1,2-a]pyrazin-8-yl)(4-(4-(oxetan-3-yl)piperazin-1-yl)-3-(2-((tetrahydro-2H-pyran-2-yl)oxy)ethoxy)phenyl)carbamate XXVII: tert-Butyl (6-bromoimidazo[1,2-a]pyrazin-8-yl)(4-(4-(oxetan-3-yl)piperazin-1-yl)-3-(2-((tetrahydro-2H-pyrazin-2-yl)oxy)ethoxy)phenyl)carbamate XXVI was reacted with XV according to the methods of CHEMISTRY B as described in Example 2 to provide the desired compound tert-butyl (6-(6-(bis(tert-butoxycarbonyl)amino)pyrazin-2-yl)imidazo[1,2-a]pyrazin-8-yl)(4-(oxetan-3-yl)piperazin-1-yl)-3-(2-((tetrahydro-2H-pyran-2-yl)oxy)ethoxy)phenyl)carbamate XXVII (313 mg, 59%).

2-(5-((6-(6-aminopyrazin-2-yl)imidazo[1,2-a]pyrazin-8-yl)amino)-2-(4-(oxetan-3-yl)piperazin-1-yl)phenoxy)ethano (5): The compound tert-butyl (6-(6-(bis(tert-butoxycarbonyl)amino)pyrazin-2-yl)imidazo[1,2-a]pyrazin-8-yl)(4-(4-(oxetan-3-yl)piperazin-1-yl)-3-(2-((tetrahydro-2H-pyran-2-yl)oxy)ethoxy)phenyl)carbamate XXVII (313 mg, 0.35 mmol) was de-protected by the analogous method described in Example 2 to provide 2-(5-((6-(6-aminopyrazin-2-yl)imidazo[1,2-a]pyrazin-8-yl)amino)-2-(4-(oxetan-3-yl)piperazin-1-yl)phenoxy)ethanol (5). LCMS-ESI$^+$ (m/z): [M+H]$^+$: 504.3. $^1$H NMR (300 MHz, d$_6$-DMSO) δ: 9.52 (s, 1H), 8.61

(s, 1H), 8.51 (s, 1H), 8.14 (d, J=1.1 Hz, 1H), 7.89 (s, 1H), 7.81 (d, J=2.3 Hz, 1H), 7.74-7.60 (m, 2H), 6.90 (d, J=8.6 Hz, 1H), 6.47 (s, 2H), 5.74 (s, 1H), 4.86-4.76 (m, 1H), 4.50 (dt, J=25.6, 6.3 Hz, 4H), 4.04 (t, J=5.1 Hz, 2H), 3.73 (q, J=5.1 Hz, 2H), 3.51-3.42 (min, 1H), 3.02 (s, 4H), 2.40 (s, 4H).
Example 6
Preparation of 2-((4-(4-((6-(6-aminopyrazin-2-yl)imidazo[1,2-a]pyrazin-8-yl)amino)phenyl)piperazin-1-yl)methyl)propane-1,3-diol (6)
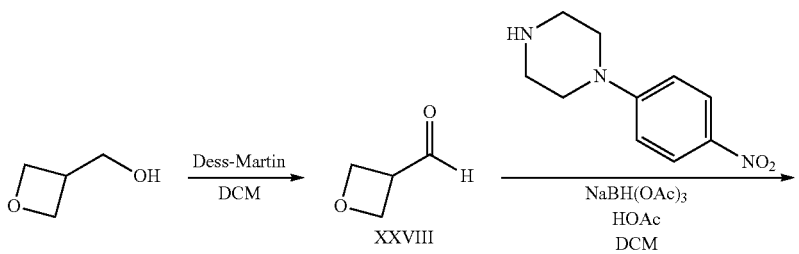
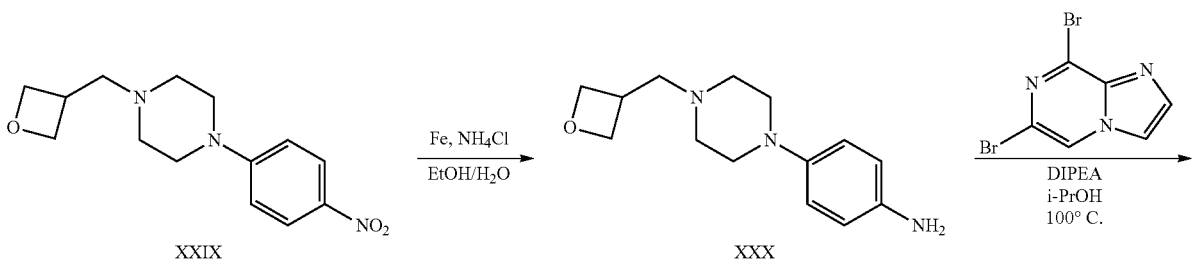
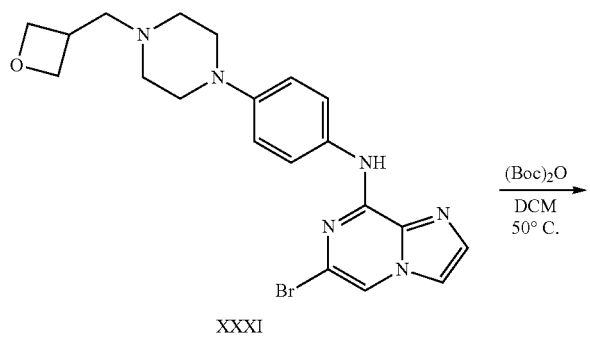
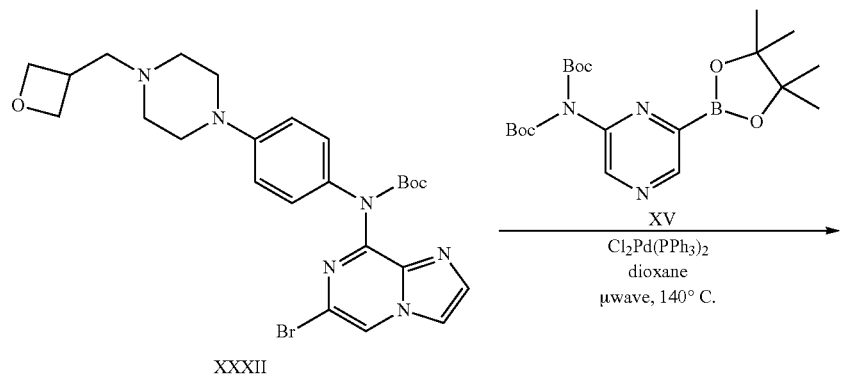

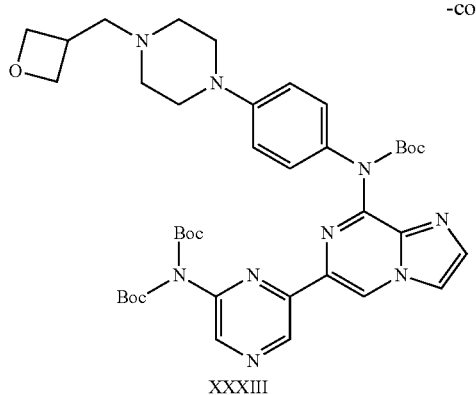

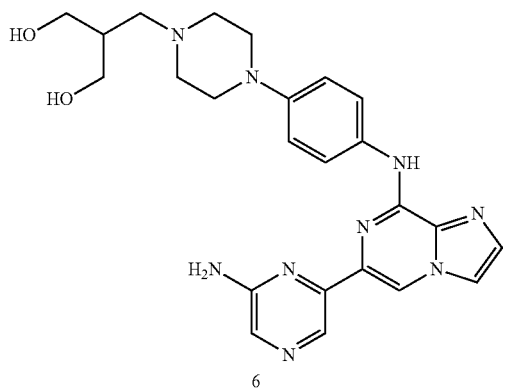

Oxetane-3 carbaldehyde XXVIII: To a round-bottomed flask equipped with a stirring bar, oxetan-3-ylmethanol (2.00 g, 22.7 mmol) was dissolved in DCM (50 mL) and Dess-Martin periodinane (10.67 g, 28.38 mmol) was added in one portion. The reaction mixture was stirred at RT overnight. The solids were filtered through celite, and washed with DCM (3 mL×5). The filtrate was removed and concentrated in vacuo and the resulting crude oxetane-3-carbaldehyde XXVIII was used in the next step directly.

1-(4-Nitrophenyl)-4-(oxetan-3-ylmethyl)piperazine XXIX: To a round-bottomed flask equipped with a stirring bar, oxetane-3-carbaldehyde XXVIII (0.977 g, 11.35 mmol), 1-(4-nitrophenyl)piperazine (1.18 g, 5.68 mmol) in DCM (100 mL), and HOAc (1.70 g, 28.38 mmol) in DCM (2 mL) were added. After 5 minutes, NaBH(OAc)$_3$ (24.06 g, 113.05 mmol) was added. The resulting mixture was stirred at room temperature for 2 h. Most volatiles were removed in vacuo. DCM (200 mL) was added, followed by saturated NaHCO$_3$ aqueous solution (20 mL), and the resulting mixture was stirred for 20 minutes. The organic phase was separated and washed with saturated NaHCO$_3$ aqueous solution (20 mL×3), brine (20 mL×1), dried over Na$_2$SO$_4$, filtered and solvents were removed in vacuo. The residue was passed through a silica gel column (MeOH:DCM=0:100 to 5:95 to 25:75) to provide the desired compound XXIX as yellow solids, 2.10 g.

4-(4-(Oxetan-3-ylmethyl)piperazin-1-yl)aniline XXX: To a round-bottomed flask equipped with a stirring bar, were added 1-(4-nitrophenyl)-4-(oxetan-3-ylmethyl)piperazine XXIX (3.20 g, 11.54 mmol), ethanol (60 mL) and water (60 mL). Following the addition of iron (4.51 g, 80.77 mmol) and ammonium chloride (4.32 g, 80.77 mmol), the reaction mixture was heated at 80° C. of or 1 h, then filtered through Celite and washed with DCM (5 mL×5). The resulting filtrate was extracted with DCM (20 mL×3). The combined organic extracts were washed with water (20 mL×2), brine (20 mL×1), dried over Na$_2$SO$_4$, and concentrated in vacuo. The desired 4-(4-(oxetan-3-ylmethyl)piperazin-1-yl)aniline XXX was obtained, 1.19 g.

6-Bromo-N-(4-(4-(oxetan-3-ylmethyl)piperazin-1-yl)phenyl)imidazo[1,2-a]pyrazin-8-amine XXXI: To a seal tube equipped with a stirring bar, 4-(4-(oxetan-3-ylmethyl)piperazino-1-yl)aniline XXX (1.19 g, 4.81 mmol), 6,8-dibromoimidazo[1,2-a]pyrazine (1.33 g, 4.81 mmol), isopropanol (24.1 mL), and diisopropylethylamine (1.37 g, 10.58 mmol) were added, and the reaction mixture was heated at 100° C. overnight. Most solvents were removed in vacuo and DCM (200 mL) was added to the mixture. The solution was washed with H$_2$O (20 mL×2), brine (20 mL×1) dried over Na$_2$SO$_4$, filtered and solvents were removed in vacuo. The resulting residue was passed through a silica gel column (MeOH:DCM=5:95) and light red solids were obtained as the desired compound XXXI, 0.692 g (yield 32.4%).

tert-Butyl (6-bromoimidazo[1,2-a]pyrazin-8-yl)(4-(1-(oxetan-3-ylmethyl)piperidin-4-yl)phenyl)carbamate XXXII: To a round-bottomed flask equipped with a stirring bar, were added 6-bromo-N-(4-(4-(oxetan-3-ylmethyl)piperazin-1-yl)phenyl)imidazo[1,2-a]pyrazin-8-amine XXXI (560 mg, 1.27 mmol), DCM (11 mL), di-tert-butyl dicarbonate (414.4 mg, 1.90 mmol), and triethylamine (640.5 mg, 6.33 mmol). The reaction mixture was heated at 50° C. overnight. DCM (200 mL) was added, and the resulting solution was washed with water (20 mL×2), brine (20 mL×1), dried over Na$_2$SO$_4$, filtered and solvents were removed in vacuo. Column chromatography gave the desired compound XXXII as yellow solids; 640 mg (yield 93.2%).

tert-Butyl (6-6-(bis(tert-butoxycarbonyl)amino)pyrazin-2-yl)imidazo[1,2-a]pyrazin-8-yl)(4-(4-(oxetan-3-yl ethyl) piperazin-1-yl)phenyl)carbamate XXXIII: To a round-bottomed flask equipped with a stirring bar, tert-butyl (6-bromoimidazo[1,2-a]pyrazin-8-yl)(4-(4-(oxetan-3-yl ethyl)piperazin-1-yl)phenyl)carbamate XXXII (150 mg, 0.276 mmol), N,N-BisBoc 6-(4,4,5,5-tetramethyl-1,3,2-dioxaborolan-2-yl)pyrazin-2-amine XV (255.8 mg, 0.607 mmol) in DME (2.3 mL), Pd(PPh$_3$)$_4$ (16.0 mg, 0.14 mmol), Na$_2$CO$_3$ aqueous solution (1.0 N, 0.91 mL, 0.91 mmol), and DME (2 mL) were added. The mixture was heated at 75° C. for 2, then DCM (200 mL) was added and the resulting mixture was washed with water (30 mL×3), brine (30 mL×1), dried over MgSO$_4$, filtered, and solvents were removed in vacuo. Purification by silica gel column (MeOH:DCM=5:95) gave the desired compound XXXIII 250 mg.

2-((4-(4-((6-(6-aminopyrazin-2-yl)imidazo[1,2-a] pyrazin-8-yl)amino)phenyl)piperazin-1-yl)methyl)propane-1,3-diol (6): To a solution of tert-butyl (6-(6-(bis(tertbutoxycarbonyl)amino)pyrazin-2-yl)imidazo[1,2-a]pyrazin-8-yl) (4-(4-(oxetan-3-ylmethyl)piperazin-1-yl)phenyl)carbamate XXXIII (250 mg, 0.33 mmol) in DCM (30 mL) was added TFA (940.3 mg, 8.25 mmol). The resulting mixture was stirred at room temperature for overnight. More TFA (752.2 mg, 6.60 mmol) was added and stirred at room temperature overnight. Most solvents were removed in vacuo, DCM (200 mL) and saturated NaHCO$_3$ aqueous solution (30 mL) were added and the resulting mixture was stirred for 30 minutes. The organic phase was separated, washed with saturated NaHCO$_3$ aqueous solution (20 mL×4), brine (20 mL×1).

The aqueous phase was extracted with DCM (30 mL×2). The combined organic phases were washed with brine (20 mL×1), dried over Na$_2$SO$_4$, filtered, and solvents were removed in vacuo. The crude material was purified on ISCO column, MeOH:DCM=0:100 to 5:95 to 7.5:92.5 to 25:75 to elute the desired compounds. Two compounds were obtained, the first is the oxetane compound (26.8 mg); and the other the desired compound (6, 49.3 mg, yield 31.4%). LCMS-ESI$^+$ (m/z): [M+H]$^+$: 476. $^1$H NMR (300 MHz, d$_6$-DMSO) δ: 9.51 (s, 1 H), 8.60 (s, 1 H), 8.49 (s, 1 H), 8.14 (d, J=1.5 Hz, 1 H), 7.95 (d, J=9 Hz, 2 H), 7.90 (s, 1 H), 7.64 (s, 1 H), 6.99 (d, J=9 Hz, 2 H), 6.48 (s, 2 H), 4.51 (broad S, 2 H), 3.43 (d, J=6 Hz, 4 H), 3.12 (broad m, 4 H), 2.54 (broad m, 4 H), 2.34 (d, J=7.2 Hz, 2 H), 1.83 (m, 1 H).

Example 7

Preparation of 2-(5-(((6-(6-amino-5-methylpyrazin-2-yl)imidazo[1,2-a]pyrazin-8-yl)amino)-2-(4-(oxetan-3-yl)piperazin-1-yl)phenoxy)ethanol (7)

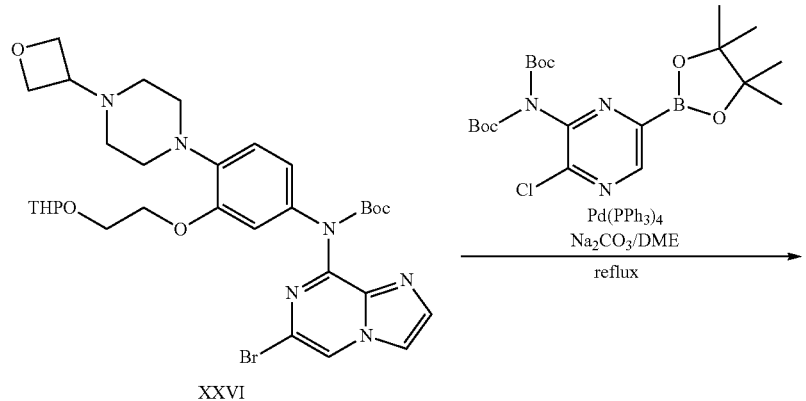

XXVI

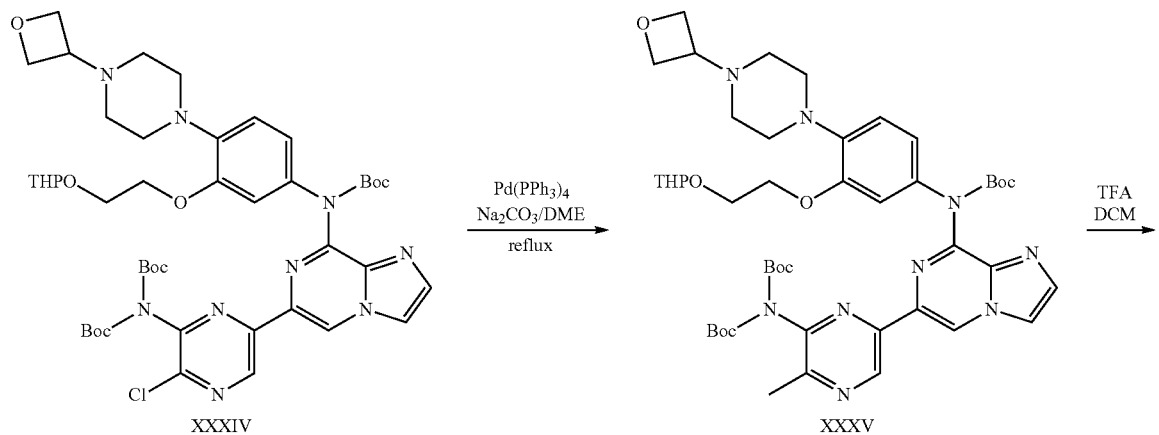

XXXIV

XXXV

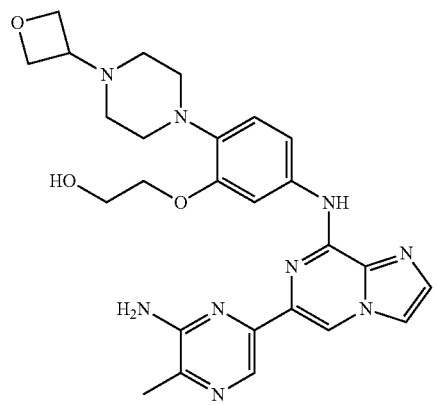

7 tert-butyl tert-butoxycarbonyl(6-(8-((tert-butoxycarbonyl)(4-(4-(oxetan-3-yl)piperazin-1-yl)-3-(2-((tetrahydro-2H-pyran-2-yl)oxy)ethoxy)phenyl)amino)imidazo[1,2-a]pyrazin-6-yl)-3-chloropyrazin-2-yl)carbamate XXXIV: A flask equipped with a reflux condenser was charged with tert-butyl (6-bromoimidazo[1,2-a]pyrazin-8-yl)(4-(4-(oxetan-3-yl)piperazin-1yl)-3-(2-((tetrahydro-2H-pyran-2-yl)oxy)ethoxy)phenyl)carbamate XXVI (prepared as described in Example 5) (352 mg, 0.52 mmol), 2-(bis-boc-amino)-3-chloro-6-(4,4,5,5-tetramethyl-1,3,2-dioxaborolan-2-yl)pyrazine (prepared by analogous method as used in Example 2 for the preparation of compound XV) (500 mg, 1.1 mmol), Pd(PPh$_3$)$_4$ (30 mg, 0.03 mmol) in sodium carbonate (1.6 mL, 1M in H$_2$O) and DME (4.8 mL). The mixture was heated to reflux for 1 h. The reaction was cooled to room temperature, diluted with DCM and H$_2$O. The aqueous layer was separated and extracted with DCM. The combined organic extracts were washed with brine, dried over sodium sulfate, filtered and concentrated under reduced pressure. The resulting residue was purified by column chromatography ISCO Rf (4 g column) eluting with a gradient of 100% DCM—100% 60/35/5 DCM/Et$_2$O/MeOH, appropriate fractions were combine d an concentrated to provide the desired compound tert-butyl tert-butoxycarbonyl(6-(8-((tert-butoxycarbonyl)(4-(4-(oxetan-3-yl)piperazin-1-yl)-3-(2-((tetrahydro-2H-pyran-2-yl)oxy)ethoxy)phenyl)amino)imidazo[1,2-a]pyrazin-6-yl)-3-chloropyrazin-2-yl)carbamate XXXIV (258 mg, 53%).

tert-butyl tert-butoxycarbonyl(6-(8-((tert-butoxycarbonyl)(4-(4-(oxetan-3-yl)piperazin-1-yl)-3-(2-((tetrahydro-2H-pyran-2-yl)oxy)ethoxy)phenyl)amino)imidazo[1,2-a]pyrazin-6-yl)-3-methylpyrazin-2-yl)carbamate XXXV: A microwave vial was charged with tert-butyl tert-butoxycarbonyl(6-(8-((tert-butoxycarbonyl)(4-(4-(oxetan-3-yl)piperazin-1-yl)-3-(2-((tetrahydro-2H-pyran-2-yl)oxy)ethoxy)phenyl)amino)imidazo[1,2-a]pyrazin-6-yl)-3-chloropyrazin-2-yl)carbamate XXXIV (258 mg, 0.28 mmol), methylboronic acid (503 mg, 8.4 mmol), Pd(PPh$_3$)$_4$ (32 mg, 0.03 mmol) in sodium carbonate (0.8 mL, 1M in H$_2$O) and DME (2.5 mL). The mixture was heated at 150° C. for 20 min. The reaction was cooled to room temperature, diluted with DCM and H$_2$O. The aqueous layer was separated and extracted with DCM. The combined organic extracts were washed with brine, dried over sodium sulfate, filtered and concentrated under reduced pressure. The resulting residue was purified by column chromatography ISCO Rf (4 g column) eluting with a gradient of 100% DCM—100% 75/18/7 DCM/Et$_2$O/MeOH to provide the desired compound tertbutyl tert-butoxycarbonyl(6-(8-((tert-butoxycarbonyl)(4-(4-(oxetan-3-yl)piperazin-1-yl)-3-(2-((tetrahydro-2H-pyran-2-yl)oxy)ethoxy)phenyl)amino)imidazo[1,2-a]pyrazin-6-yl)-3-methylpyrazin-2-yl)carbamate XXXV (165 mg, 65%).

2-(5-((6-(6-Amino-5-methylpyrazin-2-yl)imidazo[1,2-a]pyrazin-8-yl)amino)-2-(4-(oxetan-3-yl)piperazin-1-yl)phenoxy)ethanol (7): To a solution of tert-butyl tert-butoxycarbonyl(6-(8-((tert-butoxycarbonyl)(4-(4-(oxetan-3-yl)piperazin-1-yl)-3-(2-((tetrahydro-2H-pyran-2-yl)oxy)ethoxy)phenyl)amino)imidazo[1,2-a]pyrazin-6-yl)-3-methylpyrazin-2-yl)carbamate XXXV (165 mg, 0.18 mmol) in DCM (2.2 mL) was added TFA (1.1 mL, 0.11 mmol). The mixture was stirred at rt for 16 h. The reaction was diluted with 9:1 DCM:MeOH and H$_2$O. The aqueous layer was separated and extracted with 9:1 DCM:MeOH. The combined organic extracts were washed with brine, dried over sodium sulfate, filtered and concentrated under reduced pressure. The resulting residue was purified by column chromatography eluting with a gradient of 100% 75/18/7 DCM/Et$_2$O/MeOH-100% 70/20/10 DCM/Et$_2$O/MeOH to provide the desired compound 2-(5-((6-(6-amino-5-methylpyrazin-2-yl)imidazo[1,2-a]pyrazin-8-yl)amino)-2-(4-(oxetan-3-yl)piperazin-1yl)phenoxy)ethanol (7, 56 mg, 59%). LCMS-ESI$^+$ (m/z): [M+H]$^+$: 518.2. $^1$H NMR (300 MHz, d$_6$-DMSO) δ: 9.49 (s, 1H), 8.56 (s, 1H), 8.44 (s, 1H), 8.13 (d, J=1.1 Hz, 1H), 7.85-7.66 (m, 2H), 7.62 (d, J=1.1 Hz, 1H), 6.90 (d, J=8.6 Hz, 1H), 6.25 (s, 2H), 4.87-4.77 (m, 1H), 4.50 (dt, J=25.2, 6.3 Hz, 4H), 4.04 (t, J=5.1 Hz, 2H), 3.74 (q, J=5.2 Hz, 2H), 3.51-3.39 (m, 1H), 3.10-2.95 (m, 4H), 2.45-2.35 (m, 4H), 2.34 (s, 3H). Alternatively, compound XXXIV could be taken directly to this step and similarly de-protected to provide the 5-chloropyrazine substituted analog.

Biological Examples

Example 8

High Throughput Syk Biochemical Assay

Syk activity was measured using KinEASE (Cisbio), a time-resolved fluorescence resonance energy transfer (TR-FRET) immunoassay. In this assay, Syk-catalyzes the phosporylation of a XL665-labeled peptide substrate. Europium conjugated phospho-tyrosine specific antibody binds the resulting phosphorylated peptide. Formation of phosphorylated peptide is quantified by TR-FRET with Europium as the donor and XL665 the acceptor in a 2-step endpoint assay. In brief, test compounds serially diluted in DMSO were delivered into Corning white, low volume, non-binding 384 well plates using the Echo 550 acoustic liquid dispenser (Labcyte®). Syk enzyme and substrates were dispensed into assay plates using a Multi-Flo (Bio-Tek Instruments). The standard 5 μL reaction mixture contained 20 μM ATP, 1 μM biotinylated peptide, 0.015 nM of Syk in reaction buffer (50 mM Hepes, pH 7.0, 0.02% NaN$_3$, 0.1% BSA, 0.1 mM Orthovanadate, 5 mM MgCl$_2$, 1 mM DTT, 0.025% NP-40). After 30 minutes of incubation at room temperature, 5 μL of Stop and Detect Solution (1:200 Europium Cryptate labeled anti-phosphorylated peptide antibody solution and 125 nM strepavidin-XL665 Tracer in a 50 mM Hepes pH 7.0 detection buffer containing sufficient EDTA) was added. The plate was then further incubated for 120 minutes at room temperature and read using an Envision 2103 Multilabeled reader (PerkinElmer) with excitation/emission/FRET emission at 340 nm/615 nm/665 nm, respectively. Fluorescence intensities at 615 nm and 665 nm emission wavelengths were expressed as a ratio (665 nm/615 nm). Percent inhibition was calculated as follows: % Inhibition=100×(Ratio$_{sample}$−Ratio$_{0\%\ Inhibition}$)(Ratio$_{100\%\ Inhibition}$−Ratio$_{0\%\ Inhibition}$) where 0.1% DMSO (0% inhibition) was the negative control and 1 μM K252a (100% inhibition) was used as the positive control. Activity of the compounds of Examples 1-7 are provided in the following table, demonstrating the compounds are Syk inhibitors with IC$_{50}$ below 50 nM.

| Example No.: Compound Name | Syk IC$_{50}$ (nM) |
|---|---|
| Ex.-1: 6-(6-amino-5-methylpyrazin-2-yl)-N-(4-(4-(oxetan-3-yl)piperazin-1-yl)phenyl)imidazo[1,2-a]pyrazin-8-amine | 6.2 |
| Ex.-2: 6-(6-aminopyrazin-2-yl)-N-(4-(4-(oxetan-3-yl)piperazin-1-yl)phenyl)imidazo[1,2-a]pyrazin-8-amine | 13.5 |

-continued

| Example No.: Compound Name | Syk IC$_{50}$ (nM) |
|---|---|
| Ex.-3: (R)-(4-(4-((6-(6-aminopyrazin-2-yl)imidazo[1,2-a]pyrazin-8-yl)amino)phenyl)morpholin-2-yl)methanol | 13.3 |
| Ex.-4: 6-(6-aminopyrazin-2-yl)-5-methyl-N-(4-(4-(oxetan-3-yl)piperazin-1-yl)phenyl)imidazo[1,2-a]pyrazin-8-amine | 44 |
| Ex.-5: 2-(5-((6-(6-aminopyrazin-2-yl)imidazo[1,2-a]pyrazin-8-yl)amino)-2-(4-(oxetan-3-yl)piperazin-1-yl)phenoxy)ethanol | 12.2 |
| Ex.-6: 2-((4-(4-((6-(6-aminopyrazin-2-yl)imidazo[1,2-a]pyrazin-8-yl)amino)phenyl)piperazin-1-yl)methyl)propane-1,3-diol | 14.5 |
| Ex.-7: 2-(5-((6-(6-amino-5-methylpyrazin-2-yl)imidazo[1,2-a]pyrazin-8-yl)amino)-2-(4-(oxetan-3-yl)piperazin-1-yl)phenoxy)ethanol | 8.7 |

Example 9

384-well HTBS Whole Blood CD63 Basophil Assay

Syk activity was assessed in relation to reduced activation of basophils as measured by the expression of CD63 in a human whole blood basophil cellular assay (25% blood). Basophil activation was measured in human whole blood using the Flow CAST kit (Buhlmann Laboratories AG, Baselstrasse, Switzerland) following the protocol provided by the manufacturer with minor modifications. Fresh human whole blood in heparin was collected and delivered same day (AllCells, Emeryville, Calif.). Whole blood samples were incubated with either DMSO (1% final) or serial diluted compounds in DMSO for 60 minutes at 37° C. Basophils were activated using the anti-FceRI mAb and stained with anti-CD63-FITC and anti-CCR3-PE for 20 minutes at 37° C. (per well: 50 µL of whole blood was mixed with 113 µL of stimulation buffer, 8.5 µL anti-FceRI mAb, 8.5 µL Ab stain. CCR3-PE/CD63-FITC). Cells were centrifuged at 1000×g for 18 minutes and 150 L/well of supernatant removed. Red blood cells were lysed and cells fixed by 2 rounds of cell lysing: resuspending cell pellets with 150 µL/well 1× lysis buffer, incubating at room temperature for 10 minutes, and collecting cell pellets by centrifuging for 1200 rpms for 5 minutes. Cells were washed with 150 µL/well wash buffer twice, and resuspended in a final volume of 75 µL/well of wash buffer for either immediate flow cytometery analysis or overnight incubation at 4° C. followed by flow cytometry analysis. Degranulation (basophil activation) was detected by CD63 surface expression on CCR3 positive cells. The percent CD63 positive cells within the gated basophil population were determined and normalized to the DMSO (negative control) and control compound (positive control). Activity of the compounds of Examples 1-7 are provided in the following table, demonstrating the compounds are effective in reducing the activation of basophils, with EC$_{50}$ below 200 nM.

| Example No.: Compound Name | CD63 EC$_{50}$ (nM) |
|---|---|
| Ex.-1: 6-(6-amino-5-methylpyrazin-2-yl)-N-(4-(4-(oxetan-3-yl)piperazin-1-yl)phenyl)imidazo[1,2-a]pyrazin-8-amine | 51 |
| Ex.-2: 6-(6-aminopyrazin-2-yl)-N-(4-(4-(oxetan-3-yl)piperazin-1-yl)phenyl)imidazo[1,2-a]pyrazin-8-amine | 80 |
| Ex.-3: (R)-(4-(4-((6-(6-aminopyrazin-2-yl)imidazo[1,2-a]pyrazin-8-yl)amino)phenyl)morpholin-2-yl)methanol | 63 |

-continued

| Example No.: Compound Name | CD63 EC$_{50}$ (nM) |
|---|---|
| Ex.-4: 6-(6-aminopyrazin-2-yl)-5-methyl-N-(4-(4-(oxetan-3-yl)piperazin-1-yl)phenyl)imidazo[1,2-a]pyrazin-8-amine | 157 |
| Ex.-5: 2-(5-((6-(6-aminopyrazin-2-yl)imidazo[1,2-a]pyrazin-8-yl)amino)-2-(4-(oxetan-3-yl)piperazin-1-yl)phenoxy)ethanol | 120 |
| Ex.-6: 2-((4-(4-((6-(6-aminopyrazin-2-yl)imidazo[1,2-a]pyrazin-8-yl)amino)phenyl)piperazin-1-yl)methyl)propane-1,3-diol | 128 |
| Ex.-7: 2-(5-((6-(6-amino-5-methylpyrazin-2-yl)imidazo[1,2-a]pyrazin-8-yl)amino)-2-(4-(oxetan-3-yl)piperazin-1-yl)phenoxy)ethanol | 167 |

Example 10

Kinetic Solubility

The kinetic solubility of compounds in phosphate buffer at pH 7.4 was assessed. The compounds to be tested were dissolved in dimethylsulfoxide at a 10 mM concentration. Stock samples were diluted, 3 µl with 297 µl of the phosphate buffer at pH 7.4 (DulBecco's phosphate buffered saline (Sigma-Aldrich D8662), overall molarity is 0.149M and pH 7.43). The samples were then incubated for 24 hours at 37° C. with shaking, the centrifuged and an aliquot taken and tested relative to a known standard concentration of 0.1 mM. The kinetic solubility of the compounds of Examples 1-7 are provided in the following table, demonstrating the compounds have kinetic solubility at pH 7.4 of greater than 90 µM.

| Example No.: Compound Name | Solubility pH 7.4 (µM) |
|---|---|
| Ex.-1: 6-(6-amino-5-methylpyrazin-2-yl)-N-(4-(4-(oxetan-3-yl)piperazin-1-yl)phenyl)imidazo[1,2-a]pyrazin-8-amine | 95 |
| Ex.-2: 6-(6-aminopyrazin-2-yl)-N-(4-(4-(oxetan-3-yl)piperazin-1-yl)phenyl)imidazo[1,2-a]pyrazin-8-amine | 95 |
| Ex.-3: (R)-(4-(4-((6-(6-aminopyrazin-2-yl)imidazo[1,2-a]pyrazin-8-yl)amino)phenyl)morpholin-2-yl)methanol | 91 |
| Ex.-4: 6-(6-aminopyrazin-2-yl)-5-methyl-N-(4-(4-(oxetan-3-yl)piperazin-1-yl)phenyl)imidazo[1,2-a]pyrazin-8-amine | 100 |
| Ex.-5: 2-(5-((6-(6-aminopyrazin-2-yl)imidazo[1,2-a]pyrazin-8-yl)amino)-2-(4-(oxetan-3-yl)piperazin-1-yl)phenoxy)ethanol | 97 |
| Ex.-6: 2-((4-(4-((6-(6-aminopyrazin-2-yl)imidazo[1,2-a]pyrazin-8-yl)amino)phenyl)piperazin-1-yl)methyl)propane-1,3-diol | 99 |

Example 11

Human Hepatocyte Stability Assay

The human hematocyte stability of the compounds as predicted hepatocyte clearance in L/hr/kg was assessed. Compounds to be tested were diluted to 200 µM (4 µl of 10 mM DMSO stock into 196 µl ACN:H$_2$O (50:50). Propranolol was used as a positive control, and buffer only without hepatocytes as 0% control. These were further diluted 4 µl with 891 µl KHB buffer (InVitroGRO catalog number Z99074) to provide 2× dosing solution. To each well of 24 well plate, 250 µl of the 2× dosing solution was added to each well with 250 µl of hepatocytes cells (1×10$^6$ viable cells/ml per well) or KHB for control samples to achieve a final compound concentration of 1 μM during incubation. The final solvent concentration was 0.01% DMSO and 0.25% ACN. The culture plate was placed on a rocker and incubated at 37° C., 5% $CO_2$. Samples were collected at time 0, 1, 3, and 6 hours. The loss of parent compound was determined using LC-MS methods against a standard curve. Activity of the compounds of Examples 1-7 are provided in the following table, showing hepatocyte clearance of about 0.12 L/hr/kg or less.

| Example No.: Compound Name | Hheps CL (L/hr/kg) |
|---|---|
| Ex.-1: 6-(6-amino-5-methylpyrazin-2-yl)-N-(4-(4-(oxetan-3-yl)piperazin-1-yl)phenyl)imidazo[1,2-a]pyrazin-8-amine | 0.12 |
| Ex.-2: 6-(6-aminopyrazin-2-yl)-N-(4-(4-(oxetan-3-yl)piperazin-1-yl)phenyl)imidazo[1,2-a]pyrazin-8-amine | 0.055 |
| Ex.-3: (R)-(4-(4-((6-(6-aminopyrazin-2-yl)imidazo[1,2-a]pyrazin-8-yl)amino)phenyl)morpholin-2-yl)methanol | 0.09 |
| Ex.-4: 6-(6-aminopyrazin-2-yl)-5-methyl-N-(4-(4-(oxetan-3-yl)piperazin-1-yl)phenyl)imidazo[1,2-a]pyrazin-8-amine | 0.08 |
| Ex.-5: 2-(5-((6-(6-aminopyrazin-2-yl)imidazo[1,2-a]pyrazin-8-yl)amino)-2-(4-(oxetan-3-yl)piperazin-1-yl)phenoxy)ethanol | 0.07 |
| Ex.-6: 2-((4-(4-((6-(6-aminopyrazin-2-yl)imidazo[1,2-a]pyrazin-8-yl)amino)phenyl)piperazin-1-yl)methyl)propane-1,3-diol | 0.08 |
| Ex.-7: 2-(5-((6-(6-amino-5-methylpyrazin-2-yl)imidazo[1,2-a]pyrazin-8-yl)amino)-2-(4-(oxetan-3-yl)piperazin-1-yl)phenoxy)ethanol | 0.05 |

Example 12

Comparison to Known Syk Inhibitors

The assays of Examples 8-11 were used to compare the compounds as described herein with compounds known in the art. The data comparing the compounds of Examples 1-7 to previously described compounds is provided in the following table. From these results, it is clear that compounds as described herein are desirable as Syk inhibitors, with improved Syk and CD63 activity relative to the known compounds, improved kinetic solubility (at least about 9-fold more soluble) and hepatocyte clearance (at least about 2-fold less clearance). As such, the combination of improved Syk and CD63 inhibitory activity with improved kinetic solubility and clearance provides compounds that are expected to be effective at treating diseases as described herein with improved pharmacokinetic properties.

| Compound Name | Syk $IC_{50}$ (nM) | CD63 $IC_{50}$ (nM) | Solubility pH 7.4 (μM) | Hheps CL (units) |
|---|---|---|---|---|
| Ex.-1: 6-(6-amino-5-methylpyrazin-2-yl)-N-(4-(4-(oxetan-3-yl)piperazin-1-yl)phenyl)imidazo[1,2-a]pyrazin-8-amine | 6.2 | 51 | 95 | 0.12 |
| Ex.-2: 6-(6-aminopyrazin-2-yl)-N-(4-(4-(oxetan-3-yl)piperazin-1-yl)phenyl)imidazo[1,2-a]pyrazin-8-amine | 13.5 | 80 | 95 | 0.055 |
| Ex.-3: (R)-(4-(4-((6-(6-aminopyrazin-2-yl)imidazo[1,2-a]pyrazin-8-yl)amino)phenyl)morpholin-2-yl)methanol | 13.3 | 63 | 91 | 0.09 |
| Ex.-4: 6-(6-aminopyrazin-2-yl)-5-methyl-N-(4-(4-(oxetan-3-yl)piperazin-1-yl)phenyl)imidazo[1,2-a]pyrazin-8-amine | 44 | 157 | 100 | 0.08 |
| Ex.-5: 2-(5-((6-(6-aminopyrazin-2-yl)imidazo[1,2-a]pyrazin-8-yl)amino)-2-(4-(oxetan-3-yl)piperazin-1-yl)phenoxy)ethanol | 12.2 | 120 | 97 | 0.07 |
| Ex.-6: 2-((4-(4-((6-(6-aminopyrazin-2-yl)imidazo[1,2-a]pyrazin-8-yl)amino)phenyl)piperazin-1-yl)methyl)propane-1,3-diol | 14.5 | 128 | 99 | 0.08 |
| Ex.-7: 2-(5-((6-(6-amino-5-methylpyrazin-2-yl)imidazo[1,2-a]pyrazin-8-yl)amino)-2-(4-(oxetan-3-yl)piperazin-1-yl)phenoxy)ethanol | 8.7 | 167 | nd | 0.05 |
| Known compounds: | | | | |
| 6-(5-aminopyridin-3-yl)-N-(4-morpholinophenyl)imidazo[1,2-a]pyrazin-8-amine | 31 | 101 | 5 | 0.68 |
| 6-(3-aminophenyl)-N-(3,4-dimethoxyphenyl)imidazo[1,2-a]pyrazin-8-amine | 188 | 809 | 3 | 0.24 |
| 6-(5-amino-6-methylpyridin-3-yl)-N-(4-morpholinophenyl)imidazo[1,2-a]pyrazin-8-amine | 16 | 250 | 5 | 0.80 |
| 6-(6-aminopyridin-3-yl)-N-(3,4-dimethoxyphenyl)imidazo[1,2-a]pyrazin-8-amine | 53 | 734 | 10 | 0.90 |

The following examples are included to illustrate embodiments of the disclosure, and are not intended to limit the scope of the disclosure. It should be appreciated by those of skill in the art that the techniques disclosed herein represent techniques that apply in the practice of the disclosure. Those of skill in the art would appreciate that, in light of the present disclosure, changes can be made in the examples herein without departing from the spirit and scope of the disclosure.

Example 13

Comparison Effect of the Combination of a Compound of Formula I, 6-(6-aminopyrazin-2-yl)-N-(4-(4-oxetan-3-yl)piperazin-1-yl)phenyl)imidazo[1,2-a]pyrazin-8-amine, with Vincristine versus Effect of the Combination of the Compound of Formula I, 6-(6-aminopyrazin-2-yl)-N-(4-(4-(oxetan-3-yl)piperazin-1-yl)phenyl)imidazo[1,2-a]pyrazin-8-amine, with Vinblastine in the malignant DLBCL B-cell line, DHL-10

This Example evaluates the efficacy of a compound of Formula I, 6-(6-aminopyrazin-2-yl)-N-(4-(4-(oxetan-3-yl) piperazin-1-yl)phenyl)imidazo[1,2-a]pyrazin-8-amine, or a pharmaceutically acceptable salt thereof, in combination with vincristine to inhibit malignant B-cell viability in the malignant diffuse large B-cell lymphoma (DLBCL) cell line DHL-10. This Example also evaluates and compares the efficacy of a compound of Formula I, 6-(6-aminopyrazin-2-yl)-N-(4-(4-(oxetan-3-yl)piperazin-1-yl)phenyl)imidazo[1,2-a]pyrazin-8-amine, or a pharmaceutically acceptable salt thereof, in combination with vinblastine to inhibit malignant B-cell viability in the malignant diffuse large B-cell lymphoma (DLBCL) cell line DHL 10.

Cell Titer Glo Viability Assay: Vincristine and vinblastine were tested alone, or in combination with 100 nM of the compound of formula (I). The DLBCL cell line, DHL-10 was plated at 10,000 cells per well in duplicate and incubated at 37° C. with 5% $CO_2$ for 72 hours in RPMI supplemented with 10% FBS and 100 U/L penicillin-streptomycin. Cell viability was assessed using Cell Titer Glo (CTG) (Promega, Madison, Wis.) following the manufacturer's protocol. CTG signals were recorded for individual compound treatment and combinations. Results are shown in FIG. 1.

FIG. 1 depicts and summarizes the inhibitory effects the inhibitory effects of the combination of a compound of FIG. 1, 6-(6-aminopyrazin-2-yl)-N-(4-(4-(oxetan-3-yl)piperazin-1-yl)phenyl)imidazo[1,2-a]pyrazin-8-amine, and one of two of the vinca alkaloids, vincristine (FIG. 1A) and vinblastine (FIG. 1B) respectively, in the DLBCL cell line, DHL-10 when compounds were co-administered (FIG. 1).

Example 14

Comparison Effect of the Compound of Formula I, 6-(6-aminopyrazin-2-yl)-N-(4-(4-(oxetan-3-yl)piperazin-1-yl)phenyl)imidazo[1,2-a]pyrazin-8-amine, in Combination with Vincristine in a Syk-expressing Solid Tumor Cell Line versus Effect of the Compound of Formula I, 6-(6-aminopyrazin-2-yl)-N-(4-(4-(oxetan-3-yl)piperazin-1-yl)phenyl)imidazo[1,2-a]pyrazin-8-amine, in Combination with Vincristine in a non Syk-expressing Solid Tumor Cell line This Example evaluates the efficacy of the compound of Formula I, 6-(6-aminopyrazin-2-yl)-N-(4-(4-(oxetan-3yl) piperazin-1 yl)phenyl)imidazo[1,2-a]pyrazin-8-amine, or a pharmaceutically acceptable salt thereof, in combination with vincristine to inhibit cell viability in the Syk-expressing malignant colon cell line, MiaPaca. This Example also evaluates the efficacy of the combination of the compound of Formula I, 6-(6-aminopyrazin-2-yl)-N-(4-(4-(oxetan-3-yl)piperazin-1-yl)phenyl)imidazo[1,2-a]pyrazin-8-amine, and vincristine to inhibit cell viability in the non-Syk expressing cell line, HepG2.

Cell Titer Glo Viability Assay: Vincristine was tested alone, or in combination with 4 concentrations of the compound of formula (I) (300, 100, 33, and 11 nM), in the malignant colon cell line, MiaPaca and in HepG2 cells. Cells were plated at 5,000 cells per well in duplicate and incubated at 37° C. with 5% $CO_2$ for 72 hours in RPMI supplemented with 10% FBS and 100 U/L penicillin-streptomycin. Cell viability was assessed using Cell Titer Glo (CTG) (Promega, Madison, Wis.) following the manufacturer's protocol. CTG signals were recorded for individual compound treatment and combinations. Results are shown in FIG. 2.

FIG. 2 summarizes the inhibition of cell viability by the combination of the compound of Formula I, 6-(6-aminopyrazin-2-yl)-N-4-(4-(oxetan-3-yl)piperazin-1-yl)phenyl)imidazo[1,2-a]pyrazin-8-amine (Compound A), and vincristine in the Syk-expressing malignant colon cell line, MiaPaca (FIG. 2A), and in the non-Syk expressing malignant colon cell line, HepG2 (FIG. 2B).

Syk Protein Assay: Cell lines were grown logarithmically overnight in RPMI supplemented with 10% FBS and 100 U/L penicillin-streptomycin. $1 \times 10^7$ were collected by centrifugation at 300×g at room temperature for 8 minutes in 50 mL tubes. Cell pellets were lysed on ice for 15 minutes in 200 uL of 1×RIPA buffer (Cell. Signaling Technology, Danvers Mass.) containing protease (Roche, Palo Alto Calif.) and phosphatase inhibitors (Sigma, Saint Louis Mo.; Santa Cruz Technologies, Dallas Tex.). Cells lysates were transferred to 96-well V-bottom plates and used directly or frozen at −80° C. for use the next day. Proteins were separated with 4-12% SDS-Bis/Tris gels and blotted onto nitrocellulose. Blots were blocked in Rockland Odyssey blocking buffer and incubated with a total Syk antibody, 4D10 (Santa Cruz) and pSyk-$Y_{52576}$ (Cell Signaling Technologies). The primary antibodies were diluted 1:1000 and incubated for 1 hour at room temperature. Blots were washed 3 times 5 minutes in Tris-buffered saline containing 1.0% Tween (TBS-T). Blots were then incubated goat αmouse IgG (H+L), AlexaFluor 680 (Life Sciences, Inc) and Goat αRabbit IgG (H+L), DyLight 800 (Thermo Scientific), each diluted 1:20,000 in blocking buffer, for 1 hour at room temperature. Blots were washed 3 times 5 minutes in TBS-T and analyzed on an Odyssey gel imager (LI-COR).

FIG. 3 depicts the level of Syk expression in the MiaPaca and HepG2 malignant colon cell lines (FIG. 3).

Example 15

Determination of Syk Expression in Certain Malignant Solid Tumor Cell Lines

Figure 4:
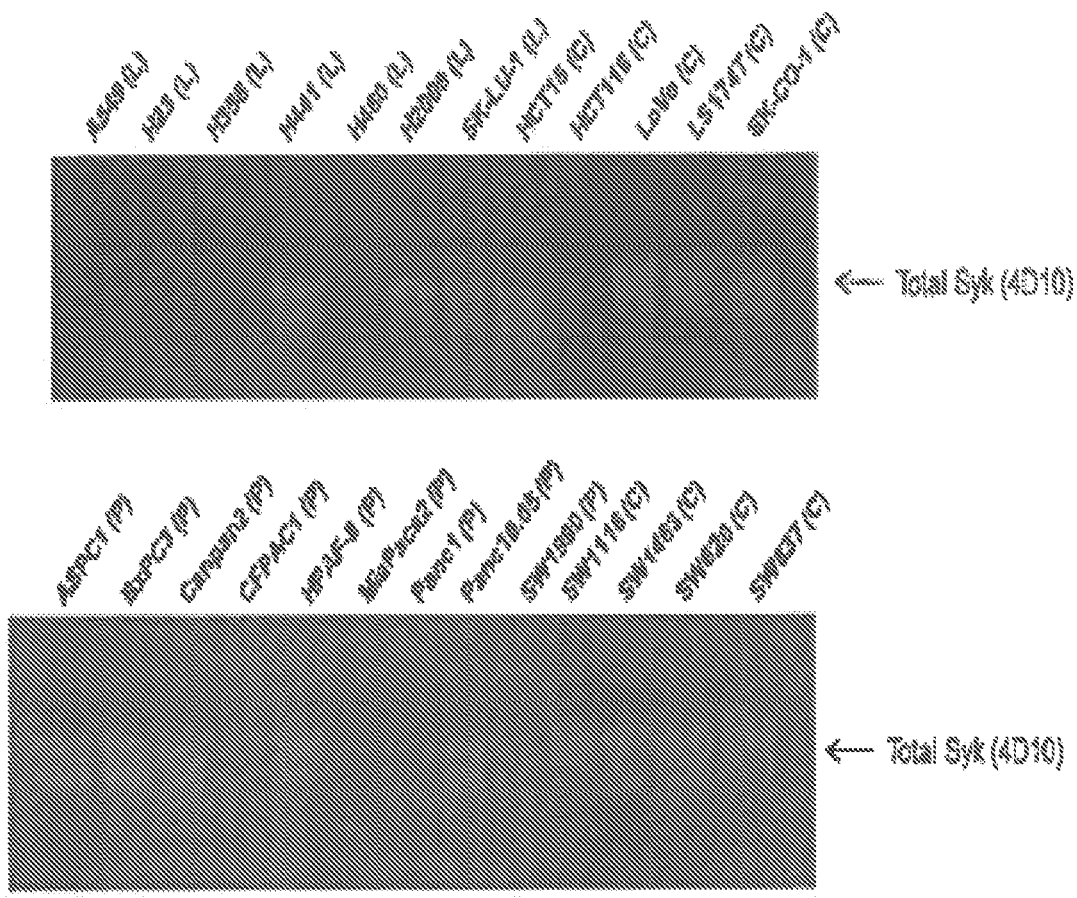
FIG. 4 summarizes the levels of Syk expression in malignant cell lines from lung, pancreas, and colon.

Syk Protein Assay: Cell lines were grown logarithmically in overnight and $1 \times 10^7$ were collected by centrifugation at 300×g at room temperature for 8 minutes in 50 mL tubes. Cell pellets were lysed on ice for 15 minutes in 200 uL of 1×RIPA buffer (Cell Signaling Technology, Danvers Mass.) containing protease (Roche, Palo Alto Calif.) and phosphatase inhibitors (Sigma, Saint Louis Mo.; Santa Cruz Technologies, Dallas Tex.). Cells lysates were transferred to 96-well V-bottom plates and used directly or frozen at −80° C. for use the next day. Proteins were separated with 4-12% SDS-Bis/Tris gels and blotted onto nitrocellulose, Blots were blocked in Rockland Odyssey bloc king buffer and incubated with a total Syk antibody, 4D10 (Santa Cruz). The primary antibodies were dilated 1:1000 and incubated for 1 hour at room temperature. Blots were washed 3 times 5 minutes in Tris-buffered saline containing 1.0% Tween (TBS-T). Blots were then incubated goat αmouse IgG (H+L), AlexaFluor 680 (Life Sciences, Inc), diluted 1:20,000 in blocking buffer, for 1 hour at room temperature. Blots were washed 3 times 5 minutes in TBS-T and analyzed on an Odyssey gel imager (LI-COR), See FIG. 4.

Throughout this specification, various patents, patent applications and other types of publications (e.g., journal articles) are referenced. The disclosure of all patents, patent applications, and publications cited herein are hereby incorporated by reference in their entirety for all purposes.

What is claimed:

1. A method for inhibiting activity of a SYK kinase in a human in need thereof, the method comprising administering to the human a therapeutic effective amount of a vinca-alkaloid, or a pharmaceutically acceptable salt thereof, and a therapeutically effective amount of a compound having the structure of Formula I;

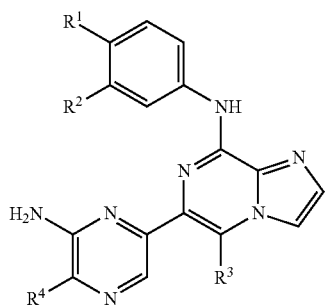

Formula I or a pharmaceutically acceptable salt thereof, wherein:
R$^1$ is selected from the group consisting of

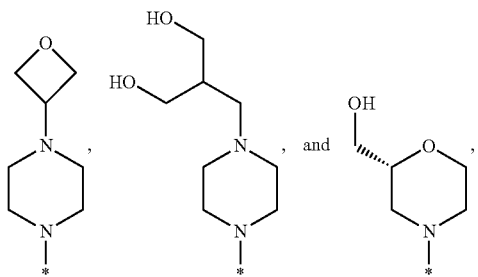

wherein * indicates the carbon atom of the indicated phenyl ring of Formula I to which R$^1$ is attached:
R$^2$ H or 2hydroxyethoxyl:
R$^3$ is H or methyl: and
R$^4$ is H or methyl;
wherein said SYK kinase mediates a disease or condition selected from the group consisting of an inflammatory disorder, an allergic disorder, an autoimmune disease, and cancer.

2. The method of claim 1, wherein the disease or condition is a cancer selected from the group consisting of a hematologic malignancy and a solid tumor.

3. The method of claim 2, wherein the disease or condition is a hematologic malignancy selected from the group consisting of lymphoma, multiple myeloma, or leukemia.

4. The method of claim 2, wherein the disease or condition is selected from the group consisting of small lymphocytic- lymphoma, non-Hodgkin's lymphoma,
indolent non-Hodgkin's lymphoma, refractory iNHL, mantle cell lymphoma, follicular lymphoma, lymphoplasmacytic lymphoma, marginal zone lymphoma, immunoblastic large cell lymphoma, lymphoblastic lymphoma, Splenic marginal zone B-cell lymphoma (+/−villous lymphocytes), Nodal marginal zone lymphoma (+/−N monocytoid B-cells), Extranodal marginal zone B-cell lymphoma of mucosa-associated lymphoid tissue type, cutaneous T-cell lymphoma, extranodal T-cell lymphoma, anaplastic large cell lymphoma, angioimmunoblastic T-cell lymphoma, mycosis fungoides, B-cell lymphoma, diffuse large B-cell lymphoma, Mediastinal large B-cell lymphoma, Intravascular large B-cell lymphoma, Primary effusion lymphoma, small non-cleaved cell lymphoma, Burkitt's lymphoma, multiple myeloma, piasmacytoma, acute lymphocytic leukemia, T-cell acute lymphoblastic leukemia, B-cell acute lymphoblastic leukemia, B-cell prolymphocytic leukemia, acute myeloid leukemia, chronic lymphocytic leukemia, juvenile myelomonocytic leukemia, minimal residual disease, hairy cell leukemia, primary myelofibrosis, secondary myelofibrosis, chronic myeloid leukemia, myelodysplastic syndrome, myeloproliferative disease, and Waldestrom's macroglobulinemia.

5. The method of claim 2, wherein the disease or condition is a solid tumor, wherein the solid tumor is from a cancer selected from the group consisting of pancreatic cancer, urological cancer, bladder cancer, colorectal cancer, colon cancer, breast cancer, prostate cancer, renal cancer, hepatocellular cancer, thyroid cancer, gall bladder cancer, lung cancer (e,g, non-small cell lung cancer, small-cell lung cancer), ovarian cancer, cervical cancer, gastric cancer, endometrial cancer, esophageal cancer, head and neck cancer, meianoma, neuroendocrine cancer, CNS cancer, brain tumors (e.g., glioma, anaplastic oligodendroglioma, adult glioblastoma multiforme, and adult anaplastic astrocytoma), bone cancer, soft tissue sarcoma, retinoblastomas, neuroblastomas, peritoneal effusions, malignant pleural effusions, mesotheilomas, Wilms tumors, trophoblastic neoplasms, hemangiopericytomas, Kaposi's sarcomas, myxoid carcinoma, round cell carcinoma, squamous cell carcinomas, esophageal squamous call carcinomas, oral carcinomas, cancers of the adrenal cortex, and ACTH-producing tumors.

6. The method of claims 2, wherein the disease or condition is selected from the group consisting of systemic lupus erythematosus, myestenia gravis, Goodpasture's syndrome, glomerulonephritis, hemorrhage, pulmonary hemorrhage, atherosclerosis, rheumatoid arthritis, psoriatic, arthritis, monoarticular arthritis, osteoarthritis, gouty arthritis, spondylitis, Behçet disease, autoimmune thyroiditis, Reynaud's syndrome, acute disseminated encephalomyelitis, chronic idiopathic thrombocytopenic purpura, multipie sclerosis, Sjögren's syndrome, autoimmune hemolytic anemia, tissue graft rejection, hyperacute rejection of transplanted organs, allograft rejection, graft-versus-host disease, diseases involving leukocyte diapedesis, disease states due to leukocyte dyscrasia and metastasis, granulocyte transfusion-associated syndromes, cytokine-induced toxicity, scleroderma, vasculitis, asthma, psoriasis, chronic inflammatory bowel disease, ulcerative colitis, Crohn's disease, necrotizing enterocolitis, irritable bowel syndrome, dermatomyositis, Addison's disease, Parkinson's disease, Alzheimer's disease, diabetes, type 1 diabetes mellitus, sepsis, septic shock, endotoxic shock, gram negative sepsis, gram positive sepsis, and toxic shock syndrome, multiple organ injury syndrome secondary to septicemia, trauma, hypovolemic shock, allergic conjunctivitis, vernal conjunctivitis, and thyroid-associated ophthalmopathy, eosinophilic granuiorna, eczema, chronic bronchitis, acute respiratory distress syndrome, ailergic rhinitis, coryza, hay fever, bronchial asthma, silicosis, pulmonary sarcoidosis, pleurisy, alveolitis, emphysema, pneumonia, bacterial pneumonia, bronchiectasis, and pulmonary oxygen toxicity, reperfusion injury of the myocardium, brain, or extremities, thermal injury, cystic fibrosis, keloid formation or scar tissue formation, fever and myalgias due to infection, and brain or spinal cord injury due to minor trauma, diseases involving leukocyte diapedesis, acute hypersensitivity, delayed hypersensitivity, urticaria, food allergies, skin sunburn, inflammatory pelvic disease, urethritis, uveitis, sinusitis, pneumonitis, encephalitis, meningitis, myocarditis, neph riti s, osteomyelitis, rnyositis, hepatitis, alcoholic hepatitis, gastritis, enteritis, contact dermatitis, atopic dermatitis, gingivitis, appendicrtis, pancreatitis, cholecystitis, polycythemie vera, essential thrombocythemia, and polycystic kidney disease.

7. The method of claim 2, wherein the disease or condition is selected from the group consisting of systemic lupus erythematosus, myestenia gravis, rheumatoid arthritis, acute disseminated encephalomyelitis, idiopathic thrombocytopenic purpura, multiple sclerosis, Sjoegren's syndrome, psoriasis, autoimmune hemolytic anemia, asthma, ulcerative colitis'Crohn's disease, irritable bowel disease, and chronic obstructive pulmonary disease, systemic lupus erythematosus, myestenia gravis, rheumatoid arthritis, acute disseminated encephalomyelitis, idiopathic thrombocytopenic purpura, multiple sclerosis, Sjoegren's syndrome, psoriasis, autoimmune hemolytic anemia, asthma, ulcerative colitis, Crohn's disease, irritable bowel disease, and chronic obstructive pulmonary disease.

8. The method of claim 2, wherein the disease or condition is selected from the group consisting of asthma, rheumatoid arthritis, multiple sclerosis, chronic obstructive pulmonary disease, and systemic lupus erythematosus.

9. The method of claim 2, wherein the compound of formula I is

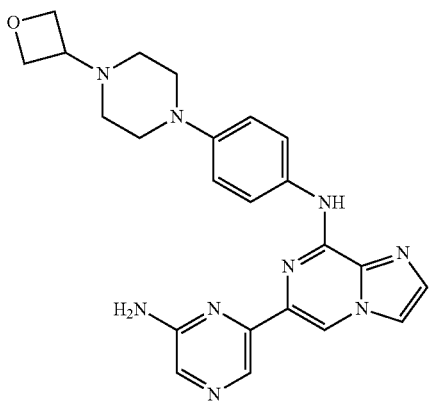 [SMILES: Nc1cncc(-c2cn3ccnc3c(Nc3ccc(N4CCN(C5COC5)CC4)cc3)n2)n1]

and the vinca-alkaloid is seiected from the group consisting of vincristine., vinblastine, vindesine, vinorelbine, desoxyvincaminol, vincaminol, vinburnine, vincamajine, and vineridine.

10. The method of claim 9, wherein the vinca-alkaloid is selected from the group consisting of vincristine, vinblastine, vindesine, and vinoreibine.

11. The method of claim 10 wherein the vinca-alkalod is vincristine.

12. The method of claims 10 wherein the vinca-alkalod is vinblastine.

13. The method of claim 10, wherein the compound of formula (I) or a pharmaceutically acceptable salt thereof, is administered before the vinca-alkaloid, or a pharmaceutically acceptable salt thereof.

14. The method of claim 10, wherein the vinca alkaloid, or a pharmaceutically acceptable salt thereof, is administered before the compound of formula(I) or a pharmaceutically acceptable salt thereof.

15. The method of claim 10, wherein the compound of formula (I) or a pharmaceutically acceptable salt thereof, and the vinca-aikaloid, or a pharmaceutically acceptable salt thereof, are administered simultaneously.

16. The method of claim 10, wherein the compound of formula (I) or a pharmaceutically acceptable salt thereof is administered at a dose between 50 mg and 300 mg and the vinca-alkaloid, or a pharmaceutically acceptable salt thereof, is administered at a dose between 0.1 mg-$M^2$ and 1,5 mg-$M^2$.

17. The method of claim 10, wherein the compound of formula (I) or a pharmaceutically acceptable salt thereof is administered at a dose between 100 mg and 250 mg and the vinca-alkaloid or a pharmaceutically acceptable salt thereof is administered at a dose between 0.25 mg-$M^2$ and 1.0 mg-$M^2$, wherein the vinca-alkaloid is selected from the group consisting of vincristine and vinblastine.

18. The method of claim 10, wherein the human who has cancer is (i) refractory to at least one chemotherapy treatment, or (ii) is in relapse after treatment with chemotherapy, or a combination thereof.

19. The method of claim 10, wherein the cancer is a hematologic malignancy.

20. The method of claim 19, wherein the cancer is a leukemia.

21. The method of claim 19, wherein the leukemia is chronic lymphocytic leukemia (CLL).

22. The method of claim 19, wherein the cancer is a lymphoma.

23. The method of claim 22, wherein the lymphoma is non-Hodgkin's lymphoma (NHL).

24. The method of claim 19, wherein the NHL is diffuse large B-cell lymphoma (DLBCL), mantle cell lymphoma (MCL), follicular lymphoma (FL), small lymphocytic lymphoma (SLL), lymphoplasmacytic lymphoma (LPL), and marginal zone lymphoma (MZL).

25. The method of claim 19, wherein the cancer is selected from the group consisting of acute lymphocytic leukemia (ALL), acute myeloid leukemia (AML), Burkitt's lymphoma (BL), chronic lymphocytic leukemia (CLL), small lymphocytic lymphoma (SLL), myelodysplastic syndrome (MDS), myeloproliferative disease (MPD), chronic myeloid leukemia (CML), multiple myeloma (MM), non-Hodgkin's lymphoma (NHL), indolent non-Hodgkin's lymphoma (iNHL), refractory iNHL, mantle cell lymphoma (MCL), follicular lymphoma (FL). Waldestrom's macroglobulinemia (WM), T-cell lymphoma, B-cell lymphoma, Hodgkin's lymphoma, diffuse large B-cell lymphoma (DLBCL), lymphoplasmacytic lymphoma (LPL), and marginal zone lymphoma (MZL).

26. The method of claim 19, wherein the cancer is a solid tumor and expresses spleen tyrosine kinase (Syk) activity.

27. The method of claim 26, wherein the solid tumor cancer is selected from the group consisting of pancreatic, lung, colorectal cancer, ovarian, breast, adenocarcinoma, esophageal and hepatocellular.

28. A method for treating cancer in a subject in need thereof, comprising administering to the subject a therapeutically effective amount of a compound of formula I:

Formula I

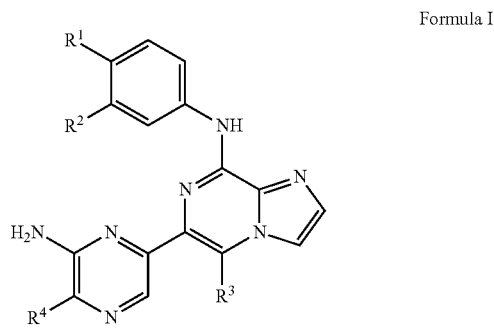

or a pharmaceutically acceptable salt thereof, wherein,
$R^1$ is selected from the group consisting of

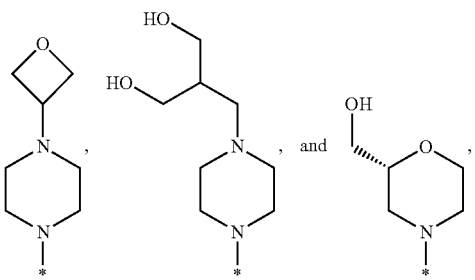

wherein * indicates the carbon atom of the indicated phenyl ring of Formula I to which $R^1$ is attached:
$R^2$ is H or 2hydroxyethoxyl:
$R^3$ is H or methyl:
$R^4$ is H or methyl; and
a therapeutically effective amount of a vinca-alkaloid, or a pharmaceutically acceptable salt;
wherein said cancer is a hematologic malignancy selected from the group consisting of lymphoma, multiple myeloma, or leukemia.

29. The method of claim 28, wherein the compound of formula I is

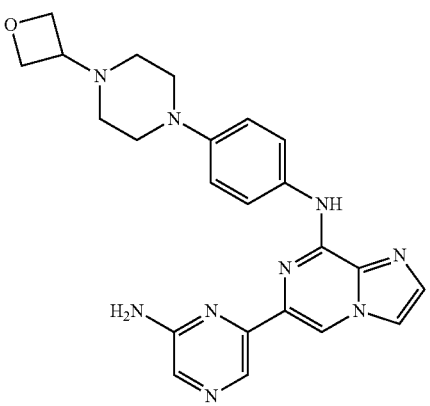 [SMILES: Nc1cncc(-c2cn3ccnc3c(Nc3ccc(N4CCN(C5COC5)CC4)cc3)n2)n1]

or a pharmaceutically acceptable salt thereof.

30. The method of claim 29, wherein said vinca-alkaloid is selected from the group consisting of vincristine, vinblastine, vindesine, vinorelbine, desoxyvincaminol, vincaminol, vinburnine, vincamajine, and vineridine, or a pharmaceutically acceptable salt thereof.

* * * * *